(12) United States Patent
Curran et al.

(10) Patent No.: US 7,321,046 B2
(45) Date of Patent: *Jan. 22, 2008

(54) ANALOGS OF DICTYOSTATIN, INTERMEDIATES THEREFOR AND METHODS OF SYNTHESIS THEREOF

(75) Inventors: Dennis P. Curran, Pittsburgh, PA (US);
Youseung Shin, Pittsburgh, PA (US);
Jean-Hugues Fournier, Montreal (CA);
John Mancuso, Montreal (CA); Billy W. Day, Pittsburgh, PA (US); Arndt Bruckner, Hallstadt (DE); Yoshikazu Fukui, Otsu (JP)

(73) Assignee: University of Pittsburgh, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/139,949

(22) Filed: May 27, 2005

(65) Prior Publication Data

US 2006/0025395 A1 Feb. 2, 2006

Related U.S. Application Data

(63) Continuation-in-part of application No. 10/655,916, filed on Sep. 5, 2003, now Pat. No. 7,122,686.

(60) Provisional application No. 60/574,858, filed on May 27, 2004, provisional application No. 60/408,503, filed on Sep. 6, 2002, provisional application No. 60/437,736, filed on Jan. 2, 2003.

(51) Int. Cl.
*C07D 313/04* (2006.01)
*C07D 313/16* (2006.01)
(52) U.S. Cl. ...................................... 549/271
(58) Field of Classification Search .............. 549/271
See application file for complete search history.

(56) References Cited

U.S. PATENT DOCUMENTS 5,430,053 A 7/1995 Pettit (Continued)

FOREIGN PATENT DOCUMENTS

EP 0 680 958 11/1995

(Continued)

OTHER PUBLICATIONS

Shin et al., Organic Letters, 2002, "Discodermolide/Dictyostatin Hybrids: Synthesis and Biological Evaluation", vol. 4, pp. 4443-4446.*

(Continued)

*Primary Examiner*—Margaret D. Seaman
*Assistant Examiner*—Niloofar Rahmani
(74) *Attorney, Agent, or Firm*—Bartony & Hare, LLP

(57) ABSTRACT

Dictyostatin and its analogs show great promise as new anticancer agents. The present invention provides dictyostatin analogs, synthetic intermediates for the synthesis of dictyostatin analogs, and synthetic methods for the synthesis of such analogs and intermediates. Dictyostatin analogs can have the following structure or its enantiomer

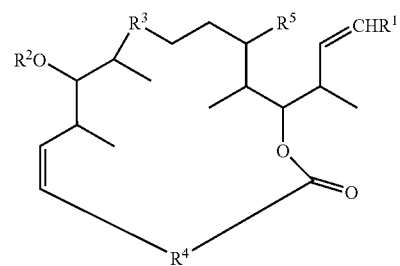

wherein $R^1$ is H, an alkyl group, an aryl group, an alkenyl group, an alkynyl group, or a halogen atom; $R^2$ is H, a protecting group, an alkyl group, a benzyl group, a trityl group, —$SiR^aR^bR^c$, $CH_2OR^d$, or $COR^e$; $R^a$, $R^b$ and $R^c$ are independently an alkyl group or an aryl group; $R^d$ is an alkyl group, an aryl group, an alkoxylalkyl group, —$R^iSiR^aR^bR^c$ or a benzyl group, wherein $R^i$ is an alkylene group; $R^e$ is an alkyl group, an allyl group, a benzyl group, an aryl group, an alkoxy group, or —$NR^gR^h$, wherein $R^g$ and $R^h$ are independently H, an alkyl group or an aryl group; $R^3$ is $(CH_2)_n$ where n is and integer in the range of 0 to 5, —$CH_2CH(CH_3)$—, —CH=CH—, —CH=C(CH_3)—, or —C≡C—; $R^4$ is

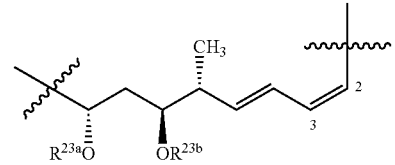

wherein $R^{23a}$ is H, a protecting group, an alkyl group, a benzyl group, a trityl group, —$SiR^aR^bR^c$, $CH_2OR^d$, or $COR^e$; $R^{23b}$ is H, a protecting group, an alkyl group, a benzyl group, a trityl group, —$SiR^aR^bR^c$, $CH_2OR^d$, or $COR^e$, or $R^{23a}$ and $R^{23b}$ together form a portion of six-membered acetal ring incorporating $CR^tR^u$; $R^t$ and $R^u$ are independently H, an alkyl group, an aryl group or an alkoxyaryl group; and $R^5$ is H or $OR^{2b}$, wherein $R^{2b}$ is H, a protecting group, an alkyl group, an aryl group, a benzyl group, a trityl group, —$SiR^aR^bR^c$, $CH_2OR^d$, or $COR^e$; provided that the compound is not dictyostatin 1.

6 Claims, 10 Drawing Sheets

U.S. PATENT DOCUMENTS

2004/0186165 A1* 9/2004 Curran et al. .............. 514/450

FOREIGN PATENT DOCUMENTS

| WO | WO 01/62239 | 8/2001 |
| WO | WO 02/12220 | 2/2002 |
| WO | WO 02/057251 | 7/2002 |
| WO | WO 2004/022552 | 9/2003 |
| WO | WO 2005/117588 | 12/2005 |

OTHER PUBLICATIONS

James A. Marshall et. al.; Synthesis of Enantioenriched Propargylic Alcohols Related to Polyketide Natural Products. A Comparison of Methodologies; Organic Letters; 2003; vol. 5, No. 18, pp. 3197-3199.

Markus Kalesse; The Chemistry and Biology of Discodermolide; Chembiochem; 2000; 1; pp. 171-175.

Ian Paterson et. al.; The Development of a Practical Total Synthesis of Discodermolide, a Promising Microtubule-Stabilizing Anticancer Agent; Eur. J. org. Chem; 2003; pp. 2193-2208.

George R. Pettit et. al.; Isolation and Structure of the Cancer Cell Growth Inhibitor Dictyostatin 1; J. Chem. Soc., Chem. Commun., 1994; pp. 1111-1112.

Richard A. Isbrucker et. al.; Tubulin Polymerizing Activity of Dictyostatin-1, a Polyketide of Marine Sponge Origin; Biochemical Pharmacology; 2003; 66 pp. 75-82.

Ian Paterson et. al.; Stereochemical Determination of Dictyostatin, a Novel Microtubule-Stabilising Macrolide from the Marine Sponge Corallistidae; Chem. Commun.; 2004; pp. 632-633.

Prodeep Phukan et. al.; Flexible Routes to the 5-Hydroxy Acid Fragment of the Cryptophycins; Eur. J. Org. Chem. 2003, pp. 1733-1740.

Merritt B. Andrus et. al.; Synthesis of Octalactin Lactone and Side Chain; Tetrahedron Letters; 1996; vol. 37; No. 29; pp. 5049-5052.

Amos B. Smith III et. al.; Evolution of a Gram-Scale Synthesis of (+)-Discodermolide; J. Am. Chem. Soc.; 2000; 122; pp. 8654-8664.

Andrew G. Myers et. al.; Pseudophedrine as a Practical Chiral Auxiliary for the Synthesis of Highly Enantlomerically Enriched Carboxylic Acids, Alcohols, Aldehydes, and Ketones; J. Am. Chem. Soc.; 1997; 119, pp. 6496-6511.

Kazuhiko Matsumura et. al.; Asymmetric Transfer Hydrogenation of Alfa, Beta-Acetylenic Ketones; J. Am. Chem. Soc.; 1997; 119; pp. 8738-8739.

Junji Inanaga et. al.; A rapid Esterification by Means of Mixed Anhydride and Its Application to Large-ring Lactonization; Bulletin of the Chemical Society of Japan; 1979; Vo.52; (7); pp. 1989-1993.

Nerenberg, J. B. et.al. Total synthesis of the immunosuppressive agent (−)- discodeermolide. J. Am. Chem. Soc. 1993, 115, 12621-12622.

Smith, A. B. et.al.;Total Synthesis of (−)- Discodermolide. J. Am. Chem. Soc. 1995, 117, 12011-12012.

Marshall, J. A. et.al.; Total synthesis of (+)-discodermolide. J. Org. Chem. 1998, 63, 7885-7892.

Paterson, I.et.al; Total synthesis of the antimicrotubule agent (+)-discodermolide using boron mediated aldol reactions of chiral ketones. Angew. Chem., Int. Ed. Eng. 2000, 39, 377-380.

Paterson, I.et.al.; Synthesis of (+)-discodermolide and analogues by control of asymmetric induction in aldol reactions of gamma-chiral (Z)-enals. Tetrahedron Lett. 2000, 41, 6935-6939.

Roush, W. R.et.al.; Asymmetric synthesis using tartrate Ester modified allylboronates. 2. Single and double asymmetric reactions with alkoxy-substituted aldehydes, J. Org. Chem. 1990, 55, 4117-4126.

Paterson, I.et.al.; A practical synthesis of (+)-discodermolide and analogues: Fragment union by complex aldol reactions. J. Am. Chem. Soc. 2001, 123, 9535-9544.

Martello, L. A. et al. The relationship between taxol and (+)-discodermolide: synthetic analogs and modeling studies. Chemistry Biol. 2001, 8, 843-855.

Harried, S. et.al. Total Synthesis of (−)-Discodermolide: An Application of a Chelation-Controlled Alkylation Reaction. J. Org. Chem. 1997, 62, 6098-6099.

Evans, D. A.et.al.. Diasteroselective magnesium halide-catalyzed anti-aldol reactions of chiral N-acyloxazolidinones. J. Am. Chem. Soc. 2002, 124, 392-393.

CAS ONLINE, STN, Columbus, Ohio, USA, 135: 371269, RN 374568-47-5.

Day, B. W., et.al;. Convenient syntheses of (2R,3S,4R)-3-(tert-butyldimethylsilanyloxy)-2,4-dimethyl-5-oxopentanoic acid methoxymethyl-amide from methacrolein. Preparation of C1-C7 and C17-C24 fragments of (+)-discodermolide. Tetrahedron Asymmetry 2002, 13, 1161-1165.

Clark, D. L. et. al.; Studies on the alkylation of chiral enolates: application toward the total synthesis of discodermolide. J. Org. Chem. 1993, 58 5878-5879.

Heathcock, C. H.et.al.;. Acyclic stereoselection-13; Aryl esters: reagents for threo-aldolization. Tetrahedron 1981, 37, 4087-4095.

Paterson, I.et.al.; A. Studies towards the total synthesis of the marine-derived immunosuppresant discodermolide: stereoselective synthesis of a C9-C24 subunit. Synlett. 1995, 498-500.

Kocovsky, P. Carbamates: a method of synthesis and some synthetic applications. Tetrahedron Lett. 1986, 27 5521-5524.

Fujiwara et. al. Synthesis of the Tetrahydropyran Ring Part of a Marine Toxin Polycavernoside-A. Chemistry Letters. 1994, pp. 2147-2150.

CAS ONLINE, STN, Columbus, Ohio, USA, 124: 86679, RN 172269-30-6P.

CAS ONLINE, STN, Columbus, Ohio, USA, 66: 94583, RN 16078-24-3P.

Shin et al., Discodermolide/Dictyostatin Hybrids: Synthesis and Biological Evaluation; Organic Letters; 2002; vol. 4(25): pp. 4443-4446.

Querolle et al., Synthesis of Novel Macrocyclic Docetaxel Analogues. Influence of their Macrocyclic Ring Size on Tubulin Activity; J. Med. Chem.; 2003; 46:3623-3630.

* cited by examiner

Figure 1.

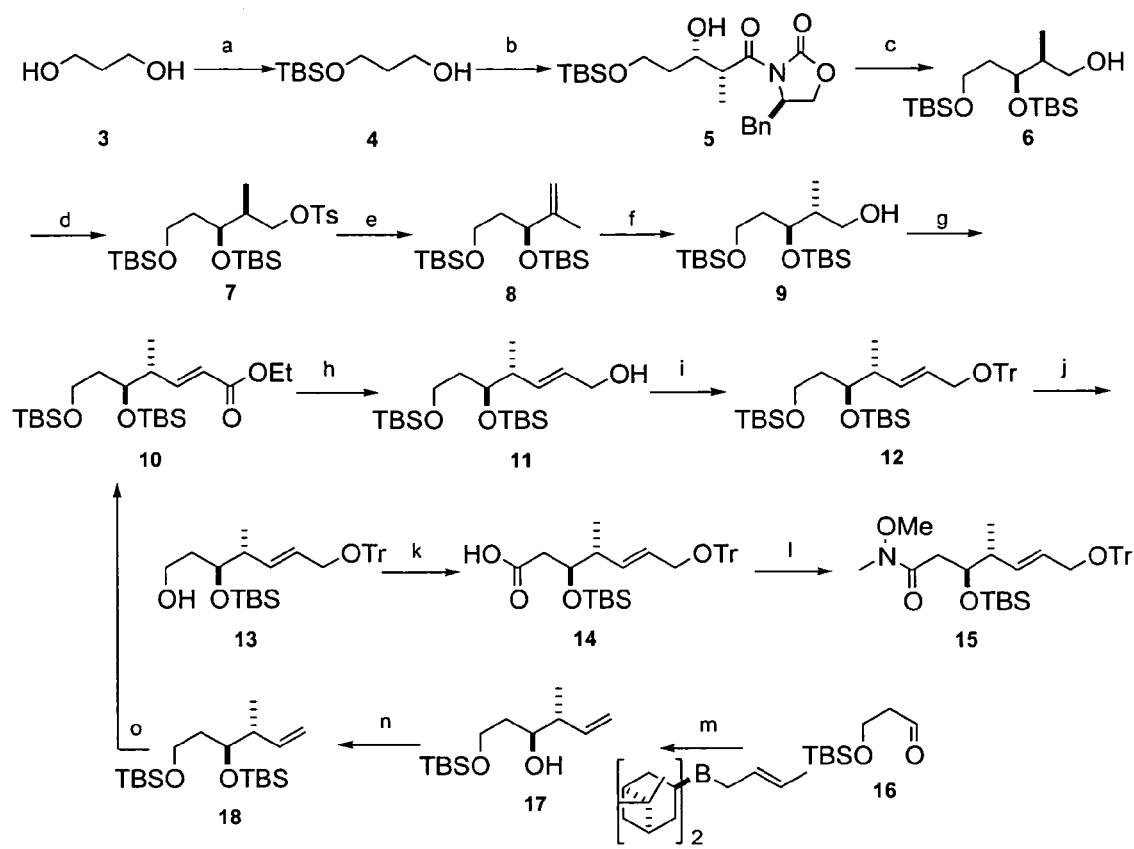

(a) TBSCl, NaH, THF, quant. (b) (i) pyridine-SO₃, Et₃N, DMSO-CH₂Cl₂; (ii) n-Bu₂OTf, DIPEA, 65% (2 steps). (c) LiBH₄, MeOH, THF, 87%. (d) TsCl, pyridine, 90%. (e) NaI, DBU, glyme, 70%. (f) 9-BBN, 72%. (g) (i) Dess-Martin; (ii) Horner-Emmons Wittig, 59% (2 steps). (h) DIBAL-H, CH₂Cl₂, 97%. (i) TrCl, 4-DMAP, pyridine. (j) HF-pyridine, pyridine, THF, 89% (2 steps). (k) (i) pyridine-SO₃, Et₃N, DMSO-CH₂Cl₂; (ii) NaClO₂, NaHPO₄, 2-methyl-2-butene, THF-H₂O. (l) NH(Me)(OMe)·HCl, DCC, Et₃N, DMAP, CH₂Cl₂, 73% (3 steps). (m) THF, hexane, −90 °C, 55%, 95% ee. (n) TBSCl, imidazole, DMAP, 95%. (o) OsO₄, NMO, THF, H₂O, then NaIO₄; (ii) Horner-Wadsworth-mmons, 83% (2 steps).

(a) TBSOTf, 2,6-lutidine. (b) LiBH₄, MeOH, THF, 90%. (c) (i) pyridine-SO₃, Et₃N, DMSO-CH₂Cl₂; (ii) Horner-Wadsorth-Emmons, 70%. (d) NiCl₂, NaBH₄, 97%. (e) 1N LiOH, acetone. (f) Evans auxiliary, pivaloyl chloride, Et₃N, LiCl, 70% (2 steps). (g) NaHMDS, MeI, 74%. (h) LiBH₄, 83%. (i) (i) TBSCl, imidazole; (ii) DDQ, 81% (2 steps). (j) (i) pyridine-SO₃, DMSO-CH₂Cl₂; (ii) PPh₃, CBr₄; (iii) n-BuLi, 73% (3 steps). (k) (i) PPh₃, I₂, imidazole, DIPEA; (ii) LDA, LiCl, 30, 87% (2 steps); (l) BH₃NH₃, LDA, 96%.

(a) n-BuLi, THF, 93%. (b) (S, S)-Noyori catalyst (20 mol %), i-PrOH, 79%. (c) Lindlar catalyst, $H_2$ (balloon), toluene, 91%. (d) TBSOTf, 2,6-lutidine, $CH_2Cl_2$, 99%. (e) HF-pyridine, pyridine, THF, 0 °C, 1 day, 67%. (f) (i) Dess-Martin oxidation; (ii) Ba(OH)$_2$, 38, THF-H$_2$O, 80% (2 steps). (g) NiCl$_2$, NaBH$_4$, MeOH-THF, 76%. (h) NaBH$_4$, MeOH-THF, 70%(β), 29%(α).

(a) TBSOTf, 2,6-lutidine, $CH_2Cl_2$, 99%. (b) DIBAL-H, $CH_2Cl_2$, 88%. (c) (i) Dess-Martin oxidation; (ii) A, $CrCl_2$, THF; (iii) NaH, THF, 89% (3 steps). (d) $ZnBr_2$, $CH_2Cl_2$-MeOH, 69%. (e) (i) Dess-Martin oxidation; (ii) $(CF_3CH_2O)P(O)CH_2CO_2Me$, KHMDS, 18-crown-6, THF, 86% (2 steps). (f) DDQ, $CH_2Cl_2$-$H_2O$, 88%. (g) 1N KOH, EtOH-THF. (h) 2,4,6-trichlorobenzoyl chloride, $Et_3N$, THF then 4-DMAP(10 eq.), toluene, 78% (2 steps). (i) 3N HCl-MeOH, THF, 55%.

Figure 5.

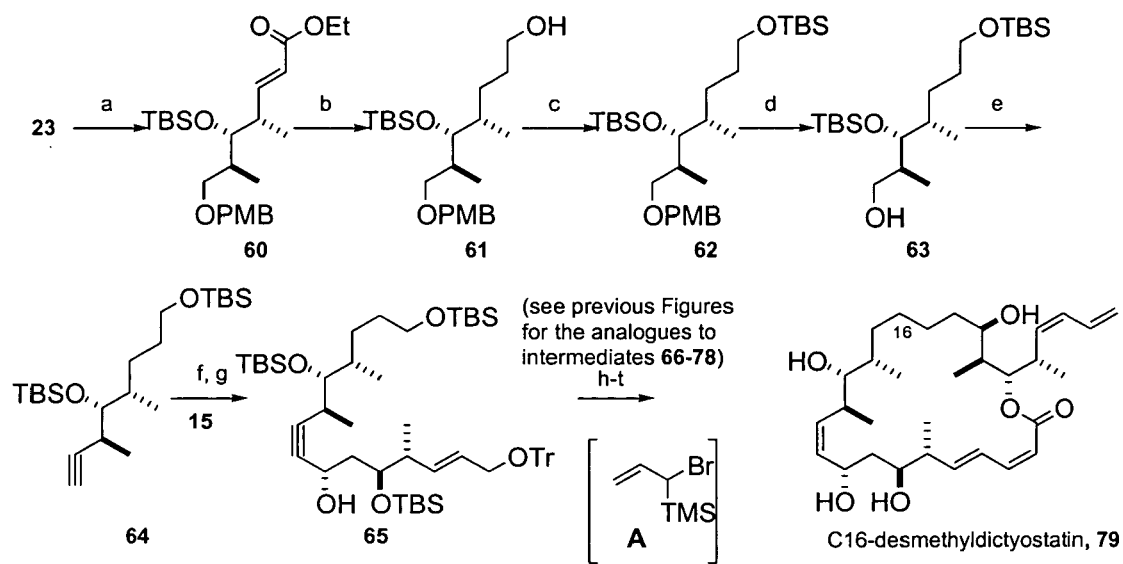

(a) (i) pyridine•SO₃, Et₃N; (ii) Horner-Wadsworth-Emmons, 63% (2 steps). (b) (i) NiCl₂, NaBH₄, MeOH-THF, 97%; (ii) DIBAL-H, 77%. (c) TBSCl, imidazole, quant. (d) DDQ, 90%. (e) (i) pyridine•SO₃, Et₃N; (ii) Corey-Fuchs, 55% (3 steps). (f) n-BuLi, THF, 86%; (g) (S,S)-Noyori catalyst, i-PrOH, 95%. (h) Lindlar catalyst, H₂, quant. (i) TBSOTf, 2,6-lutidine, 96%. (j) HF-pyridine, 0°C, 21h, 71%. (k) (i) Dess-Martin; (ii) 38, Ba(OH)₂, THF-H₂O, 83% (2 steps). (l) NiCl₂, NaBH₄, MeOH-THF, 65%. (m) LiAl(O-t-Bu)₃H, THF, 95%. TBSOTf. (n) DIBAL-H, 90%. (o) (i) Dess-Martin; (ii) CrCl₂, A; (iii) NaH, 82% (3 steps). (p) ZnBr₂, CH₂Cl₂-MeOH, 89%. (q) (i) Dess-Martin; (ii) Still-Gennari, 86% (2 steps). (r) DDQ, 82%. (s) (i) 1N KOH-THF; (ii) Yamaguchi macrolactonization, 76% (2 steps). (t) 3N HCl-MeOH, THF, 24%.

(a) n-BuLi, THF, 98%. (b) Noyori cat. (20 mol %), i-PrOH, 87%. (c) Lindlar cat., H$_2$, 90%. (d) TBSOTf, 2,6-lutidine, 100%. (e) DDQ, 84%. (f) TBSOTf, 94%. (g) HF-pyridine, 0 °C, 2 days, 66%. (h) (i) Dess-Martin; (ii) 38, Ba(OH)$_2$, THF-H$_2$O, 78% (2 steps). (i) NiCl$_2$, NaBH$_4$, MeOH-CH$_2$Cl$_2$, 76%. (j) NaBH$_4$, MeOH, 96%. (k) TBSOTf, 2,6-lutidine, 86%. (l) DIBAL-H, 97%. (m) (i) Dess-Martin; (ii) CrCl$_2$, A; NaH. 85% (3 steps). (n) ZnBr$_2$, CH$_2$Cl$_2$-MeOH, 83%.

(a) (i) Dess-Martin; (ii) Still-Gennari, 90% (2 steps). (b) DDQ, 90%. (c) 1N KOH, EtOH-THF. (d) Yamaguchi, 78% (2 steps. (e) 3N HCl, 25%.

(a) TBSOTf, 93%. (b) DIBAL-H, 87%. (c) (i) Dess-Martin; (ii) CrCl$_2$, A; (iii) NaH, 88% (3 steps). (d) ZnBr$_2$, 65%. (e) (i) Dess-Martin; (ii) Still-Gennari, 84% (2 steps). (f) DDQ, 90%. (g) (i) 1N KOH; (ii) Yamaguchi, 45% (2 steps). (h) 3N HCl, 45% and 15%

Figure 9.
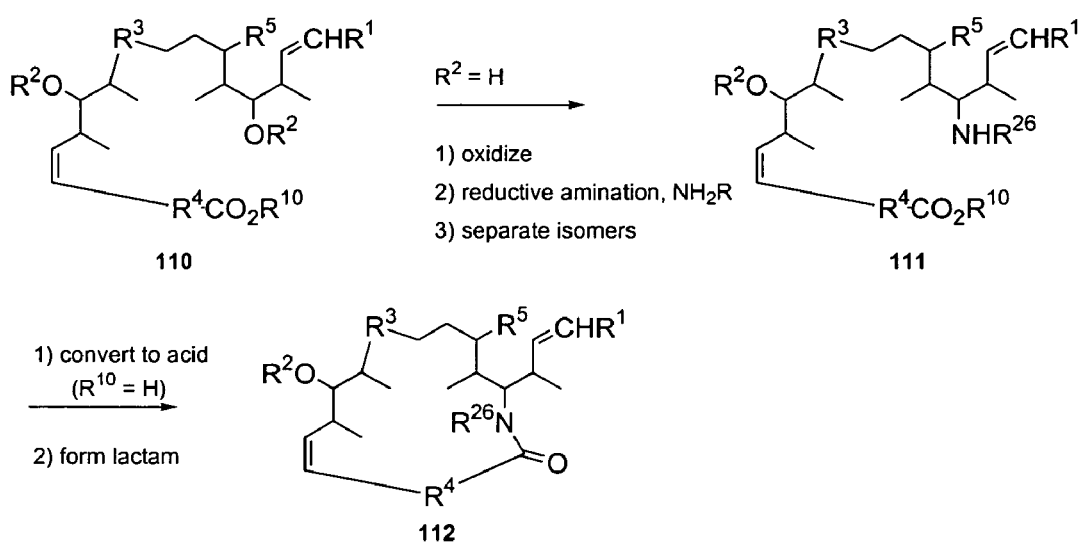
*Example:*
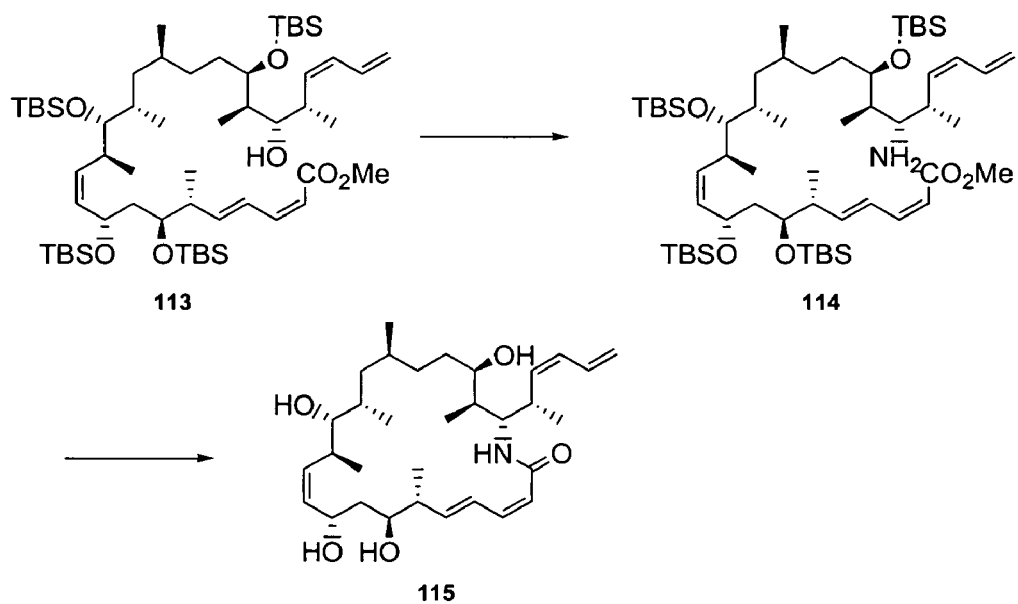

ANALOGS OF DICTYOSTATIN, INTERMEDIATES THEREFOR AND METHODS OF SYNTHESIS THEREOF

CROSS-REFERENCE TO RELATED APPLICATIONS

This application, which claims benefit of U.S. Provisional Patent Application No. 60/574,858 filed May 27, 2004, the disclosure of which is incorporated herein by reference, is a continuation in part of U.S. patent application Ser. No. 10/655,916, filed Sep. 5, 2003, now U.S. Pat. No. 7,122,686, the disclosure of which is incorporated herein by reference, which claims the benefit of U.S. Provisional Patent Application Ser. No. 60/408,503, filed Sep. 6, 2002 and U.S. Provisional Patent Application Ser. No. 60/437,736 filed Jan. 2, 2003, the disclosures of which are incorporated herein by reference.

GOVERNMENT INTEREST

This invention was made with government support under grant CA 78039 awarded by the National Institutes of Health. The government has certain rights in this invention.

BACKGROUND OF THE INVENTION

The present invention relates to analogs of dictyostatin, intermediates for the synthesis of such analogs and methods of synthesis of such intermediates and analogs.

References set forth herein may facilitate understanding of the present invention or the background of the present invention. Inclusion of a reference herein, however, is not intended to and does not constitute an admission that the reference is available as prior art with respect to the present invention.

The discovery and development of new chemotherapeutic agents for the treatment of cancer is currently of high importance. Some of the best currently available chemotherapeutic agents are natural products or natural product analogs. For example, Taxol (paclitaxel) is a natural product that is currently being used to treat patients with breast and ovarian cancer among others. A number of analogs of Taxol, including Taxotere (docetaxel), are also powerful anticancer agents.

Recently, the natural product (+)-discodermolide and its analogs have shown great promise as anticancer agents. Discodermolide has been shown to have a mechanism of action similar to Taxol, but it is active against Taxol-resistant cell lines and it is more water soluble than Taxol. Accordingly, it may have a different and/or broader spectrum of action than Taxol and be easier to formulate and administer. Analogs of discodermolide have been made and tested for activity. For example, see Myles, D. C. Emerging microtubule stabilizing agents for cancer chemotherapy, *Annual Reports In Medicinal Chem*; Academic Press: San Diego, Calif., 2002; pp 125-132. An interesting feature of discodermolide is that both enantiomers are biologically active.

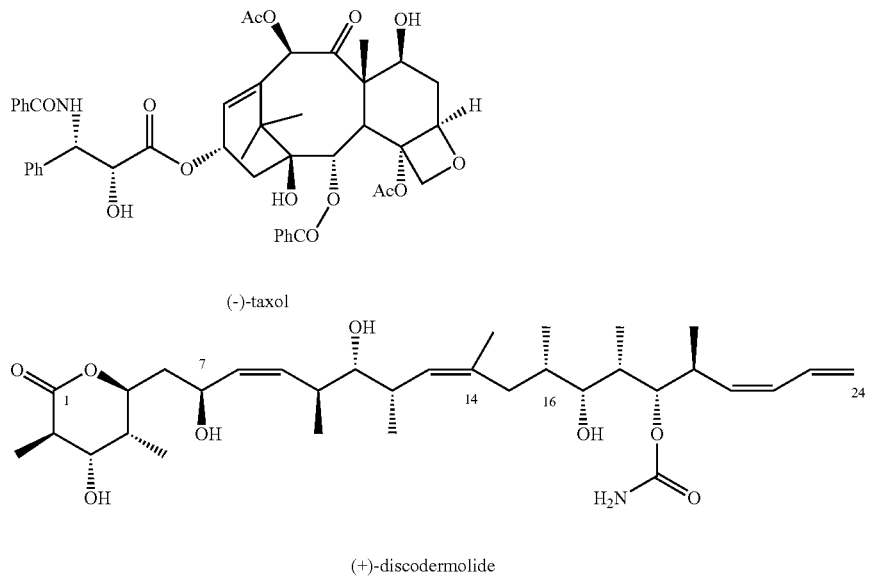

(−)-taxol (+)-discodermolide

Recently, an unusual macrolactone natural product dictyostatin 1 (sometimes called simply "dictyostatin") was isolated from two different sponges and a partial structure was assigned as shown below. See Pettit, G. R.; Cichacz, Z. A. Isolation and structure of dictyostatin 1. In U.S. Pat. No. 5,430,053; 1995; Pettit, G. R.; Cichacz, Z. A.; Gao, F.; Boyd, M. R.; Schmidt, J. M. Isolation and structure of the cancer cell growth inhibitor dictyostatin 1. *J Chem. Soc., Chem. Commun.* 1994, 1111-1112. The configurations at C16 and C19 were not yet assigned in the natural product and the absolute configuration was not known. Dictyostatin shows extremely high potencies against and array of cancer cell lines.

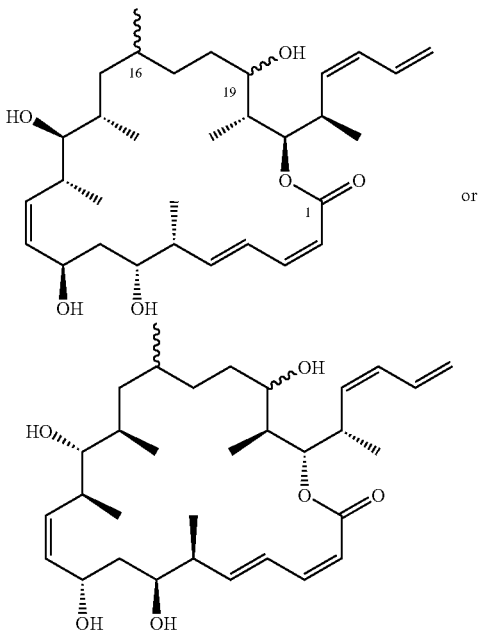

originally suggested structures dictyostatin 1
absolute configuration unknown, configurations at C16 and C19 unassigned Dictyostatin was also shown to stabilize microtubules, like discodermolide and Taxol. See Wright, A. E.; Cummins, J. L.; Pomponi, S. A.; Longley, R. E.; Isbrucker, R. A. Dictyostatin compounds for stabilization of microtubules. In PCT Int. Appl.; WO62239, 2001. Accordingly, dictyostatin and its analogs show great promise as new anticancer agents. In U.S. patent application Ser. No. 10/655,916, it was shown that novel analogs of dictyostatin are promising anti-cancer agents with potential advantages over Taxol and discodermolide, and taught the syntheses of these analogs.

It remains desirable to further develop analogs of dictyostatin as well at to develop methods of synthesis of dictyostatin analogs and intermediates for use in such methods.

SUMMARY OF THE INVENTION

The inventors of the present invention have shown that the proposed structures of (−)-dictyostatin set forth above are incorrect and that the correct structure is as shown below.

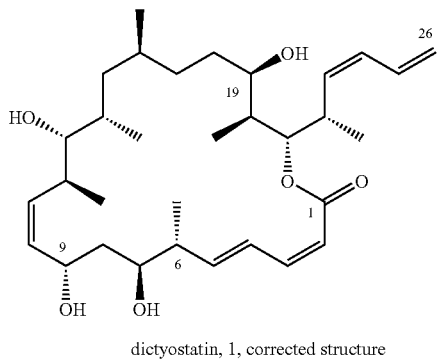

dictyostatin, 1, corrected structure

In several aspects of the present invention, new and improved methods and new intermediates for the synthesis of dictyostatin and analogs are provided. In several other aspects of the present invention, analogs of dictyostatin as well as methods and intermediates for the synthesis of these analogs are provided.

The present inventors have shown that of the dictyostatin analogs set forth in the specification and claims of U.S. patent application Ser. No. 10/655,916, those analogs having a stereostructure similar to that of dictyostatin are relatively highly biologically active. In that regard, compounds having the following structure were found to be relatively highly active:

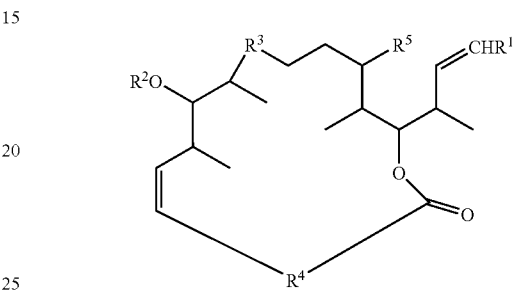

wherein $R^1$ is H, an alkyl group, an aryl group, an alkenyl group, an alkynyl group, or a halogen atom;

$R^2$ is H, a protecting group, an alkyl group, a benzyl group, a trityl group, —SiR$^a$R$^b$R$^c$, CH$_2$OR$^d$, or COR$^e$;

$R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein $R^i$ is an alkylene group;

$R^e$ is an alkyl group, an allyl group, a benzyl group, an aryl group, an alkoxy group, or —NR$^g$R$^h$, wherein $R^g$ and $R^h$ are independently H, an alkyl group or an aryl group;

$R^3$ is $(CH_2)_n$ where n is and integer in the range of 0 to 5, —CH$_2$CH(CH$_3$)—, —CH=CH—, —CH=C(CH$_3$)—, or —C≡C—;

$R^4$ is

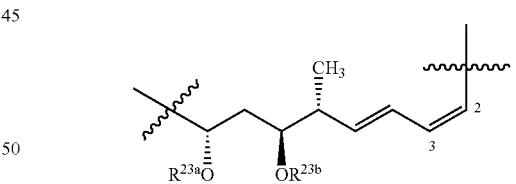

wherein $R^{23a}$ is H, a protecting group, an alkyl group, a benzyl group, a trityl group, —SiR$^a$R$^b$R$^c$, CH$_2$OR$^d$, or COR$^e$, $R^{23b}$ is H, a protecting group, an alkyl group, a benzyl group, a trityl group, —SiR$^a$R$^b$R$^c$, CH$_2$OR$^d$, or COR$^e$, or $R^{23a}$ and $R^{23b}$ together form a portion of six-membered acetal ring incorporating CR$^t$R$^u$;

$R^t$ and $R^u$ are independently H, an alkyl group, an aryl group or an alkoxyaryl group; and $R^5$ is H or OR$^{2b}$, wherein $R^{2b}$ is H, a protecting group, an alkyl group, an aryl group, a benzyl group, a trityl group, —SiR$^a$R$^b$R$^c$, CH$_2$OR$^d$, or COR$^e$; provided that the compound is not dictyostatin 1.

When groups including, but not limited to, —SiR$^a$R$^b$R$^c$, CH$_2$OR$^d$, and/or COR$^e$ are set forth as a substituent for more than one group in compounds of the claims and the specification of the present invention (for example, as a substituent of $R^2$ and $R^{23a}$ above), it is to be understood that the groups of those substituents ($R^a$, $R^b$, $R^c$, $R^d$, and $R^e$ in this example), are independently, the same of different within each group and among the groups.

In one embodiment, the compound has the followings stereostructure or its enantiomer:

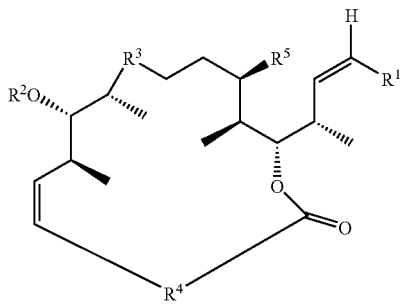

wherein $R^1$ is alkenyl; $R^2$ is H; $R^3$ is —CH$_2$CH(CH$_3$), CH$_2$CH$_2$, —CH=CH, or —CH=C(CH$_3$). In one such compound (16-desmethyldictyostatin), $R^3$ is CH$_2$CH$_2$, $R^5$ is OH, $R^1$ is CH=CH$_2$ and $R^{23a}$, $R^{23b}$ are H. In another embodiment, $R^5$ is OH or OSiR$^a$R$^b$R$^c$. In several embodiments, C2-C3 E-stereoisomers of the compounds or their enantiomers are provided.

Several intermediates are useful in synthesizing such compounds. For example, one such intermediate is a compound of the following structure or its enantiomer.

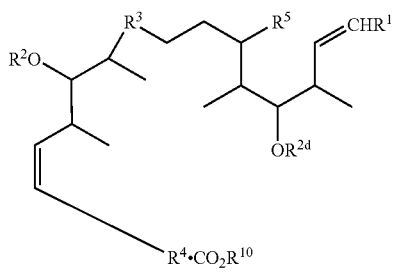

wherein $R^1$ is H, an alkyl group, an aryl group, an alkenyl group, an alkynyl group, or a halogen atom;
$R^2$ and $R^{2d}$ are independently H, a protecting group, an alkyl group, a benzyl group, a trityl group, —SiR$^a$R$^b$R$^c$, CH$_2$OR$^d$ or COR$^e$;
$R^a$, $R^b$ and $R^c$ are independently an alkyl group or an aryl group;
$R^d$ is an alkyl group, an aryl group, an alkoxylalkyl group, —R$^i$SiR$^a$R$^b$R$^c$ or a benzyl group, wherein $R^i$ is an alkylene group;
$R^e$ is an alkyl group, an allyl group, a benzyl group, an aryl group, an alkoxy group, or —NR$^g$R$^h$, wherein $R^g$ and $R^h$ are independently H, an alkyl group or an aryl group;
$R^3$ is (CH$_2$)$_n$ where n is and integer in the range of 0 to 5, —CH$_2$CH(CH$_3$)—, —CH=CH—, —CH=C(CH$_3$)—, or —C≡C—;

$R^4$ is

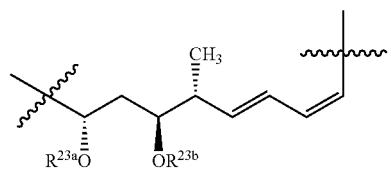

wherein $R^{23a}$ is H, a protecting group, an alkyl group, a benzyl group, a trityl group, —SiR$^a$R$^b$R$^c$, CH$_2$OR$^d$, or COR$^e$, $R^{23b}$ is H, a protecting group, an alkyl group, a benzyl group, a trityl group, —SiR$^a$R$^b$R$^c$, CH$_2$OR$^d$, or COR$^e$, or $R^{23a}$ and $R^{23b}$ together form a portion of six-membered acetal ring incorporating CR$^t$R$^u$;
$R^t$ and $R^u$ are independently H, an alkyl group, an aryl group or an alkoxyaryl group;
$R^5$ is H or OR$^{2b}$, wherein $R^{2b}$ is H, a protecting group, an alkyl group, an aryl group, a benzyl group, a trityl group, —SiR$^a$R$^b$R$^c$, CH$_2$OR$^d$, or COR$^e$; and $R^{10}$ is H or alkyl.

In one embodiment, the compound has the following stereostructure, or its enantiomer:

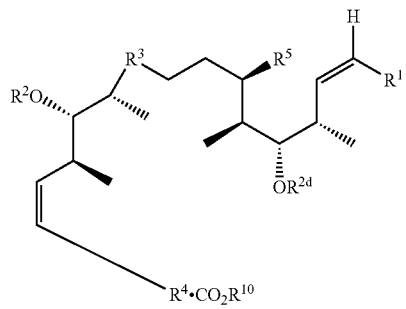

wherein $R^1$ is alkenyl; $R^2$ is H; $R^{2d}$ is H, OC(O)CH$_3$ or OC(O)NR$^g$R$^h$ wherein $R^g$ and $R^h$ are independently H, an alkyl group or an aryl group; $R^3$ is CH$_2$CH(CH$_3$), CH$_2$CH$_2$, CH=CH or CH=C(CH$_3$); and $R^5$ is OH or OSiR$^a$R$^b$R$^c$; and $R^{10}$ is H or alkyl. In one embodiment, $R^1$ is —CH=CH$_2$, and $R^{2d}$ is H, C(O)CH$_3$ or C(O)NH$_2$.

In another aspect, a compound of the following structure or its enantiomer is provided:

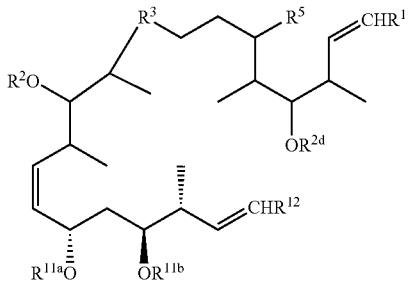

wherein $R^1$ is H, an alkyl group, an aryl group, an alkenyl group, an alkynyl group, or a halogen atom;
$R^2$ and $R^{2d}$ are independently H, a protecting group, an alkyl group, a benzyl group, a trityl group, —SiR$^a$R$^b$R$^c$, CH$_2$OR$^d$, or COR$^e$;

R$^a$, R$^b$ and R$^c$ are independently an alkyl group or an aryl group;

R$^d$ is an alkyl group, an aryl group, an alkoxylalkyl group, —R$^i$SiR$^a$R$^b$R$^c$ or a benzyl group, wherein R$^i$ is an alkylene group;

R$^e$ is an alkyl group, an allyl group, a benzyl group, an aryl group, an alkoxy group, or —NR$^g$R$^h$, wherein R$^g$ and R$^h$ are independently H, an alkyl group or an aryl group;

R$^3$ is (CH$_2$)$_n$ where n is and integer in the range of 0 to 5, —CH$_2$CH(CH$_3$)—, —CH=CH—, —CH=C(CH$_3$)—, or —C≡C—;

R$^5$ is H or OR$^{2b}$, wherein R$^{2b}$ is H, a protecting group, an alkyl group, an aryl group, a benzyl group, a trityl group, —SiR$^a$R$^b$R$^c$, CH$_2$OR$^d$, or COR$^e$;

R$^{11a}$ and R$^{11b}$ are independently H, an alkyl group, a benzyl group, a trityl group, —SiR$^a$R$^b$R$^c$, CH$_2$OR$^d$, COR$^e$, or R$^{11a}$ and R$^{11b}$ together form a portion of six-membered acetal ring incorporating CR$^t$R$^u$;

R$^t$ and R$^u$ are independently H, an alkyl group, an aryl group or an alkoxyaryl group; and R$^{12}$ is a halogen atom, CH$_2$OR$^{2c}$, CHO, CO$_2$R$^{10}$, CH=CHCH$_2$OR$^{2c}$, CH=CHCHO, wherein R$^{2c}$ is H, a protecting group, an alkyl group, a benzyl group, a trityl group, —SiR$^a$R$^b$R$^c$, CH$_2$OR$^d$, or COR$^e$, and R$^{10}$ is H or alkyl.

In one embodiment, the compound has the following stereostructure or its enantiomer:

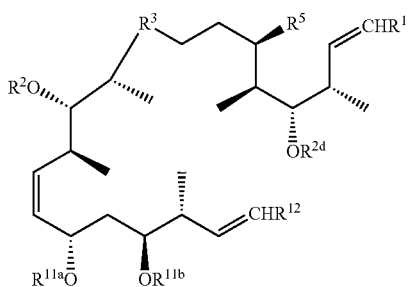

wherein R$^1$ is alkenyl; R$^2$ and R$^{2d}$ are independently, H, OC(O)CH$_3$ or OC(O)NR$^g$R$^h$ wherein R$^g$ and R$^h$ are independently H, an alkyl group or an aryl group; R$^3$ is CH$_2$CH(CH$_3$)CH$_2$CH$_2$, CH=CH or CH=C(CH$_3$); R$^{11a}$ and R$^{11b}$ are H or together form a portion of a six-membered acetal ring containing C(H)(p-C$_6$H$_4$OCH$_3$) or C(CH$_3$)$_2$; R$^{12}$ is a halogen atom, CH$_2$OR$^{2c}$, CHO, CO$_2$R$^{10}$, CH=CHCH$_2$OR$^{2c}$, CH=CHCHO, wherein R$^{2c}$ is H, an alkyl group, a benzyl group, a trityl group, —SiR$^a$R$^b$R$^c$, CH$_2$OR$^d$, or COR$^e$, and R$^{10}$ is H or alkyl. In one embodiment, R$^1$ is —CH=CH$_2$, R$^{2d}$ is H, —C(O)CH$_3$ or —O(O)NH$_2$, and R$^{12}$ is —CH$_2$OH, —CHO or —CO$_2$R$^{10}$.

In another aspect, a compound having the following stereostructure or its enantiomer is provided:

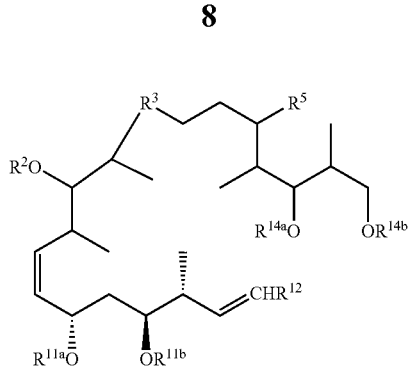

wherein R$^2$ is H, a protecting group, an alkyl group, a benzyl group, a trityl group, —SiR$^a$R$^b$R$^c$, CH$_2$OR$^d$, or COR$^e$;

R$^a$, R$^b$ and R$^c$ are independently an alkyl group or an aryl group;

R$^d$ is an alkyl group, an aryl group, an alkoxylalkyl group, —R$^i$SiR$^a$R$^b$R$^c$ or a benzyl group, wherein R$^i$ is an alkylene group;

R$^e$ is an alkyl group, an allyl group, a benzyl group, an aryl group, an alkoxy group, or —NR$^g$R$^h$, wherein R$^g$ and R$^h$ are independently H, an alkyl group or an aryl group;

R$^3$ is (CH$_2$)$_n$ where n is and integer in the range of 0 to 5, —CH$_2$CH(CH$_3$)—, —CH=CH—, —CH=C(CH$_3$)—, or —C≡C—;

R$^5$ is H or OR$^{2b}$, wherein R$^{2b}$ is H, a protecting group, an alkyl group, a benzyl group, a trityl group, —SiR$^a$R$^b$R$^c$, CH$_2$OR$^d$, or COR$^e$;

R$^{11a}$ and R$^{11b}$ are independently H, a protecting group, an alkyl group, a benzyl group, a trityl group, —SiR$^a$R$^b$R$^c$, CH$_2$OR$^d$, COR$^e$, or R$^{11a}$ and R$^{11b}$ together form a portion of six-membered acetal ring containing CR$^t$R$^u$;

R$^t$ and R$^u$ are independently H, an alkyl group, an aryl group or an alkoxyaryl group;

R$^{12}$ is a halogen atom, CH$_2$OR$^{2c}$, CHO, CO$_2$R$^{10}$, CH=CHCH$_2$OR$^{2c}$ or CH=CHCHO, CH=CHCO$_2$R$^{10}$, wherein R$^{2c}$ is H, a protecting group, an alkyl group, a benzyl group, a trityl group, —SiR$^a$R$^b$R$^c$, CH$_2$OR$^d$, or COR$^e$, and R$^{10}$ is H or alkyl; and R$^{14a}$ and R$^{14b}$ are independently H, a protecting group, an alkyl group, a benzyl group, a trityl group, —SiR$^a$R$^b$R$^c$, CH$_2$OR$^d$, COR$^e$, or R$^{14a}$ and R$^{14b}$ together form a six-membered ring containing CR$^v$R$^w$, wherein R$^v$ and R$^w$ are independently H, an alkyl group, an aryl group or an alkoxyaryl group.

In one embodiment, the compound has the following stereostructure or its enantiomer:

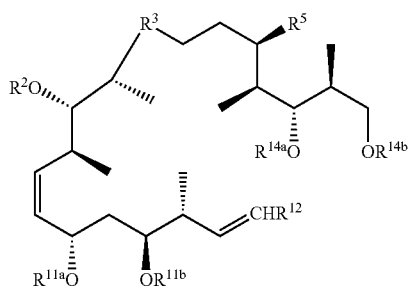

wherein $R^2$ is H; $R^3$ is $CH_2CH(CH_3)$ or $CH=C(CH_3)$; $R^{11a}$ and $R^{11b}$ are H or together form a portion of a six-membered acetal ring containing $C(H)(p-C_6H_4OCH_3)$ or $C(CH_3)_2$; $R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl.

In another aspect, a compound having the following formula, or its enantiomer is provided:

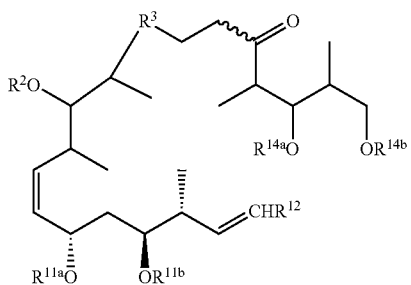

$R^2$ is H, a protecting group, an alkyl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^{11a}$ and $R^{11b}$ are independently H, an alkyl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group, an aryl group or an alkoxyaryl group;

$R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, a protecting group, an alkyl group, a benzyl group, a trityl group, —$SiR^aR^bR^c$, $CH_2OR^d$, or $COR^e$, and $R^{10}$ is H or alkyl; and $R^{14a}$ and $R^{14b}$ are independently H, a protecting group, an alkyl group, a benzyl group, a trityl group, —$SiR^aR^bR^c$, $CH_2OR^d$, $COR^e$, or $R^{14a}$ and $R^{14b}$ together form a six-membered ring containing $CR^vR^w$, wherein $R^v$ and $R^w$ are independently H, an alkyl group, an aryl group or an alkoxyaryl group.

In one embodiment, the compound has the following stereostructure or its enantiomer:

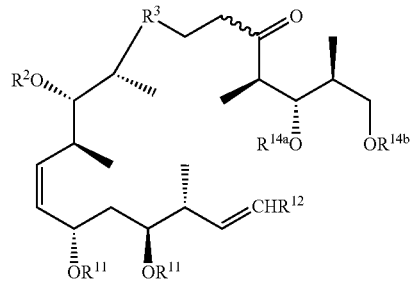

wherein $R^3$ is $CH_2CH_2$, $CH=CH$, $CH_2CH(CH_3)$ or $CH=C(CH_3)$; $R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl.

In a further aspect, a compound having the following formula or its enantiomer is provided:

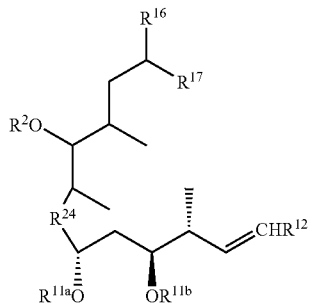

wherein $R^2$ is H, a protecting group, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^{11a}$ and $R^{11b}$ are independently H, an alkyl group, and aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group or an aryl group;

$R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, a protecting group, an alkyl group, an aryl group, a benzyl group, a trityl group, —$SiR^aR^bR^c$, $CH_2OR^d$, or $COR^e$, and $R^{10}$ is H or alkyl;

$R^{16}$ is H or alkyl; and $R^{17}$ is $CH_2OR^{2f}$, CHO, $CO_2R^{10}$, wherein $R^{2f}$ is H, a protecting group, an alkyl group, an aryl group, a benzyl group, a trityl group, —$SiR^aR^bR^c$, $CH_2OR^d$, or $COR^e$; and $R^{24}$ is C≡C, cis or trans CH=CH, or $CH_2CH_2$.

In one embodiment, the compound has the following stereostructure or its enantiomer:

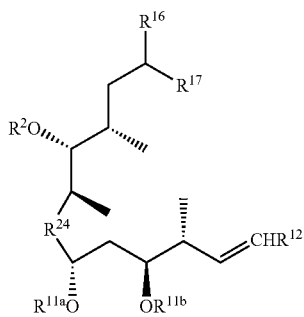

wherein $R^2$ is H, an alkyl group, a benzyl group, a trityl group, —$SiR^aR^bR^c$, $CH_2OR^d$, or $COR^e$, and $R^{24}$ is C≡C or cis CH=CH.

In one embodiment, a process for synthesizing dictyostatin analogs includes a process for conversion of a first compound having the following formula or its enantiomer:

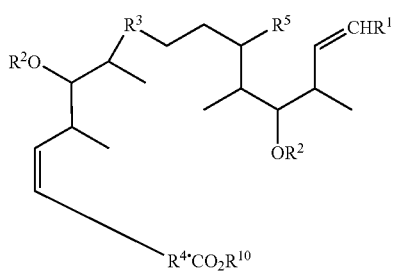

wherein $R^1$ is H, an alkyl group, an aryl group, an alkenyl group, an alkynyl group, or a halogen atom;

$R^2$ is H, a protecting group, an alkyl group, a benzyl group, a trityl group, —$SiR^aR^bR^c$, $CH_2OR$, or $COR^e$;

$R^{2d}$ is H;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C($CH_3$)—, or —C≡C—;

$R^4$ is

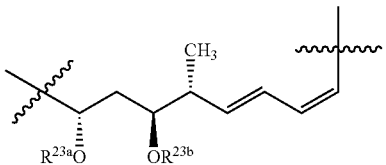

wherein $R^{23a}$ is H, a protecting group, an alkyl group, a benzyl group, a trityl group, —$SiR^aR^bR^c$, $CH_2OR^d$, or $COR^e$, $R^{23b}$ is H, a protecting group, an alkyl group, a benzyl group, a trityl group, —$SiR^aR^bR^c$, $CH_2OR^d$, or $COR^e$, or $R^{23a}$ and $R^{23b}$ together form a portion of six-membered acetal ring incorporating $CR^tR^u$;

$R^t$ and $R^u$ are independently H, an alkyl group, an aryl group or an alkoxyaryl group; and $R^{10}$ is H;

to a second compound with the formula

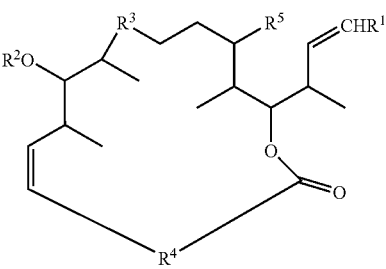

comprising the step of reacting the first compound under conditions suitable to effect macrolactonization.

In one embodiment, the first compound has the following stereostructure or its enantiomer:

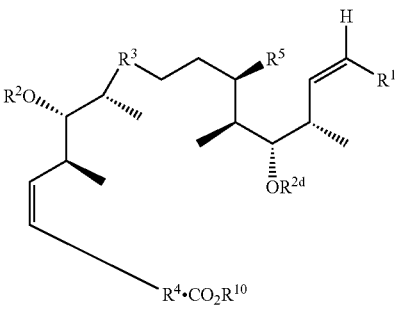

wherein $R^1$ is H, an alkyl group, an alkenyl group, an alkynyl group, or a halogen atom;

$R^2$ is H, an alkyl group, a benzyl group, a trityl group, —$SiR^aR^bR^c$, $CH_2OR^d$, or $COR^e$;

$R^{2d}$ is H;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C(CH_3)—, or —C≡C—; and
$R^{10}$ is H;

and the second compound has the following formula or its enantiomer

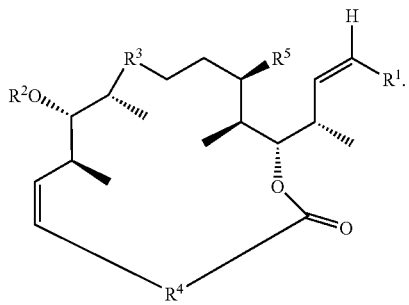

In one embodiment, $R^1$ is alkenyl; $R^3$ is $CH_2CH_2$, CH=CH, $CH_2CH(CH_3)$ or CH=C(CH_3); and $R^5$ is $OR^{2b}$. In one embodiment of the process, the first compound is reacted with 2,4,6-trichlorobenzoylchloride.

In another aspect, the present invention provides a compound having the following formula, or its enantiomer

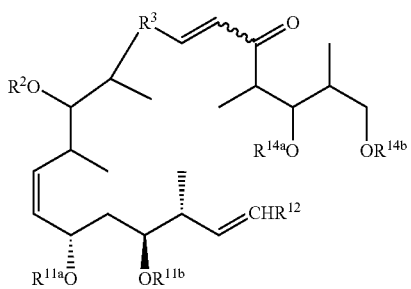

$R^2$ is H, a protecting group, an alkyl group, a benzyl group, a trityl group, —$SiR^aR^bR^c$, $CH_2OR^d$, or $COR^e$;
$R^a$, $R^b$ and $R^c$ are independently an alkyl group or an aryl group;
$R^d$ is an alkyl group, an aryl group, an alkoxylalkyl group, —$R^iSiR^aR^bR^c$ or a benzyl group, wherein $R^i$ is an alkylene group;
$R^e$ is an alkyl group, an allyl group, a benzyl group, an aryl group, an alkoxy group, or —$NR^gR^h$, wherein $R^g$ and $R^h$ are independently H, an alkyl group or an aryl group;
$R^3$ is $(CH_2)_n$ where n is and integer in the range of 0 to 5, —$CH_2CH(CH_3)$—, —CH=CH—, —CH=C(CH_3)—, or —C≡C—;
$R^{11a}$ and $R^{11b}$ are independently H, a protecting group, an alkyl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^rR^u$;
$R^r$ and $R^u$ are independently H, an alkyl group, an aryl group or an alkoxyaryl group;
$R^{12}$ is a halogen atom, $CH_2OR^{2c}$, CHO, $CO_2R^{10}$, CH=$CHCH_2OR^{2c}$, CH=CHCHO or CH=$CHCO_2R^{10}$, wherein $R^{2c}$ is H, a protecting group, an alkyl group, an aryl group, a benzyl group, a trityl group, —$SiR^aR^bR^c$, $CH_2OR^d$, or $COR^e$, and $R^{10}$ is H or alkyl; and $R^{14a}$ and $R^{14b}$ are independently H, an alkyl group, a benzyl group, a trityl group, —$SiR^aR^bR^c$, $CH_2OR^d$, $COR^e$, or $R^{14a}$ and $R^{14b}$ together form a six-membered ring containing $CR^vR^w$, wherein $R^v$ and $R^w$ are independently H, an alkyl group, an aryl group or an alkoxyaryl group.

In one embodiment, the compound has the following stereostructure, or its enantiomer

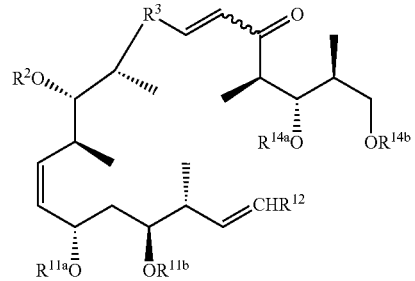

wherein $R^3$ is $CH_2CH(CH_3)CH_2CH_2$, CH=CH, or CH=C(CH_3); and $R^{11a}$ and $R^{11b}$ are H or together form a portion of a six-membered acetal ring containing $C(H)(p-C_6H_4OCH_3)$ or $C(CH_3)_2$.

In another aspect, the present invention provides a compound having the following formula, or its enantiomer

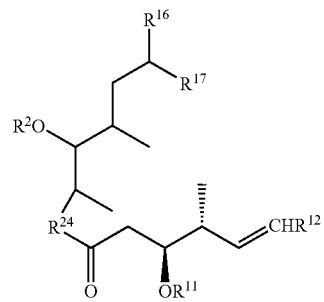

wherein $R^2$ is H, a protecting group, an alkyl group, an aryl group, a benzyl group, a trityl group, —$SiR^aR^bR^c$, $CH_2OR^d$, or $COR^e$;
$R^a$, $R^b$ and $R^c$ are independently an alkyl group or an aryl group;
$R^d$ is an alkyl group, an aryl group, an alkoxylalkyl group, —$R^iSiR^aR^bR^c$ or a benzyl group, wherein $R^i$ is an alkylene group;
$R^e$ is an alkyl group, an allyl group, a benzyl group, an aryl group, an alkoxy group, or —$NR^gR^h$, wherein $R^g$ and $R^h$ are independently H, an alkyl group or an aryl group;
$R^{11}$ is a protecting group, an alkyl group, and aryl group, a benzyl group, a trityl group, —$SiR^aR^bR^c$, $CH_2OR^d$, or $COR^e$;
$R^{12}$ is a halogen atom, $CH_2OR^{2c}$, CHO, $CO_2R^{10}$, CH=$CHCH_2OR^{2c}$, CH=CHCHO or CH=$CHCO_2R^{10}$, wherein $R^{2c}$ is H, a protecting group, an alkyl group, an aryl group, a benzyl group, a trityl group, —$SiR^aR^bR^c$, $CH_2OR^d$, or $COR^e$, and $R^{10}$ is H or alkyl;
$R^{16}$ is H or alkyl;
$R^{17}$ is $CH_2OR^{2f}$, CHO, $CO_2R^{10}$, wherein $R^{2f}$ is H, an alkyl group, an aryl group, a benzyl group, a trityl group, —$SiR^aR^bR^c$, $CH_2OR^d$, or $COR^e$; and
$R^{24}$ is C≡C, cis or trans CH=CH, or $CH_2CH_2$.

In one embodiment, the compound has the following stereostructure, or its enantiomer

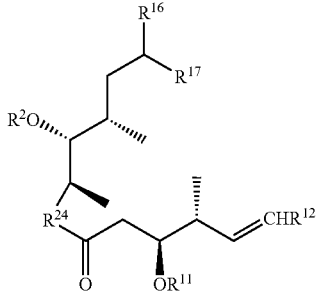

wherein $R^2$ is H, an alkyl group, a benzyl group, a trityl group, —$SiR^aR^bR^c$, $CH_2OR^d$, or $COR^e$; and
$R^{24}$ is C≡C or cis CH=CH.

In another aspect, the present invention provides a compound having the following formula, or its enantiomer

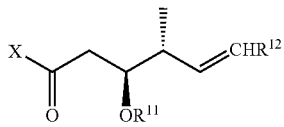

wherein X is H, $NCH_3(OCH_3)$, or a leaving group;
$R^{11}$ is H, a protecting group, an alkyl group, and aryl group, a benzyl group, a trityl group, —$SiR^aR^bR^c$, $CH_2OR^d$, or $COR^e$;
$R^t$ and $R^u$ are independently H, an alkyl group or an aryl group;
$R^{12}$ is a halogen atom, $CH_2OR^{2c}$, CHO, $CO_2R^{10}$, $CH=CHCH_2OR^{2c}$, CH=CHCHO or $CH=CHCO_2R^{10}$, wherein $R^{2c}$ is H, a protecting group, an alkyl group, an aryl group, a benzyl group, a trityl group, —$SiR^aR^bR^c$, $CH_2OR^d$, or $COR^e$, and $R^{10}$ is H or alkyl.

In a further aspect, the present invention provides a compound having the following formula, or its enantiomer

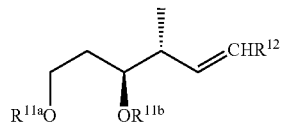

wherein $R^{11a}$ and $R^{11b}$ are independently H, a protecting group, an alkyl group, and aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;
$R^t$ and $R^u$ are independently H, an alkyl group, an aryl group or an alkoxyaryl group;
$R^{12}$ is a halogen atom, $CH_2OR^{2c}$, CHO, $CO_2R^{10}$, $CH=CHCH_2OR^{2c}$, CH=CHCHO or $CH=CHCO_2R^{10}$, wherein $R^{2c}$ is H, a protecting group, an alkyl group, an aryl group, a benzyl group, a trityl group, —$SiR^aR^bR^c$, $CH_2OR^d$, or $COR^e$, and $R^{10}$ is H or alkyl;

In another aspect, the present invention provides a process of conversion of a compound with the following formula, or its enantiomer

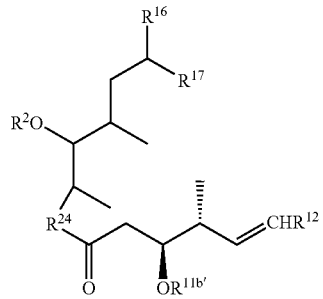

wherein $R^2$ a protecting group, an alkyl group, an aryl group, a benzyl group, a trityl group, —$SiR^aR^bR^c$, $CH_2OR^d$, or $COR^e$;
$R^a$, $R^b$ and $R^c$ are independently an alkyl group or an aryl group;
$R^d$ is an alkyl group, an aryl group, an alkoxylalkyl group, —$R^iSiR^aR^bR^c$ or a benzyl group, wherein $R^i$ is an alkylene group;
$R^e$ is an alkyl group, an allyl group, a benzyl group, an aryl group, an alkoxy group, or —$NR^gR^h$, wherein $R^g$ and $R^h$ are independently H, an alkyl group or an aryl group;
$R^{11b'}$ is an alkyl group, and aryl group, a benzyl group, a trityl group, —$SiR^aR^bR^c$, $CH_2OR^d$, $COR^e$;
$R^{12}$ is a halogen atom, $CH_2OR^{2c}$, $CO_2R^{10}$, $CH=CHCH_2OR^{2c}$, or $CH=CHCO_2R^{10}$, wherein $R^{2c}$ is a protecting group, an alkyl group, an aryl group, a benzyl group, a trityl group, —$SiR^aR^bR^c$, $CH_2OR^d$, or $COR^e$, and $R^{10}$ is H or alkyl;
$R^{16}$ is H or alkyl; and
$R^{17}$ is $CH_2OR^{2f}$, $CO_2R^{10}$, wherein $R^{2f}$ is H, a protecting group, an alkyl group, an aryl group, a benzyl group, a trityl group, —$SiR^aR^bR^c$, $CH_2OR^d$, or $COR^e$; and
$R^{24}$ is C≡C to a compound of the following formula, or its enantiomer

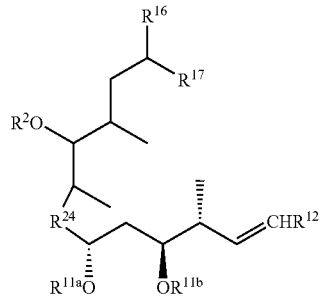

wherein $R^{11a}$ is H, an alkyl group, and aryl group, a benzyl group, a trityl group, —$SiR^aR^bR^c$, $CH_2OR^d$, $COR^e$ and $R^{11b}$ is an alkyl group, and aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;
$R^t$ and $R^u$ are independently H, an alkyl group or an aryl group; and
$R^{24}$ is cis CH=CH, including at least the steps of semi-reduction of the alkyne and asymmetric reduction of the ketone, or asymmetric reduction of the ketone and semi-hydrogentation of the alkyne.

In one embodiment, the process includes at least the steps of semi-reduction of the alkyne, asymmetric reduction of the ketone and protection of a resulting alcohol, or asymmetric reduction of the ketone, protection of a resulting alcohol and semihydrogentation of the alkyne, or asymmetric reduction of the ketone, semi-hydrogentation of the alkyne and protection of a resulting alcohol.

In a further aspect, the present invention provides a compound of the following formula, or its enantiomer

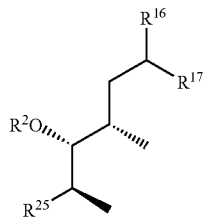

wherein $R^2$ is H, a protecting group, an alkyl group, an aryl group, a benzyl group, a trityl group, —SiR$^a$R$^b$R$^c$, CH$_2$OR$^d$, or COR$^e$;

$R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein R$^i$ is an alkylene group;

$R^e$ is an alkyl group, an allyl group, a benzyl group, an aryl group, an alkoxy group, or —NR$^g$R$^h$, wherein R$^g$ and R$^h$ are independently H, an alkyl group or an aryl group;

$R^{16}$ is H or alkyl; and $R^{17}$ is CH$_2$OR$^{2f}$, CHO, CONHCH(CH$_3$)CH(OH)Ph, CO$_2$R$^{10}$, wherein R$^{2f}$ is H, a protecting group, an alkyl group, an aryl group, a benzyl group, a trityl group, —SiR$^a$R$^b$R$^c$, CH$_2$OR$^d$, or COR$^e$;

$R^{25}$ is CO$_2$R$^{10}$, CHO, CH=CBr$_2$, C≡CH, or C≡C SiR$^a$R$^b$R$^c$; and $R^{10}$ is H or an alkyl group.

In another aspect the present invention provides a process for reacting a first compound of the following formula, or its enantiomer

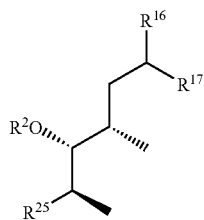

wherein $R^2$ a protecting group, an alkyl group, an aryl group, a benzyl group, a trityl group, —SiR$^a$R$^b$R$^c$, CH$_2$OR$^d$, or COR$^e$;

$R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein R$^i$ is an alkylene group;

$R^e$ is an alkyl group, an allyl group, a benzyl group, an aryl group, an alkoxy group, or —NR$^g$R$^h$, wherein R$^g$ and R$^h$ are independently H, an alkyl group or an aryl group;

$R^{16}$ is H or alkyl; and $R^{17}$ is CH$_2$OR$^{2f}$, CHO, CO$_2$R$^v$, wherein R$^{2f}$ is H, an alkyl group, an aryl group, a benzyl group, a trityl group, —SiR$^a$R$^b$R$^c$, CH$_2$OR$^d$, or COR$^e$;

$R^{25}$ CH=CX$_2$, C≡CH or C≡CSiR$^a$R$^b$R;

X is Cl, Br or I with a second compound of the following formula, or its enantiomer

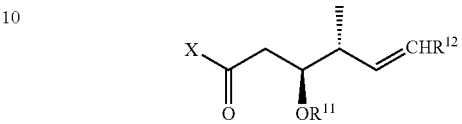

wherein X is NCH$_3$(OCH$_3$), or a leaving group;

$R^{11}$ an alkyl group, and aryl group, a benzyl group, a trityl group, —SiR$^a$R$^b$R$^c$, CH$_2$OR$^d$, COR$^e$;

$R^{12}$ is a halogen atom, CH$_2$OR$^{2c}$, CO$_2$R$^v$, CH=CHCH$^2$OR$^{2c}$ or CH=CHCO$_2$R$^v$, wherein R$^{2c}$ is an alkyl group, an aryl group, a benzyl group, a trityl group, —SiR$^a$R$^b$R$^c$, CH$_2$OR$^d$, or COR$^e$, and R$^v$ is alkyl, including the steps of metalation of the first compound and addition of the second compound to produce a compound of the following formula, or its enantiomer

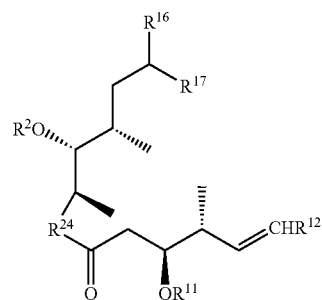

wherein $R^{24}$ is C≡C.

In another aspect, the present invention provides a process for reacting a first compound of the following formula, or its enantiomer

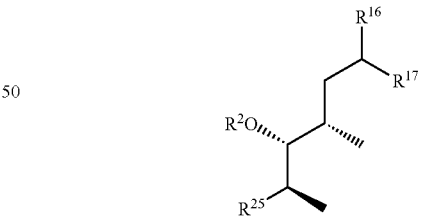

wherein $R^2$ a protecting group, an alkyl group, an aryl group, a benzyl group, a trityl group, —SiR$^a$R$^b$R$^c$, CH$_2$OR$^d$, or COR$^e$;

$R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein R$^i$ is an alkylene group;

$R^e$ is an alkyl group, an allyl group, a benzyl group, an aryl group, an alkoxy group, or —NR$^g$R$^h$ wherein R$^g$ and R$^h$ are independently H, an alkyl group or an aryl group;

$R^{16}$ is H or alkyl;

$R^{17}$ is $CH_2OR^{2f}$, CHO, $CO_2R^{10}$, wherein $R^{2f}$ is H, an alkyl group, an aryl group, a benzyl group, a trityl group, —$SiR^aR^bR^c$, $CH_2OR^d$, or $COR^e$;

$R^{25}$ $CH=CX_2$, $C\equiv CH$ or $C\equiv CSiR^aR^bR$;

with a second compound of the following formula, or its enantiomer

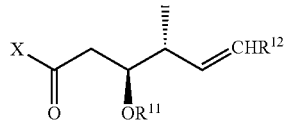

wherein X is H;

$R^{11}$ an alkyl group, and aryl group, a benzyl group, a trityl group, —$SiR^aR^bR^c$, $CH_2OR^d$, $COR^e$;

$R^{12}$ is a halogen atom, $CH_2OR^{2c}$, $CO_2R^{10}$, $CH=CHCH_2OR^{2c}$ or $CH=CHCO_2R^{10}$, wherein $R^{2c}$ is an alkyl group, an aryl group, a benzyl group, a trityl group, —$SiR^aR^bR^c$, $CH_2OR^d$, or $COR^e$, and $R^{10}$ is alkyl, including the steps of metalation of the first compound and addition of the second compound to produce a compound of the following formula, or its enantiomer

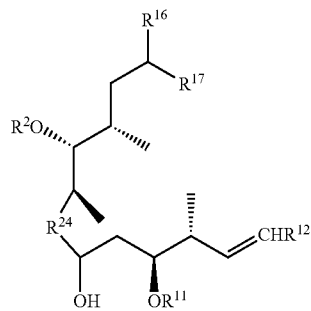

wherein $R^{24}$ is $C\equiv C$

In another aspect, the present invention provides a compound of the following structure

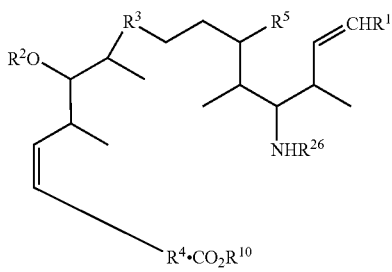

wherein $R^1$ is H, an alkyl group, an aryl group, an alkenyl group, an alkynyl group, or a halogen atom;

$R^2$ is H, a protecting group, an alkyl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —$CH=C(CH_3)$—, or —$C\equiv C$—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k4})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, —$(CHR^{k1})_{y1}(CHR^{k2})_{y2}(CHR^{k3})_{y3}(CHR_{k4})_{y4}(CHR^{k5})_{y5}CH(R^{s1})CH(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, a protecting group, an alkyl group, a benzyl group, a trityl group, —$SiR^aR^bR^c$, $CH_2OR^d$, or $COR^e$; and $R^5$ is H or $OR^{2b}$, wherein $R^{2b}$ is H, a protecting group, an alkyl group, an aryl group, a benzyl group, a trityl group, —$SiR^aR^bR^c$, $CH_2OR^d$, or $COR^e$; and $R^{26}$ is H, a protecting group, an alkyl group, an aryl group, —$SiR^aR^bR^c$, or $COR^e$;

In one embodiment, the compound of has the following stereostructure, or its enantiomer

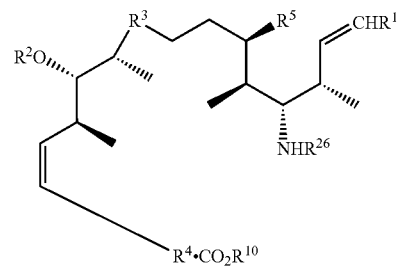

wherein $R^1$ is alkenyl; $R^3$ is —$CH_2CH_2$, —CH=CH, —$CH_2CH(CH_3)$ or —$CH=C(CH_3)$; and $R^4$ is

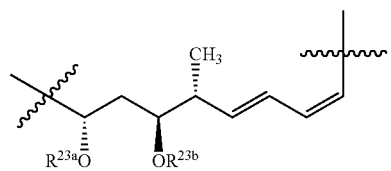

wherein $R^{23a}$ is H, a protecting group, an alkyl group, a benzyl group, a trityl group, —$SiR^aR^bR^c$, $CH_2OR^d$, or $COR^e$, $R^{23b}$ is H, a protecting group, an alkyl group, a benzyl group, a trityl group, —$SiR^aR^bR^c$, $CH_2OR^d$, or $COR^e$, or $R^{23a}$ and $R^{23b}$ together form a portion of six-membered acetal ring incorporating $CR^tR^u$;

$R^t$ and $R^u$ are independently H, an alkyl group, an aryl group or an alkoxyaryl group.

In another aspect, the present invention provides a compound of the following structure

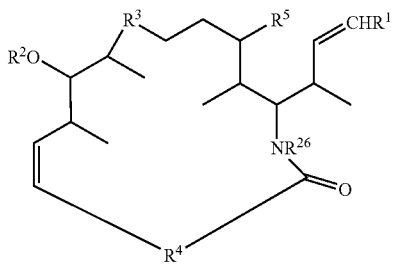

wherein $R^1$ is H, an alkyl group, an aryl group, an alkenyl group, an alkynyl group, or a halogen atom;

$R^2$ is H, a protecting group, an alkyl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, a benzyl group, a trityl group, —$SiR^aR^bR^c$, $CH_2OR^d$, or $COR^e$; and $R^5$ is H or $OR^{2b}$, wherein $R^{2b}$ is H, a protecting group, an alkyl group, an aryl group, a benzyl group, a trityl group, —$SiR^aR^bR^c$, $CH_2OR^d$, or $COR^e$; and $R^{26}$ is H, a protecting group, an alkyl group, an aryl group, —$SiR^aR^bR^c$, or $COR^e$;

In one embodiment, the compound has the following stereostructure, or its enantiomer

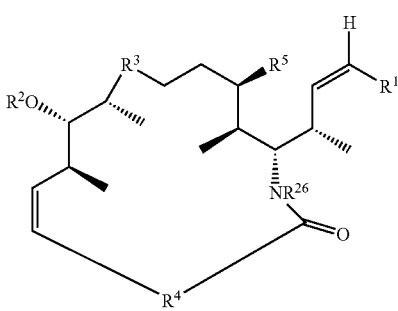

wherein $R^1$ is alkenyl; $R^3$ is —$CH_2CH_2$—, —$CH=CH$—, —$CH_2CH(CH_3)$— or —$CH=C(CH_3)$—; and $R^4$ is

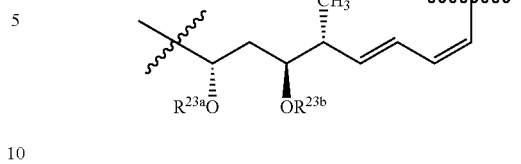

wherein $R^{23a}$ is H, a protecting group, an alkyl group, a benzyl group, a trityl group, —$SiR^aR^bR^c$, $CH_2OR^d$, or $COR^e$, $R^{23b}$ is H, a protecting group, an alkyl group, a benzyl group, a trityl group, —$SiR^aR^bR^c$, $CH_2OR^d$, or $COR^e$, or $R^{23a}$ and $R^{23b}$ together form a portion of six-membered acetal ring incorporating $CR^tR^u$;

$R^t$ and $R^u$ are independently H, an alkyl group, an aryl group or an alkoxyaryl group In another aspect, the present invention provides a process for synthesizing a compound having the following structure

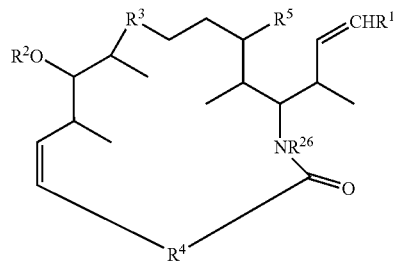

wherein $R^1$ is H, an alkyl group, an aryl group, an alkenyl group, an alkynyl group, or a halogen atom;

$R^2$ is H, a protecting group, an alkyl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})C(R^{s3})=C(R^{s4})$—, —$(CHR^{k1})_1(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, —$(CHR^{k1})_{y1}(CHR^{k2})_{y2}(CHR^{k3})CHR^{k4})_{y4}(CHR^{k5})_{y5}CH(R^{s1})CH(R^{s2})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, a benzyl group, a trityl group, —$SiR^aR^bR^c$, $CH_2OR^d$, or $COR^e$; and $R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; and $R^{26}$ is H, a protecting group, an alkyl group, an aryl group, —$SiR^aR^bR^c$, or $COR^e$;

including the step of reacting a starting compound having the formula:

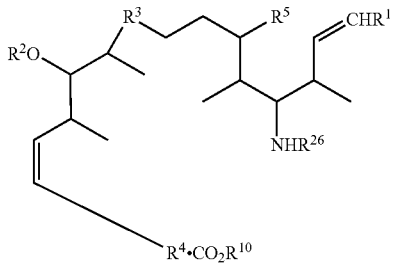

wherein $R^{10}$ is H, under conditions suitable to form the macrolactam ring.

In one embodiment of the process, the starting compound has the following structure, or its enantiomer

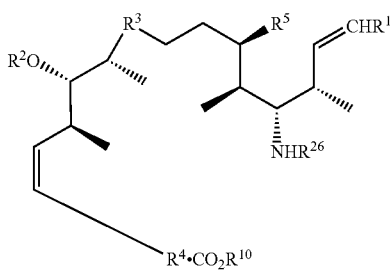

wherein $R^1$ is alkenyl; $R^3$ is —CH$_2$CH(CH$_3$) or —CH=C(CH$_3$); and $R^4$ is

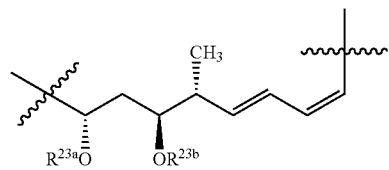

wherein $R^{23a}$ is H, a protecting group, an alkyl group, a benzyl group, a trityl group, —SiR$^a$R$^b$R$^c$, CH$_2$OR$^d$, or COR$^e$, $R^{23b}$ is H, a protecting group, an alkyl group, a benzyl group, a trityl group, —SiR$^a$R$^b$R$^c$, CH$_2$OR$^d$, or COR$^e$, or $R^{23a}$ and $R^{23b}$ together form a portion of six-membered acetal ring incorporating CR$^t$R$^u$;

R$^t$ and R$^u$ are independently H, an alkyl group, an aryl group or an alkoxyaryl group and the product compound has the following structure, or its enantiomer

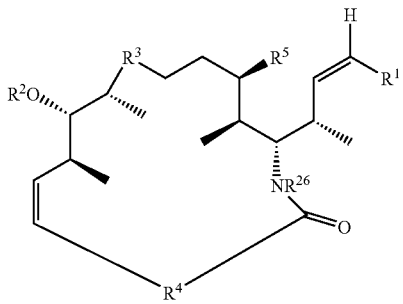

In a further aspect, the present invention provides a process for converting a starting compound of the following structure

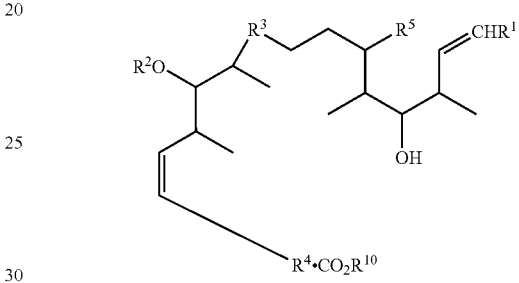

wherein $R^1$ is H, an alkyl group, an aryl group, an alkenyl group, an alkynyl group, or a halogen atom;
$R^2$ and $R^{2d}$ are independently H, a protecting group, an alkyl group, a benzyl group, a trityl group, —SiR$^a$R$^b$R$^c$, CH$_2$OR$^d$, or COR$^e$;
R$^a$, R$^b$ and R$^c$ are independently an alkyl group or an aryl group;
R$^d$ is an alkyl group, an aryl group, an alkoxylalkyl group, —R$^i$SiR$^a$R$^b$R$^c$ or a benzyl group, wherein R$^i$ is an alkylene group;
R$^e$ is an alkyl group, an allyl group, a benzyl group, an aryl group, an alkoxy group, or —NR$^g$R$^h$, wherein R$^g$ and R$^h$ are independently H, an alkyl group or an aryl group;
$R^3$ is (CH$_2$)$_n$ where n is and integer in the range of 0 to 5, —CH$_2$CH(CH$_3$)—, —CH=CH—, —CH=C(CH$_3$)—, or —C≡C—;
$R^4$ is (CH$_2$)$_p$ where p is an integer in the range of 4 to 12, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$C(R$^{s1}$)=C(R$^{s2}$)C(R$^{s3}$)=C(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$CH(R$^{s1}$)CH(R$^{s2}$)C(R$^{s3}$)=C(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$C(R$^{s1}$)=C(R$^{s2}$)CH(R$^{s3}$)CH(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$CH(R$^{s1}$)CH(R$^{s2}$)CH(R$^{s3}$)CH(R$^{s4}$)—, wherein y1 and y2 are 1 and y3, y4 and y5 are independently 0 or 1, R$^{k1}$, R$^{k2}$, R$^{k3}$, R$^{k4}$ and R$^{k5}$ are independently H, —CH$_3$, or OR$^{2a}$, and R$^{s1}$, R$^{s2}$, R$^{s3}$, and R$^{s4}$ are independently H or CH$_3$, wherein R$^{2a}$ is H, an alkyl group, an aryl group, a benzyl group, a trityl group, —SiR$^a$R$^b$R$^c$, CH$_2$OR$^d$, or COR$^e$; and
$R^5$ is H or OR$^{2b}$, wherein R$^{2b}$ is H, a protecting group an alkyl group, an aryl group, a benzyl group, a trityl group, —SiR$^a$R$^b$R$^c$, CH$_2$OR$^d$, or COR$^e$; and
$R^{10}$ is H or alkyl to a compound of the following structure

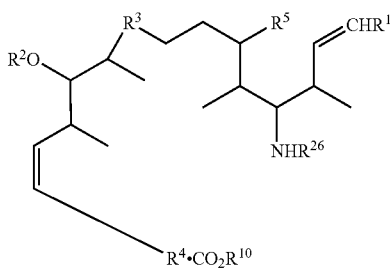

where $R^{26}$ is H, a protecting group, an alkyl group, a aryl group, —$SiR^aR^bR^c$, or $COR^e$, including at least the steps of alcohol oxidation and reductive amination.

In one embodiment of the process, the starting compound has the following structure, or its enantiomer

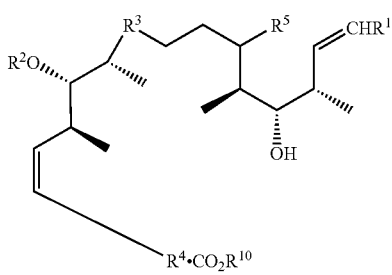

wherein $R^1$ is alkenyl; $R^3$ is —$CH_2CH(CH_3)$ or —$CH$=$C(CH_3)$; and $R^4$ is

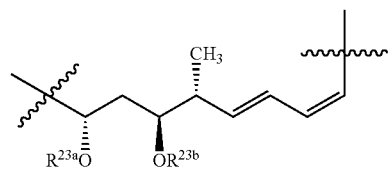

wherein $R^{23a}$ is H, a protecting group, an alkyl group, a benzyl group, a trityl group, —$SiR^aR^bR^c$, $CH_2OR^d$, or $COR^e$, $R^{23b}$ is H, a protecting group, an alkyl group, a benzyl group, a trityl group, —$SiR^aR^bR^c$, $CH_2OR^d$, or $COR^e$, or $R^{23a}$ and $R^{23b}$ together form a portion of six-membered acetal ring incorporating $CR^tR^u$;

$R^t$ and $R^u$ are independently H, an alkyl group, an aryl group or an alkoxyaryl group and the product compound has the following structure, or its enantiomer

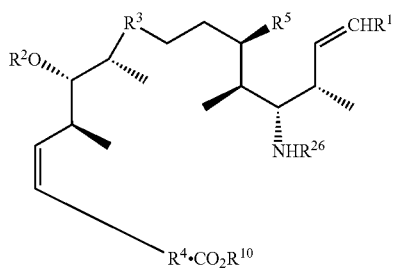

In a further aspect, the present invention provides a compound of the following structure or its enantiomer

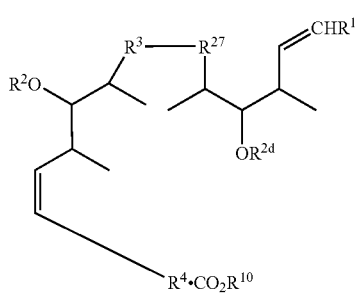

wherein $R^1$ is H, a protecting group, an alkyl group, an aryl group, an alkenyl group, an alkynyl group, or a halogen atom;

$R^2$ and $R^{2d}$ are independently H, a protecting group, an alkyl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH$=$CH$—, —$CH$=$C(CH_3)$—, or —$C$≡$C$—;

$R^4$ is

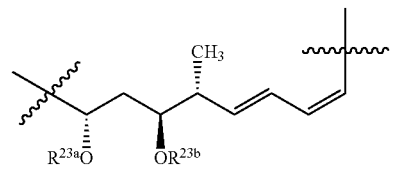

wherein $R^{23a}$ is H, a protecting group, an alkyl group, a benzyl group, a trityl group, $-SiR^aR^bR^c$, $CH_2OR^d$, or $COR^e$, $R^{23b}$ is H, a protecting group, an alkyl group, a benzyl group, a trityl group, $-SiR^aR^bR^c$, $CH_2OR^d$, or $COR^e$, or $R^{23a}$ and $R^{23b}$ together form a portion of six-membered acetal ring incorporating $CR^tR^u$;

$R^t$ and $R^u$ are independently H, an alkyl group, an aryl group or an alkoxyaryl group;

$R^5$ is H or $OR^{2b}$, wherein $R^{2b}$ is H, a protecting group, an alkyl group, an aryl group, a benzyl group, a trityl group, $-SiR^aR^bR^c$, $CH_2OR^d$, or $COR^e$;

$R^{10}$ is H or alkyl; and $R^{27}$ is $CH=CHC(O)$, $CH=CHCH(OH)$, or $CH_2CH_2C(O)$.

In still a further aspect, the present invention provides a compound of the following structure or its enantiomer

[Chemical structure diagram showing a macrocyclic compound with substituents $R^3$, $R^{27}$, $CHR^1$, $R^2O$, $OR^{2d}$, $CHR^{12}$, $R^{11a}O$, $OR^{11b}$]

wherein $R^1$ is H, a protecting group, an alkyl group, an aryl group, an alkenyl group, an alkynyl group, or a halogen atom;

$R^2$ and $R^{2d}$ are independently H, a protecting group, an alkyl group, a benzyl group, a trityl group, $-SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, $-R^iSiR^aR^bR^c$ or a benzyl group, wherein $R^i$ is an alkylene group;

$R^e$ is an alkyl group, an allyl group, a benzyl group, an aryl group, an alkoxy group, or $-NR^gR^h$, wherein $R^g$ and $R^h$ are independently H, an alkyl group or an aryl group;

$R^3$ is $(CH_2)_n$ where n is and integer in the range of 0 to 5, $-CH_2CH(CH_3)-$, $-CH=CH-$, $-CH=C(CH_3)-$, or $-C\equiv C-$;

$R^5$ is H or $OR^{2b}$, wherein $R^{2b}$ is H, an alkyl group, an aryl group, a benzyl group, a trityl group, $-SiR^aR^bR^c$, $CH_2OR^d$, or $COR^e$;

$R^{11a}$ and $R^{11b}$ are independently H, a protecting group, an alkyl group, a benzyl group, a trityl group, $-SiR^aR^bR^c$, $CH_2OR^d$, $COR^e$, or $R^{11a}$ and $R^{11b}$ together form a portion of six-membered acetal ring incorporating $CR^tR^u$;

$R^t$ and $R^u$ are independently H, an alkyl group, an aryl group or an alkoxyaryl group;

$R^{12}$ is a halogen atom, $CH_2OR^{2c}$, CHO, $CO_2R^{10}$, $CH=CHCH_2OR^{2c}$, $CH=CHCHO$, wherein $R^{2c}$ is H, an alkyl group, a benzyl group, a trityl group, $-SiR^aR^bR^c$, $CH_2OR^d$, or $COR^e$, and $R^{10}$ is H or alkyl; and $R^{27}$ is $CH=CHC(O)$, $CH=CHCH(OH)$, or $CH_2CH_2C(O)$.

The above general structures for the compounds of the present invention include all stereoisomers thereof (other than the natural compound dictyostatin 1). Moreover, the structures of the compounds of the present invention include the compounds in racemic form, enantiomerically enriched form or enantiomerically pure form. Wherein double bonds (for example, with the groups $-CH=CH-$ or $-CH=C(CH_3)-$) a present in $R^3$, a preferred stereoisomer is Z.

The terms "alkyl", "aryl" and other groups refer generally to both unsubstituted and substituted groups unless specified to the contrary. In that regard, the groups set forth above can be substituted with a wide variety of substituents to synthesize analogs retaining biological activity. Unless otherwise specified, alkyl groups are hydrocarbon groups and are preferably $C_1$-$C_{15}$ (that is, having 1 to 15 carbon atoms) alkyl groups, and more preferably $C_1$-$C_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or naphthyl. As used herein, the terms "halogen" or "halo" refer to fluoro, chloro, bromo and iodo.

The term "alkoxy" refers to —OR, wherein R is an alkyl group. The term "alkenyl" refers to a straight or branched chain hydrocarbon group with at least one double bond, preferably with 2-15 carbon atoms, and more preferably with 2-10 carbon atoms (for example, $-CH=CHR$ or $-CH_2CH=CHR$; wherein R can be a group including, but not limited to, an alkyl group, an alkoxyalkyl group, an amino alkyl group, an aryl group, or a benzyl group). The term "alkynyl" refers to a straight or branched chain hydrocarbon group with at least one triple bond, preferably with 2-15 carbon atoms, and more preferably with 2-10 carbon atoms (for example, $-C\equiv CR$ or $-CH_2-C\equiv CR$; wherein R can be a group including, but not limited to, an alkyl group, an alkoxyalkyl group, an amino alkyl group, an aryl group, or a benzyl group). The terms "alkylene," "alkenylene" and "alkynylene" refer to bivalent forms of alkyl, alkenyl and alkynyl groups, respectively.

The term "trityl" refers to a triphenyl methyl group or $-C(Ph)_3$.

Certain groups such as amino and hydroxy groups may include protective groups as known in the art. Preferred protective groups for amino groups include tert-butyloxycarbonyl, formyl, acetyl, benzyl, p-methoxybenzyloxycarbonyl, trityl. Preferred protecting groups for alcohol include trialkylsilyl (for example, triethylsilyl, triisopropylsilyl and tributyldimethylsilyl), p-methoxybenzyl, trityl, and (in the case of 1,3-diols) p-methoxyphenyl acetals. Other suitable protecting groups as known to those skilled in the art are disclosed in Greene, T., Wuts, P. G. M., *Protective Groups in Organic Synthesis*, Wiley (1991), the disclosure of which is incorporated herein by reference.

Other aspects of the present invention include the synthesis of the compounds of the present invention as well as the biological assaying of such compounds and the biological activity of such compounds against, for example, cancer (such as breast, prostate cancer and ovarian cancer). For example, in another aspect, the present invention provides a method of treating a patient for cancer, including the step of administering a pharmaceutically effective amount of a biologically active compound of the present invention or a pharmaceutically acceptable salt thereof.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1 illustrates two embodiments of the synthesis of dictyostatin bottom fragment 15.

FIG. 5 illustrates an embodiment of the synthesis of representative analog C16-desmethyldictyostatin 79.

FIG. 9 illustrates representative examples and methods of synthesis of lactam analogs of the present invention.

DETAILED DESCRIPTION OF THE INVENTION

Figure 2:
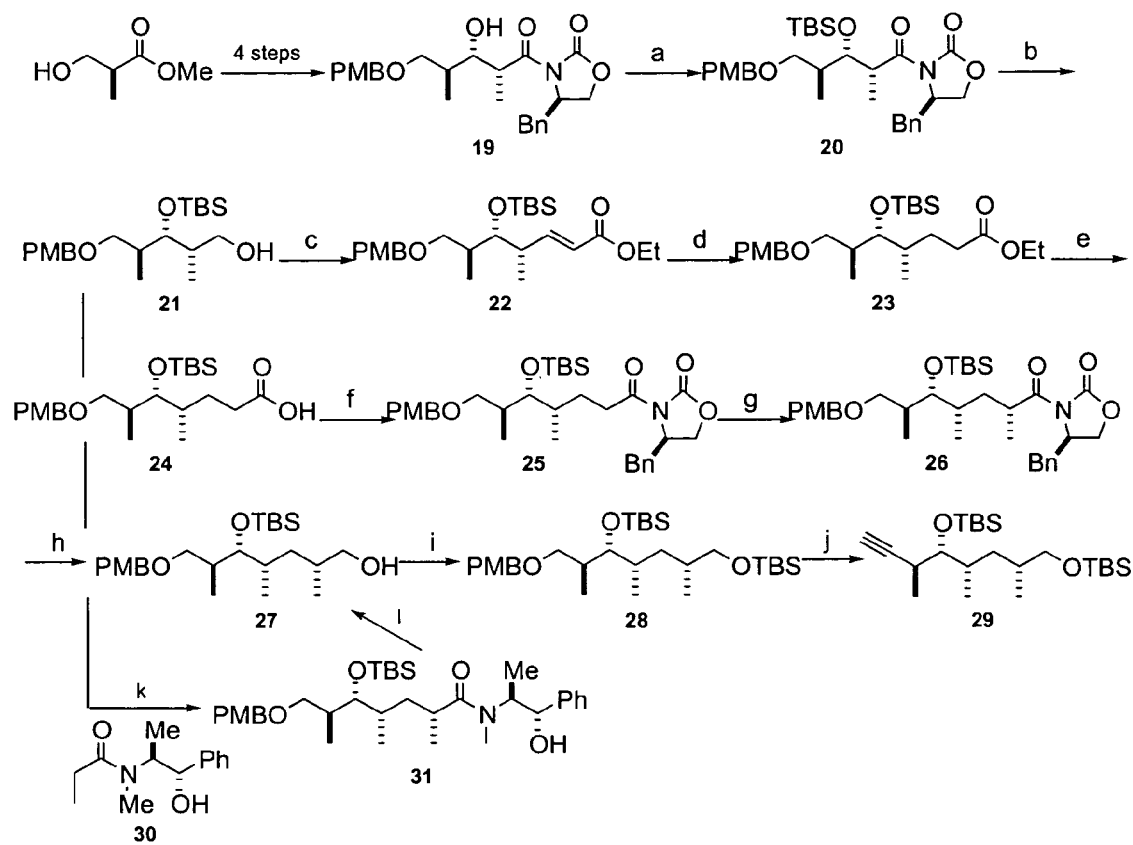
FIG. 2 illustrates two embodiments of the syntheses of dictyostatin middle fragment 29.

FIGS. 1-9 show exemplary synthetic pathways and intermediates for the synthesis of dictyostatin analogs.

The synthesis of an exemplary "bottom fragment" 15 for making dictyostatin and analogs is shown in FIG. 1. 1,3-Propanediol 3 was elaborated via Evans chiral auxiliary-based methods to the known, bis-TBS-protected Horner-Wadsworth-Emmons product 10 in nine steps. See, Phukan, P.; Sasmal, S.; Maier, M. E. *Eur. J. Org. Chem.* 2003, 1733, and Andrus, M. B.; Argade, A. B. *Tetrahedron Lett.* 1996, 37, 5049. This unsaturated ester was reduced to the allylic alcohol 11, which was protected with a trityl group and its primary TBS group removed with HF-pyridine to give alcohol 13, which was oxidized in two steps to the carboxylic acid and coupled with the Weinreb reagent to give amide 15. The fifteen-step process from 3 to 15 yielded this intermediate in 9.5% overall yield.

A shorter route to 10, also illustrated in FIG. 1, was also deployed. Brown crotylmetalation of TBS-protected 3-hydroxypropanal 16 (prepared quantitatively in two steps from 3), was followed by protection of the resulting alcohol 17, $OsO_4$-catalyzed dihydroxylation and diol cleavage with periodate, and finally Horner-Wadsworth-Emmons homologation. This second generation route improved the overall yield of 15 from 3 to 27%.

The synthesis of an exemplary "middle fragment" 29 for making dictyostatin and analogs is shown in FIG. 2. The secondary alcohol of known compound 19 (see, Smith, A. B.; Beauchamp, T. J.; LaMarche, M. J.; Kaufman, M. D.; Qiu, Y. P.; Arimoto, H.; Jones, D. R.; Kobayashi, K. *J. Am. Chem. Soc.* 2000, 122, 8654-8664. ), prepared in four steps from the (S)-Roche ester, was protected with a TBS group and the Evans auxiliary was removed with $LiBH_4$ to give alcohol 21. Oxidation to the aldehyde and Horner-Emmons reaction gave the ester 22. Alkene reduction with nickel boride, saponification with LiOH and coupling with the Evans auxiliary gave amide 25. Asymmetric methylation provided one diastereomer 26 very predominantly. Removal of the chiral auxiliary, TBS protection, and PMB deprotection with DDQ gave the primary alcohol 28. Corey-Fuchs reaction gave the desired alkyne 29. This route from 19 to 29 proceeded in 16% overall yield.

Another route to 29, also illustrated in FIG. 2, involved conversion of 21 to its iodide and asymmetric alkylation with Myers' auxiliary 30 to give amide 31. See, Myers, A.; Yang, B. Y.; Chen, H.; McKinstry, L.; Kopecky, D. J.; Gleason, J. *J. Am. Chem. Soc.* 1997, 119, 6496-6511. Removal of the auxiliary gave 27 in high yield, which was converted to 29 by the steps described above. This second generation approach to 29 doubled the overall yield from 19 to 31%. By using the enantiomer of Myers' auxiliary 30, the epimer of 29 at C16 (dictyostatin numbering) is prepared.

Figure 3:
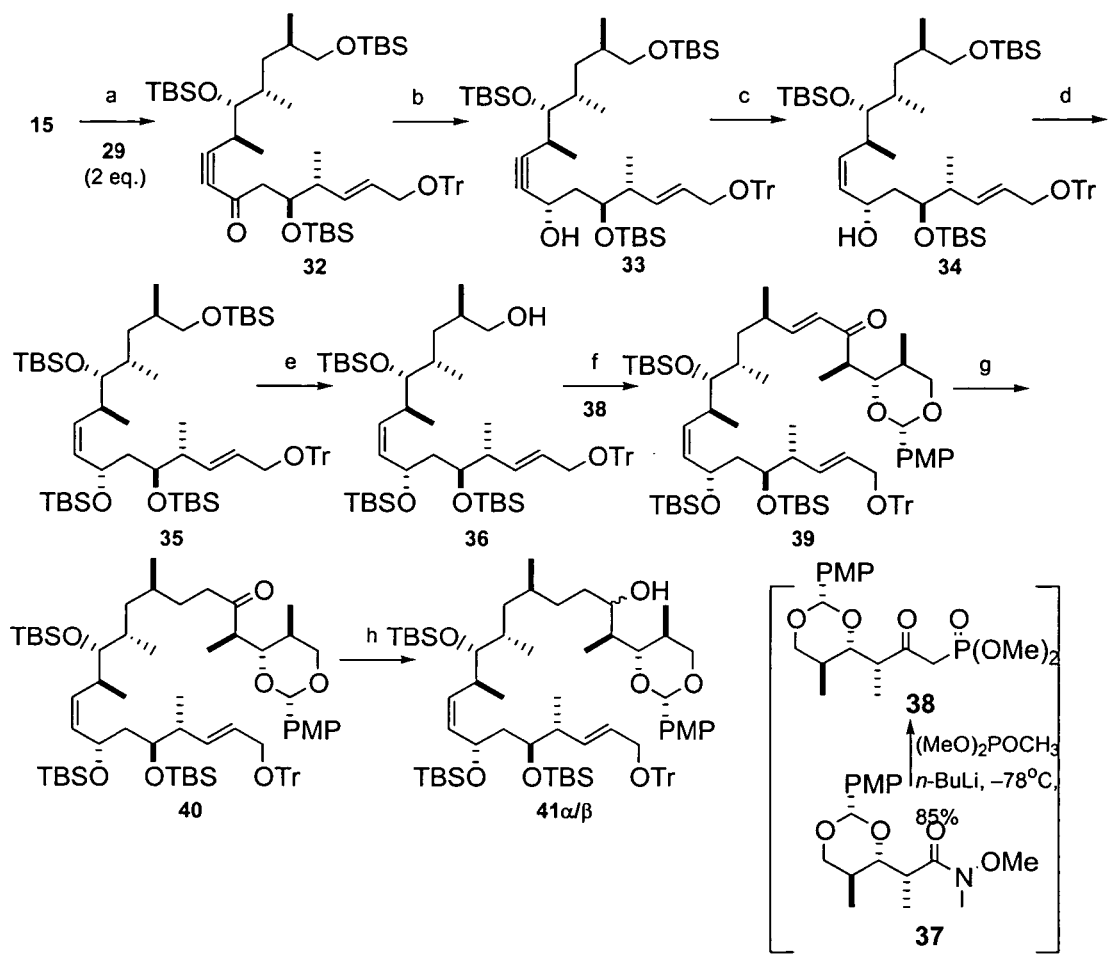
FIG. 3 illustrates one embodiment of the coupling of bottom and middle fragments of dictyostatin and elaboration to build the upper fragment.
Figure 4:
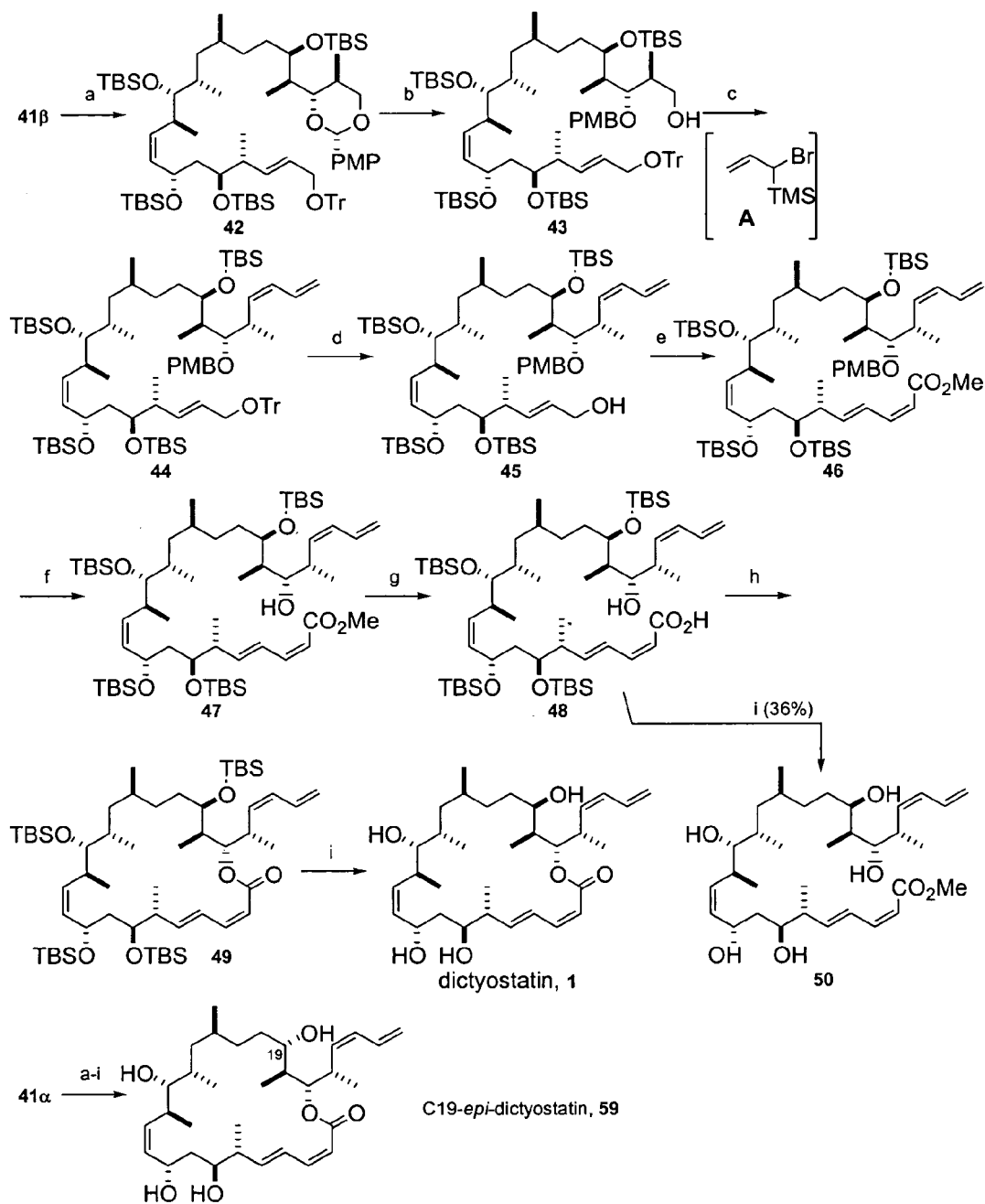
FIG. 4 illustrates one embodiment of the construction of dictyostatin 1 and representative analogs 50 and 59.

The bottom and middle fragments were then coupled and the synthesis of dictyostatin was completed as summarized in FIGS. 3 and 4. The route is flexible and generally allows access to many analogs. The Weinreb amide 15 was reacted with two equivalents of the anion from alkyne 29 to give the coupling product 32 in high yield. Reduction with the (S,S)-Noyori catalyst gave predominantly one isomer of the alcohol 33 (see, Matsumura, K.; Hashiguchi, S.; Ikariya, T.; Noyori, R. *J. Am. Chem. Soc.* 1997, 119, 8738-8739), whose alkyne group was reduced by Lindlar hydrogenation to alkene 34.

The newly generated secondary hydroxy group was protected with a TBS group to give 35. Selective deprotection of the primary TBS group with HF-pyridine in buffered pyridine at 0° C. gave 36. The aldehyde formed by Dess-Martin oxidation was reacted with the phosphonate 38 (prepared from 37) under Horner-Wadsworth-Emmons conditions to give the conjugated alkene 39 in good yield. Selective reduction with nickel boride gave the ketone 40, which was reduced in a purposefully unselective manner with $NaBH_4$ to give a 2.4:1 mixture of C19 epimers of 41, with the β isomer, necessary for preparation of (−)-dictyostatin, predominating. The isomers of 41 were readily separated by silica gel chromatography. A ratio favoring 41β (5:1) was obtained by use of the bulkier reducing agent $LiAl(O\text{-}t\text{-}Bu)_3H$, whereas a 1:1 ratio of the α and β isomers was obtained when L-Selectride was employed.

Alcohol 41β was protected with a TBS group to give 42, whose PMP acetal was cleaved with DIBAL-H to give alcohol 43 (FIG. 4). Oxidation to the aldehyde followed by Nozaki-Hiyama addition and Peterson-type elimination installed the (E,Z)-diene to give 44 in high yield. The allylic trityl group was removed with $ZnBr_2$ to give alcohol 45. Dess-Martin oxidation to the aldehyde and Still-Gennari reaction gave the (E,Z)-conjugated ester 46. The PMB group was removed with DDQ to give 47 and saponification with aqueous KOH in EtOH-THF to give acid 48. Yamaguchi macrolactonization gave 49 in good yield. Global deprotection with 3N HCl in MeOH-THF gave (−)-dictyostatin 1. The sample exhibited spectral data identical to the natural product and the optical rotation matched well. Thus, the previously proposed structures of dictyostatin are incorrect.

Also shown in FIG. 4 are the synthetic steps leading to two representative analogs, the open-chain methyl ester 50 and C19-epi-dictyostatin 59. Ester 50 was prepared by global removal of the TBS groups from 48 in 36% yield. The C19-epi analog 59 was prepared from alcohol 41α, as made in FIG. 3, by the same methods used for preparation of 1.

Synthesis of C16-desmethyl dictyostatin 79, another exemplary analog, is shown in FIG. 5. The synthesis proceeded from ester 23 in a manner similar to the existing route to 1, but with omission of the C16-methyl group. Thus, a considerably simpler-to-make middle fragment 64 lacking the awkward C16 stereocenter was used for construction of 79. Intermediate 23 was elongated to ester 60 by Horner- Wadsorth-Emmons reaction. Nickel boride then DIBAL-H reduction of the ester gave alcohol 61 in 76% yield. The primary hydroxy group was protected with TBSCl to give 62 quantitatively, then the PMB group was removed to give alcohol 63 in 90% yield. Oxidation of 63 to the aldehyde by using Parikh-Doering conditions, followed by Corey-Fuchs reaction, afforded the middle fragment alkyne 64.

The remainder of the synthesis from 64 to C16-desmethyldictyostatin 79 was then completed by using the same synthetic pathway described above for 1. Interestingly, reduction of ketone 70 (not shown, the desmethyl homologue of 40) with 3 equivalents of LiAl(O-t-Bu)$_3$H gave the desired 71β in 95% yield, with only 5% of the α-isomer.

Figure 6:
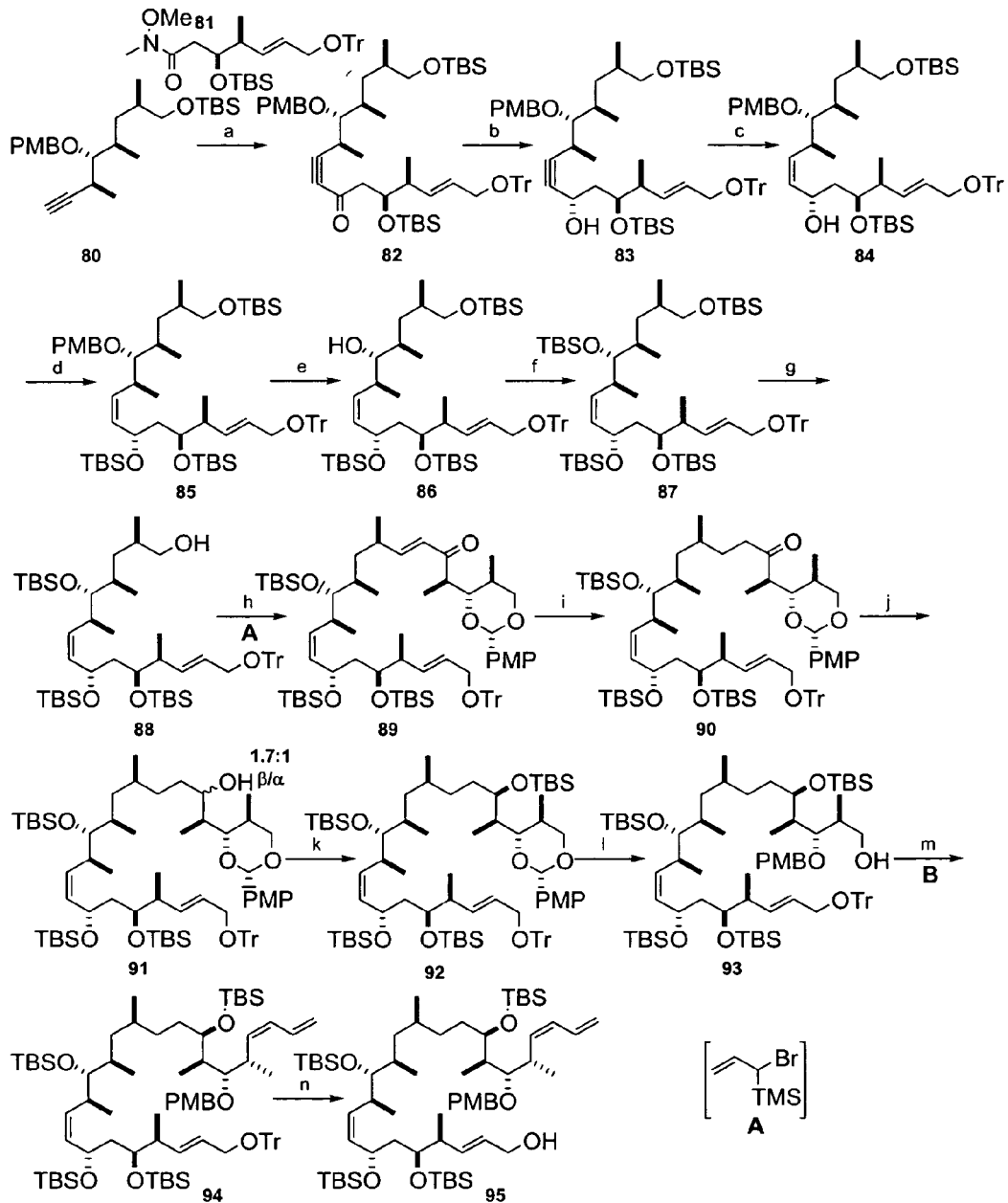
FIG. 6 illustrates an embodiment of the synthesis representative C6-epi,C14-epi intermediate 95.
Figure 7:
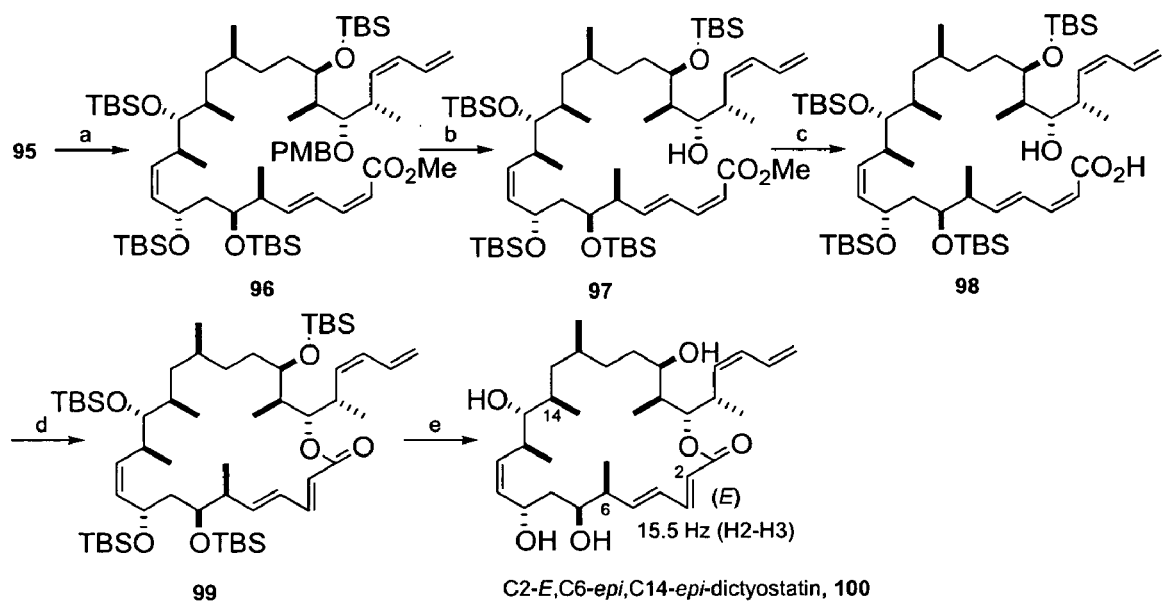
FIG. 7 illustrates an embodiment of the synthesis of representative analog C2-E,C6-epi,C14-epi dictyostatin 100 and its C2-C3 Z-isomer.
Figure 8:
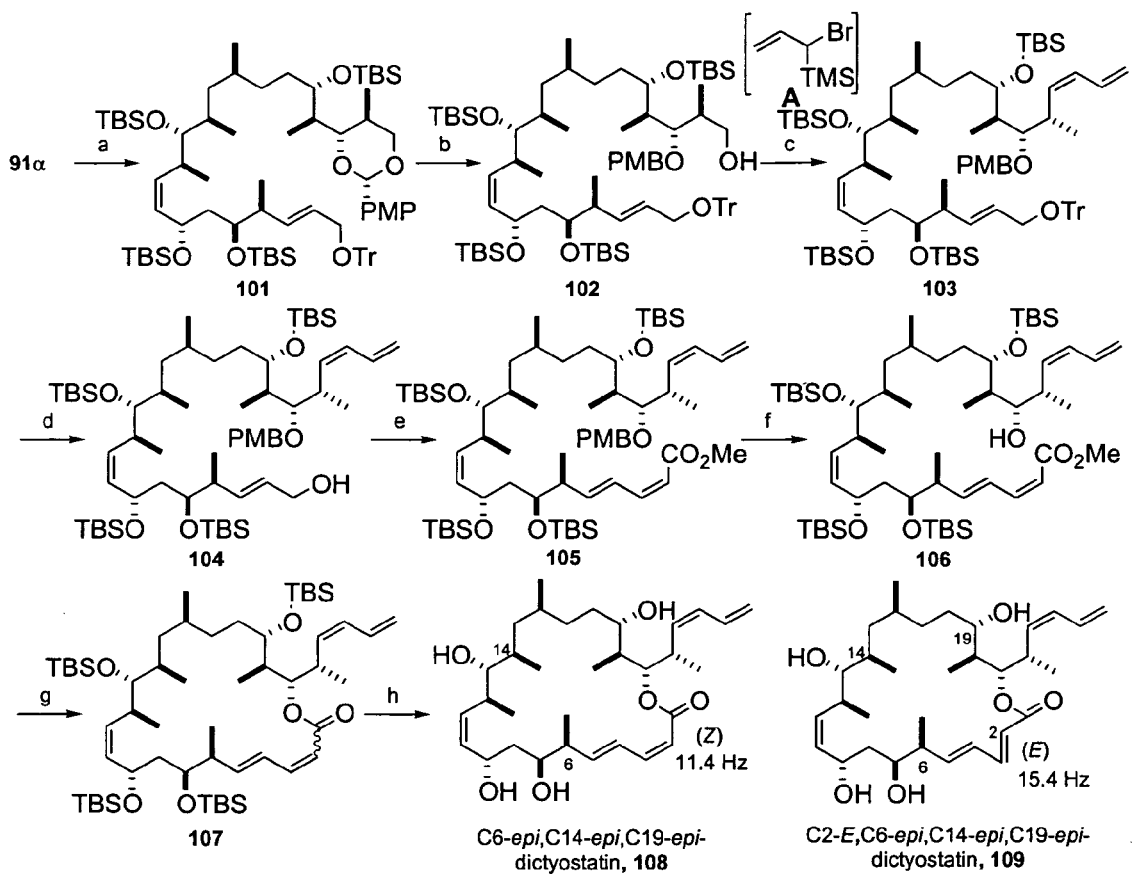
FIG. 8 illustrates an embodiment of the synthesis of representative analog C6-epi,C14-epi,C19-epi dictyostatin 108 and its C2-C3 E-isomer.

The synthesis of yet other representative analogs are shown in FIG. 6-8. These are epimers of dictyostatin at C6, C14 and/or C19. The alkyne 80 was added to bottom fragment 81 to give alkyne 82 in 98% yield (FIG. 8). When this alkynyl ketone was subjected to Noyori reduction conditions, one major isomer 83 was formed in 87% yield. Also in this case, about 20 mol % of the (S,S)-Noyori catalyst was preferred. The Noyori product 83 was reduced by using Lindlar catalyst to give the cis-alkene 84 in 90% yield. When the reaction time was extended (~1 day), partial over-reduction of other multiple bonds occurred.

In order to assign the configuration of the newly generated stereocenter at C9, 84 was treated with TBAF to remove both TBS groups. The resulting triol was reacted with excess 2,2-dimethoxypropane (3.0 equiv) to form the acetal, whose HMQC (500 MHz) NMR spectrum showed the two methyl groups of the acetonide at similar chemical shifts (24.5 ppm and 25.1 ppm) and the tertiary carbon at 100.4 ppm. These data show an anti-relationship between the C7 and C9 hydroxy groups based on the Rychnovsky method. The C9 hydroxy group in 84 was protected with a TBS group to give 85 in quantitative yield. The PMB group was then removed with DDQ to give 86 in 84% yield. The resulting secondary hydroxy group was protected again by a TBS group, giving 87 in 94% yield. Selective deprotection of the primary TBS group was accomplished in 66% yield by treatment with HF-pyridine complex in buffered pyridine at 0° C. for 2 days to give 88 along with other deprotected byproducts. After the successful coupling of the middle and bottom fragments, 88 was oxidized to the aldehyde, which then was subjected to Horner-Emmons reaction with the phosphonate 38, yielding 89 in 78% yield.

The alkene in α,β-unsaturated ketone 89 was reduced with nickel boride giving 90 in 76% yield. As a side reaction, some over-reduction of the C4-C5 alkene in the bottom fragment was also observed. The C19 ketone was reduced by NaBH$_4$ yielding a 1.7:1 ratio of diastereomers of 91, with the β isomer as the major (62%), less polar product and the α isomer as the minor (36%), more polar product. These two diastereomers could be separated by silica gel column chromatography. The newly generated C19 hydroxy group in 91β was protected by a TBS group to give 92 in 86% yield, then the PMB acetal was cleaved with DIBAL-H to give the primary alcohol 93 in 97% yield. Oxidation to the aldehyde and subsequent Nozaki-Hiyama and Peterson syn-elimination reactions gave the diene 94 in 85% yield.

Removal of the trityl group in 94 with ZnBr$_2$ in CH$_2$Cl$_2$-MeOH gave 95 in 83% yield. This was oxidized to the aldehyde and the (E,Z)-diene was installed by Still-Gennari reaction in 90% yield (FIG. 7). The PMB group in 96 was removed by DDQ to give 97 in 90% yield, and the resulting methyl ester was hydrolyzed with 1N aqueous KOH in EtOH-THF. Macrolactonization by the Yamaguchi method gave, surprisingly, mainly the C2E,C4E macrolactone 99 in 78% yield. Final global TBS deprotection yielded 100 in 25% yield.

The C19 epimer of 100 was prepared from 91α using similar reaction pathways (FIG. 8). After Yamaguchi lactonization, and global TBS deprotection, the (E,Z)-isomer 108 (less polar, 45%) could be isolated along with the isomerized (E,E)-isomer 109 (more polar, 15%) in a 3:1 ratio.

The methods outlined in FIGS. 1-8 are only exemplary of many possible variants. For example, analogs containing a C15-C16 Z-alkene can be prepared by the methods outlined in U.S. patent application Ser. No. 10/655,916. Analogs lacking the C9 oxygen atom (C9-deoxy analogs) can likewise be prepared by methods shown in that application. See, for example, FIGS. 8 and 11, among others.

The preferred method for forming the macrolactones (often called macrocyclic lactones or macrolides) is the Yamaguchi lactonization. See, for example, Inanaga, J.; Kuniko, H.; Hiroko, S.; Katsuki, T.; Yamaguchi, M. *Bull. Chem. Soc. Jpn.* 1979, 52, 1989. An example of the Yamaguchi lactonization is the conversion of hydroxy acid 48 to lactone 49 in FIG. 4. Many other commons conditions suitable to effect macrolactone formation from hydroxy acids are well known to those skilled in the art, and these can also be used. See, for example, Kirst, H. A. Macrolides. *Large Ring Molecules*; Wiley: NY; 1996; pp 345-375, and Boeckman, R. K., Jr; Goldstein, S. W. The Total Synthesis of Macrocyclic Lactones. *The Total Synthesis of Natural Products*; Wiley: New York, 1988; p 1.

The steps of semi-reduction of the C10-C11 alkyne, asymmetric reduction of the C9 ketone and (optionally) protection of the resulting alcohol can be conducted under and assortment of different reaction conditions. For one example, see the conversion of alkynyl ketone 32 to alkynyl alcohol 33, to alkenyl alcohol 34, to silyl ether 35 in FIG. 3. The preferred conditions for reduction of the ketone involve use of the Noyori reagent, see K. Matsumura, S. Hashiguchi, T. Ikariya, R. Noyori, *J. Am. Chem. Soc.* 1997, 119, 8738-39. However, many other common ketone reducing agents, both chiral and achiral, can also be used. See, for example, Itsuno, S. Enantioselective Reduction of Ketones. *Org. React.* (N.Y.) 1998, 52, 395-576. In cases were two epimers of the alcohol are formed, chromatographic separation is used to isolate the individual epimers (see, for example, separation of 41 in FIG. 3). The Lindlar reduction is the preferred method of semi-reduction of the alkyne to the Z-alkene, but other methods can also be used. See for example, Siegel, S. Heterogeneous Catalytic Hydrogenation of C═C and Alkynes. *Comprehensive Organic Synthesis*; Pergamon Press: Oxford, 1991; pp 417, and Takaya, H. Homogeneous Catalytic Hydrogenation of C═C and Alkynes. *Comprehensive Organic Synthesis*; Pergamon Press: Oxford, 1991; pp 443.

The reactions in this sequence of steps can also be conducted in several orders. The preferred order is semi-reduction of the C10-C11 alkyne, followed by asymmetric reduction of the C9 ketone followed by (optionally) protection of the resulting alcohol. Other orders of reactions are asymmetric reduction of the ketone, protection of the alcohol and semi-reduction of the alkyne, or asymmetric reduction of the ketone, semi-reduction of the alkyne and protection of the alcohol.

The preceding steps of coupling of an alkynyl anion with an activated carboxylic acid, see for example conversion of 15 and 29 to 32 in FIG. 3, also can be conducted under different sets of conditions. A preferred method is the deprotonation of the alkyne with a strong base, for example BuLi, followed by addition of a carboxylic acid derivative that is activated with a suitable leaving group. Preferred activated carboxylic acids for acylation (acylating agents) are Weinreb amides where the leaving group is the N-methoxy-N-methyl amide group. Many other agents such as esters, acid halides, acid imidazolides, etc. can also be used. These have standard leaving groups such as alkoxide, imidazole and halide. The alkynyl anion can also be generated in situ from a silylalkyne by desilylation or from a geminal-haloalkene by treatment with two or more equivalents of a lithiating agent like BuLi.

In an alternative route, the alkynyl anion can be reacted with an aldehyde instead of an activated carboxylic acid to produce a C9 alcohol directly after workup. This route is more direct, but mixtures of epimers at C9 may result and chromatographic separation of the epimers may be required. One epimer of a C9 (or other) alcohol can be converted to the other by a Mitsunobu reaction.

Lactam analogs of dictyostatin are important as anticancer agents because of their increased hydrolytic stability compared to the lactones, both in vivo and in vitro. These analogs are readily made by starting with intermediates of the current invention, as exemplified in FIG. 9. Standard oxidation of the free C21 alcohol of 110 to a ketone followed by reductive amination provides 111. If desired, the C21 amine stereoisomers can be separated by chromatography. Hydrolysis of the ester to the acid followed by macrolactamization provides lactam 112. The specific example of dictyostatin macrolactam 115, made for example by the sequence 113→114→115, is exemplary of a lactam analog of this invention.

The steps in the sequence can be conducted in different orders and also on different intermediates. When the C21 nitrogen atom is installed earlier in the synthesis, it is optionally protected with a standard nitrogen protecting group for the subsequent steps prior to macrolactamization. In another approach, this nitrogen can be installed by a Mitsunobu reaction of a suitably acidic nitrogen nucleophile (for example, azide) with a C21 alcohol. This reaction occurs with inversion, so the configuration of C23 is chosen accordingly.

For exemplary methods and conditions of reductive amination, see Baxter, E. W.; Reitz, A. B. Reductive aminations of carbonyl compounds with borohydride and borane reducing agents. *Org. React.* (N.Y.) 2002, 59, 1-714. Methods of synthesizing macrolactams (macrocyclic lactams) are related to those for macrolactones. For exemplary methods and conditions, see Nubbemeyer, U. *Top. Curr. Chem.* 2001, 216, 125-196. For exemplary methods and conditions for Mitsunobu reactions, see Hughes, D. L. *Org. Prep. Proced. Int.* 1996, 28, 127-164.

Biology

Tubulin Polymerization.

The abilities of the new compounds to cause tubulin polymerization were determined under reaction conditions consisting of purified bovine brain tubulin (1 mg/mL) in the presence or absence of microtubule-associated proteins (MAPs, 0.75 mg/mL) and GTP (100 µM). Test agents were initially screened at 10 and 40 µM. In these experiments, test agent-induced assembly of soluble tubulin into polymer, with respect to the presence and absence of cofactors and at different temperatures, was monitored in a multi-cuvette, temperature-controlled spectrophotometer via development of turbidity in the solution. The initial temperature was closely controlled at 0° C., then rapidly raised to 10° C., to 20° C., then finally to 30° C. to determine both the temperature at which a test agent induced assembly as well as the extent of agent-induced assembly. The temperature increases were followed by a rapid decrease in temperature back to 0° C. to determine the cold-stability of polymer formed. The effects of dictyostatin 1 and discodermolide 2 were similar and far more potent than those of paclitaxel.

Figure 10:
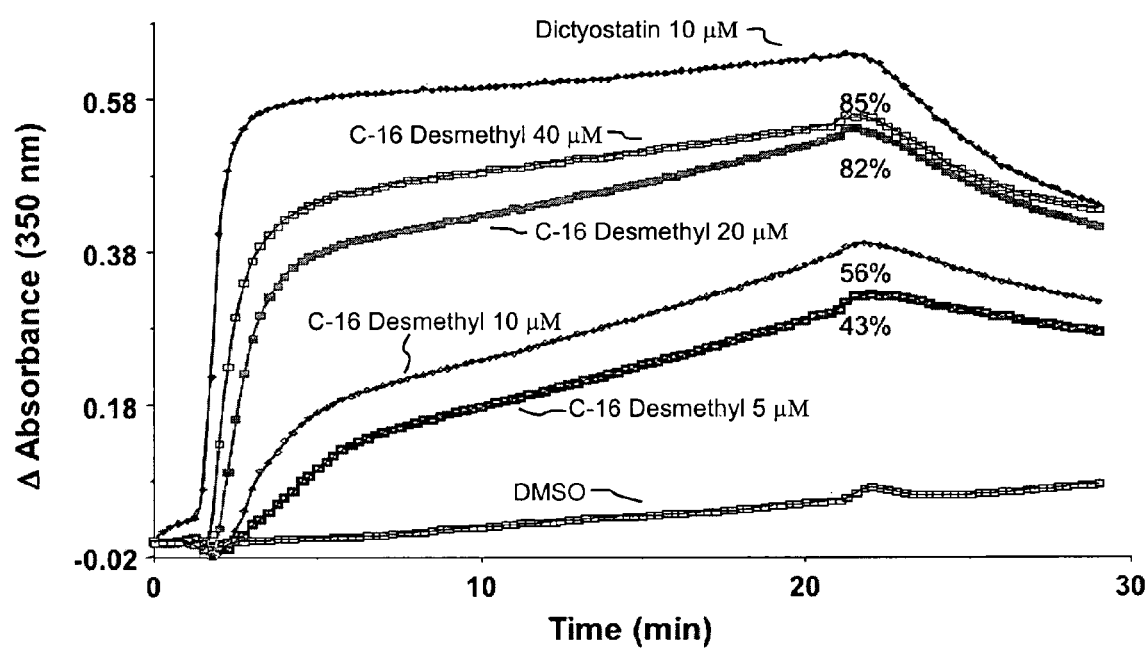
FIG. 10 illustrates representative turbidity profiles of 16-desmethyldictyostatin in comparison to that of dictyostatin 1 in a tubulin-only (no MAPs, no GTP, assembly supported by monosodium glutamate) assay.

The C16-desmethyl compound 79 is especially potent among the analogs. FIG. 10 shows the simplest of its turbidity profiles in comparison to that of dictyostatin 1 in a tubulin-only (no MAPs, no GTP, assembly supported by monosodium glutamate) assay wherein initial temperature was 0° C. for 2 min, followed by rapid rise in temperature to 30° C. for 20 min, then rapid decrease to 0° C. Turbidity profiles showed that analogs 50 and 59 also caused tubulin assembly at temperatures lower than 30° C. The results showed that all of the compounds had effects on the isolated target, tubulin, but with a range of potencies.

Antiproliferative Activity.

Representative analogs were examined for their antiproliferative activities against human ovarian carcinoma 1A9 cells and their paclitaxel-resistant mutants, 1A9/Ptx10 and 1A9/Ptx22. Each of these resistant lines contains single mutations in the major β-tubulin gene that confer to the cells, which do not express drug efflux pumps, appreciable tolerance to paclitaxel. Paclitaxel had subnanomolar potency against the parental 1A9 cells, but the mutant cells showed ca. 90- and 70-fold resistance to the drug (Table 1). Analogs 50 and 59 gave GI50 values in the mid-nanomolar range. C6-epi,C14-epi-C19-epi-dictyostatin 108 and its C2E-diene derivative 109 were antiproliferative agents, giving mid micromolar GI50 values. Even though 100 also had three stereo/geometric alterations (C2E,C6-epi,C14-epi), it was a more potent antiproliferative agent than 108 and 109, showing high nanomolar GI50 values. With one notable exception (vide infra), the fold-resistance values for 1 and its analogs against 1A9/Ptx10 and 1A9/Ptx22 cell lines were much lower than that observed for paclitaxel. The one exception was compound 79, which appeared to be essentially equipotent to 1 against the parental 1A9 cells and the Ala364→Thr β-tubulin mutant 1A9/Ptx22 cells, but experienced resistance from the Phe270→Val β-tubulin mutant 1A9/Ptx10 cells. Because these mutant cells are not clinically relevant, the result of reduced potency is primarily of mechanistic importance.

TABLE 1

Antiproliferative potencies of dictyostatin (1) and analogs as compared to discodermolide (2) and paclitaxel against human ovarian carcinoma cells (1A9) and their paclitaxel-resistant, β-tubulin mutant clones (1A9/Ptx10 and 1A9/Ptx22).

| | GI50 ± S.D., nM (fold-resistance) | | |
| --- | --- | --- | --- |
| Compound | 1A9 | 1A9/Ptx10 (Phe270 -> Val) | 1A9/Ptx22 (Ala364 -> Thr) |
| dictyostatin-1 (1) | 0.69 ± 0.80 | 3.2 ± 2.4 (4.6) | 1.3 ± 1.0 (1.9) |
| discodermolide (2) | 1.7 ± 1.2 | 6.2 ± 3.6 (3.6) | 7.0 ± 8.4 (4.1) |
| paclitaxel | 0.71 ± 0.11 | 64 ± 8 (90) | 51 ± 9 (72) |
| 50 | 56 ± 16 | 79 ± 13 (1.4) | 85 ± 2 (1.5) |
| 59 | 21 ± 14 | 120 ± 60 (5.7) | 43 ± 12 (2.0) |
| 79 | 0.41 ± 0.52 | 470 ± 70 (1146) | 5.6 ± 4.7 (14) |
| 107 | >500 | >500 (—) | >500 (—) |
| 100 | 310 ± 40 | 780 ± 200 (2.5) | 790 ± 560 (2.5) |

TABLE 1-continued

Antiproliferative potencies of dictyostatin (1) and analogs as compared to discodermolide (2) and paclitaxel against human ovarian carcinoma cells (1A9) and their paclitaxel-resistant, β-tubulin mutant clones (1A9/Ptx10 and 1A9/Ptx22).

| | GI50 ± S.D., nM (fold-resistance) | | |
|---|---|---|---|
| Compound | 1A9 | 1A9/Ptx10 (Phe270 -> Val) | 1A9/Ptx22 (Ala364 -> Thr) |
| 108 | 28 ± 1 µM | 26 ± 0 µM (0.9) | 30 ± 1 µM (1.1) |
| 109 | 25 ± 2 µM | 25 ± 1 µM (1) | 30 ± 1 µM (1.2) |

Pelleting Assay ($EC_{50}$ Determination).

Dictyostatin and representative analogs were evaluated in a quantitative assay for their ability to promote tubulin polymerization. The $EC_{50}$ value (defined as test agent concentration required to polymerize 50% of tubulin compared to control) observed for dictyostatin 1 under these conditions was 3.1±0.2 µM, similar to that obtained for discodermolide 2 (3.6±0.4 µM). Both were far superior to paclitaxel, which gave an $EC_{50}$ value of 25±3 µM. The C16-desmethyl analog 79 an $EC_{50}$ of 14±7 µM. When the percent polymer formed was determined in the reactions, a comparison of the activities of all the analogs could be made. Compounds 50 and 59 showed moderate activity. These $EC_{50}$ data correlated well with the relative antiproliferative potencies of the analogs.

TABLE 2

Tubulin Assembly $EC_{50}$ determinations.[a]

| Compound | $EC_{50}$ (µM) ± SD (N) | % Tubulin polymerized by 50 µM test agent |
|---|---|---|
| dictyostatin (1) | 3.1 ± 0.2 (3) | 99 ± 4 |
| discodermolide (2) | 3.6 ± 0.4 (3) | 98 ± 5 |
| paclitaxel | 25 ± 3 (3) | 89 ± 6 |
| 50 | >50 (2) | 39 ± 7 |
| 59 | >50 (2) | 30 ± 2 |
| 79 | 14 ± 7 (3) | 91 ± 6 |
| 100 | >50 (2) | 1 ± 1 |
| 108 | >50 (2) | 5 ± 1 |
| 109 | >50 (2) | 5 ± 4 |

[a]Bovine brain tubulin (10 µM) in 0.2 M MSG, 15 min at 20° C., centrifugation and Lowry determination of remaining soluble tubulin Radiolabeled Ligand Binding Assays.

The abilities of test agents to inhibit the binding of radiolabeled forms of the microtubule stabilizers paclitaxel, discodermolide and epothilone B from tubulin polymer were determined. Dictyostatin 1 was equipotent to discodermolide in inhibition of the binding of radiolabeled paclitaxel and epothilone B to microtubules. These two compounds were the most potent of all agents tested. The open chain methyl ester 50 and the 16-desmethyl analog 79 were ca. 60% as potent as 1 in inhibiting the binding of radiolabeled paclitaxel to microtubules.

TABLE 4

Percent inhibition of radiolabel from microtubules (±SD (N, number of independent determinations)).

| Test Agent (4 µM) | [$^3$H]Paclitaxel | [$^3$H]Discodermolide | [$^{14}$C]Epothilone B |
|---|---|---|---|
| dictyostatin (1) | 75 ± 5 (3) | 40 ± 3 (3) | 88 ± 1 (3) |
| discodermolide (2) | 76 ± 6 (4) | nd | 90 ± 1 (3) |
| paclitaxel | nd | 6 ± 5 (3) | 26 ± 1 (3) |
| 50 | 42 ± 1 (3) | nd | nd |
| 59 | 7 ± 2 (3) | nd | nd |
| 79 | 48 ± 3 (3) | nd | nd |
| 100 | 0 ± 1 | nd | nd |
| 108 | 0 ± 1 | nd | nd |
| 109 | 0 ± 1 | nd | nd |
| epothilone B | nd | 14 ± 3 | nd |
| docetaxel | 63 ± 8 (4) | 8 ± 6 (3) | 36 ± 1 (3) |
| epothilone A | 53 ± 4 (4) | 6 ± 6 (3) | 25 ± 3 (3) |

Multiparameter Fluorescence Analysis of Cellular Effects.

HeLa cells were plated on collagen-coated 384-well microtiter plates, allowed to attach, then treated for 24 h with test agents. Test agent concentrations began at 1 µM, and two-fold dilutions were made to levels below 1 nM. After the treatment period, the cells were fixed with formalin and their chromatin stained with Hoechst 33342. Cells were permeabilized and treated with primary antibodies for α-tubulin and phosphohistone H3, and then with fluorophore-labeled secondary antibodies. The three fluorescent channels were then examined on an ArrayScan II, which gives quantitative pixel distribution and density information in each channel on a per cell basis. Dictyostatin 1 was the most potent of all compounds tested, followed by paclitaxel, discodermolide and the 16-desmethyl analog 79.

TABLE 5

Minimum detectable cellular changes determined by multiparameter fluorescence high information content analysis.

| Compound | Nuclear condensation | Phosphohistone H3 | Tubulin polymer intensity |
|---|---|---|---|
| dictyostatin (1) | 32.7 ± 11.7 (3) | 9.6 ± 2.4 (4) | 7.4 ± 2.5 (4) |
| 50 | 479 ± 182 (4) | 149 ± 23.6 (4) | 219 ± 36 (4) |
| 59 | 363 ± 146 (2) | 261 ± 91 (4) | 284 ± 108 (4) |
| 79 | 71.5 ± 18.0 (4) | 34.4 ± 10.5 (4) | 26.9 ± 2.9 (4) |
| 100 | >5000 (4) | >5000 (4) | >5000 (4) |
| 108 | >5000 (4) | >5000 (4) | >5000 (4) |
| 109 | >5000 (4) | >5000 (4) | >5000 (4) |
| discodermolide (2) | 62.5 (1) | 38.4 ± 21.9 (2) | 64.6 ± 0.0 (2) |
| Paclitaxel | 40.2 ± 13.9 (4) | 17.5 ± 6.8 (4) | 8.0 ± 2.9 (4) |

EXAMPLES

Chemistry

Ethyl (4R,5S,2E)-5,7-bis(tert-butyldimethylsilyloxy)-4-methylhept-2-enoate (10)

A solution of triethyl phosphonoacetate (3.5 mL, 17.6 mmol) was added to a cooled (0° C.) stirred suspension of NaH (0.43 g, 17.0 mmol, 95% dispersion in mineral oil) in THF (46 mL) dropwise over a 10 min period. The mixture was brought to room temperature with a water bath (30 min)

and then cooled back to −78° C. and the aldehyde (2.73 g, 7.58 mmol) in THF (5 mL) was added. The resulting mixture was stirred for 1 h at 0° C. then pH7 phosphate buffer solution (10 mL) and Et$_2$O (50 mL) were added. The mixture was allowed to warm to room temperature and the phases were separated. The organic phase was washed with sat'd NH$_4$Cl solution (30 mL) and brine (30 mL), dried with MgSO$_4$, filtered and concentrated to give oily crude product. Purification by flash chromatography (EtOAc/hexane 1:9) afforded pure ester 10 (2.92 g, 59% for 2 steps) as a colorless oil: IR (CHCl$_3$) 2956, 2930, 2857, 1724, 1651, 1472, 1463, 1367, 1256, 1180, 1098, 1036, 836, 775 cm$^{-1}$; $^1$H NMR (300 MHz, CDCl$_3$) ϵ6.88 (dd, J=15.8, 7.6 Hz, 1H), 5.74 (d, J=15.8 Hz, 1H), 4.19 (q, J=7.1 Hz, 2H), 3.79 (ddd, J=6.7, 4.7, 4.4 Hz, 1H), 3.59 (m, 2H), 2.43 (m, 1H), 1.53 (m, 3H), 1.22 (t, J=7.1 Hz, 3H), 1.01 (d, J=6.8 Hz, 3H), 0.83 (s, 18H), 0.02 (m, 12H); $^{13}$C NMR (75 MHz, CDCl$_3$) δ 166.4, 150.9, 121.3, 71.8, 59.9, 59.5, 42.0, 36.8, 25.82, 25.78, 26.1, 18.1, 18.0, 14.4, 14.2, −4.6, −4.7, −5.4; LRMS (EI) 415 (M−CH$_3$), 373, 303, 147; HRMS (EI) calcd for C$_{21}$H$_{43}$O$_4$Si 415.2710 (M−CH$_3$), found 415.2712; [α]$^{20}$$_D$+3.8 (c 0.21, CHCl$_3$).

(4R,5S,2E)-5,7-bis(tert-Butyldimethylsilyloxy)-4-methylhept-2-en-1-ol (11)

DIBAL-H (26.5 mL, 26.5 mmol, 1.0 M solution in hexane) was added to the ester 10 (3.14 g. 7.30 μmol) in CH$_2$Cl$_2$ (35 mL) at −78° C. dropwise and stirred for 1 h. The reaction mixture was quenched by EtOAc (5 mL) and sat'd sodium potassium tartrate solution (20 mL) followed by vigorous stirring for 4 h. The aqueous phase was extracted with CH$_2$Cl$_2$ (3×30 mL) and the combined organic layers were washed with brine (10 mL). After drying over MgSO$_4$ and evaporation under vacuum, flash column chromatography (hexane/EtOAc 4:1) provided 2.75 g of alcohol 11 (97%) as a colorless oil: IR (CHCl$_3$) 3349, 2956, 2928, 2857, 1471, 1462, 1255, 1099, 836, 774 cm$^{-1}$; $^1$H NMR (300 MHz, CDCl$_3$) ϵ5.57 (m, 2H), 4.03 (m, 2H), 3.70 (ddd, J=9.7, 6.0, 3.8 Hz, 1H), 3.59 (m, 2H), 2.27 (m, 1H), 2.00 (s, 1H), 1.53 (q, J=6.5 Hz, 2H), 0.96 (d, J=6.9 Hz, 3H), 0.85 (s, 9H), 0.84 (s, 9H), 0.00 (m, 12H); $^{13}$C NMR (75 MHz, CDCl$_3$) δ 134.7, 129.2, 72.4, 63.6, 60.1, 41.8, 36.3, 25.9, 18.2, 18.0, 15.1, 10.7, −4.6, −5.4; LRMS (EI) 370 (M−H$_2$O), 303, 171, 147; HRMS (EI) calcd for C$_{20}$H$_{42}$O$_2$Si$_2$ 370.2723 (M−H$_2$O), found 370.2725; [α]$^{20}$$_D$−3.0 (c 0.57, CHCl$_3$).

((4R,5S,2E)-5,7-bis(tert-Butyldimethylsilyloxy)-4-methylhept-2-enyloxy)triphenylmethane (12)

Trityl chloride (4.1 g, 14.7 mmol) and DMAP (1.8 g, 14.7 mmol) were added to a solution of alcohol 11 (2.75 g, 7.1 mmol) in pyridine (71 mL). The mixture was heated to reflux for 18 h, cooled to ambient temperature and added to a solution of sat'd CuSO$_4$ (200 mL). The mixture was extracted with Et$_2$O (2×20 mL) and the combined organic extracts were washed sat'd CuSO$_4$ (2×20 mL). The organic layer was separated, dried (MgSO$_4$), filtered, and concentrated in vacuo. Flash column chromatography (EtOAc/hexane 1:19) provided 12 (4.46 g, quantitative) as a pale yellow oil: IR (CHCl$_3$) 2954, 2856, 1471, 1448, 1254, 1095, 835, 773, 705 cm$^{-1}$; $^1$H NMR (300 MHz, CDCl$_3$) ϵ7.56 (m, 6H), 7.32 (m, 9H), 5.79 (dd, J=15.6, 6.7 Hz, 1H), 5.65 (dd, J=15.7, 5.0 Hz, 1H), 3.85 (m, 1H), 3.74 (m, 1H), 3.66 (d, J=4.9 Hz, 1H), 2.43 (m, 1H), 1.70 (q, J=6.5 Hz, 2H), 1.21 (d, J=6.9 Hz, 3H), 0.99 (s, 9H), 0.97 (s, 9H), 0.154 (s, 3H), 0.150 (s, 3H), 0.13 (s, 3H), 0.12 (s, 3H); $^{13}$C NMR (75 MHz, CDCl$_3$) δ 144.4, 134.2, 128.7, 127.7, 126.9, 126.8, 86.8, 72.6, 65.1, 60.2, 42.1, 36.6, 26.0, 18.3, 18.1, 15.3, −4.4, −5.3; LRMS (EST) 653.3 [M+Na]+, 422.4, 243.2; HRMS (ESI) calcd for C$_{39}$H$_{58}$O$_3$Si$_2$Na 653.3822 [M+Na]$^+$, found 653.3851; [α]$^{20}$$_D$−1.9 (c 0.42, CHCl$_3$).

(3S,4R,5E)-3-(tert-Butyldimethylsilyloxy)-4-methyl-7-(trityloxy)hept-5-en-1-ol (13)

HF-pyridine in pyridine (40 mL, prepared by slow addition of 12 mL pyridine to 3 mL HF-pyridine complex followed by dilution with 25 mL THF) was added to a solution of TBS ether 12 (4.46 g, 7.07 mmol) in THF (10 mL). The mixture was stirred overnight at room temperature and quenched with sat'd NaHCO$_3$ (100 mL). The aqueous layer was separated and extracted with Et$_2$O (3×50 mL). The combined organic layers were washed with sat'd CUSO$_4$ (3×50 mL), dried over MgSO$_4$, and concentrated. Flash column chromatography (EtOAc/hexane 1:4) afforded 3.26 g (89%) of alcohol 13 as a colorless oil: IR (CHCl$_3$) 3407, 2955, 2928, 2856, 1490, 1471, 1448, 1254, 1058, 1031, 836, 773, 705 cm$^{-1}$; $^1$H NMR (300 MHz, CDCl$_3$) ϵ7.57 (m, 6H), 7.37 (m, 9H), 5.78 (dd, J=15.6, 6.5 Hz, 1H), 5.73 (dt, J=15.5, 4.8 Hz, 1H), 3.91 (m, 1H), 3.82 (d, J=5.9 Hz, 2H), 3.69 (d, J=4.4 Hz, 2H), 2.51 (m, 1H), 2.22 (br, 1H), 1.77 (m, 2H), 1.13 (d, J=6.8 Hz, 3H), 1.03 (s, 9H), 0.21 (s, 3H), 0.19 (s, 3H); $^{13}$C NMR (75 MHz, CDCl$_3$) δ 144.2, 134.1, 128.6, 127.7, 127.1, 126.9, 86.8, 74.3, 64.9, 60.4, 42.0, 34.8, 25.9, 18.0, 14.5, −4.4, −4.6; LRMS (ESI) 539.2 [M+Na]+, 243.2; HRMS (ESI) calcd for C$_{33}$H$_{44}$O$_3$Si$_1$Na 539.2957 [M+Na]$^+$, found 539.2976; [α]$^{20}$$_D$−2.8 (c 2.0, CHCl$_3$).

(3S,4R,5E)-3-(tert-Butyldimethylsilyloxy)-N-methoxy-N,4-dimethyl-7-(trityloxy)hept-5-enamide (15)

Sulfur trioxide pyridine complex (3.02 g, 19.1 mmol) was added to a stirred solution of alcohol 13 (3.26 g, 6.31 mmol) and triethylamine (2.6 mL, 19.1 mmol) in anhydrous CH$_2$Cl$_2$ (6 mL) and DMSO (12 mL) at 0° C. The reaction mixture was stirred at the ambient temperature for 1 h. The mixture was diluted with Et$_2$O (100 mL) and washed with aqueous 0.5 N HCl (50 mL) and brine (10 mL). The separated organic layer was dried over MgSO$_4$. Filtration and concentration followed by short flash column chromatography (hexane/EtOAc 4:1) provided the crude aldehyde as a colorless oil, which was used without further purification. A solution of the aldehyde in THF (25 mL) and H$_2$O (12 mL) was treated with 2-methyl-2-butene in THF (2M, 18 mL, 9.0 mmol), NaH$_2$PO$_4$·H$_2$O (2.6 g, 18.8 mmol) and NaClO$_2$ (2.1 g, 18.6 mmol). The reaction mixture was stirred for 2 h, diluted with 1N HCl (20 mL) and extracted with CH$_2$Cl$_2$ (2×40 mL). The combined organic layers were dried over MgSO$_4$, concentrated in vacuo and the crude acid was used for the next reaction without further purification. N,O-Dimethylhydroxylamine hydrochloride (0.62 g, 6.36 mmol), Et$_3$N (0.88 mL, 6.31 mmol), DMAP (0.63 mmol) were successively added to a solution of the crude acid in CH$_2$Cl$_2$ (10 mL). The reaction mixture was cooled to 0° C. and DCC (1.30 g, 6.30 mmol) was added. The mixture was stirred at ambient temperature for 15 h and filtered. The filtrate was washed with 0.5 N HCl, saturated aqueous NaHCO$_3$, and brine, dried over anhydrous MgSO$_4$ and concentrated. Purification by column chromatography over silica gel (hexane/EtOAc 4:1) gave the Weinreb amide 15 (2.65 g, 73% for 3 steps) as a colorless oil: IR (CHCl$_3$) 2956, 2929, 2855, 1663, 1448, 1252, 1083, 1032, 836 cm$^{-1}$; $^1$H NMR (300 MHz, CDCl$_3$) ϵ7.58 m, 6H), 7.37 (m, 9H), 5.89 (dd, J=15.6, 7.6 Hz, 1H), 5.72 (dt, J=15.6, 5.2 Hz, 1H), 4.38 (ddd, J=8.0, 5.0, 3.0 Hz, 1H), 3.74 (s, 3H), 3.70 (d, J=5.1 Hz, 2H), 3.27 (s, 3H), 2.79 (dd, J=15.1, 7.4 Hz, 1H), 2.52 (m, 2H), 1.20 (d, J=6.9 Hz, 3H), 1.02 (s, 9H), 0.22 (s, 3H), 0.16 (s, 3H); $^{13}$C NMR (75 MHz, CDCl$_3$) δ 172.6, 144.2, 133.3, 128.5, 127.7, 127.5, 126.8, 86.7, 72.4, 64.8, 61.2, 42.4, 36.3, 31.9, 25.8, 18.0, 15.7, −4.6, −5.0; LRMS (ESI) 596.2 [M+Na]$^+$, 449.2, 243.0; HRMS (ESI) calcd for C$_{35}$H$_{47}$O$_4$NSiNa 596.3172 [M+Na]$^+$, found 596.3165; [α]$^{20}_D$−14.7 (c 0.65, CHCl$_3$).

(R)-3-((2R,3S,4S)-5-(4-Methoxybenzyloxy)-3-(tert-butyldimethylsilyloxy)-2,4-dimethylpentanoyl)-4-benzyloxazolidin-2-one (20)

2,6-Lutidine (5.14 mL, 44.2 mmol) and TBSOTf (9.36 mL, 40.8 mmol) were added to a solution of 19 (15.0 g, 33.9 mmol) in CH$_2$Cl$_2$ (340 mL) stirred at 0° C. The mixture was stirred at 0° C. for 2 h and then quenched by the addition of saturated aqueous NaHCO$_3$. The phases were separated and the aqueous layer was extracted with CH$_2$Cl$_2$. The combined organic phases were washed with 0.5 M aqueous NaHSO$_4$. The organic phase was dried over Na$_2$SO$_4$, filtered and concentrated under reduced pressure. The residue was purified by flash chromatography (hexane/EtOAc 4:1) to give 20 (17.9 g, 95%) as a colorless oil: IR (film) 1781, 1696, 1513, 1383, 1248, 1209, 1110, 1042 cm$^{-1}$; $^1$H NMR (300 MHz, CDCl$_3$) ϵ7.35-7.28 (m, 7H), 6.85 (d, J=8,7 Hz, 1H), 4.49 (m, 1H), 4.38 (d, J=11.7 Hz, 1H), 4.34 (d, J=11.7 Hz), 4.03 (m, 3H), 3.81 (m, 3H), 3.77 (s, 3H), 3.54 (dd, J=9.2, 5.6 Hz, 1H), 3.22 (dd, J=13.3, 3.1 Hz, 1H), 3.17 (dd, J=9.1, 5.9 Hz, 1H), 2.72 (dd, J=13.3, 9.6 Hz, 1H), 1.97 (m, 1H), 1.25 (d, J=6.5 Hz, 3H), 1.02 (d, J=7.0 Hz, 3H), 0.91 (s, 9H), 0.07 (s, 6H); $^{13}$C NMR (75 MHz, CDCl$_3$) δ 176.4, 159.4, 153.1, 135.8, 131.1, 129.8, 129.3, 129.2, 127.6, 75.6, 72.9, 72.0, 66.1, 55.8, 55.6, 41.9, 39.3, 38.0, 26.4, 18.7, 15.3, 15.2, −3.5, −3.6; HRMS (ESI) calcd for C$_{31}$H$_{45}$NO$_6$SiNa 578.2914 [M+Na]$^+$, found 578.2923; [α]$^{20}_D$−8.1 (c 7.6, CHCl$_3$).

(2S,3R,4S)-5-(4-Methoxybenzyloxy)-3-(tert-butyldimethylsilyloxy)-2,4-dimethylpentan-1-ol (21)

Dry MeOH (1.05 mL, 26.0 mmol) then LiBH$_4$ (13 mL, 2.0 M solution in THF, 26 mmol) were added to a stirred solution of 20 (4.79 g, 8.62 mmol) in THF (75 mL) at 0° C. The resulting mixture was stirred at 0° C. for 45 min and at room temperature for 1 h. The solution was cooled to 0° C. and treated carefully with a 1.0 M aqueous NaOH (50 mL). The phases were separated and the aqueous phase was extracted with CH$_2$Cl$_2$. The combined organic phases were washed with brine, dried over MgSO$_4$, filtered and concentrated under reduced pressure. The residue was purified by flash chromatography (hexane/EtOAc 7:3) to give the alcohol 21 (2.98 g, 90%) as a colorless oil: IR (film) 3425, 1613, 1513, 1463, 1249, 1091, 1037 cm$^{-1}$; $^1$H NMR (300 MHz, CDCl$_3$) δ 7.26 (d, J=8.5 Hz, 2H), 6.88 (d, J=8.5 Hz, 2H), 4.47 (d, J=11.7 Hz, 1H), 4.40 (d, J=11.7 Hz, 1H), 3.84 (s, 3H), 3.75 (dd, J=5.7, 2.9 Hz, 1H), 3.52 (m, 3H), 3.28 (dd, J=9.1, 7.1 Hz, 1H), 2.10 (br, 1H), 2.05 (m, 1H), 1.93-1.81 (m, 1H), 0.97 (d, J=7.0 Hz, 3H), 0.90 (s, 9H), 0.87 (d, J=7.1 Hz, 3H), 0.07 (s, 3H), 0.05 (s, 3H); $^{13}$C NMR (75 MHz, CDCl$_3$) δ 159.2, 130.7, 129.3, 113.8, 74.8, 72.8, 72.7, 66.3, 55.4, 39.0, 37.7, 26.2, 18.4, 15.2, 12.0, −4.1; HRMS (ESI) calcd for C$_{18}$H$_{31}$O$_3$SiNa 323.2042 [M+Na]$^+$, found 323.2035; [α]$^{20}_D$−0.76 (c 2.9, CHCl$_3$).

(4S,5R,6S,2E)-Ethyl-7-(4-methoxybenzyloxy)-5-(tert-butyldimethylsilyloxy)-4,6-dimethylhept-2-enoate (22)

The procedure for 10 was used with the aldehyde from 21 (17.5 g, 31.6 mmol), Py.SO$_3$ (15.2 g, 95.5 mmol) and Et$_3$N (13.3 mL, 95.5 mmol), NaH (0.90 g, 39.7 mmol) and triethylphosphonoacetate (7.2 mL, 40.3 mmol) to yield 8.96 g (63% for 3 steps) of the ester 22 by flash column chromatography (EtOAc/Hexane 1:9) as a colorless oil: IR (CHCl$_3$) 2957, 2931, 2856, 1720, 1651, 1613, 1513, 1463, 1366, 1250, 1180, 1093, 1077, 837 cm$^{-1}$; $^1$H NMR (300 MHz, CDCl$_3$) ϵ7.31-7.27 (m, 2H), 7.03 (dd, J=15.8, 7.8 Hz, 1H), 6.93-6.91 (m, 2H), 5.83 (dd, J=15.8, 1.3 Hz, 1H), 4.48b-4.40 (m, 2H), 4.23 (q, J=7.1 Hz, 2H), 3.84 (s, 3H), 3.67 (m, 1H), 3.52 (m, 1H), 3.30 (dd, J=9.1, 7.2 Hz, 1H), 2.59 (m, 1H), 2.00 (m, 1H), 1.33 (t, J=7.1 Hz, 3H), 1.09 (d, J=6.8 Hz, 3H), 1.01 (d, J=7.0 Hz, 3H), 0.94 (s, 9H), 0.08 (m, 6H); $^{13}$C NMR (75 MHz, CDCl$_3$) δ 166.5, 159.0, 152.7, 130.6, 129.0, 120.4, 113.6, 76.8, 72.5, 71.8, 60.0, 55.1, 40.2, 38.0, 26.0, 18.2, 14.8, 14.3, 14.2, −4.0, −4.2; LRMS (ESI) 473.2 [M+Na]+; HRMS (ESI) calcd for C$_{25}$H$_{42}$O$_5$SiNa 473.2699 [M+Na]$^+$, found 473.2716; [α]$^{20}_D$−28.3 (c 0.41, CHCl$_3$).

(4S,5R,6S)-Ethyl-7-(4-methoxy)benzyloxy-5-(tert-butyldimethylsilyloxy)-4,6-dimethylheptanoate (23)

NiCl$_2$.6H$_2$O (2.4 g, 10.1 mmol) then portionwise NaBH$_4$ (1.50 g, 39.7 mmol) were added to a stirred solution of unsaturated ketone 22 (8.96 g, 19.9 μmol) in MeOH (66 mL), THF (20 mL) at 0° C. After 1 h, the solvent was evaporated and filtered with Celite using Et$_2$O as an eluent (60 mL). The organic phase was concentrated and the residue was purified by flash chromatography (EtOAc/hexane 1:9) to yield 8.76 g of 23 (97%) as a colorless oil: IR (CHCl$_3$) 2957, 2856, 1737, 1613, 1513, 1463, 1374, 1249, 1172, 1091, 1038, 836, 773 cm$^{-1}$; $^1$H NMR (300 MHz, CDCl$_3$) ϵ7.40-7.37 (m, 2H), 7.02-6.99 (m, 2H), 4.59-4.50 (m, 2H), 4.25 (q, J=7.1 Hz, 2H), 3.91 (s, 3H), 3.66-3.62 (m, 2H), 3.40 (dd, J=8.8, 7.3 Hz, 1H), 2.52-2.33 (m, 2H), 2.13-2.02 (m, 1H), 1.90-1.82 (m, 1H), 1.78-1.57 (m, 2H), 1.38 (t, J=7.1 Hz, 3H), 1.09 (d, J=6.9 Hz, 3H), 1.03 (s, 9H), 1.00 (d, J=6.5 Hz, 3H), 0.19 (s, 3H), 0.18 (s, 3H); $^{13}$C NMR (75 MHz, CDCl$_3$) δ 173.6, 158.9, 130.7, 129.0, 113.5, 76.8, 72.5, 60.0, 55.0, 38.0, 35.6, 32.5, 29.9, 26.0, 18.3, 14.9, 14.1, 13.7, −3.9, −4.2; LRMS (ESI) 475.3 [M+Na]$^+$; HRMS (ESI) calcd for C$_{25}$H$_{44}$O$_5$SiNa 475.2856 [M+Na]$^+$, found 473.2877; [α]$^{20}_D$−6.0 (c 1.9, CHCl$_3$).

(4S,5R,6S)-7-(4-Methoxybenzyloxy)-5-(tert-butyldimethylsilyloxy)-4,6-dimethylheptanoic acid (24)

Aqueous LiOH (1N, 193 mL, 0.19 mol) was added to a THF-H$_2$O solution of 23 (8.76 g, 19.4 mmol). The resulting solution was warmed to 60° C. and stirred with heating for 6 h. Aqueous 1N HCl was added to give a neutral pH and the mixture was extracted with CH$_2$Cl$_2$, dried over MgSO4, filtered and evaporated to yield 8.22 g of crude acid 24, which was used without further purification: $^1$H NMR (300 MHz, CDCl$_3$) δ 7.24-7.22 (m, 2H), 6.86-6.83 (m, 2H), 4.39 (m, 2H), 3.77 (s, 3H), 3.69 (q, J=7.0 Hz, 1H), 3.52 (m, 1H), 3.47 (q, J=7.0 Hz, 1H), 3.19 (t, J=8.5 Hz, 1H), 2.16 (m, 1H), 1.90 (m, 1H), 1.65-1.51 (m, 2H), 1.21 (t, J=7.0 Hz, 2H), 0.92-0.85 (m, 12H), 0.81 (d, J=6.3 Hz, 3H), 0.00 (m, 6H); $^{13}$C NMR (75 MHz, CDCl$_3$) δ 181.0, 158.9, 130.6, 129.1, 113.6, 72.5, 65.8, 58.0, 55.1, 37.8, 30.6, 26.1, 18.3, 18.1, 15.2, 14.0, −3.5, −4.1.

(R)-3-((4S,5R,6S)-7-(4-Methoxybenzyloxy)-5-(tert-butyldimethylsilyloxy)-4,6-dimethylheptanoyl)-4-benzyloxazolidin-2-one (25)

A solution of the acid 24 (8.22 g, 19.4 mmol) and Et$_3$N (5.40 mL, 38.8 mmol) in 100 mL of dry THF was cooled to −78° C. and treated dropwise with pivaloyl chloride (2.86 g, 23.3 mmol), stirred in the cold for 2 h and warmed to 0° C. prior to the addition of the oxazolidinone (3.5 g, 19.8 mmol) and LiCl (2.46 g, 58.8 mmol). This mixture was stirred overnight at room temperature and diluted with water (200 mL). The separated aqueous phase was extracted with ether (100 mL) and the combined organic layers were dried and evaporated to give a residue that was chromatographed to yield 7.91 g (70% for 2 steps) of imide 25 by flash column chromatography (EtOAc/hexane 1:4) as a colorless oil: $^1$H NMR (300 MHz, CDCl$_3$) δ 7.41-7.23 (m, 7H), 6.94-6.91 (m, 2H), 4.71 (m, 1H), 4.51 (d, J=11.6 Hz, 1H), 4.46 (d, J=11.6 Hz, 1H), 4.25-4.16 (m, 2H), 3.84 (s, 3H), 3.63-3.58 (m, 2H), 3.37-3.31 (m, 2H), 3.14-3.04 (m, 1H), 2.94-2.86 (m, 1H), 2.79 (dd, J=13.3, 9.7 Hz, 1H), 2.04 (m, 1H), 1.87-1.60 (m, 3H), 1.03 (d, J=6.9 Hz, 3H), 0.99-0.97 (m, 12H), 0.14 (s, 3H), 0.12 (s, 3H); $^{13}$C NMR (75 MHz, CDCl$_3$) δ 173.1, 158.8, 153.3, 135.2, 130.7, 129.3, 129.0, 128.8, 127.1, 113.5, 77.1, 72.5, 72.4, 65.9, 55.1, 54.9, 37.9, 37.7, 35.6, 33.7, 29.2, 26.0, 18.3, 14.9, 13.9, −3.8, −4.2.

(R)-3-((2R,4S,5R,6S)-7-(4-Methoxybenzyloxy)-5-(tert-butyldimethylsilyloxy)-2,4,6-trimethylheptanoyl)-4-benzyloxazolidin-2-one (26)

NaHMDS (1 M in THF, 14.9 mL, 14.9 mmol) was added dropwise over a 30 min period to a cooled (−78° C.) suspension of the imide 25 (7.91 g, 13.6 mmol) in THF (45 mL). After 15 min of stirring, the resulting cold solution was treated with MeI (2.53 mL, 40.8 mmol) and allowed to stir at −78° C. for 3 h before being warmed to 25° C. overnight (12 h) The reaction was quenched with H$_2$O (100 mL), and the aqueous layer was extracted with Et$_2$O (3×150 mL). The combined organic extracts were dried (MgSO$_4$), concentrated in vacuo and chromatographed (EtOAc/hexane 1:9) to provide 5.97 g (74%) of 26 as a colorless oil: $^1$H NMR (300 MHz, CDCl$_3$) δ 7.42-7.26 (m, 7H), 6.95-6.92 (m, 2H), 4.71 (m, 1H), 4.51 (m, 2H), 4.18 (m, 2H), 3.95 (m, 1H), 3.84 (s, 3H), 3.63 (dd, J=8.9, 3.8 Hz, 1H), 3.57 (dd, J=6.4, 2.7 Hz, 1H), 3.35 (t, J=8.5 Hz, 1H), 3.28 (dd, J=13.3, 3.1 Hz, 1H), 2.83 (dd, J=13.3, 9.4 Hz, 1H), 2.10-1.95 (m, 2H), 1.68 (m, 1H), 1.38 (ddd, J=14.1, 9.8, 4.9 Hz, 1H), 1.31 (d, J=6.8 Hz, 3H), 1.04 (d, J=6.9 Hz, 3H), 0.98 (s, 9H), 0.95 (d, J=6.7 Hz, 3H), 0.14 (s, 3H), 0.13 (s, 3H); $^{13}$C NMR (75 MHz, CDCl$_3$) δ 176.8, 158.8, 152.8, 135.1, 130.8, 129.3, 128.9, 128.7, 127.1, 113.5, 77.6, 72.6, 72.4, 65.7, 55.0, 38.9, 38.0, 37.6, 35.3, 33.8, 26.0, 18.8, 18.3, 14.9, 13.8, −3.8, −4.2.

(2R,4S,5R,6S)-7-(4-Methoxybenzyloxy)-5-(tert-butyldimethylsilyloxy)-2,4,6-trimethylheptan-1-ol (27)

n-BuLi (2.5 M in hexane, 17.6 mL, 44 mmol) was added to a solution of diisopropylamine (6.65 mL, 47.4 mmol) in THF (48 mL) stirred at −78° C. The solution was stirred at −78° C. for 5 min and warmed to 0° C. for 15 min. Borane-ammonia complex (90%, 1.55 g, 45.2 mmol) was added and the resulting mixture was stirred at 0° C. for 15 min, warmed to room temperature for 15 min and then cooled to 0° C. A solution of amide 26 (6.62 g, 11.3 mmol) in THF (35 mL) was added dropwise and the reaction was stirred at 0° C. for 1 h and then at room temperature for 2 h. The mixture was cooled to 0° C. and quenched carefully with saturated aqueous NH$_4$Cl. The mixture was extracted with Et$_2$O and the combined organic extracts were washed with brine, dried over MgSO$_4$, filtered and concentrated under reduced pressure. The residue was purified by flash chromatography (step gradient of 4:1 to 7:3 hexane/EtOAc) to afford the alcohol 27 (4.57 g, 96%) as a colorless oil: IR (film) 3410, 1612, 1513, 1249, 1067, 1038 cm$^{-1}$; $^1$H NMR (300 MHz, CDCl$_3$) δ 7.26 (d, J=8.6 Hz, 2H), 6.88 (d, J=8.6 Hz, 2H), 4.44 (d, J=11.7 Hz, 1H), 4.39 (d, J=11.7 Hz, 1H), 3.81 (s, 3H), 3.51 (m, 2H), 3.44 (dd, J=5.6, 3.4 Hz, 1H), 3.37 (dd, J=10.6, 6.5 Hz, 1H), 3.22 (dd, J=9.0, 7.0 Hz, 1H), 2.03-1.95 (m, 1H), 1.78-1.62 (m, 2H), 1.53 (br, 1H), 1.41 (ddd, J=13.5, 7.5, 5.8 Hz, 1H), 0.95 (d, J=6.9 Hz, 3H), 0.94 (d, J=6.7 Hz, 3H), 0.88 (s, 9H), 0.87 (d, J=6.9 Hz, 3H), 0.04 (s, 3H), 0.03 (s, 3H); $^{13}$C NMR (75 MHz, CDCl$_3$) δ 159.2, 130.9, 129.4, 113.9, 77.5, 72.8, 67.7, 55.4, 38.3, 38.0, 33.6, 33.2, 26.3, 18.6, 18.0, 15.6, 15.5, −3.5, −3.8; [α]$^{20}_D$−6.3 (c 1.7, CHCl$_3$).

(2S,3R,4S,6R)-3,7-bis(tert-Butyldimethylsilyloxy)-2,4,6-trimethylheptan-1-ol (28)

TBSCl (4.16 g, 27.6 mmol) was added to a solution of alcohol 27 (5.86 g, 13.8 mmol), imidazole (2.89 g, 41.4 mmol), and DMAP (169 mg, 1.38 mmol) in CH$_2$Cl$_2$ (55 mL). The resulting white suspension was stirred at room temperature for 2 h and the volatiles were removed under reduced pressure. The residue was dissolved in hexane and brine. The phases were separated and the organic layer was washed with brine, dried over MgSO$_4$, filtered and concentrated under reduced pressure. The residue was purified by flash chromatography (hexane/EtOAc 19:1) to afford the TBS protected alcohol (7.04 g, 95%) as a colorless oil: IR (film) 1513, 1471, 1463, 1249, 1091, 1039 cm$^{-1}$; $^1$H NMR (300 MHz, CDCl$_3$) δ 7.30 (d, J=8.6 Hz, 2H), 6.91 (d, J=8.6 Hz, 2H), 4.48 (d, J=11.9 Hz, 1H), 4.44 (d, J=11.9 Hz, 1H), 3.82 (s, 3H), 3.60-3.49 (m, 3H), 3.39-3.28 (m, 3H), 2.05-1.95 (m, 1H), 1.80-1.66 (m, 2H), 1.49-1.40 (m, 2H), 1.02 (d, J=6.9 Hz, 3H), 1.0-0.91 (m, 24 H), 0.10 (s, 3H), 0.09 (s, 3H), 0.08 (s, 3H); $^{13}$C NMR (75 MHz, CDCl$_3$) δ 159.2, 131.1, 129.3, 127.9, 77.3, 73.1, 72.8, 68.4, 55.3, 38.9, 38.5, 33.5, 26.4, 26.2, 18.7, 18.6, 18.1, 15.3, 15.1, −3.4, −3.8, −5.2; [α]$^{20}_D$−15.9 (c 0.47, CHCl$_3$). A solution of above TBS protected alcohol (5.28 g, 9.8 mmol) in CH$_2$Cl$_2$ (332 mL) and pH 7 phosphate buffer solution (33 mL) was treated with DDQ (3.34 g, 14.7 mmol). The reaction was stirred at room temperature for 1 h and was quenched with saturated aqueous NaHCO$_3$ solution. The phases were separated and the aqueous layer was extracted with CH$_2$Cl$_2$. The combined organic extracts were washed with water, dried over MgSO$_4$, filtered, and concentrated under reduced pressure. The residue was purified by flash chromatography (hexane/EtOAc 97:3 to 93:7) to afford 28 (4.01 g, 98%) as a colorless oil: IR (film) 3353, 1472, 1463, 1388, 1360, 1255, 1091, 1030, 1005 cm$^{-1}$; $^1$H NMR (300 MHz, CDCl$_3$) δ 3.60 (d, J=5.3 Hz, 2H), 3.55-3.45 (m, 2H), 3.32 (dd, J=9.7, 6.7 Hz, 1H), 2.49 (br, 1H), 1.45 (ddd, J=13.5, 7.5, 5.3 Hz, 1H), 0.95 (d, J=7.1 Hz, 3H), 0.92 (s, 9H), 0.89 (s, 9H), 0.93-0.87 (m, 6H), 0.11 (s, 3H), 0.09 (s, 3H), 0.04 (s, 6H); $^{13}$C NMR (75 MHz, CDCl$_3$) δ 80.9, 68.0, 66.2, 38.4, 37.8, 35.4, 33.5, 26.3, 26.1, 18.5, 18.3, 16.2, 15.7, −3.6, −3.9, −5.3; [α]$^{20}_D$−16.1 (c 4.4, CHCl$_3$).

(3S,4R,5S,7R)-4-(tert-Butyldimethylsilyloxy)-7-((tert-butyldimethylsilyloxy)methyl)-3,5-dimethyloct-1-yne (29)

Sulfur trioxide pyridine complex (5.44 g, 34.2 mmol) was added to a solution of 28 (4.78 g, 11.4 mmol) and triethylamine (4.77 mL, 34.2 mmol) in $CH_2Cl_2$ (23 mL) and DMSO (46 mL) at 0° C. The mixture was stirred at 0° C. for 1 h and then diluted with $Et_2O$. The organic phase was washed with cold 0.5 M aqueous $NaHSO_4$ and then with brine. The organic layer was dried over $MgSO_4$, filtered and concentrated under reduced pressure. The residue was purified by short flash chromatography (hexane/EtOAc 9:1) to afford the crude aldehyde as a golden oil which was used directly in the next reaction without further purification. Carbon tetrabromide (7.56 g, 22.8 mmol) was added to a solution of triphenylphosphine (12.3 g, 45.6 mmol) in $CH_2Cl_2$ (56 mL) at 0° C. The resulting dark-red mixture was stirred at 0° C. for 10 min. A solution of the crude aldehyde and 2,6-lutidine (2.66 mL, 22.8 mmol) in $CH_2Cl_2$ (45 mL) was added dropwise. The dark-brown mixture was stirred at 0° C. for 1 h and then quenched with a saturated aqueous $NH_4Cl$. The layers were separated and the aqueous phase was extracted with $CH_2Cl_2$. The combined organic extracts were washed with $H_2O$, dried over $MgSO_4$, filtered and concentrated under reduced pressure. The residue was purified by short flash chromatography (hexane 100%) to afford the dibromoolefin (4.76 g, 73% yield from the alcohol) as a colorless oil that was used without further purification. A solution of the dibromoolefin (4.76 g, 8.2 mmol) in THF (40 mL) stirred at −78° C. was treated with n-BuLi (1.6 M in hexane, 15.4 mL, 24.6 mmol). The solution was stirred at −78° C. for 2 h and then quenched with saturated aqueous $NH_4Cl$. The mixture was allowed to reach room temperature and was diluted with $Et_2O$. The aqueous layer was extracted with $Et_2O$. The combined organic extracts were washed with brine, dried over $MgSO_4$, filtered and concentrated under reduced pressure. The residue was purified by flash chromatography (hexane:EtOAc 97:3) to afford the pure alkyne 29 (3.26 g, 95%) as a colorless oil: IR (film) 3313, 2100, 1472, 1463, 1252, 1088, 1005 $cm^{-1}$; $^1$H NMR (300 MHz, $CDCl_3$) δ 3.53-3.48 (m, 2H), 3.33 (d, J=9.7, 6.8 Hz, 1H), 2.62 (ddddd, J=7.2, 7.2, 7.2, 5.1, 2.5 Hz, 1H), 2.03 (d, J=2.5 Hz, 1H), 1.97-1.80 (m, 1H), 1.73-1.6 (m, 1H), 1.47 (m, 1H), 1.21 (d, J=7.1 Hz, 3H), 0.99-0.91 (m, 6H), 0.95 (s, 9H), 0.93 (s, 9H), 0.13 (s, 3H), 0.11 (s, 3H), 0.08 (s, 6H); $^{13}$C NMR (75 MHz, $CDCl_3$) δ 87.9, 77.8, 70.2, 68.5, 39.2, 33.9, 33.7, 32.3, 26.4, 26.3, 18.6, 17.9, 17.5, 15.7, −3.6, −5.1; HRMS (ESI) calcd for $C_{22}H_{45}O_2Si_2Na$ 397.2958 [M+Na]$^+$, found 397.2950; $[\alpha]^{20}_D$ −8.2 (c 3.1, $CHCl_3$).

(2R,4S,5R,6S)-7-(4-Methoxybenzyloxy)-5-(tert-butyldimethylsilyloxy)-N-((1S,2S)-1-hydroxy-1-phenylpropan-2-yl)-N,2,4,6-tetramethylheptanamide (31)

$PPh_3$ (7.05 g, 26.2 mmol), imidazole (1.78 g, 26.2 mmol), diisopropylethylamine (4.6 mL, 26.2 mmol) in benzene (80 mL), diethyl ether (165 mL) and acetonitrile (33 mL) were stirred at room temperature and treated with iodine (6.65 g, 26.2 mmol). The resulting mixture was vigorously stirred until the formation of a beige suspension. A solution of the alcohol 21 (5.0 g, 13.1 mmol) in $Et_2O$ (20 mL) was added dropwise to the suspension and the resulting mixture was stirred at room temperature for 30 min. The reaction was quenched with saturated aqueous $NaHCO_3$ and diluted with $Et_2O$. The aqueous phase was extracted with $Et_2O$ and the combined organic extracts were washed with brine, dried over $MgSO_4$, filtered and concentrated under reduced pressure. The residue was triturated with hexane and the triturate was concentrated under reduced pressure. This procedure was repeated two more times to afford the iodide as a colorless oil that was used directly in the next reaction. A solution of n-BuLi in hexane (2.5 M, 21 mL, 52.4 mmol) was added to a suspension of LiCl (7.05 g, 166.4 mmol) and diisopropylamine (7.85 mL, 56.3 mmol) in THF (40 mL) at −78° C. The suspension was stirred at −78° C. for 5 min, 0° C. for 15 min and then cooled to −78° C. A solution of (S,S)-pseudoephedrine propionamide (Meyer's auxiliary, 30) (6.09 g, 27.5 mmol) in THF (70 mL) was added dropwise. The resulting mixture was stirred at −78° C. for 1 h, at 0° C. for 15 min and at room temperature for 5 min. The suspension was cooled to 0° C. and the iodide was added as a solution in THF (6 mL followed by a 6 mL rinse). The reaction mixture was stirred at room temperature for 24 h and quenched with half-saturated aqueous $NH_4Cl$. The aqueous layer was extracted with EtOAc and the combined organic extracts were dried over $Na_2SO_4$, filtered and concentrated under reduced pressure to give a residue which was purified by flash chromatography (hexane/EtOAc 1:1) to afford the amide 31 (6.69 g, 87%) as a colorless oil: IR (film) 3387, 1616, 1513, 1463, 1248, 1087, 1037 $cm^{-1}$; HRMS (ESI) calcd for $C_{34}H_{56}NO_5Si$ 586.3928, found 586.3940; $[\alpha]^{20}_D$ +23.2 (c 1.26, $CHCl_3$).

(4R,5S,10S,11R,12S,14R,2E)-5,11,15-tris(tert-Butyldimethylsilyloxy)-4,10,12,14-tetramethyl-1-(trityloxy)pentadec-2-en-8-yn-7-one (32)

Alkyne 29 (4.12 g, 10.0 mmol) was dissolved in THF (100 mL) and cooled to −78° C. n-BuLi (6.25 mL, 1.6 M hexane solution) was added slowly. After 5 min, the mixture was warmed to 0° C. and stirred for 30 min. The mixture was then cooled to −78° C. and amide 15 (6.47 g, 11.3 mmol) in THF (5 mL) was added slowly. After 5 min, the solution was warmed to 0° C. and stirred for 30 min. The reaction was quenched with saturated aqueous $NH_4Cl$ and the mixture was partitioned in a separatory funnel. The aqueous phase was extracted with $Et_2O$ (3×20 mL). The combined organic extracts were washed with brine and dried over $MgSO_4$. Filtration and concentration under reduced pressure, followed by flash chromatography on silica gel (hexane/EtOAc 19:1), afforded the ynone 32 (9.70 g, 93%) as a pale yellow oil: IR ($CHCl_3$) 2955, 2928, 2856, 2209, 1676, 1471, 1462, 1252, 1085, 836, 774 $cm^{-1}$; $^1$H NMR (300 MHz, $CDCl_3$) ε7.56 m, 6H), 7.36 (m, 9H), 5.80 (dd, J=15.6, 7.1 Hz, 1H), 5.69 (dt, J=15.7, 4.8 Hz, 1H), 4.37 (m, 1H), 3.69 (d, J=4.7 Hz, 2H), 3.61 (m, 1H), 3.58 (dd, J=9.7, 5.0 Hz, 1H), 3.43 (dd, J=9.7, 6.5 Hz, 1H), 2.87 (m, 1H), 2.73 (m, 1H), 2.46 (m, 1H), 1.88 (m, 1H), 1.76 (m, 1H), 1.59 (m, 1H), 1.31 (d, J=7.1 Hz, 3H), 1.15 (d, J=6.8 Hz, 3H), 1.05 (m, 1H), 1.00 (m, 3H), 0.194 (s, 3H), 0.190 (s, 3H), 0.17 (s, 3H), 0.15 (s, 3H), 0.14 (s, 6H); $^{13}$C NMR (75 MHz, $CDCl_3$) δ 186.1, 144.2, 132.9, 128.6, 127.7, 126.9, 96.8, 86.8, 83.1, 71.5, 68.0, 64.9, 50.0, 42.3, 38.1, 34.4, 33.2, 32.1, 26.01, 25.96, 25.85, 18.3, 18.0, 17.9, 17.2, 15.5, 15.4, −3.8, −4.1, −4.6, −4.7, −5.4; LRMS (ESI) 947.5 [M+Na]+, 562.3, 243.1; HRMS (ESI) calcd for $C_{56}H_{88}O_5Si_3Na$ 947.5837 [M+Na]$^+$, found 947.5875; $[\alpha]^{20}_D$ −12.0 (c 0.54, $CHCl_3$).

(4R,5S,7S,10S,11R,12S,14R,2E)-5,11,15-tris(tert-Butyldimethylsilyloxy)-4,10,12,14-tetramethyl-1-(trityloxy)pentadec-2-en-8-yn-7-ol (33)

Ynone 32 (5.28 g, 5.71 mmol) was taken up in i-PrOH (58 mL). The (S,S)-Noyori catalyst (0.77 g, 1.15 mmol, 20 mol %) was added in one portion and the solution was stirred overnight. The solvent was removed under vacuum, and the crude residue was purified by flash chromatography on silica gel (hexane/EtOAc 97:3), affording propargylic alcohol 33 (4.18 g, 79%) as a pale yellow oil: IR (CHCl$_3$) 3469, 2955, 2856, 1471, 1448, 1252, 1084, 836, 774 cm$^{-1}$; $^1$H NMR (300 MHz, CDCl$_3$) δ 7.55 (m, 6H), 7.36 (m, 9H), 5.71 (m, 2H), 4.59 (m, 1H), 4.03 (quint, J=3.9 Hz, 1H), 3.65 (d, J=3.9 Hz, 2H), 3.58 (dd, J=4.6, 3.2 Hz, 1H), 3.55 (dd, J=10.1, 5.1 Hz, 1H), 3.38 (dd, J=9.7, 6.8 Hz, 1H), 2.71 (m, 1H), 2.50 (m, 1H), 2.32 (d, J=5.4 Hz, 1H), 1.88 (m, 1H), 1.80 (m, 2H), 1.55 (m, 1H), 1.23 (d, J=7.1 Hz, 3H), 1.11 (d, J=6.8 Hz, 3H), 0.98 (m, 34H), 0.20 (s, 3H), 0.17 (s, 3H), 0.16 (s, 3H), 0.14 (s, 3H), 0.12 (s, 6H); $^{13}$C NMR (75 MHz, CDCl$_3$) δ 144.3, 134.0, 128.6, 127.8, 127.1, 126.9, 88.1, 86.8, 83.0, 72.6, 68.3, 65.8, 65.1, 59.5, 41.9, 40.3, 38.7, 33.5, 33.2, 32.1, 26.0, 25.9, 18.4, 18.1, 17.7, 17.4, 15.7, 15.3, 14.2, −3.9, −4.0, −4.4, −4.5, −5.3; LRMS (ESI) 949.7 [M+Na]+, 413.3, 243.1; HRMS (ESI) calcd for C$_{56}$H$_{90}$O$_5$Si$_3$Na 949.5994 [M+Na]$^+$, found 949.6018; [α]$^{20}$$_D$ −10.0 (c 1.2, CHCl$_3$).

(2E,4R,5S,7S,8Z,10S,11R,12S,14R)-5,11,15-tris(tert-Butyldimethylsilyloxy)-4,10,12,14-tetramethyl-1-(trityloxy)pentadeca-2,8-dien-7-ol (34)

A catalytic amount of Lindlar catalyst (ca. 200 mg) was added to a solution of alcohol 33 (4.18 g, 4.51 mmol) in toluene (100 mL). The flask was flushed with H$_2$ via a balloon several times, then stirred under an atmosphere of H$_2$ until starting material was consumed (usually 1 h) as indicated by TLC analysis. The mixture was filtered through a pad of Celite and concentrated under reduced pressure to afford the alkene 34 as a colorless oil (3.82 g, 91%): IR (CHCl$_3$) 3436, 2954, 2926, 2855, 1461, 1378, 1252, 1061, 836, 773 cm$^{-11}$; $^1$H NMR (300 MHz, CDCl$_3$) δ 7.56 (m, 6H), 7.34 (m, 9H), 5.73 (m, 2H), 5.60 (t, J=10.3 Hz, 1H), 5.43 (dd, J=10.9, 8.4 Hz, 1H), 4.73 (m, 1H), 3.98 (q, J=5.0 Hz, 1H), 3.68 (d, J=4.1 Hz, 1H), 3.59 (dd, J=9.7, 4.7 Hz, 1H), 3.48 (m, 1H), 3.36 (dd, J=9.0, 7.3 Hz, 1H), 2.79 (m, 1H), 2.58 (m, 1H), 2.23 (br, 1H), 1.78 (m, 1H), 1.71 (m, 1H), 1.66 (m, 2H), 1.50 (m, 1H), 1.11 (d, J=6.8 Hz, 3H), 1.07 (d, J=6.8 Hz, 3H), 1.00 (m, 34H), 0.22 (s, 3H), 0.18 (s, 3H), 0.14 (s, 6H), 0.13 (s, 6H); $^{13}$C NMR (75 MHz, CDCl$_3$) δ 144.3, 135.3, 134.6, 131.5, 128.7, 127.7, 127.0, 126.8, 86.8, 79.6, 73.0, 68.2, 65.0, 64.7, 42.0, 39.6, 38.0, 36.4, 34.9, 33.4, 26.2, 26.0, 25.9, 19.9, 18.4, 18.3, 18.1, 18.0, 15.2, 14.5, −3.4, −3.7, −4.2, −4.4, −4.5, −5.4; LRMS (ESI) 951.7 [M+Na]+, 413.3, 243.1; HRMS (ESI) calcd for C$_{56}$H$_{92}$O$_5$Si$_3$Na 951.6150 [M+Na]$^+$, found 951.6172; [α]$^{20}$$_D$ 1.0 (c 0.62, CHCl$_3$).

((2E,4R,5S,7S,8Z,10S,11R,12S,14R)-5,7,11,15-tetrakis(tert-Butyldimethylsilyloxy)-4,10,12,14-tetramethylpentadeca-2,8-dienyloxy)triphenylmethane (35)

TBSOTf (2.08 mL, 9.07 mmol) was added to a stirred solution of the alcohol 34 (3.82 g, 4.11 mmol) and 2,6-lutidine (1.14 mL, 9.85 mmol) in CH$_2$Cl$_2$ (14 mL) at 0° C. The reaction mixture was stirred for 1 h at 0° C. The reaction mixture was quenched by the addition of H$_2$O (25 mL). The reaction mixture was extracted with CH$_2$Cl$_2$ which was dried over MgSO$_4$, filtered and the solvent was evaporated under reduced pressure. The residue was purified by short column chromatography (hexane/EtOAc 19:1) to obtain 35 (4.27 g, 99%) as a colorless oil: IR (CHCl$_3$) 2956, 2929, 2856, 1471, 1462, 1449, 1255, 1089, 1005, 836, 773, 705 cm$^{-1}$; $^1$H NMR (300 MHz, CDCl$_3$) δ 7.60 (m, 6H), 7.39 (m, 9H), 5.77 (m, 2H), 5.56 (t, J=10.8 Hz, 1H), 5.42 (dd, J=11.0, 8.2 Hz, 1H), 4.69 (m, 1H), 4.07 (m, 1H), 3.71 (d, J=3.8 Hz, 2H), 3.64 (dd, J=9.8, 4.8 Hz, 1H), 3.53 (m, 1H), 3.40 (dd, J=9.6, 7.5 Hz, 1H), 2.74 (m, 1H), 2.55 (m, 1H), 1.89 (m, 3H), 1.59 (m, 3H), 1.12 (d, J=6.2 Hz, 6H), 1.04 (m, 42H), 0.26 (s, 3H), 0.24 (s, 3H), 0.19 (s, 6H), 0.18 (s, 3H), 0.17 (s, 6H), 0.16 (s, 3H); $^{13}$C NMR (75 MHz, CDCl$_3$) δ 144.4, 134.5, 132.9, 132.6, 128.7, 127.7, 126.8, 86.8, 79.9, 72.3, 68.3, 66.5, 65.1, 64.1, 42.4, 41.6, 37.9, 36.0, 35.3, 33.6, 26.3, 26.02, 25.97, 25.7, 19.4, 18.5, 18.4, 18.20, 18.15, 18.1, 15.5, 13.3, −2.9, −3.5, −3.7, −4.1, −4.2, −4.3, −5.3; LRMS (ESI) 1065.9 [M+Na]$^+$, 413.3, 359.3, 328.3, 243.1; HRMS (ESI) calcd for C$_{62}$H$_{106}$O$_5$Si$_4$Na 1065.7015 [M+Na]$^+$, found 1065.7026; [α]$^{20}$$_D$ −10.4 (c 0.53, CHCl$_3$).

(2R,4S,5R,6S,7Z,9S,11S,12R,13E)-5,9,11-tris(tert-Butyldimethylsilyloxy)-2,4,6,12-tetramethyl-15-(trityloxy)pentadeca-7,13-dien-1-ol (36)

HF-pyridine in pyridine (40 mL, prepared by slow addition of 12 mL pyridine to 3 mL HF-pyridine complex followed by dilution with 25 mL THF) was slowly added to a solution of TBS ether 35 (4.27 g, 4.10 mmol) in THF (5 mL) at 0° C. The mixture was stirred for 21 h at 0° C. and quenched with saturated aqueous NaHCO$_3$ (100 mL). The aqueous layer was separated and extracted with Et$_2$O (3×50 mL). The combined organic layers were washed with saturated aqueous CuSO$_4$ (3×50 mL), dried over MgSO$_4$, filtered and concentrated. Flash column chromatography (EtOAc/hexane 1:4) afforded 2.55 g (67%) of the alcohol 36 as a colorless oil: IR (CHCl$_3$) 3350, 2956, 2928, 2856, 1471, 1448, 1254, 1086, 836, 773, 705 cm$^{-1}$; $^1$H NMR (300 MHz, CDCl$_3$) δ 7.52 (m, 6H), 7.32 (m, 9H), 5.68 (m, 2H), 5.50 (t, J=10.6 Hz, 1H), 5.35 (dd, J=10.9, 8.5 Hz, 1H), 4.61 (t, J=8.5 Hz, 1H), 4.00 (t, J=8.1 Hz, 1H), 3.62 (d, J=3.2 Hz, 2H), 3.58 (dd, J=10.6, 4.3 Hz, 1H), 3.45 (m, 1H), 3.36 (dd, J=9.9, 7.3 Hz, 1H), 2.66 (m, 1H), 2.48 (m, 1H), 1.70 (m, 3H), 1.49 (m, 3H), 1.04 (d, J=6.6 Hz, 6H), 0.97 (s, 18H), 0.93 (m, 6H), 0.87 (s, 9H), 0.18 (s, 3H), 0.16 (s, 3H), 0.11 (s, 6H), 0.10 (s, 3H), 0.08 (s, 3H); $^{13}$C NMR (75 MHz, CDCl$_3$) δ 144.3, 134.4, 133.0, 132.1, 128.7, 127.7, 126.8, 86.7, 79.8, 72.3, 67.7, 66.5, 65.1, 42.4, 41.5, 37.3, 35.7, 35.5, 33.3, 26.2, 26.0, 25.9, 19.6, 18.4, 18.14, 18.06, 17.98, 15.7, 13.2, −2.9, −3.6, −3.7, −4.1, −4.2, −4.3; LRMS (ESI) 951.8 [M+Na]$^+$, 771.6, 328.3; HRMS (ESI) calcd for C$_{56}$H$_{92}$O$_5$Si$_3$Na 951.6150 [M+Na]$^+$, found 951.6162; [α]$^{20}$$_D$ −12.0 (c 0.71, CHCl$_3$).

(2R,4E,6R,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-6,8,10,16-tetramethyl-19-(trityloxy)nonadeca-4,11,17-trien-3-one (39)

The alcohol 36 (2.55 g, 2.75 μmol) in CH$_2$Cl$_2$ (30 mL) was treated with Dess-Martin periodinane (1.74 g, 4.10 μmol). After 1 h, the mixture was quenched with saturated aqueous NaHCO$_3$ (30 mL) and Na$_2$S$_2$O$_3$ (30 mL). The aqueous layer was extracted with Et$_2$O (2×30 mL) and the combined extracts were dried over anhydrous MgSO$_4$. Filtration and concentration followed by short flash column chromatography (hexane/EtOAc 4:1) provided the crude aldehyde as a colorless oil, which was used without further purification. A mixture of ketophosphonate 38 (1.06 g, 2.75 mmol) and Ba(OH)$_2$ (0.38 g, activated by heating to 100° C. for 1-2 h before use) in THF (40 mL) was stirred at room temperature for 30 min. A solution of the above aldehyde in wet THF (4×1 mL washings, 40:1 THF/H$_2$O) was then added. After stirring for 12 h, the reaction mixture was diluted with Et$_2$O (30 mL) and washed with saturated aqueous NaHCO$_3$ (50 mL) and brine (50 mL). The organic solution was dried (MgSO$_4$), filtered and the solvent was evaporated in vacuo. The residue was chromatographed (hexane/EtOAc 9:1) to yield 39 (2.60 g, 80% for 2 steps) as a colorless oil: IR (CHCl$_3$) 2956, 2928, 2855, 1688, 1618, 1518, 1471, 1461, 1338, 1251, 1080, 1038, 836, 773 cm$^{-1}$; $^1$H NMR (300 MHz, CDCl$_3$) δ 7.50 (m, 6H), 7.40 (m, 2H), 7.30 (m, 9H), 6.89 (m, 2H), 6.73 (dd, J=15.6, 8.5 Hz, 1H), 6.29 (d, J=15.6 Hz, 1H), 5.66 (m, 2H), 5.46 (t, J=10.4 Hz, 1H), 5.46 (s, 1H), 5.31 (dd, J=11.0, 8.4 Hz, 1H), 4.58 (t, J=8.1 Hz, 1H), 4.12 (dd, J=11.3, 4.6 Hz, 1H), 3.96 (m, 1H), 3.92 (dd, J=10.0, 4.2 Hz, 1H), 3.80 (s, 3H), 3.60 (d, J=2.8 Hz, 2H), 3.56 (m, 1H), 3.39 (t, J=3.3 Hz, 1H), 2.93 (m, 1H), 2.64 (m, 1H), 2.45 (m, 1H), 2.37 (m, 1H), 2.01 (m, 1H), 1.61 (m, 1H), 1.54 (m, 2H), 1.50 (m, 1H), 1.44 (m, 1H), 1.27 (d, J=7.0 Hz, 3H), 1.06 (d, J=6.6 Hz, 3H), 1.02 (d, J=6.5 Hz, 3H), 0.99 (d, J=6.6 Hz, 3H), 0.95 (s, 9H), 0.94 (s, 9H), 0.88 (d, J=6.6 Hz, 3H), 0.84 (s, 9H), 0.79 (d, J=6.7 Hz, 3H), 0.15 (s, 3H), 0.14 (s, 3H), 0.07 (s, 3H), 0.06 (s, 3H), 0.05 (s, 3H), 0.03 (s, 3H); $^{13}$C NMR (75 MHz, CDCl$_3$) δ 200.7, 159.8, 152.3, 144.3, 134.3, 132.8, 132.1, 131.0, 128.6, 127.7, 127.1, 126.8, 126.6, 113.4, 100.8, 86.7, 82.7, 80.0, 72.8, 72.1, 66.4, 65.0, 55.2, 47.1, 42.4, 41.4, 39.3, 35.8, 34.7, 34.6, 32.2, 26.1, 25.92, 25.86, 20.8, 19.7, 18.3, 18.1, 18.0, 15.0, 13.0, 12.4, 10.8, −2.9, −3.7, −3.8, −4.18, −4.25, −4.35; LRMS (ESI) 1209.6 [M+Na]$^+$, 828.4, 715.3, 449.2, 243.1; HRMS (ESI) calcd for C$_{72}$H$_{110}$O$_8$Si$_3$Na 1209.7406 [M+Na]$^+$, found 1209.7474; [α]$^{20}_D$ −6.7 (c 0.11, CHCl$_3$).

(2R,6S,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-6,8,10,16-tetramethyl-19-(trityloxy)nonadeca-11,17-dien-3-one (40)

NiCl$_2$.6H$_2$O (0.26 g, 1.09 mmol) then portionwise NaBH$_4$ (0.17 g, 4.49 mmol) were added to a stirred solution of unsaturated ketone 39 (2.60 g, 2.19 μmol) in 80 mL of 3:2 MeOH/THF at 0° C. After 1 h, the reaction mixture was evaporated and filtered through Celite using Et$_2$O (30 mL) as an eluent. The organic phase was concentrated and the residue was purified by flash chromatography (EtOAc/hexane 1:9) to yield 1.98 g of 40 (76%) as a colorless oil: IR (CHCl$_3$) 2955, 2927, 2855, 1711, 1614, 1518, 1461, 1251, 1076, 835, 773 cm$^{-1}$; $^1$H NMR (300 MHz, CDCl$_3$) δ 7.46 (m, 6H), 7.27 (m, 1H), 6.85 (m, 2H), 5.60 (m, 2H), 5.43 (s, 1H), 5.40 (m, 1H), 5.27 (m, 1H), 4.52 (m, 1H), 4.11 (dd, J=11.1, 4.7 Hz, 1H), 3.91 (m, 2H), 3.78 (s, 3H), 3.55 (m 2H), 3.50 (m, 1H), 3.35 (m, 1H), 2.67 (m, 1H), 2.58 (m, 1H), 2.51 (m, 1H), 2.41 (m, 1H), 2.01 (m, 1H), 1.68 (m, 3H), 1.41 (m, 5H), 1.23 (d, J=7.1 Hz, 3H), 0.96 (d, J=6.7 Hz, 3H), 0.90 (s, 9H), 0.89 (s, 9H), 0.88 (m, 1H), 0.87 (m, 3H), 0.80 (s, 9H), 0.78 (m, 6H), 0.10 (s, 3H), 0.08 (s, 3H), 0.04 (s, 3H), 0.03 (s, 6H), 0.01 (s, 3H); $^{13}$C NMR (75 MHz, CDCl$_3$) δ 211.9, 159.8, 144.5, 144.3, 134.4, 132.9, 132.4, 130.9, 128.6, 127.9, 127.8, 127.7, 127.1, 126.8, 113.4, 100.8, 86.7, 83.1, 79.9, 72.8, 72.2, 66.4, 65.1, 55.1, 48.3, 42.3, 41.2, 38.1, 35.7, 35.0, 31.2, 29.8, 29.7, 26.2, 25.92, 25.87, 20.2, 19.4, 18.4, 18.1, 18.0, 15.2, 13.2, 12.1, 9.6, −3.0, −3.5, −3.7, −4.2, −4.28, −4.34; LRMS (ESI) 1211.9 (30 mL), 1031.8, 870.4, 684.3, 366.4, 243.1; HRMS (ESI) calcd for C$_{72}$H$_{112}$O$_8$Si$_3$Na 1211.7563 (30 mL), found 1211.7616; [α]$^{20}_D$ +1.6 (c 0.50, CHCl$_3$).

(2S,3R,6S,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-6,8,10,16-tetramethyl-19-(trityloxy)nonadeca-7,11-dien-3ol (41β)

NaBH$_4$ (0.095 g, 2.51 mmol) was added to a solution of ketone 40 (1.98 g, 1.67 mmol) in MeOH (28 mL) at 0° C. After stirring for 2 h at 0° C., the reaction mixture was evaporated and water (30 mL) was added. The reaction mixture was extracted with ether (2×40 mL) and washed with brine (50 mL), dried over MgSO$_4$ and concentrated in vacuo. The residue was purified by flash chromatography (EtOAc/hexane 1:9) to yield major product the title compound 41β (1.39 g, 70%, less polar) and minor product 41α (0.58 g, 28%, more polar) as a colorless oil. 41β: IR (CHCl$_3$) 3398, 2954, 2926, 2854, 1517, 1460, 1251, 1072, 835 cm$^{-1}$; $^1$H NMR (300 MHz, CDCl$_3$) δ 7.50 (m, 6H), 7.39 (m, 2H), 7.33 (m, 9H), 6.89 (m, 2H), 5.66 (m, 2H), 5.54 (s, 1H), 5.46 (m, 1H), 5.32 (m, 1H), 4.58 (m, 1H), 4.14 (dd, J=11.3, 4.6 Hz, 1H), 3.95 (m, 1H), 3.87 (m, 1H), 3.80 (s, 3H), 3.72 (d, J=9.8 Hz, 1H), 3.61 (m, 2H), 3.55 (m, 1H), 3.41 (m, 1H), 3.24 (br, 1H), 2.64 (m, 1H), 2.46 (m, 1H), 2.16 (m, 1H), 1.82 (m, 1H), 1.71 (m, 2H), 1.53 (m, 5H), 1.35 (m, 2H), 1.06 (d, J=7.2 Hz, 3H), 1.01 (d, J=6.6 Hz, 3H), 0.95 (s, 9H), 0.93 (s, 9H), 0.90 (m, 9H), 0.85 (s, 9H), 0.78 (d, J=6.6 Hz, 3H), 0.14 (m, 6H), 0.09 (m, 12H); $^{13}$C NMR (75 MHz, CDCl$_3$) δ 160.0, 144.5, 144.3, 134.4, 132.9, 132.4, 130.7, 128.7, 127.9, 127.8, 127.7, 127.6, 127.2, 127.1, 126.8, 113.6, 101.2, 89.1, 86.7, 80.0, 76.9, 73.1, 72.2, 66.5, 65.1, 42.3, 41.5, 41.4, 37.0, 36.7, 35.1, 32.5, 32.1, 30.4, 30.3, 26.2, 25.93, 25.87, 20.4, 19.4, 18.4, 18.1, 18.0, 15.4, 13.2, 11.8, 5.4, −3.0, −3.5, −3.7, −4.2, −4.27, −4.33; LRMS (ESI) 1213.7 [M+Na]$^+$, 1033.6, 570.9, 364.3, 243.1; HRMS (ESI) calcd for C$_{72}$H$_{114}$O$_8$Si$_3$Na 1213.7719 [M+Na]$^+$, found 1213.7861; [α]$^{20}_D$ +6.5 (c 0.31, CHCl$_3$). 41α: IR (CHCl$_3$) 3540, 2956, 2929, 2855, 1615, 1518, 1461, 1383, 1251, 1074, 835, 773 cm$^{-1}$; $^1$H NMR (300 MHz, CDCl$_3$) δ 7.61 (m, 6H), 7.51 (m, 2H), 7.44-7.32 (m, 9H), 7.00 (m, 2H), 5.77 (m, 2H), 5.61 (s, 1H), 5.55 (m, 1H), 5.45 (m, 1H), 4.71 (m, 1H), 4.24 (dd, J=11.1, 4.5 Hz, 1H), 4.07 (m, 1H), 4.01 (m, 1H), 3.88 (s, 3H), 3.73-3.60 (m, 4H), 3.54 (m, 1H), 2.76 (m, 1H), 2.56 (m, 1H), 2.49 (m, 1H), 2.24 (m, 1H), 1.94-1.78 (m, 4H), 1.72-1.46 (m, 6H), 1.42-1.31 (m, 2H), 1.22 (d, J=7.0 Hz, 3H), 1.13 (d, J=5.9 Hz, 3H), 1.06 (s, 18H), 1.03 (m, 6H), 0.96 (s, 9H), 0.86 (d, J=6.6 Hz, 3H), 0.27-0.18 (m, 18H); $^{13}$C NMR (75 MHz, CDCl$_3$) δ 159.9, 144.4, 144.3, 134.3, 132.9, 132.4, 131.0, 128.6, 127.6, 127.2, 126.8, 113.5, 101.0, 86.7, 82.8, 79.8, 74.8, 73.2, 72.2, 66.4, 65.0, 55.1, 42.3, 41.5, 37.8, 35.9, 34.9, 33.2, 32.4, 30.3, 30.2, 26.2, 25.92, 25.87, 20.4, 19.3, 18.4, 18.1, 18.0, 15.3, 13.2, 11.8, 11.0, −3.0, −3.4, −3.7, −3.9, −4.2, −4.28, −4.34; LRMS (ESI) 1213.9 [M+Na]$^+$, 987.7, 659.3, 437.2, 243.1; HRMS (ESI) calcd for C$_{72}$H$_{114}$O$_8$Si$_3$Na 1213.7719 [M+Na]$^+$, found 1213.7760; [α]$^{20}_D$ +2.3 (c 0.75, CHCl$_3$).

(4S,5S)-4-((2R,3R,6S,8S,9R,10S,11Z,13S,15S,16R, 17E)-3,9,13,15-tetrakis(tert-Butyldimethylsilyloxy)-6,8,10,16-tetramethyl-19-(trityloxy)nonadeca-11,17-dien-2-yl)-2-(4-methoxyphenyl)-5-methyl-1,3-dioxane (42)

TBSOTf (0.40 mL, 1.74 mmol) was added to a stirred solution of alcohol 41β (1.39 g, 1.17 mmol) and 2,6-lutidine (0.27 mL, 2.33 mmol) in $CH_2Cl_2$ (23 mL) at 0° C. After stirring for 1 h at ambient temperature, the reaction mixture was quenched by the addition of water (50 mL) and extracted by $CH_2Cl_2$. After drying over $MgSO_4$, followed by the evaporation of the solution under reduced pressure, the residue was purified by short column chromatography (hexane/EtOAc 9:1) to yield 42 (1.51 g, 99%) as a colorless oil: IR ($CHCl_3$) 2955, 2928, 2855, 1615, 1517, 1461, 1250, 1074, 1039, 835, 773 $cm^{-1}$; $^1H$ NMR (300 MHz, $CDCl_3$) δ 7.59 (m, 6H), 7.52 (m, 2H), 7.41 (m, 9H), 7.01 (m, 2H), 5.74 (m, 2H), 5.57 (s, 1H), 5.50 (m, 1H), 5.43 (m, 1H), 4.67 (m, 1H), 4.25 (dd, J=11.3, 4.6 Hz, 1H), 4.04 (m, 1H), 3.94 (s, 3H), 3.78 (m, 1H), 3.70 (m, 3H), 3.49 (m, 1H), 3.16 (m, 1H), 2.72 (m 1H), 2.54 (m, 1H), 2.18 (m, 1H), 2.01 (m, 1H), 1.82 (m, 3H), 1.54 (m, 6H), 1.14 (d, J=6.9 Hz, 3H), 1.11 (d, J=6.8 Hz, 3H), 1.10 (d, J=6.5 Hz, 3H), 1.05 (s, 9H), 1.03 (s, 9H), 1.02 (s, 12H), 0.98 (d, J=6.3 Hz, 3H), 0.94 (s, 9H), 0.87 (d, J=6.7 Hz, 3H), 0.24 (s, 3H), 0.22 (s, 3H), 0.17 (m, 18H); $^{13}C$ NMR (75 MHz, $CDCl_3$) δ 159.6, 144.5, 144.3, 134.4, 133.1, 132.6, 131.5, 128.6, 127.7, 127.6, 127.1, 126.8, 126.7, 113.3, 100.4, 86.7, 81.9, 79.8, 74.9, 73.3, 72.2, 66.4, 65.1, 55.1, 42.3, 41.5, 38.8, 35.9, 34.5, 31.3, 31.2, 30.8, 30.7, 26.3, 25.99, 25.97, 25.91, 22.6, 20.3, 19.2, 18.5, 18.10, 18.05, 15.1, 14.1, 13.1, 12.4, 10.6, −3.0, −3.2, −3.6, −4.2, −4.25, −4.30; LRMS (ESI) 1327.8 [M+Na]$^+$, 1147.7, 833.3, 631.3, 429.2, 364.3, 301.1; HRMS (ESI) calcd for $C_{78}H_{128}O_8Si_4Na$ 1327.8584 [M+Na]$^+$, found 1327.8693; $[α]^{20}_D$+7.6 (c 0.17, $CHCl_3$).

(2S,3S,4R,5R,8S,10S,11R,12S,13Z,15S,17S,18R, 19E)-3-(4-Methoxybenzyloxy)-5,11,15,17-tetrakis (tert-butyldimethylsilyloxy)-2,4,8,10,12,18-hexamethyl-21-(trityloxy)henicosa-13,19-dien-1-ol (43)

DIBAL-H (1.0 M in hexane, 11.7 mL, 11.7 mmol) was added dropwise to a stirred solution of TBS protected acetal 42 (1.53 g, 1.17 mmol) in anhydrous $CH_2Cl_2$ (2.3 mL) under an atmosphere of $N_2$ at 0° C. After stirring for additional 30 min at 0° C. the reaction mixture was quenched by the careful addition of aqueous saturated aqueous potassium sodium tartrate (30 mL). The resulting mixture was stirred for 3 h at room temperature. The organic layer was separated, and the aqueous layer was extracted by $CH_2Cl_2$ (20 mL). The combined organic layers were washed with brine and dried over $MgSO_4$ followed by the evaporation of the organic solution under reduced pressure. The residue was purified by column chromatography (EtOAc/hexane 1:9) to obtain pure 43 (1.35 g, 88%) as a colorless oil: IR ($CHCl_3$) 3464, 2956, 2929, 2856, 1613, 1514, 1471, 1252, 1087, 836, 773 $cm^{-1}$; $^1H$ NMR (300 MHz, $CDCl_3$) δ 7.46 (m, 6H), 7.28 (m, 1H), 6.88 (m, 2H), 5.61 (m, 2H), 5.39 (m, 1H), 5.28 (m, 1H), 4.57 (m, 1H), 4.53 (s, 2H), 3.92 (m, 2H), 3.83 (m, 1H), 3.80 (s, 3H), 3.60 (m, 2H), 3.56 (m, 2H), 3.46 (dd, J=6.2, 4.5 Hz, 1H), 3.37 (m, 1H), 3.03 (m, 1H), 2.86 (m 1H), 2.59 (m, 1H), 2.41 (m, 1H), 1.93 (m, 1H), 1.88 (m, 1H), 1.66 (m, 3H), 1.35 (m, 5H), 1.11 (d, J=7.0 Hz, 3H), 1.01 (d, J=6.8 Hz, 3H), 0.97 (d, J=6.8 Hz, 3H), 0.92 (m, 27H), 0.85 (m, 10H), 0.81 (s, 9H), 0.11 (s, 3H), 0.09 (s, 3H), 0.07 (s, 3H), 0.06 (s, 6H), 0.05 (s, 6H), 0.04 (s, 3H); $^{13}C$ NMR (75 MHz, $CDCl_3$) δ 159.2, 144.4, 144.3, 134.3, 133.0, 132.4, 130.5, 129.1, 128.6, 127.6, 126.7, 113.8, 86.7, 85.4, 79.8, 75.1, 73.8, 72.2, 66.4, 65.0, 55.0, 42.3, 41.6, 41.5, 40.5, 37.1, 35.8, 34.8, 32.0, 31.9, 30.7, 26.2, 25.94, 25.86, 20.3, 19.2, 18.4, 18.1, 18.0, 15.6, 15.2, 13.2, 10.0, −3.0, −3.4, −3.8, −3.9, −4.2, −4.28, −4.34, −4.4; LRMS (ESI) 1329.8 [M+Na]$^+$, 707.3, 413.2, 243.1; HRMS (ESI) calcd for $C_{78}H_{130}O_8Si_4Na$ 1329.8741 [M+Na]$^+$, found 1329.8779; $[α]^{20}_D$−8.9 (c 0.46, $CHCl_3$).

((2E,4R,5S,7S,8Z,10S,11R,12S,14S,17R,18R,19S,20S, 21Z)-19-(4-Methoxybenzyloxy)-5,7,11,17-tetrakis(tert-butyldimethylsilyloxy)-4,10,12,14,18,20-hexamethyltetracosa-2,8,21,23-tetraenyloxy)triphenylmethane (44)

The alcohol 43 (1.35 g, 1.03 μmol) in $CH_2Cl_2$ (20 mL) was treated with Dess-Martin periodinane (0.66 g, 1.56 μmol). After 1 h, the mixture was quenched with saturated aqueous $NaHCO_3$ (20 mL) and $Na_2S_2O_3$ (20 mL). The aqueous layer was extracted with $Et_2O$ (2×20 mL) and the combined extracts were dried over anhydrous $MgSO_4$. Filtration and concentration followed by short flash column chromatography (hexane/EtOAc 9:1) provided the crude aldehyde as a colorless oil, which was used without further purification. $CrCl_2$ (1.06 g, 8.62 mmol) was added to a stirred solution of the crude aldehyde and 1-bromoallyl trimethylsilane (1.28 g, 5.20 mmol) in anhydrous THF (26 mL) under an atmosphere of $N_2$ at room temperature and the mixture was stirred for additional 14 h at ambient temperature. The reaction mixture was diluted with hexane followed by filtration through celite. After the evaporation of the solvent under reduced pressure, the residue was purified by short silica gel column chromatography using EtOAc/hexane (1:9) as eluent. The foregoing product in THF (40 mL) was cooled to 0° C. and NaH (95% w/w, 0.52 g, 20.6 mmol) was added in one portion. The ice bath was removed after 15 min and the mixture was stirred for 2 h at ambient temperature. The reaction mixture was cooled to 0° C., quenched with $H_2O$ (5 mL) and extracted with $Et_2O$ (2×20 mL). The combined organic layers were washed with brine, dried over $MgSO_4$, filtered and the solvent removed under reduced pressure. The residue was purified by column chromatography (hexane/EtOAc 49:1) to obtain 44 (1.17 g, 85% for 3 steps) as a colorless oil: IR ($CHCl_3$) 2956, 2928, 2856, 1614, 1514, 1471, 1462, 1249, 1088, 836, 772 $cm^{-1}$; $^1H$ NMR (300 MHz, $CDCl_3$) δ 7.46 (m, 6H), 7.27 (m, 1H), 6.86 (m, 2H), 6.58 (ddd, J=17.0, 10.6, 10.5 Hz, 1H), 6.00 (t, J=11.0 Hz, 1H), 5.60 (m, 3H), 5.31 (m, 2H), 5.17 (d, J=16.9 Hz, 1H), 5.09 (d, J=10.4 Hz, 1H), 4.51 (m, 3H), 3.90 (m, 2H), 3.80 (s, 3H), 3.61 (m, 1H), 3.56 (d, J=3.7 Hz, 1H), 3.33 (m, 2H), 3.00 (m, 1H), 2.56 (m, 1H), 2.40 (m, 1H), 2.21 (m, 1H), 1.63 (m, 3H), 1.38 (m, 2H), 1.27 (m, 3H), 1.21 (m, 2H), 1.10 (d, J=6.7 Hz, 3H), 0.96 (m, 3H), 0.93 (s, 9H), 0.91 (s, 9H), 0.89 (s, 9H), 0.86 (m, 6H), 0.82 (m, 6H), 0.80 (s, 9H), 0.79 (m, 3H), 0.08 (m, 6H), 0.05 (m, 6H), 0.04 (m, 6H), 0.01 (m, 6H); $^{13}C$ NMR (75 MHz, $CDCl_3$) δ 159.0, 146.2, 144.5, 144.4, 134.6, 134.5, 133.1, 132.7, 132.3, 131.4, 129.0, 128.9, 128.7, 127.7, 126.8, 117.1, 113.7, 86.8, 84.4, 79.9, 75.0, 72.9, 72.3, 66.5, 65.1, 55.2, 42.4, 41.9, 41.6, 40.6, 36.0, 35.6, 35.3, 34.5, 32.5, 31.7, 30.5, 26.3, 26.0, 25.9, 20.2, 19.2, 18.8, 18.5, 18.2, 18.1, 15.1, 13.3, 9.3, −2.9, −3.0, −3.3, −3.6, −3.7, −4.2, −4.3, −4.4; LRMS (ESI) 1351.8 [M+Na]$^+$, 1171.7, 1043.7, 889.6, 707.3, 536.1, 453.3, 413.2, 359.2; HRMS (ESI) calcd for $C_{81}H_{132}O_7Si_4Na$ 1351.8948 [M+Na]$^+$, found 1351.9012; $[α]^{20}_D$+1.1 (c 1.7, $CHCl_3$).

(2E,4R,5S,7S,8Z,10S,11R,12S,14S,17R,18R,19S, 20S,21Z)-19-(4-Methoxybenzyloxy)-5,7,11,17-tetrakis(tert-butyldimethylsilyloxy)-4,10,12,14,18,20-hexamethyltetracosa-2,8,21,23-tetraen-1-ol (45)

ZnBr$_2$ (0.41 g) in 1.2 mL of 5:1 CH$_2$Cl$_2$/MeOH was added dropwise for 30 min to a stirred solution of trityl compound 44 (0.24 g, 0.18 µmol) in 1.4 mL of 6:1 CH$_2$Cl$_2$/MeOH at 0° C. After 4 h, the reaction mixture was quenched with saturated aqueous NaHCO$_3$ (20 mL) and extracted with Et$_2$O (2×10 mL). The organic phase were separated, dried with MgSO$_4$, filtered and concentrated. The residue was purified by flash chromatography (EtOAc/hexane 1:9) to yield 45 (0.15 g, 77%) as a colorless oil: IR (CHCl$_3$) 3432, 2956, 2856, 1613, 1514, 1471, 1462, 1360, 1250, 1082, 835, 773 cm$^{-1}$; $^1$H NMR (300 MHz, CDCl$_3$) δ 7.29 (m, 2H), 6.88 (m, 2H), 6.58 (ddd, J=16.9, 10.6, 10.6 Hz, 1H), 6.00 (t, J=11.0 Hz, 1H), 5.63 (m, 3H), 5.38 (t, J=11.0 Hz, 1H), 5.27 (dd, J=11.2, 8.3 Hz, 1H), 5.17 (d, J=16.8 Hz, 1H), 5.10 (d, J=10.3 Hz, 1H), 4.53 (m, 3H), 4.08 (d, J=4.4 Hz, 2H), 3.90 (m, 1H), 3.81 (s, 3H), 3.62 (m, 1H), 3.33 (m, 2H), 2.99 (ddd, J=10.0, 6.8, 3.2 Hz, 1H), 2.57 (m, 1H), 2.39 (m, 1H), 1.63 (m, 3H), 1.42 (m, 3H), 1.28 (m, 5H), 1.11 (d, J=6.8 Hz, 3H), 0.97 (d, J=6.8 Hz, 3H), 0.96 (d, J=6.9 Hz, 3H), 0.93 (s, 9H), 0.91 (s, 18H), 0.89 (m, 3H), 0.88 (s, 9H), 0.81 (d, J=6.7 Hz, 3H), 0.80 (d, J=6.2 Hz, 3H), 0.10 (s, 3H), 0.09 (s, 3H), 0.08 (s, 6H), 0.06 (s, 3H), 0.05 (s, 6H), 0.03 (s, 3H); $^{13}$C NMR (75 MHz, CDCl$_3$) δ 159.0, 146.9, 135.2, 134.6, 133.0, 132.7, 132.3, 131.4, 129.2, 129.1, 128.9, 127.93, 127.90, 127.2, 84.4, 80.0, 75.0, 72.8, 72.2, 66.6, 63.9, 55.2, 42.4, 41.8, 41.7, 40.5, 35.9, 35.2, 34.6, 32.6, 31.6, 30.5, 26.3, 25.99, 25.96, 25.93, 20.2, 19.2, 18.8, 18.5, 18.2, 18.1, 15.1, 13.2, 9.2, −3.0, −3.3, −3.6, −3.7, −4.2, −4.4, −4.5; LRMS (ESI) 1109.8 [M+Na]$^+$, 823.6, 691.5, 559.4; HRMS (ESI) calcd for C$_{62}$H$_{118}$O$_7$Si$_4$Na 1109.7852 [M+Na]$^+$, found 1109.7897; [α]$^{20}_D$+1.6 (c 0.94, CHCl$_3$).

(2Z,4E,6R,7S,9S,10Z,12S,13R,14S,16S,19R,20R, 21S,22S,23Z)-Methyl-21-(4-methoxy-benzyloxy)-7, 9,13,19-tetrakis(tert-butyldimethylsilyloxy)-6,12,14, 16,20,22-hexamethylhexacosa-2,4,10,23,25-pentaenoate (46)

The alcohol 45 (127 mg, 0.117 µmol) in CH$_2$Cl$_2$ (4 mL) was treated with Dess-Martin periodinane (75 mg, 0.18 µmol). After 1 h, the mixture was quenched with saturated aqueous NaHCO$_3$ (5 mL) and Na$_2$S$_2$O$_3$ (5 mL). The aqueous layer was extracted with Et$_2$O (2×10 mL) and the combined extracts were dried over anhydrous MgSO$_4$. Filtration and concentration followed by short flash column chromatography (hexane/EtOAc 9:1) provided the crude aldehyde as a colorless oil, which was used for the next reaction without further purification. KHMDS (0.28 mL, 0.14 µmol, 0.5M solution in toluene) was added dropwise to a stirred solution of bis(2,2,2-trifluoroethyl)-(methoxycarbonylmethyl) phosphate (0.030 mL, 0.14 µmol) and 18-crown-6 (0.15 g, 0.57 mmol) in THF (2.3 mL) at −78° C. Thereafter, the aldehyde in THF (0.5 mL) was added and the solution was stirred for 4 h at −78° C. The reaction mixture was quenched by addition of a saturated aqueous NH$_4$Cl (5 mL) and diluted with Et$_2$O (20 mL). The organic phase was washed with brine (30 mL), dried with MgSO$_4$, filtered and concentrated. The residue was purified by flash chromatography (EtOAc/hexane 1:19) yielding (E,Z)-doubly unsaturated ester 46 (0.12 g, 86% for 2 steps) as a colorless oil: IR (CHCl$_3$) 2955, 2929, 2856, 1722, 1514, 1471, 1462, 1250, 1174, 1085, 1041, 836, 773 cm$^{-1}$; $^1$H NMR (300 MHz, CDCl$_3$) δ 7.39 (dd, J=15.4, 11.3 Hz, 1H), 7.29 (m, 2H), 6.88 (m, 2H), 6.59 (ddd, J=16.9, 10.8, 10.6 Hz, 1H), 6.55 (t, J=11.3 Hz, 1H), 6.01 (t, J=11.0 Hz, 1H), 6.00 (dd, J=15.7, 7.0 Hz, 1H), 5.60 (d, J=11.3 Hz, 1H), 5.59 (t, J=10.4 Hz, 1H), 5.39 (t, J=10.4 Hz, 1H), 5.27 (dd, J=11.0, 8.3 Hz, 1H), 5.18 (d, J=16.8 Hz, 1H), 5.11 (d, J=10.3 Hz, 1H), 4.54 (m, 3H), 3.96 (m, 1H), 3.81 (s, 3H), 3.74 (s, 3H), 3.63 (m, 1H), 3.34 (m, 2H), 3.00 (m, 1H), 2.57 (m, 2H), 1.64 (m, 3H), 1.55 (m, 1H), 1.46 (t, J=5.9 Hz, 2H), 1.26 (m, 5H), 1.11 (d, J=6.8 Hz, 3H), 1.05 (d, J=6.7 Hz, 3H), 0.97 (d, J=6.9 Hz, 3H), 0.96 (d, J=7.1 Hz, 3H), 0.94 (s, 9H), 0.92 (s, 9H), 0.91 (s, 9H), 0.87 (s, 9H), 0.83 (d, J=6.4 Hz, 3H), 0.82 (d, J=6.0 Hz, 3H), 0.13 (s, 3H), 0.11 (s, 3H), 0.10 (s, 3H), 0.09 (s, 3H), 0.06 (s, 3H), 0.05 (s, 6H), 0.04 (s, 3H); $^{13}$C NMR (75 MHz, CDCl$_3$) δ 166.8, 159.0, 147.3, 145.5, 134.6, 132.9, 132.8, 132.4, 131.4, 129.0, 128.9, 126.9, 117.1, 115.5, 113.7, 84.4, 80.0, 75.0, 72.9, 72.1, 66.5, 55.2, 50.9, 43.5, 42.5, 41.8, 40.5, 36.0, 35.3, 34.5, 32.5, 31.6, 30.5, 26.3, 25.99, 25.96, 25.91, 20.2, 19.2, 18.8, 18.5, 18.2, 18.1, 15.0, 13.4, 9.2, −3.0, −3.2, −3.3, −3.6, −3.7, −4.1, −4.4, −4.5; LRMS (ESI) 1163.9 [M+Na]$^+$, 1009.8, 684.3, 610.2, 513.4; HRMS (ESI) calcd for C$_{65}$H$_{120}$O$_8$Si$_4$Na 1163.7958 [M+Na]$^+$, found 1163.7985; [α]$^{20}_D$−9.3 (c 1.2, CHCl$_3$).

(2Z,4E,6R,7S,9S,10Z,12S,13R,14S,16S,19R,20R, 21S,22S,23Z)-Methyl-7,9,13,19-tetrakis(tert-butyldimethylsilyloxy)-21-hydroxy-6,12,14,16,20,22-hexamethylhexacosa-2,4,10,23,25-pentaenoate (47)

The ester 46 (81 mg, 71 µmol) was added to CH$_2$Cl$_2$ (2 mL) and H$_2$O (0.1 mL) and DDQ (20 mg, 88 µmol) was added at 0° C. After 1 h of stirring at 0° C., the reaction mixture was quenched by adding saturated aqueous NaHCO$_3$ (5 mL). The organic phase was washed with saturated aqueous NaHCO$_3$ (3×10 mL) and brine, dried over MgSO$_4$, filtered and concentrated. Purification by flash column chromatography (EtOAc/hexane 1:9) furnished 47 (64 mg, 88%) as a colorless oil: IR (CHCl$_3$) 3541, 2956, 2929, 2856, 1722, 1639, 1471, 1462, 1377, 1360, 1254, 1175, 1086, 836, 773 cm$^{-1}$; $^1$H NMR (300 MHz, CDCl$_3$) δ 7.34 (dd, J=15.4, 11.2 Hz, 1H), 6.61 (ddd, J=16.8, 10.7, 10.6 Hz, 1H), 6.51 (t, J=11.3 Hz, 1H), 6.06 (t, J=11.0 Hz, 1H), 5.96 (dd, J=15.4, 7.1 Hz, 1H), 5.56 (d, J=11.3 Hz, 1H), 5.39 (t, J=10.1 Hz, 1H), 5.38 (t, J=10.3 Hz, 1H), 5.22 (dd, J=11.0, 8.5 Hz, 1H), 5.17 (d, J=18.7 Hz, 1H), 5.09 (d, J=10.1 Hz, 1H), 4.50 (m, 1H), 3.92 (m, 1H), 3.71 (m, 1H), 3.70 (s, 3H), 3.44 (m, 1H), 3.32 (m, 1H), 2.74 (m, 1H), 2.52 (m, 2H), 2.31 (br, 1H), 1.61 (m, 4H), 1.39 (m, 2H), 1.31 (m, 2H), 1.26 (m, 3H), 1.00 (d, J=6.7 Hz, 3H), 0.93 (d, J=6.9 Hz, 3H), 0.92 (d, J=6.7 Hz, 3H), 0.86 (m, 27H), 0.84 (m, 6H), 0.82 (m, 12H), 0.05 (s, 9H), 0.02 (s, 3H), 0.01 (s, 6H), 0.00 (s, 6H); $^{13}$C NMR (75 MHz, CDCl$_3$) δ 166.8, 147.3, 145.5, 135.3, 132.7, 132.6, 132.3, 129.9, 126.8, 117.7, 115.5, 79.9, 77.6, 76.6, 72.1, 66.5, 51.0, 43.5, 42.4, 41.5, 37.7, 36.1, 35.7, 35.0, 32.1, 31.5, 30.6, 26.3, 25.9, 25.9, 20.4, 19.4, 18.5, 18.1, 17.9, 17.7, 15.3, 13.3, 6.9, −3.0, −3.4, −3.7, −4.1, −4.2, −4.4; LRMS (ESI) 1043.6 [M+Na]$^+$, 889.6, 757.5, 625.4, 393.3; HRMS (ESI) calcd for C$_{57}$H$_{112}$O$_7$Si$_4$Na 1043.7383 [M+Na]$^+$, found 1043.7417; [α]$^{20}_D$−25.3 (c 0.61, CHCl$_3$).

(2Z,4E,6R,7S,9S,10Z,12S,13R,14S,16S,19R,20R, 21S,22S,23Z)-7,9,13,19-tetrakis(tert-Butyldimethylsilyloxy)-21-hydroxy-6,12,14,16,20,22-hexamethylhexacosa-2,4,10,23,25-pentaenoic acid (48)

A stirred solution of alcohol 47 (25 mg, 24 µmol) in 3.4 mL of 12:5 EtOH/THF was treated with 1N aqueous KOH (0.24 mL) and the mixture was refluxed gently for 3 h. The ethanolic solution was concentrated and then diluted with Et$_2$O (4 mL). After the solution was acidified to pH3 with 1N aqueous HCl, the organic phase was separated and aqueous phase was extracted with Et$_2$O (2×5 mL). The combined organic phase was dried with MgSO$_4$, filtered, concentrated and the residue was used without further purification: IR (CHCl$_3$) 2956, 2929, 2857, 1693, 1635, 1600, 1471, 1462, 1254, 1088, 836, 773 cm$^{-1}$; $^1$H NMR (300 MHz, CDCl$_3$) δ 7.33 (dd, J=15.2, 11.3 Hz, 1H), 6.61 (t, J=11.4 Hz, 1H), 6.61 (m, 1H), 6.07 (t, J=11.0 Hz, 1H), 6.02 (dd, J=15.8, 7.2 Hz, 1H), 5.58 (d, J=11.3 Hz, 1H), 5.39 (m, 2H), 5.23 (dd, J=11.0, 8.2 Hz, 1H), 5.18 (d, J=16.8 Hz, 1H), 5.09 (d, J=10.2 Hz, 1H), 4.50 (m, 1H), 3.92 (m, 1H), 3.73 (m, 1H), 3.46 (dd, J=7.3, 2.6 Hz, 1H), 3.34 (m, 1H), 2.78 (m, 1H), 2.54 (m, 2H), 1.66 (m, 4H), 1.42 (m, 4H), 1.24 (m, 3H), 1.01 (d, J=6.8 Hz, 3H), 0.95 (d, J=6.7 Hz, 3H), 0.94 (d, J=6.7 Hz, 3H), 0.88 (m, 30H), 0.84 (m, 15H), 0.09 (s, 3H), 0.07 (s, 3H), 0.06 (s, 6H), 0.02 (s, 6H), 0.01 (s, 6H); $^{13}$C NMR (75 MHz, CDCl$_3$) δ 171.2, 148.2, 147.3, 135.2, 133.2, 132.7, 132.3, 123.0, 127.0, 117.7, 115.2, 79.9, 77.6, 76.5, 72.1, 66.4, 43.5, 42.6, 41.6, 37.8, 36.0, 35.8, 34.9, 32.1, 31.5, 30.6, 26.2, 25.93, 25.87, 20.3, 19.4, 18.4, 18.10, 18.05, 17.7, 15.3, 13.6, 6.9 −3.0, −3.4, −3.7, −4.1, −4.19, −4.24, −4.4; LRMS (ESI) 1029.7 [M+Na]$^+$, 875.6, 743.6, 611.4, 593.4, 393.3; HRMS (ESI) calcd for C$_{56}$H$_{110}$O$_7$Si$_4$Na 1029.7226 [M+Na]$^+$, found 1029.7274; [α]$^{20}_D$−25.7 (c 0.54, CHCl$_3$).

(8S,10S,14R,20R)-tetrakis(tert-Butyldimethylsilyloxy)-(7R,13S,15S,17S,21S)-pentamethyl-(22S)-((1S)-methylpenta-2,4-dienyl)oxacyclodocosa-3,5,11-trien-2-one (49)

A solution of 48 in THF (2 mL) was treated at 0° C. with Et$_3$N (0.020 mL, 147 μmol) and 2,4,6-trichlorobenzoyl chloride (0.019 mL, 122 μmol). The reaction mixture was stirred at 0° C. for 30 min and then added to 4-DMAP (12 mL, 0.02 M solution in toluene) at 25° C. After stirring for 12 h, the reaction mixture was concentrated, Et$_2$O (10 mL) was added and the crude was washed with 1N HCl (2×5 mL) and dried over MgSO$_4$. Purification by flash column chromatography (EtOAc/hexane 1:49) furnished the macrolactone (19 mg, 78% for 2 steps) as a colorless oil: IR (CHCl$_3$) 2955, 2929, 2857, 1716, 1642, 1474, 1225, 1043, 836, 773 cm$^{-1}$; $^1$H NMR (300 MHz, CDCl$_3$) δ 6.98 (dd, J=14.8, 11.3 Hz, 1H), 6.55 (m, 1H), 6.52 (t, J=11.2 Hz, 1H), 6.04 (t, J=10.5 Hz, 1H), 6.01 (dd, J=15.4, 6.4 Hz, 1H), 5.59 (d, J=11.2 Hz, 1H), 5.58 (m, 1H), 5.38 (t, J=10.6 Hz, 1H), 5.33 (dd, J=11.3, 8.1 Hz, 1H), 5.19 (d, J=16.6 Hz, 1H), 5.11 (d, J=10.5 Hz, 1H), 5.06 (dd, J=7.6, 3.7 Hz, 1H), 4.52 (m, 1H), 4.01 (m, 1H), 3.63 (m, 1H), 3.19 (d, J=6.2 Hz, 1H), 3.03 (m, 1H), 2.58 (m, 1H), 2.52 (m, 2H), 1.81 (m, 4H), 1.45 (m, 3H), 1.25 (m, 3H), 1.09 (m, 3H), 1.02 (d, J=6.8 Hz, 3H), 1.01 (d, J=7.0 Hz, 3H), 0.97 (d, J=6.6 Hz, 3H), 0.95 (d, J=6.4 Hz, 3H), 0.91 (s, 9H), 0.89 (s, 9H), 0.88 (s, 9H), 0.86 (s, 9H), 0.77 (d, J=6.4 Hz, 3H), 0.75 (d, J=6.5 Hz, 3H), 0.10 (s, 3H), 0.07 (s, 3H), 0.06 (s, 3H), 0.04 (s, 3H), 0.033 (s, 6H), 0.026 (s, 6H); $^{13}$C NMR (75 MHz, CDCl$_3$) δ 166.5, 143.1, 141.8, 133.9, 132.7, 131.8, 130.2, 129.8, 128.0, 118.4, 118.1, 81.0, 78.0, 70.4, 66.5, 62.5, 43.1, 42.3, 41.4, 39.1, 35.2, 34.8, 34.5, 31.6, 30.3, 29.7, 29.3, 26.2, 26.0, 25.94, 25.85, 20.2, 19.7, 18.5, 18.24, 18.16, 18.08, 16.2, 14.0, 9.9, −2.7, −3.4, −3.5, −3.8, −3.9, −4.2, −4.3; [α]$^{20}_D$−18.1 (c 0.24, CHCl$_3$).

(8S,10S,14R,20R)-Tetrahydroxy-(7R,13S,15S,17S,21S)-pentamethyl-(22S)-((1S)-methylpenta-2,4-dienyl)oxacyclodocosa-3,5,11-trien-2-one (Dictyostatin, 1)

A stirred solution of macrolactone 49 (18 mg, 18 μmol) in THF (3 mL) at 0° C. was treated with 3N HCl (10 mL, prepared by adding 2.5 mL of conc. HCl to 7.5 mL MeOH). After 24 h at room temperature, the reaction mixture was diluted with EtOAc (4 mL) and H$_2$O (4 mL). The organic phase was saved and the aqueous phase was extracted with EtOAc (2×4 mL). The combined organic phase was washed with saturated aqueous NaHCO$_3$ (10 mL), dried with MgSO$_4$, filtered and concentrated. The residue was purified by flash chromatography (EtOAc/hexane 3:2) to yield 1 as a white solid (5.3 mg, 55%): IR (CHCl$_3$) 3406, 2960, 2924, 2872, 1693, 1637, 1461, 1378, 1274, 1181, 1069, 998, 738 cm$^{-1}$; $^1$H NMR (600 MHz, CD$_3$OD) δ 7.21 (dd, J=15.6, 11.1 Hz, 1H), 6.71 (ddd, J=16.9, 11.0, 10.6 Hz, 1H), 6.65 (dd, J=11.3, 11.3 Hz, 1H), 6.17 (dd, J=15.6, 6.7 Hz, 1H), 6.06 (dd, J=11.1, 11.1 Hz, 1H), 5.56 (d, J=11.3 Hz, 1H), 5.55 (dd, J=11.0, 11.0 Hz, 1H), 5.41 (dd, J=11.1, 8.8 Hz, 1H), 5.34 (dd, J=10.7, 10.6 Hz, 1H), 5.25 (dd, J=16.8, 1.8 Hz, 1H), 5.15 (d, J=10.1 Hz, 1H), 5.14 (dd, J=7.0, 5.0 Hz, 1H), 4.65 (ddd, J=9.5, 9.5, 3.3 Hz, 1H), 4.05 (ddd, J=10.6, 3.7, 2.8 Hz, 1H), 3.17 (ddq, J=10.1, 6.8, 6.6 Hz, 1H), 3.10 (dd, J=8.1, 2.9 Hz, 1H), 2.76 (m, 1H), 2.60 (m, 1H), 1.89 (m, 1H), 1.84 (dddd, J=12.9, 11.2, 6.4, 5.4 Hz, 1H), 1.60 (m, 1H), 1.58 (m, 1H), 1.54 (m, 1H), 1.50 (ddd, J=14.1, 10.7, 3.5 Hz, 1H), 1.42 (ddd, J=14.0, 10.0, 2.7 Hz, 1H), 1.25 (ddd, J=13.7, 10.6, 3.6 Hz, 1H), 1.15 (d, J=6.9 Hz, 3H), 1.12 (d, J=7.0 Hz, 3H), 1.10 (m, 1H), 1.07 (d, J=6.9 Hz, 3H), 1.01 (d, J=6.8 Hz, 3H), 0.95 (d, J=6.5 Hz, 3H), 0.93 (d, J=6.5 Hz, 3H). 0.90 (m, 1H), 0.71 (dddd, J=12.9, 12.8, 8.7, 4.9 Hz, 1H); $^{13}$C NMR (150 MHz, CD$_3$OD) δ 168.10, 146.42, 144.90, 134.87, 134.54, 133.43, 131.32, 131.27, 128.60, 118.58, 118.04, 80.37, 78.64, 73.73, 70.41, 65.53, 44.07, 42.28, 40.84, 40.65, 35.84, 35.78, 35.33, 32.75, 32.51, 31.23, 21.81, 19.36, 18.08, 15.98, 13.80, 10.41; LRMS (ESI) 555.3 [M+Na]$^+$, 449.2, 243.1; HRMS (ESI) calcd for C$_{32}$H$_{52}$O$_6$Na 555.3662 [M+Na]$^+$, found 555.3665; [α]$^{20}_D$−22.6 (c 0.27, MeOH).

(2Z,4E,6R,7S,9S,10Z,12S,13R,14S,16S,19R,20S,21S,22S,23Z)-Methyl-7,9,13,19,21-penta-hydroxy-6,12,14,16,20,22-hexamethylhexacosa-2,4,10,23,25-pentaenoate (50)

3N HCl (10 mL, prepared by adding 2.5 mL of conc. HCl to 7.5 mL MeOH) was added to a stirred solution of the macrolactonization precursor 48 (23 mg, 23 μmol) in THF (3 mL) at 0° C. After 24 h at room temperature, the reaction mixture was diluted with EtOAc (4 mL) and H$_2$O (4 mL). The organic phase was retained and aqueous phase was extracted with EtOAc (2×4 mL). The combined organic phase was washed with saturated aqueous NaHCO$_3$ (10 mL), dried with MgSO$_4$, filtered and concentrated. The residue was purified by flash chromatography (EtOAc/hexane 3:2) to yield the product 50 (4.5 mg, 36%) as a colorless oil: IR (CHCl$_3$) 3399, 2917, 2849, 1713, 1635, 1600, 1461, 1439, 1197, 1178, 970, 757 cm$^{-1}$; $^1$H NMR (600 MHz, CD$_3$OD) δ 7.36 (dd, J=15.3, 11.2 Hz, 1H), 6.67 (ddd, J=16.9, 11.1, 10.6 Hz, 1H), 6.63 (dd, J=11.3, 11.3 Hz, 1H), 6.14 (dd, J=15.4, 8.3 Hz, 1H), 6.03 (dd, J=11.0, 1.0 Hz, 1H), 5.59 (dd, J=11.4 Hz, 1H), 5.43 (dd, J=10.7, 10.7 Hz, 1H), 5.42 (dd, J=10.8, 9.2 Hz, 1H), 5.32 (dd, J=10.4, 10.4 Hz, 1H), 5.17 (dd, J=16.8, 2.0 Hz, 1H), 5.08 (d, J=10.2 Hz, 1H), 4.61 (ddd, J=12.9, 8.5, 4.6 Hz, 1H), 3.80 (ddd, J=8.9, 4.4, 4.4 Hz, 1H), 3.69 (s, 3H), 3.63 (m, 1H), 3.46 (t, J=5.8 Hz, 1H), 3.13 (dd, J=8.0, 3.2 Hz, 1H), 2.93 (m, 1H), 2.71 (m, 1H), 2.38 (m, 1H), 1.73 (m, 1H), 1.56-1.53 (m, 3H), 1.52-1.46 (m, 2H), 1.44-1.36 (m, 3H), 1.09 (d, J=6.9 Hz, 3H), 0.98 (d, J=6.8 Hz, 3H), 0.96 (d, J=6.6 Hz, 3H), 0.95 (m, 2H), 0.94 (d, J=6.9 Hz, 3H), 0.87 (d, J=6.6 Hz, 3H), 0.86 (d, J=6.8 Hz, 3H); $^{13}C$ NMR (150 MHz, $CD_3OD$) δ 168.4, 148.5, 146.9, 135.7, 135.4, 133.85, 133.82, 130.6, 128.2, 117.7, 116.2, 79.2, 78.5, 74.8, 72.4, 65.8, 51.5, 45.1, 43.2, 43.0, 41.0, 37.2, 36.5, 34.0, 33.3, 33.1, 31.0, 20.7, 18.6, 18.4, 16.7, 13.8, 7.8; LRMS (ESI) 587.5 [M+Na]$^+$, 559.2, 485.2, 413.3, 355.1, 212.1; HRMS (ESI) calcd for $C_{33}H_{56}O_7Na$ 587.3924 [M+Na]$^+$, found 587.3953; $[α]^{20}_D$+8.7 (c 0.30, $CDCl_3$).

(4S,5S)-4-((2R,3S,6S,8S,9R,10S,11Z,13S,15S,16R, 17E)-3,9,13,15-tetrakis(tert-Butyldimethylsilyloxy)-6,8,10,16-tetramethyl-19-trityloxynonadeca-11,17-dien-2-yl)-2-(4-methoxyphenyl)-5-methyl-1,3-dioxane (51)

The procedure for 42 was used with 41α (0.58 g, 0.49 mmol), TBSOTf (0.17 mL, 0.74 mmol) and 2,6-lutidine (0.11 mL, 0.97 mmol) to yield 0.62 g (97%) of the product by flash column chromatography (EtOAc/hexane 1:9) as a colorless oil: IR ($CHCl_3$) 2955, 2856, 1615, 1518, 1462, 1385, 1251, 1082, 835, 773, 705 cm$^{-1}$; $^1H$ NMR (300 MHz, $CDCl_3$) δ 7.55 (m, 6H), 7.49 (m, 2H), 7.40-7.27 (m, 9H), 6.96 (m, 2H), 5.72 (m, 2H), 5.53 (m, 1H), 5.52 (s, 1H), 5.38 (m, 1H), 4.65 (m, 1H), 4.19 (dd, J=11.0, 4.4 Hz, 1H), 4.03 (m, 1H), 3.95 (d, J=8.7 Hz, 1H), 3.86 (m, 1H), 3.84 (s, 3H), 3.66 (d, J=3.7 Hz, 2H), 3.56 (t, J=11.1 Hz, 1H), 3.50 (m 1H), 2.71 (m, 1H), 2.52 (m, 1H), 2.12 (m, 1H), 1.90-1.79 (m, 2H), 1.75-1.68 (m, 3H), 1.61-1.37 (m, 6H), 1.08 (d, J=6.6 Hz, 6H), 1.02-0.91 (m, 36H), 0.81 (d, J=6.5 Hz, 3H), 0.22-0.13 (m, 24H); $^{13}C$ NMR (75 MHz, $CDCl_3$) δ 159.7, 144.5, 134.4, 132.8, 132.6, 131.7, 128.7, 127.7, 127.3, 126.8, 113.4, 100.9, 86.7, 81.4, 80.1, 73.4, 72.3, 71.5, 66.5, 65.1, 55.1, 42.4, 41.5, 37.9, 35.5, 35.1, 31.3, 30.8, 30.2, 27.9, 26.3, 26.01, 25.99, 25.93, 25.7, 20.6, 19.5, 18.4, 18.11, 18.07, 15.4, 13.4, 13.3, 12.2, 9.2, -2.9, -3.5, -3.7, -3.9, -4.1, -4.2, -4.3, -4.9; LRMS (ESI) 1328.0 [M+Na]$^+$, 782.5, 659.3, 437.2; HRMS (ESI) calcd for $C_{78}H_{128}O_8Si_4Na$ 1327.8584 [M+Na]$^+$, found 1327.8624; $[α]^{20}_D$+6.1 (c 0.93, $CHCl_3$).

(2S,3S,4R,5S,8S,10S,11R,12S,13Z,15S,17S,18R, 19E)-3-(4-Methoxybenzyloxy))-5,11,15,17-tetrakis (tert-butyldimethylsilyloxy)-2,4,8,10,12,18-hexamethyl-21-trityloxyhenicosa-13,19-dien-1-ol (52)

The procedure for 43 was used with 51 (0.62 g, 0.47 mmol) and DIBAL-H (1.0 M in hexane, 4.7 mL, 4.7 mmol) to yield 0.54 g (87%) of the product after flash column chromatography (EtOAc/hexane 1:9) as a colorless oil: IR ($CHCl_3$) 3479, 2955, 2928, 2856, 1613, 1514, 1471, 1251, 1084, 835, 773 cm$^{-1}$; $^1H$ NMR (300 MHz, $CDCl_3$) δ 7.56-7.52 (m, 6H), 7.38-7.33 (m, 9H), 7.30 (m, 2H), 6.94 (m, 2H), 5.72 (m, 2H), 5.52 (m, 1H), 5.38 (m, 1H), 4.67 (d, J=10.3 Hz, 1H), 4.65 (m, 1H), 4.60 (d, J=10.4 Hz, 1H), 4.03 (m, 1H), 3.83 (m, 3H), 3.70 (m, 3H), 3.65 (d, J=3.7 Hz, 2H), 3.49 (m, 1H), 3.02 (m, 1H), 2.71 (m 1H), 2.52 (m, 1H), 1.91 (m, 2H), 1.80-1.64 (m, 3H), 1.60-1.34 (m, 8H), 1.09-0.90 (m, 54H), 0.21-0.12 (m, 24H); $^{13}C$ NMR (75 MHz, $CDCl_3$) δ 159.2, 144.5, 144.3, 134.4, 132.8, 132.4, 130.6, 129.0, 128.6, 127.7, 126.8, 113.8, 86.7, 84.7, 80.0, 74.8, 74.5, 72.2, 66.5, 66.2, 65.1, 55.1, 42.3, 41.4, 38.7, 35.5, 35.2, 35.0, 31.5, 30.9, 30.7, 29.8, 26.2, 26.00, 25.95, 25.89, 20.5, 19.4, 18.4, 18.13, 18.08, 1,8.02, 15.4, 15.2, 13.2, 10.4, -3.0, -3.6, -3.7,
-3.8, -4.18, -4.24, -4.3, -4.4; LRMS (ESI) 1329.8 [M+Na]$^+$, 782.4, 413.2; HRMS (ESI) calcd for $C_{78}H_{130}O_8Si_4Na$ 1329.8741 [M+Na]$^+$, found 1329.8782; $[α]^{20}_{D-6.8}$ (c 0.66, $CHCl_3$).

((2E,4R,5S,7S,8Z,10S,11R,12S,14S,17S,18R,19S, 20S,21Z)-19-(4-Methoxybenzyloxy)-5,7,11,17-tetrakis(tert-butyldimethylsilyloxy)-4,10,12,14,18,20-hexamethyltetracosa-2, 8,21,23-tetraenyloxy) triphenylmethane (53)

The procedure for 44 was used with 52 (0.54 g, 0.41 μmol) and Dess-Martin periodinane (0.26 g, 0.61 μmol), 1-bromoallyl trimethylsilane (0.50 g, 2.60 mmol) and $CrCl_2$ (0.42 g, 3.42 mmol), NaH (95% w/w, 0.21 g, 8.31 mmol) to yield 0.46 g (83% for 3 steps) of the product by flash column chromatography (EtOAc/hexane 1:9) as a colorless oil: IR ($CHCl_3$) 2955, 2928, 2856, 1613, 1514, 1462, 1250, 1069, 835, 773, 705 cm$^{-1}$; $^1H$ NMR (300 MHz, $CDCl_3$) δ 7.58-7.54 (m, 6H), 7.40-7.35 (m, 9H), 7.33-7.30 (m, 2H), 6.96-6.93 (m, 2H), 6.69 (ddd, J=16.8, 10.6, 10.5 Hz, 1H), 6.12 (t, J=11.0 Hz, 1H), 5.80-5.67 (m, 3H), 5.52 (t, J=10.4 Hz, 1H), 5.40 (m, 1H), 5.28 (d, J=16.8 Hz, 1H), 5.19 (d, J=10.2 Hz, 1H), 4.63 (m, 3H), 4.03 (m, 1H), 3.85 (s, 3H), 3.67 (m, 2H), 3.51 (m, 1H), 3.38 (m, 1H), 2.96 (m, 1H), 2.72 (m, 1H), 2.53 (m, 1H), 1.93-1.74 (m, 2H), 1.66-1.37 (m, 7H), 1.31-1.23 (m, 3H), 1.18 (d, J=6.8 Hz, 3H), 1.09 (m, 6H), 1.03-0.92 (m, 45H), 0.23-0.10 (m, 24H); $^{13}C$ NMR (75 MHz, $CDCl_3$) δ 159.1, 144.5, 144.4, 134.7, 134.5, 133.0, 132.6, 132.2, 131.4, 129.1, 129.0, 128.7, 127.7, 126.8, 117.5, 113.7, 86.8, 84.6, 79.9, 74.7, 73.6, 72.3, 66.5, 65.1, 55.2, 42.5, 42.4, 41.6, 36.1, 35.9, 34.8, 32.0, 30.8, 29.8, 26.3, 26.02, 25.96, 20.5, 19.3, 18.6, 18.5, 18.2, 18.1, 15.4, 13.3, 10.5, -2.9, -3.4, -3.7, -4.1, -4.2, -4.3; LRMS (ESI) 1352.0 [M+Na]$^+$, 782.5, 647.6, 619.6, 437.2; HRMS (ESI) calcd for $C_{81}H_{132}O_7Si_4Na$ 1351.8948 [M+Na]$^+$, found 1351.8987; $[α]^{20}_D$-8.6 (c 1.6, $CHCl_3$).

(2E,4R,5S,7S,8Z,10S,11R,12S,14S,17S,18R,19S, 20S,21Z)-19-(4-Methoxybenzyloxy)-5,7,11,17-tetrakis(tert-butyldimethylsilyloxy)-4,10,12,14,18,20-hexamethyltetracosa-2,8,21,23-tetraen-1-ol (54)

The procedure for 45 was used with 53 (0.46 g, 0.35 μmol) and $ZnBr_2$ (0.41 g in 5.8 mL of 24:5 $CH_2Cl_2$MeOH) to yield 0.21 g (55%) of the product after flash column chromatography (EtOAc/hexane 1:9) as a colorless oil: IR ($CHCl_3$) 3410, 2956, 2929, 2856, 1614, 1514, 1471, 1462, 1251, 1075, 836, 773 cm$^{-1}$; $^1H$ NMR (300 MHz, $CDCl_3$) δ 7.28 (m, 2H), 6.87 (m, 2H), 6.60 (ddd, J=16.8, 10.7, 10.6 Hz, 1H), 6.03 (t, J=11.0 Hz, 1H), 5.67-5.57 (m, 3H), 5.41 (m, 1H), 5.29 (m, 1H), 5.20 (d, J=18.2 Hz, 1H), 5.11 (d, J=10.2 Hz, 1H), 4.56 (m, 3H), 4.10 (d, J=4.4 Hz, 1H), 3.93 (m, 1H), 3.81 (s, 3H), 3.66-3.57 (m, 2H), 3.40 (dd, J=4.6, 2.6 Hz, 1H), 3.28 (dd, J=6.2, 4.2 Hz, 1H), 2.85 (m, 1H), 2.60 (m, 1H), 2.39 (m, 1H), 1.79 (m, 1H), 1.70 (m, 1H), 1.66-1.56 (m, 2H), 1.51-1.19 (m, 8H), 1.09 (d, J=6.8 Hz, 3H), 0.98 (d, J=6.8 Hz, 3H), 0.97 (d, J=6.9 Hz, 3H), 0.92-0.86 (m, 45H), 0.11-0.00 (m, 24H); $^{13}C$ NMR (75 MHz, $CDCl_3$) δ 159.0, 135.2, 134.7, 132.8, 132.7, 132.3, 131.4, 129.2, 129.1, 129.0, 117.4, 113.7, 84.6, 80.0, 74.7, 73.6, 72.2, 66.6, 63.9, 63.3, 55.3, 42.4, 41.7, 36.1, 35.8, 34.8, 31.9, 30.8, 29.8, 26.3, 26.0, 25.9, 20.5, 19.4, 19.3, 18.6, 18.5, 18.1, 15.3, 13.3, 10.5, -3.0, -3.4, -3.7, -4.2, -4.3, -4.5; LRMS (ESI) 1109.9 [M+Na]$^+$, 947.8, 782.5, 689.2, 615.2, 541.1, 413.3, 306.3; HRMS (ESI) calcd for $C_{62}H_{118}O_7Si_4Na$ 1109.7856 [M+Na]$^+$, found 1109.7902; $[α]^{20}_D$-12.0 (c 1.7, $CHCl_3$).

(2Z,4E,6R,7S,9S,10Z,12S,13R,14S,16S,19S,20R, 21S,22S,23Z)-Methyl-21-(4-methoxybenzyloxy)-7, 9,13,19-tetrakis(tert-butyldimethylsilyloxy)-6,12, 14,16,20,22-hexamethylhexacosa-2,4,10,23,25-pentaenoate (55)

The procedure for 46 was used with 54 (117 mg, 0.108 μmol) and Dess-Martin periodinane (69 mg, 0.16 μmol), bis(2,2,2-trifluoroethyl)-(methoxycarbonylmethyl) phosphate (0.027 mL, 0.13 μmol), 18-crown-6 (0.14 g, 0.53 mmol) and KHMDS (0.26 mL, 0.13 μmol, 0.5 M solution in toluene) to yield 69 mg (56% for 2 steps) of the product after flash column chromatography (EtOAc/hexane 1:19) as a colorless oil: IR (CHCl$_3$) 2956, 2929, 2856, 1722, 1640, 1514, 1471, 1462, 1250, 1174, 1080, 836, 773 cm$^{-1}$; $^1$H NMR (300 MHz, CDCl$_3$) δ 7.44 (dd, J=15.2, 11.3 Hz, 1H), 7.28 (m, 2H), 6.88 (m, 2H), 6.60 (ddd, J=16.7, 10.6, 10.5 Hz, 1H), 6.56 (t, J=11.3 Hz, 1H), 6.04 (dd, J=15.5, 7.1 Hz, 1H), 6.00 (t, J=11.0 Hz, 1H), 5.62 (m, 2H), 5.42 (m, 1H), 5.27 (m, 1H), 5.21 (d, J=16.8 Hz, 1H), 5.11 (d, J=10.3 Hz, 1H), 4.54 (m, 3H), 3.97 (m, 1H), 3.81 (s, 3H), 3.74 (s, 3H), 3.60 (m, 1H), 3.40 (m, 1H), 3.29 (m, 1H), 2.86 (m, 1H), 2.57 (m, 2H), 1.80-1.67 (m, 3H), 1.55-1.41 (m, 4H), 1.40-1.20 (m, 4H), 1.09 (d, J=6.8 Hz, 3H), 1.06 (d, J=6.8 Hz, 3H), 0.99 (d, J=6.6 Hz, 3H), 0.98 (d, J=6.7 Hz, 3H), 0.95-0.85 (m, 42H), 0.13-0.00 (m, 24H); $^{13}$C NMR (75 MHz, CDCl$_3$) δ 166.8, 159.0, 147.3, 145.5, 134.7, 132.9, 132.7, 132.3, 131.4, 129.1, 129.0, 126.9, 117.4, 115.5, 113.7, 84.6, 80.0, 74.7, 73.6, 72.1, 66.5, 55.3, 51.0, 43.5, 42.4, 41.6, 36.1, 35.8, 34.8, 31.9, 30.7, 29.8, 26.3, 26.0, 25.9, 20.5, 19.3, 18.6, 18.5, 18.1, 15.3, 13.4, 10.5, −3.0, −3.3, −3.7, −4.10, −4.15, −4.19, −4.3, −4.4; LRMS (ESI) 1163.8 [M+Na]$^+$, 1057.7, 782.4, 541.1; HRMS (ESI) calcd for C$_{65}$H$_{120}$O$_8$Si$_4$Na 1163.7958[M+Na]$^+$, found 1163.8000; [α]$^{20}_D$ −16.7 (c 0.33, CHCl$_3$).

(2Z,4E,6R,7S,9S,10Z,12S,13R,14S,16S,19S,20R, 21S,22S,23Z)-Methyl-7,9,13,19-tetrakis(tert-butyldimethylsilyloxy)-21-hydroxy-6,12,14,16,20,22-hexamethylhexacosa-2,4,10,23, 25-pentaenoate (56)

The procedure for 47 was used with 55 (68 mg, 60 μmol) and DDQ (15 mg, 66 μmol) to yield 56 mg (92%) of the product after flash column chromatography (EtOAc/hexane 1:9) as a colorless oil: IR (CHCl$_3$) 3499, 2956, 2929, 2856, 1723, 1641, 1471, 1462, 1255, 1175, 1081, 836, 773 cm$^−$; $^1$H NMR (300 MHz, CDCl$_3$) δ 7.35 (dd, J=15.2, 11.3 Hz, 1H), 6.64 (ddd, J=16.9, 10.6, 10.5 Hz, 1H), 6.52 (t, J=11.3 Hz, 1H), 6.07 (t, J=11.0 Hz, 1H), 5.96 (dd, J=15.5, 7.1 Hz, 1H), 5.56 (d, J=11.3 Hz, 1H), 5.44-5.33 (m, 2H), 5.26-5.21 (m, 1H), 5.17 (d, J=16.7 Hz, 1H), 5.07 (d, J=10.1 Hz, 1H), 4.49 (m, 1H), 3.92 (m, 1H), 3.73-3.67 (m, 5H), 3.34 (m, 1H), 3.25 (br, 1H), 2.73 (m, 1H), 2.52 (m, 2H), 1.82-1.50 (m, 4H), 1.44-1.16 (m, 7H), 1.01 (d, J=6.8 Hz, 3H), 0.97 (d, J=7.1 Hz, 3H), 0.93 (d, J=6.9 Hz, 3H), 0.90 (d, J=6.9 Hz, 3H), 0.88-0.81 (m, 42H), 0.08-0.00 (m, 24H); $^{13}$C NMR (75 MHz, CDCl$_3$) δ 166.8, 147.3, 145.5, 136.5, 132.8, 132.7, 132.6, 129.6, 126.8, 117.3, 115.5, 79.8, 78.4, 74.2, 72.1, 66.5, 51.0, 43.5, 42.5, 41.4, 36.0, 35.9, 35.8, 35.0, 32.4, 31.9, 30.7, 26.3, 26.0, 25.9, 20.4, 19.4, 18.5, 18.12, 18.08, 17.98, 17.4, 15.3, 13.4, 10.8, −3.0, −3.4, −3.7, −4.1, −4.2, −4.3, −4.4, −4.8; LRMS (ESI) 1043.7 [M+Na]$^+$, 889.6, 758.2, 684.2, 610.1; HRMS (ESI) calcd for C$_{57}$H$_{112}$O$_7$Si$_4$Na 1043.7383 [M+Na]$^+$, found 1043.7435; [α]$^{20}_D$ −9.4 (c 0.62, CHCl$_3$).

(2Z,4E,6R,7S,9S,10Z,12S,13R,14S,16S,19S,20R, 21S,22S,23Z)-7,9,13,19-tetrakis(tert-Butyldimethylsilyloxy)-21-hydroxy-6,12,14,16,20,22-hexamethylhexacosa-2,4,10,23,25-pentaenoic acid (57)

The procedure for 48 was used with 56 (56 mg, 55 μmol) and 1N aqueous KOH (0.54 mL) to yield 57, which was used without further purification: IR (CHCl$_3$) 2956, 2929, 2857, 1693, 1634, 1471, 1462, 1254, 1082, 836, 773 cm$^{-1}$; $^1$H NMR (300 MHz, CDCl$_3$) δ 7.34 (dd, J=15.1, 11.4 Hz, 1H), 6.64 (ddd, J=16.5, 10.6, 10.5 Hz, 1H), 6.61 (t, J=11.2 Hz, 1H), 6.07 (t, J=11.0 Hz, 1H), 6.01 (dd, J=15.5, 7.2 Hz, 1H), 5.58 (d, J=11.3 Hz, 1H), 5.44-5.34 (m, 2H), 5.23 (dd, J=11.0, 8.2 Hz, 1H), 5.17 (d, J=18.0 Hz, 1H), 5.08 (d, J=10.1 Hz, 1H), 4.50 (m, 1H), 3.92 (m, 1H), 3.69 (m, 1H), 3.35 (m, 1H), 2.75 (m, 1H), 2.54 (m, 2H), 1.74-1.56 (m, 4H), 1.49-1.20 (m, 7H), 1.02 (d, J=6.8 Hz, 3H), 0.98 (d, J=7.2 Hz, 3H), 0.94 (d, J=7.0 Hz, 3H), 0.90-0.82 (m, 45H), 0.09-0.01 (m, 24H); $^{13}$C NMR (75 MHz, CDCl$_3$) δ 171.1, 148.2, 147.4, 136.4, 132.7, 132.6, 129.6, 127.0, 117.4, 115.1, 79.8, 78.4, 74.2, 72.1, 66.5, 43.5, 42.6, 41.5, 36.0, 35.9, 35.8, 35.0, 31.9, 30.8, 29.7, 26.3, 26.0, 25.9, 20.4, 19.3, 18.5, 18.13, 18.08, 17.97, 17.4, 15.4, 13.7, 10.8, −3.0, −3.4, −3.7, −4.1, −4.2, −4.3, −4.4, −4.8; LRMS (ESI) 1029.8 [M+Na]$^+$, 832.3, 758.3, 684.3, 610.2, 541.2; HRMS (ESI) calcd for C$_{56}$H$_{110}$O$_7$Si$_4$Na 1029.7226 [M+Na]$^+$, found 1029.7255; [α]$^{20}_D$ −6.5 (c 0.17, CHCl$_3$).

(8S,10S,14R,20S)-tetrakis(tert-Butyldimethylsilyloxy)-(7R,13S,15S,17S,21S)-pentamethyl-(22S)-((1S)-methylpenta-2,4-dienyl)-oxacyclodocosa-3,5, 11-trien-2-one (58)

The procedure for 49 was used with 57, Et$_3$N (0.046 mL, 33 μmol), 2,4,6-trichlorobenzoyl chloride (0.043 mL, 28 μmol) and 4-DMAP (27 mL, 0.02 M solution in toluene) to yield 42 mg (78% for 2 steps) of 58 after flash column chromatography (EtOAc/hexane 1:49) as a colorless oil: IR (CHCl$_3$) 2956, 2929, 2856, 1704, 1638, 1471, 1462, 1378, 1361, 1255, 1086, 1044, 1004, 835, 773 cm$^{-1}$; $^1$H NMR (300 MHz, CDCl$_3$) δ 6.98 (dd, J=15.3, 11.3 Hz, 1H), 6.58 (ddd, J=16.9, 10.6, 10.5 Hz, 1H), 6.42 (t, J=11.4 Hz, 1H), 5.94 (t, J=9.2 Hz, 1H), 5.92 (dd, J=9.5, 5.2 Hz, 1H), 5.55 (m, 1H), 5.42 (d, J=11.6 Hz, 1H), 5.33-5.21 (m, 3H), 5.12 (t, J=15.1 Hz, 1H), 4.99 (d, J=9.7 Hz, 1H), 4.54 (m, 1H), 3.99 (m, 1H), 3.44 (m, 1H), 3.17 (m, 1H), 2.99 (m, 1H), 2.54 (m, 1H), 2.19 (m, 1H), 1.99 (m, 1H), 1.61-1.42 (m, 7H), 1.37-1.18 (m, 3H), 1.10 (d, J=6.9 Hz, 3H), 1.05 (d, J=7.1 Hz, 3H), 1.00 (d, J=6.3 Hz, 3H), 0.98 (d, J=6.4 Hz, 3H), 0.98-0.82 (m, 36H), 0.79 (d, J=6.6 Hz, 3H), 0.66 (d, J=6.7 Hz, 3H), 0.11-0.01 (m, 24H); $^{13}$C NMR (75 MHz, CDCl$_3$) δ 166.4, 146.5, 143.9, 134.3, 132.7, 132.2, 130.8, 129.8, 127.9, 117.4, 117.1, 81.6, 78.0, 77.1, 73.0, 66.7, 46.9, 45.7, 41.2, 37.5, 35.8, 35.1, 34.5, 31.1, 29.7, 26.2, 26.1, 26.0, 25.9, 20.5, 19.5, 19.1, 18.5, 18.4, 18.2, 17.9, 17.3, 16.9, 7.9, −2.6, −3.4, −3.5, −4.3, −4.4, −4.6; LRMS (ESI) 1011.7 [M+Na]$^+$, 803.5, 633.1, 544.2, 413.2; HRMS (ESI) calcd for C$_{56}$H$_{108}$O$_6$Si$_4$Na 1011.7121 [M+Na]$^+$, found 1011.7164; [α]$^{20}_D$ −61.6 (c 2.8, CHCl$_3$).

(8S,10S,14R,20S)-Tetrahydroxy-(7R,13S,15S,17S, 21s)-pentamethyl-(22S)-((1S)-methylpenta-2,4-dienyl)-oxacyclodocosa-3,5,11-trien-2-one (59)

3N HCl (10 mL, prepared by adding 2.5 mL of conc. HCl to 7.5 mL MeOH) was added to a stirred solution of macrolactone 58 (42 mg, 42 μmol) in THF (3 mL) at 0° C.

After 24 h at room temperature, the reaction mixture was diluted with EtOAc (4 mL) and H$_2$O (4 mL). The organic phase was retained and the aqueous phase was extracted with EtOAc (2×4 mL). The combined organic phase was washed with saturated aqueous NaHCO$_3$ (10 mL), dried with MgSO$_4$, filtered and concentrated. The residue was purified by flash chromatography (EtOAc/hexane 3:2) to yield 59 (7.9 mg, 35%) as a colorless oil: IR (CHCl$_3$) 3415, 2961, 2917, 2849, 1681, 1637, 1461, 1279, 1067, 965, 758 cm$^{-1}$; $^1$H NMR (600 MHz, CD$_3$OD) δ 7.05 (dd, J=15.3, 11.3 Hz, 1H), 6.65 (ddd, J=16.9, 10.2, 10.1 Hz, 1H), 6.53 (dd, J=11.5, 11.5 Hz, 1H), 5.97 (dd, J=15.3, 9.5 Hz, 1H), 5.94 (dd, J=11.0, 11.0 Hz, 1H), 5.60 (dd, J=10.8, 9.6 Hz, 1H), 5.41 (d, J=11.5 Hz, 1H), 5.20 (dd, J=10.5, 10.3 Hz, 1H), 5.11 (dd, J=16.9, 2.0 Hz, 1H), 5.10 (dd, J=9.7, 2.1 Hz, 1H), 5.01 (d, J=10.1 Hz, 1H), 4.60 (ddd, J=10.1, 9.7, 2.7 Hz, 1H), 3.94 (ddd, J=11.0, 2.1, 2.0 Hz, 1H), 3.38 (ddd, J=9.8, 3.0,2.0 Hz, 1H), 3.09 (ddq, J=13.0, 7.0, 4.9 Hz, 1H), 3.01 (dd, J=8.3, 2.7 Hz, 1H), 2.70 (m, 1H), 2.23(ddd, J=9.3, 7.0, 2.4 Hz, 1H), 2.07 (ddd, J=7.0, 2.6, 2.5 Hz, 1H), 1.67 (m, 2H), 1.56 (ddd, J=14.0, 10.9, 2.9 Hz, 1H), 1.51 (m, 1H), 1.47 (ddd, J=14.1, 10.5, 1.9 Hz, 1H), 1.17 (d, J=6.9 Hz, 3H), 1.13 (m, 1H), 1.11 (d, j=7.1 Hz, 3H), 1.09 (d, J=7.0 Hz, 3H), 1.02 (d, J=6.7 Hz, 3H), 1.00 (m, 1H), 0.93 (d, J=6.4 Hz, 3H), 0.92 (m, 1H), 0.78 (m, 1H), 0.76 (d, J=6.7 Hz, 3H). 0.74 (m, 1H); $^{13}$C NMR (150 MHz, CD$_3$OD) δ 168.3, 147.6, 145.3, 135.4, 134.3, 133.5, 131.3, 131.0, 130.1, 118.1, 81.2, 79.9, 77.6, 72.0, 65.1, 45.9, 44.8, 42.4, 38.7, 36.0, 35.6, 31.8, 29.8, 27.8, 22.2, 19.8, 18.4, 17.6, 16.4, 9.1; LRMS (ESI) 555.3 [M+Na]$^+$, 443.2; HRMS (EST) calcd for C$_{32}$H$_{52}$O$_6$ 555.3662 [M+Na]$^+$, found 555.3655; [α]$^{20}_D$–76.2 (c 0.45, MeOH).

(4S,5R,6S)-7-(4-Methoxybenzyloxy)-5-(tert-butyldimethylsilyloxy)-4,6-dimethylheptan-1-ol (61)

DIBAL-H (19.8 mL, 19.8 mmol, 1.0 M solution in hexane) was added at –78° C. dropwise to ester 60 (3.59 g, 7.94 µmol) in CH$_2$Cl$_2$ (40 mL). After stirring for 1 h, the reaction mixture was quenched by addition of EtOAc (5 mL) and saturated aqueous sodium potassium tartrate (80 mL), followed by vigorous stirring for 4 h. The aqueous phase was extracted with CH$_2$Cl$_2$ (3×20 mL) and the combined organic layers were washed with brine (40 mL). After drying over MgSO$_4$, filtration and evaporation under vacuum, flash column chromatography (hexane/EtOAc 3:7) provided 60 (2.51 g, 77%) as a colorless oil: IR (CHCl$_3$) 3387, 2934, 2856, 1612, 1513, 1472, 1462, 1360, 1302, 1249, 1172, 1039, 836, 773 cm$^{-1}$; $^1$H NMR (300 MHz, CDCl$_3$) ϵ7.42-7.38 (m, 2H), 7.03-6.98 (m, 2H), 4.58 (d, J=11.6 Hz, 1H), 4.53 (d, J=11.6 Hz, 1H), 3.92 (s, 3H), 3.70 (d, J=6.6 Hz, 2H), 3.64 (m, 2H), 3.38 (dd, J=8.8, 7.6 Hz, 1H), 2.31 (br, 1H), 2.16-2.03 (m, 1H), 1.78-1.66 (m, 2H), 1.65-1.50 (m, 2H), 1.38-1.28 (m, 1H), 1.09 (d, J=6.9 Hz, 3H), 1.03 (s, 9H), 1.01 (d, J=6.9 Hz, 3H), 0.18 (s, 3H), 0.17 (s, 3H); $^{13}$C NMR (75 MHz, CDCl$_3$) δ 159.0, 130.7, 129.0, 113.6, 77.4, 72.6, 72.5, 62.8, 55.1, 37.8, 36.1, 30.8, 30.4, 26.0, 18.3, 15.2, 14.5, –3.8, –4.2; LRMS (ESI) 433.3 [M+Na]$^+$; HRMS (ESI) calcd for C$_{23}$H$_{42}$O$_4$SiNa 433.2750 [M+Na]$^+$, found 433.2765; [α]$^{20}_D$–10.2 (c 1.0, CHCl$_3$).

1-(((2S,3R,4S)-3,7-bis(tert-Butyldimethylsilyloxy)-2,4-dimethylheptyloxy)methyl)-4-methoxybenzene (62)

TBSCl (0.92 g, 6.11 mmol) was added to a solution of above alcohol 61 (2.51 g, 6.11 mmol) and imidazole (0.46 g, 6.76 mmol) in CH$_2$Cl$_2$ (20 mL). The resulting slurry was stirred for 1 h at room temperature. The organic phase was washed with water (100 mL) and brine (2×100 mL). After drying over MgSO$_4$, filtration and evaporation under vacuum, the residue was used directly in next step: IR (CHCl$_3$) 2930, 2856, 1613, 1513, 1471, 1360, 1250, 1098, 1040, 835, 773 cm$^{-1}$; $^1$H NMR (300 MHz, CDCl$_3$) δ 7.29-7.26 (m, 2H), 6.90-6.88 (m, 2H), 4.46 (d, J=11.6 Hz, 1H), 4.42 (d, J=11.6 Hz, 1H), 3.81 (s, 3H), 3.62 (t, J=6.3 Hz, 2H), 3.58-3.52 (m, 2H), 3.28 (dd, J=8.8, 7.7 Hz, 1H), 2.02-1.94 (m, 1H), 1.66-1.54 (m, 2H), 1.52-1.39 (m, 2H), 1.28-1.18 (m, 1H), 0.99 (d, J=6.9 Hz, 3H), 0.94 (s, 9H), 0.92 (s, 9H), 0.89 (d, J=6.8 Hz, 3H), 0.09 (s, 6H), 0.07 (s, 3H), 0.06 (3H); $^{13}$C NMR (75 MHz, CDCl$_3$) δ 159.0, 130.9, 129.0, 113.6, 77.5, 72.8, 72.6, 63.4, 55.1, 38.0, 36.3, 31.1, 30.8, 26.1, 25.9, 18.4, 18.3, 15.2, 14.4, –3.8, –4.1, –5.3; LRMS (ESI) 547.4 [M+Na]$^+$413.3, 212.1; HRMS (ESI) calcd for C$_{29}$H$_{56}$O$_4$Si$_2$Na 547.3615 [M+Na]$^+$, found 547.3638; [α]$^{20}_D$–9.9 (c 2.5, CHCl$_3$).

(2S,3R,4S)-3,7-bis(tert-Butyldimethylsilyloxy)-2,4-dimethylheptan-1-ol (63)

The PMB alcohol 62 (6.11 mmol) was added to CH$_2$Cl$_2$ (19 ML) then H$_2$O (1 mL) and DDQ (1.80 g, 7.93 µmol) were added. After 1 h of stirring, the reaction was quenched by adding saturated aqueous NaHCO$_3$ (100 mL). The organic phase was washed with saturated aqueous NaHCO$_3$ (3×100 mL) and brine, dried over MgSO$_4$ filtered and concentrated. Purification by flash column chromatography (EtOAc/hexane 1:9) furnished 63 (2.23 g, 90%) as a colorless oil: IR (CHCl$_3$) 3403, 2928, 2856, 1472, 1463, 1388, 1256, 1100, 836, 773 cm$^{-1}$; $^1$H NMR (300 MHz, CDCl$_3$) ϵ3.59-3.50 (m, 4H), 3.46 (dd, J=5.5, 3.7 Hz, 1H), 1.83-1.75 (m, 1H), 1.62-1.52 (m, 2H), 1.49-1.35 (m, 2H), 1.18-1.05 (m, 1H), 0.91 (d, J=7.0 Hz, 3H), 0.87-0.84 (m, 21H), 0.05 (s, 3H), 0.03 (s, 3H), 0.00 (s, 6H); $^{13}$C NMR (75 MHz, CDCl$_3$) δ 80.4, 65.8, 63.3, 38.1, 37.8, 31.1, 29.6, 26.0, 25.9, 18.2, 15.9, 14.9, 4.0, –4.2, –5.4; LRMS (ESI) 427.3 [M+Na]+, 256.8, 212.1; HRMS (ESI) calcd for C$_{21}$H$_{48}$O$_3$Si$_2$Na 427.3040 [M+Na]+, found 427.3050; [α]$^{20}_D$–14.0 (c 0.6, CHCl$_3$).

(3S,4R,5S)-4,8-bis(tert-Butyldimethylsilyloxy)-3,5-dimethyloct-1-yne (64)

Sulfur trioxide pyridine complex (2.63 g, 16.5 mmol) was added to a stirred solution of alcohol 63 (2.23 g, 5.51 mmol) and triethylamine (2.25 mL, 16.5 mmol) in anhydrous CH$_2$Cl$_2$ (12 mL) and DMSO (22 mL) at 0° C. The reaction mixture was stirred at ambient temperature for 1 h. The mixture was diluted with Et$_2$O (100 mL) and washed with 0.5N aqueous HCl (50 mL) and brine (10 mL). The separated organic layer was dried over MgSO$_4$. Filtration and concentration followed by short flash column chromatography (hexane/EtOAc 4:1) provided the crude aldehyde as a colorless oil, which was used without further purification. A mixture of carbon tetrabromide (3.65 g, 11.0 mmol) and triphenylphosphine (5.78 g, 22.0 mmol) in CH$_2$Cl$_2$ (50 mL) was stirred at 0° C. for 10 min. A solution of the crude aldehyde and 2,6-lutidine (1.27 mL, 11.0 mmol) in CH$_2$Cl$_2$ (5 mL) was transferred via cannula to the reaction mixture. The reaction was stirred for an additional 2 h at 0° C., then quenched with a saturated aqueous NH$_4$Cl (20 mL). The layers were separated and the aqueous layer was extracted with CH$_2$Cl$_2$ (2×20 mL). The combined layers were dried over MgSO$_4$, filtered and concentrated in vacuo. Flash column chromatography over silica gel (EtOAc/hexane 1:19) afforded the vinyl dibromide as a colorless oil. The vinyl dibromide in THF (18 mL) was cooled to −78° C. and treated with n-BuLi (8.6 mL, 13.8 mmol, 1.6 M solution in hexane). The reaction was stirred for 1 h at −78° C., warmed to 20° C. and stirred an additional 1 h. Saturated aqueous $NH_4Cl$ (5 mL) was added, the layers were separated and the aqueous layer was extracted with $Et_2O$. The combined organic layer was dried over $MgSO_4$, filtered and concentrated in vacuo. Purification by flash column chromatography (EtOAc/hexane 1:9) furnished 64 (1.20 g, 55% for 3 steps) as a colorless oil: IR ($CHCl_3$) 3313, 2930, 2857, 1472, 1463, 1387, 1361, 1254, 1099, 835, 774, 627 $cm^{-1}$; $^1H$ NMR (300 MHz, $CDCl_3$) ε3.74 (m, 2H), 3.66 (dd, J=4.7, 3.8 Hz, 1H), 2.74 (m, 1H), 2.14 (d, J=2.5 Hz, 1H), 1.85 (m, 1H), 1.74-1.56 (m, 4H), 1.31 (d, J=7.1 Hz, 3H), 1.05-1.01 (m, 18H), 0.23 (s, 3H), 0.20 (s, 3H), 0.18 (s, 6H); $^{13}C$ NMR (75 MHz, $CDCl_3$) δ 87.4, 77.9, 69.9, 63.4, 36.5, 31.5, 31.0, 30.7, 26.1, 26.0, 18.4, 18.3, 17.5, 15.0, −3.9, −5.3; LRMS (ESI) 421.3 $[M+Na]^+$, 372.8, 359.3, 256.8, 212.1; HRMS (ESI) calcd for $C_{22}H_{46}O_2Si_2Na$ 421.2934 $[M+Na]^+$, found 421.2942; $[α]^{20}_D$ −5.3 (c 1.3, $CHCl_3$).

(4R,5S,10S,11R,12S)-5,11,15-tris(tert-Butyldimethylsilyloxy)-4,10,12-trimethyl-1-trityloxypentadec-2-en-8-yn-7-one The procedure for 32 was used with 15 (1.31 g, 2.28 μmol), 64 (1.20 g, 3.01 mmol) and n-BuLi (1.88 mL, 1.20 mmol) to yield the ynone (1.79 g, 86%) after flash column chromatography (EtOAc/hexane 1:19) as a colorless oil: IR ($CHCl_3$) 2929, 2856, 2209, 1675, 1471, 1462, 1385, 1254, 1093, 836, 775, 705 $cm^{-1}$; $^1H$ NMR (300 MHz, $CDCl_3$) ε7.56-7.53 (m, 6H), 7.38-7.25 (m, 9H), 5.79 (dd, J=15.6, 7.2 Hz, 1H), 5.67 (dt, J=15.6, 4.9 Hz, 1H), 4.36 (m, 1H), 3.69-3.66 (m, 4H), 3.63 (t, J=4.1 Hz, 1H), 2.86 (m, 1H), 2.72 (m, 1H), 2.45 (m, 1H), 1.76 (m, 1H), 1.67-1.51 (m, 3H), 1.34 (m, 1H), 1.29 (d, J=7.1 Hz, 3H), 1.14 (d, J=6.8 Hz, 3H), 1.00-0.97 (m, 28H), 0.18-0.13 (m, 18H); $^{13}C$ NMR (75 MHz, $CDCl_3$) δ 186.0, 144.2, 132.8, 128.6, 127.9, 127.7, 126.8, 96.7, 86.8, 83.1, 77.8, 71.6, 64.8, 63.2, 50.1, 42.3, 37.2, 31.7, 30.9, 30.2, 26.0, 25.9, 25.8, 18.3, 18.2, 18.0, 17.3, 15.4, 14.8, −3.9, −4.1, −4.6, −4.7, −5.3; LRMS (ESI) 933.6 $[M+Na]^+$, 795.5, 665.2, 496.1, 413.2, 243. 1; HRMS (ESI) calcd for $C_{55}H_{86}O_5Si_3Na$ 933.5681 $[M+Na]^+$, found 933.5692; $[α]^{20}_D$ −9.5 (c 0.55, $CHCl_3$).

(4R,5S,7S,10S,11R,12S,2E)-5,11,15-tris(tert-Butyldimethylsilyloxy)-4,10,12-trimethyl-1-trityloxy-pentadec-2-en-8-yn-7-ol (65)

The procedure for 33 was used with the above ynone (1.77 g, 1.94 μmol), (S,S)-Noyori catalyst (0.26 g, 20 mol %) and i-PrOH (19 mL) to yield 65 (1.69 g, 95%) after flash column chromatography (EtOAc/hexane 1:19) as a pale yellow oil: IR ($CHCl_3$) 3464, 2929, 2856, 1471, 1448, 1386, 1254, 1090, 836, 774, 705 $cm^{-1}$; $^1H$ NMR (300 MHz, $CDCl_3$) δ 7.56-7.54 (m, 6H), 7.39-7.26 (m, 9H), 5.78 (dd, J=15.7, 6.4 Hz, 1H), 5.68 (dt, J=15.6, 4.9 Hz, 1H), 4.57 (m, 1H), 4.06 (m, 1H), 3.71-3.67 (m, 4H), 3.62 (t, J=4.0 Hz, 1H), 2.74 (m, 1H), 2.50 (m, 1H), 2.46 (d, J=5.4 Hz, 1H), 1.82 (m, 3H), 1.72-1.54 (m, 3H), 1.36 (m, 1H), 1.24 (d, J=7.1 Hz, 3H), 1.13 (d, J=6.8 Hz, 3H), 1.04-0.94 (m, 27H), 0.21-0.14 (m, 18H); $^{13}C$ NMR (75 MHz, $CDCl_3$) δ 144.3, 133.8, 128.6, 127.7, 127.2, 126.8, 87.8, 86.8, 83.1, 77.7, 72.5, 65.0, 63.5, 59.4, 41.9, 40.6, 36.4, 31.7, 30.7, 26.01, 25.96, 25.9, 18.3, 18.0, 17.4, 15.2, 14.5, −4.0, −4.1, −4.4, −4.5, −5.3; LRMS (ESI) 935.4 $[M+Na]^+$; HRMS (ESI) calcd for $C_{55}H_{88}O_5Si_3Na$ 935.5837 $[M+Na]^+$, found 935.5851; $[α]^{20}_D$ −10.5 (c 0.86, $CHCl_3$).

(2E,4R,5S,7S,8Z,10S,11R,12S)-5,11,15-tris(tert-Butyldimethylsilyloxy)-4,10,12-trimethyl-1-(trityloxy)pentadeca-2,8-dien-7-ol (66)

The procedure for 34 was used with alkyne 65 (1.69 g, 1.85 μmol) and Lindlar catalyst (ca. 200 mg) to yield 66 (1.70 g, quantitative) as a pale yellow oil: IR ($CHCl_3$) 3477, 2955, 2856, 1471, 1448, 1386, 1254, 1057, 835, 773, 705 $cm^{-1}$; $^1H$ NMR (300 MHz, $CDCl_3$) δ 7.63-7.60 (m, 6H), 7.43-7.27 (m, 9H), 5.88-5.77 (m, 2H), 5.70 (t, J=10.1 Hz, 1H), 5.49 (dd, J=10.6, 8.4 Hz, 1H), 4.78 (m, 1H), 4.06 (m, 1H), 3.76-3.72 (m, 4H), 3.58 (t, J=3.6 Hz, 1H), 2.89 (m, 1H), 2.63 (m, 1H), 2.20 (d, J=2.8 Hz, 1H), 1.73-1.48 (m, 7H), 1.18 (d, J=6.9 Hz, 3H), 1.15 (d, J=7.0 Hz, 3H), 1.08-1.02 (m, 27H), 0.29-0.20 (m, 18H); $^{13}C$ NMR (75 MHz, $CDCl_3$) δ 144.3, 134.9, 134.4, 131.5, 128.6, 127.7, 127.0, 126.8, 86.7, 79.8, 72.8, 65.0, 64.7, 63.5, 42.1, 39.7, 37.9, 35.9, 31.4, 29.9, 26.2, 26.0, 25.9, 20.1, 18.4, 18.3, 18.0, 14.9, 14.5, −3.6, −3.8, −4.5, −4.6, −5.3; LRMS (ESI) 937.5 $[M+Na]^+$; HRMS (ESI) calcd for $C_{55}H_{90}O_5Si_3Na$ 937.5994 $[M+Na]^+$, found 937.6016; $[α]^{20}_D$ +2.1 (c 0.92, $CHCl_3$).

((2E,4R,5S,7S,8Z,10S,11R,12S)-5,7,11,15-tetrakis(tert-Butyldimethylsilyloxy)-4,10,12-trimethylpentadeca-2,8-dienyloxy)triphenylmethane (67)

The procedure for 35 was used with alcohol 66 (1.70 g, 1.85 μmol), TBSOTf (0.94 mL, 4.07 mmol) and 2,6-lutidine (0.51 mL, 4.44 mmol) to yield 67 (1.82 g, 96%) by flash column chromatography (EtOAc/hexane 1:19) as a colorless oil: IR ($CHCl_3$) 2956, 2856, 1471, 1448, 1254, 1092, 1004, 836, 773 $cm^{-1}$; $^1H$ NMR (300 MHz, $CDCl_3$) δ 7.77-7.75 (m, 6H), 7.57-7.47 (m, 9H), 6.02-5.87 (m, 2H), 5.76 (t, J=10.8 Hz, 1H), 5.61 (dd, J=10.8, 8.5 Hz, 1H), 4.88 (m, 1H), 4.24 (m, 1H), 3.88 (m, 4H), 3.75 (m, 1H), 2.94 (m, 1H), 2.73 (m, 1H), 1.83 (m, 2H), 1.75 (m, 2H), 1.57 (m, 1H), 1.46-1.41 (m, 2H), 1.31 (d, J=6.8 Hz, 3H), 1.30 (d, J=6.3 Hz, 3H), 1.24-1.13 (m, 39H), 0.44-0.34 (m, 24H); $^{13}C$ NMR (75 MHz, $CDCl_3$) δ 144.4, 134.4, 132.9, 132.2, 128.7, 127.7, 126.8, 86.8, 80.2, 72.3, 66.6, 65.1, 63.6, 42.4, 41.6, 38.4, 35.7, 31.6, 29.9, 26.3, 26.0, 19.6, 18.5, 18.4, 18.2, 15.1, 13.2, −2.9, −3.6, −3.7, −4.2, −5.2; LRMS (ESI) 1051.6 $[M+Na]^+$, 918.6, 769.5, 637.4, 413.2; HRMS (ESI) calcd for $C_{61}H_{104}O_5Si_4Na$ 1051.6859 $[M+Na]^+$, found 1051.6848 $[α]^{20}_D$ −8.3 (c 2.4, $CHCl_3$).

(4S,5R,6S,7Z,9S,11S,12R,13E)-5,9,11-tris(tert-Butyldimethylsilyloxy)-4,6,12-trimethyl-15-(trityloxy)pentadeca-7,13-dien-1-ol (68)

The procedure for 36 was used with 67 (1.82 g, 1.77 μmol) and HF-pyridine in pyridine (100 mL) to yield 68 (1.15 g, 71%) by flash column chromatography (EtOAc/Hexane 1:9) as a colorless oil: IR ($CHCl_3$) 3349, 2956, 2929, 2856, 1471, 1448, 1254, 1060, 836, 773, 705 $cm^{-1}$; $^1H$ NMR (300 MHz, $CDCl_3$) δ 7.58-7.55 (m, 6H), 7.39-7.27 (m, 9H), 5.81-5.65 (m, 2H), 5.56 (t, J=10.7 Hz, 1H), 5.41 (dd, J=11.0, 8.4 Hz, 1H), 4.67 (m, 1H), 4.05 (m, 1H), 3.69-3.63 (m, 4H), 3.53 (m, 1H), 2.73 (m, 1H), 2.52 (m, 1H), 1.64 (m, 3H), 1.58-1.48 (m, 2H), 1.30-1.20 (m, 2H), 1.11 (d, J=6.8 Hz, 3H), 1.10 (d, J=6.6 Hz, 3H), 1.03-0.92 (m, 30H), 0.23-0.14 (m, 18H); $^{13}C$ NMR (75 MHz, $CDCl_3$) δ 144.3, 134.3, 132.9, 132.0, 128.6, 127.7, 126.8, 86.7, 80.1, 72.3, 66.4, 65.0, 63.1, 42.4, 41.7, 38.2, 35.5, 31.2, 29.5, 26.2, 25.95, 25.89, 19.6, 18.4, 18.1, 18.0, 15.1, 13.3, −2.9, −3.7, −3.8, −4.17, −4.24, −4.3; LRMS (ESI) 937.6 [M+Na]$^+$; HRMS (ESI) calcd for $C_{55}H_{90}O_5Si_3Na$ 937.5994 [M+Na]$^+$, found 937.6035; $[\alpha]^{20}_D$ −10.8 (c 0.84, $CHCl_3$).

(2R,4E,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-8,10,16-trimethyl-19-(trityloxy)nonadeca-4,11,17-trien-3-one (69)

The procedure for 39 was used with alcohol 68 (1.15 g, 1.26 μmol), Dess-Martin reagent (0.80 g, 1.89 mmol) and $Ba(OH)_2$ (0.17 g, 1.01 mmol) and 38 (0.49 g, 1.27 mmol) to yield 69 (1.22 g, 83%) after flash column chromatography (EtOAc/hexane 1:9) as a colorless oil: IR ($CHCl_3$) 2956, 2929, 2856, 1693, 1618, 1518, 1461, 1388, 1251, 1080, 836, 773 cm$^{-1}$; $^1$H NMR (300 MHz, $CDCl_3$) δ 7.70-7.68 (m, 6H), 7.60-7.57 (m, 2H), 7.52-7.39 (m, 9H), 7.11 (m, 1H), 7.07-7.04 (m, 2H), 6.54 (d, J=15.6, Hz, 1H), 5.94-5.78 (m, 2H), 5.67 (t, J=10.9 Hz, 1H), 5.64 (s, 1H), 5.54 (dd, J=11.0, 8.2 Hz, 1H), 4.80 (m, 1H), 4.28 (dd, J=11.3, 4.6 Hz, 1H), 4.18 (m, 1H), 4.11 (dd, J=9.8, 3.9 Hz, 1H), 3.94 (s, 3H), 3.81 (m, 2H), 3.71 (m, 1H), 3.66 (m, 1H), 3.12 (m, 1H), 2.87 (m, 1H), 2.66 (m, 1H), 2.47 (m, 1H), 2.34 (m, 1H), 2.19 (m, 1H), 1.90-1.73 (m, 3H), 1.67-1.51 (m, 2H), 1.45 (d, J=7.0 Hz, 3H), 1.23 (d, J=6.6 Hz, 3H), 1.22 (d, J=6.8 Hz, 3H), 1.16-1.05 (m, 30H), 0.96 (d, J=6.7 Hz, 3H), 0.36-0.26 (m, 18H); $^{13}$C NMR (75 MHz, $CDCl_3$) δ 200.4, 159.6, 147.2, 144.2, 134.1, 133.0, 131.9, 130.9, 128.5, 127.8, 127.6, 127.1, 126.7, 113.3, 100.6, 86.6, 82.7, 79.8, 72.7, 72.1, 66.3, 64.9, 55.0, 46.8, 42.3, 41.5, 37.9, 35.3, 32.0, 31.7, 30.8, 26.1, 25.9, 19.5, 18.3, 18.0, 17.9, 14.7, 13.1, 12.3, 10.4, −3.0, −3.7, −3.9, −4.3, −4.4; LRMS (ESI) 1195.7 [M+Na]$^+$, 1051.8; HRMS (ESI) calcd for $C_{71}H_{108}O_8Si_3Na$ 1195.7250 [M+Na]$^+$ found 1195.7297; $[\alpha]^{20}_D$ +9.1 (c 1.2, $CHCl_3$).

(2R,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-8,10,16-trimethyl-19-trityloxynonadeca-11,17-dien-3-one (70)

The procedure for 40 was used with 69 (1.22 g, 1.04 μmol), $NiCl_2 \cdot 6H_2O$ (0.12 g, 0.52 mmol) and $NaBH_4$ (0.079 g, 2.08 mmol) to yield 70 (0.80 g, 65%) after flash column chromatography (EtOAc/hexane 1:9) as a colorless oil: IR ($CHCl_3$) 2956, 2929, 2855, 1713, 1615, 1518, 1461, 1388, 1251, 1077, 1037, 836, 773 cm$^{-1}$; $^1$H NMR (300 MHz, $CDCl_3$) δ 7.70-7.66 (m, 6H), 7.57-7.40 (m, 1H), 7.07-7.04 (m, 2H), 5.92-5.77 (m, 2H), 5.65 (m, 1H), 5.64 (s, 1H), 5.52 (m, 1H), 4.78 (m, 1H), 4.30 (dd, J=11.2, 4.6 Hz, 1H), 4.14 (m, 2H), 3.94 (s, 3H), 3.79 (d, J=3.9 Hz, 2H), 3.73 (t, J=11.1 Hz, 1H), 3.61 (m, 1H), 2.92-2.79 (m, 2H), 2.72 (t, J=7.4 Hz, 2H), 2.65 (m, 1H), 2.22 (m, 1H), 1.91-1.71 (m, 4H), 1.65-1.56 (m, 3H), 1.51 (m, 1H), 1.43 (d, J=7.1 Hz, 3H), 1.35 (m, 1H), 1.20 (d, J=6.7 Hz, 3H), 1.14-1.12 (m, 21H), 1.08 (d, J=6.2 Hz, 3H), 1.05-1.03 (m, 9H), 0.96 (d, J=6.7 Hz, 3H), 0.34-0.25 (m, 18H); $^{13}$C NMR (75 MHz, $CDCl_3$) δ 211.5, 159.8, 144.4, 144.3, 134.3, 132.9, 132.2, 130.9, 128.6, 127.6, 127.1, 126.8, 113.4, 100.8, 86.7, 83.0, 80.1, 72.8, 72.2, 66.4, 65.0, 55.0, 48.2, 42.3, 41.6, 40.6, 38.0, 35.7, 33.5, 31.2, 27.6, 26.2, 25.91, 25.87, 23.9, 19.4, 18.4, 18.05, 17.99, 14.8, 13.2, 12.0, 9.5, −3.0, −3.6, −3.8, −4.2, −4.3, −4.4; LRMS (ESI) 1197.7 [M+Na]$^+$, 684.2, 541.1; HRMS (ESI) calcd for $C_{71}H_{110}O_8Si_3Na$ 1197.7406 [M+Na]$^+$, found 1197.7411; $[\alpha]^{20}_D$ +4.6 (c 1.1, $CHCl_3$).

(2S,3R,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-8,10,16-trimethyl-19-(trityloxy)nonadeca-11,17-dien-3-ol (71)

$LiAl(O-t-Bu)_3H$ (2.0 mL, 1.0 M solution in THF) was added to a solution of 70 (0.80 g, 0.68 mmol) in THF (7 mL). After 30 min of stirring at room temperature, the reaction was quenched with saturated aqueous $NH_4Cl$ (1 mL), stirring for 1 h, dried over $MgSO_4$, filtered, concentrated in vacuo, and chromatographed (EtOAc/hexane 3:17) to provide the β isomer of 71 (0.76 g, 95%) as a colorless oil: IR ($CHCl_3$) 3538, 2929, 2855, 1615, 1518, 1461, 1385, 1251, 1072, 835, 773, 734 cm$^{-1}$; $^1$H NMR (300 MHz, $CDCl_3$) δ 7.70-7.66 (m, 6H), 7.59-7.56 (m, 2H), 7.52-7.39 (m, 9H), 7.08-7.05 (m, 2H), 5.93-5.77 (m, 2H), 5.71 (s, 1H), 5.67 (t, J=10.2 Hz, 1H), 5.55-5.48 (m, 1H), 4.78 (m, 1H), 4.30 (dd, J=11.4, 4.8 Hz, 1H), 4.15 (m, 1H), 4.09 (m, 1H), 3.94 (s, 3H), 3.88 (dd, J=10.0, 1.5 Hz, 1H), 3.79 (d, J=3.9 Hz, 2H), 3.70 (t, J=11.1 Hz, 1H), 3.64 (m, 1H), 3.38 (br, 1H), 2.84 (m, 1H), 2.65 (m, 1H), 2.33 (m, 1H), 2.22-1.91 (m, 2H), 1.86-1.71 (m, 3H), 1.66-1.54 (m, 4H), 1.49-1.34 (m, 3H), 1.24 (d, J=7.0 Hz, 3H), 1.21 (d, J=6.6 Hz, 3H), 1.15-1.08 (m, 21H), 1.09 (d, J=6.9 Hz, 3H), 1.04 (m, 9H), 0.94 (d, J=6.7 Hz, 3H), 0.34-0.25 (m, 18H); $^{13}$C NMR (75 MHz, $CDCl_3$) δ 160.0, 144.4, 144.3, 134.3, 132.8, 132.2, 130.6, 128.6, 127.6, 127.1, 126.7, 113.6, 101.1, 88.9, 86.7, 80.1, 76.2, 73.0, 72.2, 66.4, 65.0, 55.1, 42.3, 41.6, 38.2, 37.4, 35.7, 35.0, 33.6, 30.3, 28.0, 26.5, 26.1, 25.91, 25.87, 19.5, 18.4, 18.05, 17.99, 15.0, 13.2, 11.8, 5.6, −3.0, −3.7, −3.8, −4.2, −4.3; LRMS (ESI) 1199.7 [M+Na]$^+$, 937.6, 782.4, 413.2; HRMS (ESI) calcd for $C_{71}H_{112}O_8Si_3Na$ 1199.7563 [M+Na]$^+$, found 1199.7538; $[\alpha]^{20}_D$ +8.9 (c 0.46, $CHCl_3$).

(2S,3R,8S,9R,10S,11Z,13S,15S,16R,17E)-9,13,15-tris(tert-Butyldimethylsilyloxy)-2-((4S,5S)-2-(4-methoxyphenyl)-5-methyl-1,3-dioxan-4-yl)-8,10,16-trimethyl-19-(trityloxy)nonadeca-11,17-dien-3-ol (72)

The procedure for 42 was used with 71 (0.76 g, 0.65 μmol), TBSOTf (0.22 mL, 0.98 mmol) and 2,6-lutidine (0.15 mL, 1.30 mmol) to yield 72 (0.76 g, 92%) after flash column chromatography (EtOAc/Hexane 1:9) as a colorless oil: IR ($CHCl_3$) 2955, 2929, 2856, 1615, 1518, 1471, 1388, 1251, 1074, 836, 773 cm$^{-1}$; $^1$H NMR (300 MHz, $CDCl_3$) δ 7.60-7.57 (m, 6H), 7.52-7.49 (m, 2H), 7.41-7.27 (m, 9H), 6.99-6.96 (m, 2H), 5.83-5.67 (m, 2H), 5.56 (t, J=9.2 Hz, 1H), 5.55 (s, 1H), 5.43 (dd, J=10.9, 8.4 Hz, 1H), 4.69 (m, 1H), 4.21 (m, 1H), 4.06 (m, 1H), 3.84 (s, 3H), 3.81 (m, 1H), 3.76-3.70 (m, 3H), 3.60 (t, J=11.1 Hz, 1H), 3.54 (m, 1H), 2.74 (m 1H), 2.54 (m, 1H), 2.14 (m, 1H), 2.00 (t, J=6.7 Hz, 1H), 1.68 (m, 3H), 1.58-1.40 (m, 5H), 1.34-1.20 (m, 3H), 1.13 (d, J=6.8 Hz, 3H), 1.10 (m, 3H), 1.05-0.95 (m, 42H), 0.84 (d, J=6.4 Hz, 3H), 0.25-0.17 (m, 24H); $^{13}$C NMR (75 MHz, $CDCl_3$) δ 159.7, 144.5, 144.3, 134.3, 132.9, 132.4, 131.6, 128.7, 127.7, 127.1, 126.8, 113.4, 100.5, 86.7, 81.9, 80.2, 74.7, 73.3, 72.3, 66.5, 65.0, 55.1, 42.3, 41.6, 38.9, 38.2, 35.9, 34.0, 33.7, 30.7, 28.4, 26.2, 26.0, 25.96, 25.9, 25.7, 19.4, 18.4, 18.1, 14.8, 13.2, 12.3, 10.6, −3.0, −3.5, −3.8, −4.2, −4.3; LRMS (ESI) 1313.8 [M+Na]$^+$, 782.4, 413.2; HRMS (ESI) calcd for $C_{77}H_{126}O_8Si_4Na$ 1313.8428 [M+Na]$^+$, found 1313.8402; $[\alpha]^{20}_D$ +9.5 (c 0.38, $CHCl_3$).

(2S,3S,4R,5R,10S,11R,12S,13Z,15S,17S,18R,19E)-3-(4-Methoxybenzyloxy)-5,11,15,17-tetrakis(tert-butyldimethylsilyloxy)-2,4,10,12,18-pentamethyl-21-trityloxyhenicosa-13,19-dien-1-ol (73)

The procedure for 43 was used with 72 (0.76 g, 0.59 μmol) and DIBAL-H (5.9 mL, 5.9 mmol) to yield 73 (0.69 g, 90%) after flash column chromatography (EtOAc/Hexane 3:17) as a colorless oil: IR (CHCl$_3$) 3484, 2928, 2856, 1613, 1514, 1471, 1360, 1251, 1037, 835, 773 cm$^{-1}$; $^1$H NMR (300 MHz, CDCl$_3$) δ 7.62-7.58 (m, 6H), 7.47-7.34 (m, 1H), 7.02-7.00 (m, 2H), 5.82-5.68 (m, 2H), 5.55 (t, J=10.0 Hz, 1H), 5.46-5.41 (m, 1H), 4.70 (m, 1H), 4.66 (s, 2H), 4.04 (m, 1H), 3.97 (m, 1H), 3.94 (s, 3H), 3.77 (m, 1H), 3.70 (d, J=3.3 Hz, 2H), 3.59 (dd, J=6.6, 4.3 Hz, 1H), 3.53 (m, 1H), 3.00 (dd, J=5.8, 4.4 Hz, 1H), 2.72 (m 1H), 2.55 (m, 1H), 2.10 (m, 1H), 2.02 (m, 1H), 1.77-1.61 (m, 5H), 1.55-1.47 (m, 3H), 1.41-1.33 (m, 5H), 1.25 (d, J=7.0 Hz, 3H), 1.14 (d, J=6.9 Hz, 3H), 1.11 (d, J=6.8 Hz, 3H), 1.05-0.94 (m, 42H), 0.25-0.16 (m, 24H); $^{13}$C NMR (75 MHz, CDCl$_3$) δ 159.2, 144.3, 144.2, 134.3, 132.9, 132.2, 130.5, 129.2, 128.6, 127.6, 126.8, 113.8, 86.7, 85.6, 80.1, 75.1, 73.4, 72.2, 66.4, 65.0, 55.0, 42.3, 41.5, 40.5, 38.2, 37.0, 35.7, 34.7, 33.7, 28.3, 26.2, 25.9, 19.4, 18.4, 18.1, 15.7, 14.8, 13.1, 10.1, −3.0, −3.6, −3.8, −3.9, −4.3, −4.4; LRMS (ESI) 1315.8 [M+Na]$^+$, 937.6; HRMS (ESI) calcd for C$_{77}$H$_{128}$O$_8$Si$_4$Na 1315.8584 [M+Na]$^+$, found 1315.8534; [α]$^{20}_D$ −4.2 (c 1.5, CHCl$_3$).

((2E,4R,5S,7S,8Z,10S,11R,12S,17R,18R,19S,20S,21z)-19-(4-Methoxybenzyloxy)-5,7,11,17-tetrakis(tert-butyldimethylsilyloxy)-4,10,12,18,20-pentamethyltetracosa-2,8,21,23-tetraenyloxy)triphenylmethane (74)

The procedure for 44 was used with 73 (0.69 g, 0.53 μmol), Dess-Martin reagent (0.34 g, 0.80 mmol) and 1-bromoallyltrimethylsilane (0.66 g, 2.65 mmol), CrCl$_2$ (0.54 g, 4.39 mmol) and NaH (0.27 g, 10.7 mmol) to yield 74 (0.58 g, 82% for 3 steps) after flash column chromatography (EtOAc/hexane 1:19) as a colorless oil: IR (CHCl$_3$) 2955, 2929, 2856, 1613, 1514, 1471, 1250, 1063, 836, 773 cm$^{-1}$; $^1$H NMR (300 MHz, CDCl$_3$) δ 7.63-7.60 (m, 6H), 7.43-7.31 (m, 1H), 6.99-6.97 (m, 2H), 6.74 (ddd, J=16.8, 10.6, 10.5 Hz, 1H), 6.16 (t, J=11.0 Hz, 1H), 5.86-5.71 (m, 3H), 5.58 (t, J=9.8 Hz, 1H), 5.46 (dd, J=11.0, 8.3 Hz, 1H), 5.31 (d, J=16.8 Hz, 1H), 5.23 (d, J=10.2 Hz, 1H), 4.75-4.63 (m, 3H), 4.09 (m, 1H), 3.86 (s, 3H), 3.81 (m, 1H), 3.73 (d, J=4.0 Hz, 1H), 3.55 (m, 1H), 3.49 (m, 1H), 3.18 (m, 1H), 2.77 (m, 1H), 2.57 (m, 1H), 1.91-1.78 (m, 2H), 1.73-1.50 (m, 6H), 1.49-1.35 (m, 3H), 1.26 (d, J=6.6 Hz, 3H), 1.15 (d, J=6.3 Hz, 3H), 1.13 (d, J=5.9 Hz, 3H), 1.10-0.97 (m, 42H), 0.28-0.19 (m, 24H); $^{13}$C NMR (75 MHz, CDCl$_3$) δ 159.2, 144.5, 144.4, 134.6, 134.4, 133.0, 132.5, 132.4, 131.3, 129.1, 129.0, 128.7, 127.7, 126.8, 117.2, 113.7, 86.8, 84.3, 80.3, 75.0, 72.6, 72.3, 66.5, 65.1, 55.1, 42.4, 41.6, 40.7, 38.0, 36.0, 35.3, 35.2, 34.0, 28.2, 26.3, 26.03, 26.00, 25.97, 25.7, 19.4, 18.8, 18.5, 18.2, 18.14, 18.09, 14.8, 13.3, 9.4, −2.9, −3.5, −3.6, −3.8, −4.1, −4.2, −4.3, −4.4; LRMS (ESI) 1337.8 [M+Na]$^+$, 537.4, 243.1; HRMS (ESI) calcd for C$_{80}$H$_{130}$O$_7$Si$_4$Na 1337.8791 [M+Na]$^+$, found 1337.8785; [α]$^{20}_D$ +5.1 (c 0.37, CHCl$_3$).

(2E,4R,5S,7S,8Z,10S,11R,12S,17R,18R,19S,20S,21Z)-19-(4-Methoxybenzyloxy)-5,7,11,17-tetrakis(tert-butyldimethylsilyloxy)-4,10,12,18,20-pentamethyltetracosa-2,8,21,23-tetraen-1-ol (75)

The procedure for 45 was used with 74 (0.58 g, 0.22 μmol), ZnBr (0.25 g, 1.11 mmol) to yield 75 (0.42 g, 89%) after flash column chromatography (EtOAc/hexane 3:17) as a colorless oil: IR (CHCl$_3$) 3402, 2956, 2929, 2856, 1614, 1514, 1471, 1251, 1085, 836, 773 cm$^{-1}$; $^1$H NMR (300 MHz, CDCl$_3$) δ 7.47-7.44 (m, 2H), 7.04-7.01 (m, 2H), 6.76 (ddd, J=16.8, 10.6, 10.5 Hz, 1H), 6.19 (t, J=11.0 Hz, 1H), 5.87-5.72 (m, 3H), 5.59 (t, J=10.0 Hz, 1H), 5.45 (dd, J=10.9, 8.3 Hz, 1H), 5.35 (d, J=16.8 Hz, 1H), 5.27 (d, J=10.2 Hz, 1H), 4.75-4.65 (m, 3H), 4.22 (d, J=4.5 Hz, 2H), 4.09 (m, 1H), 3.94 (s, 3H), 3.83 (m, 1H), 3.56 (m, 1H), 3.51 (m, 1H), 3.17 (m, 1H), 2.77 (m, 1H), 2.57 (m, 1H), 1.95 (m, 1H), 1.85 (m, 1H), 1.78-1.55 (m, 8H), 1.53-1.40 (m, 3H), 1.29 (d, J=6.7 Hz, 3H), 1.56-1.06 (m, 45H), 1.01 (d, J=6.7 Hz, 3H), 0.29-0.22 (m, 24H); $^{13}$C NMR (75 MHz, CDCl$_3$) δ 158.9, 134.8, 134.5, 132.8, 132.4, 132.3, 131.2, 129.2, 129.1, 128.9, 117.1, 113.6, 84.3, 80.2, 75.0, 72.4, 72.2, 66.5, 63.6, 55.1, 42.3, 41.5, 40.5, 37.9, 35.7, 35.2, 33.8, 28.1, 26.2, 25.9, 25.6, 19.3, 18.8, 18.4, 18.2, 18.0, 14.6, 13.0, 9.2, −3.0, −3.5, −3.7, −3.9, −4.3, −4.4, −4.5; LRMS (ESI) 1095.7 [M+Na]$^+$, 809.6, 677.5, 537.4, 413.2; HRMS (ESI) calcd for C$_{61}$H$_{116}$O$_7$Si$_4$Na 1095.7696 [M+Na]$^+$, found 1095.7712; [α]$^{20}_D$ +4.8 (c 1.7, CHCl$_3$).

(2Z,4E,6R,7S,9S,10Z,12S,13R,14S,19R,20R,21S,22S,23Z)-Methyl-21-(4-methoxybenzyloxy)-7,9,13,19-tetrakis(tert-butyldimethylsilyloxy)-6,12,14,20,22-pentamethylhexacosa-2,4,10,23,25-pentaenoate (76)

The procedure for 46 was used with 75 (0.42 g, 0.39 μmol), Dess-Martin reagent (0.25 g, 0.59 mmol) and bis(2,2,2-trifluoroethyl)-(methoxycarbonylmethyl) phosphate (0.10 mL, 0.47 μmol), 18-crown-6 (0.52 g, 1.97 mmol) and KHMDS (0.94 mL, 0.47 mmol) to yield 76 (0.38 g, 86% for 2 steps) by flash column chromatography (EtOAc/hexane 1:19) as a colorless oil: IR (CHCl$_3$) 2955, 2856, 1722, 1640, 1514, 1462, 1250, 1174, 1084, 836, 773 cm$^{-1}$; $^1$H NMR (300 MHz, CDCl$_3$) δ 7.44 (dd, J=15.3, 11.3 Hz, 1H), 7.31-7.29 (m, 2H), 6.90-6.87 (m, 2H), 6.04 (t, J=11.0 Hz, 1H), 6.02 (m, 1H), 5.66-5.60 (m, 2H), 5.44 (t, J=10.0 Hz, 1H), 5.30 (dd, J=11.1, 8.3 Hz, 1H), 5.20 (d, J=16.8 Hz, 1H), 5.12 (d, J=10.2 Hz, 1H), 4.61-4.51 (m, 3H), 3.98 (m, 1H), 3.80 (s, 3H), 3.73 (s, 3H), 3.68 (m, 1H), 3.42 (m, 1H), 3.37 (dd, J=7.6, 3.1 Hz, 1H), 3.03 (m, 1H), 2.60 (m, 2H), 1.72 (m, 2H), 1.61-1.41 (m, 1H), 1.38-1.27 (m, 3H), 1.20-1.15 (m, 2H), 1.14 (d, J=6.7 Hz, 3H), 1.08 (d, J=6.8 Hz, 3H), 1.01 (d, J=6.6 Hz, 3H), 1.00 (d, J=6.7 Hz, 3H), 0.99-0.87 (m, 39H), 0.16-0.07 (m, 24H); $^{13}$C NMR (75 MHz, CDCl$_3$) δ 166.7, 159.0, 147.1, 145.4, 134.5, 132.6, 132.3, 131.3, 129.0, 128.9, 126.8, 117.1, 115.4, 113.6, 84.3, 80.2, 75.0, 72.5, 72.1, 66.4, 55.1, 50.8, 43.4, 42.4, 40.6, 37.9, 35.9, 35.2, 33.9, 28.1, 26.2, 26.0, 25.90, 25.87, 25.6, 19.3, 18.8, 18.4, 18.1, 18.05, 18.04, 14.6, 13.3, 9.3, −3.0, −3.5, −3.7, −3.8, −4.2, −4.3, −4.4, −4.5; LRMS (ESI) 1149.7 [M+Na]$^+$, 995.7, 436.2; HRMS (ESI) calcd for C$_{64}$H$_{118}$O$_8$Si$_4$Na 1149.7802 [M+Na]$^+$, found 1149.7813; [α]$^{20}_D$ −3.8 (c 0.85, CHCl$_3$).

(2Z,4E,6R,7S,9S,10Z,12S,13R,14S,19R,20R,21S,22S,23Z)-Methyl-7,9,13,19-tetrakis(tert-butyldimethylsilyloxy)-21-hydroxy-6,12,14,20,22-pentamethylhexacosa-2,4,10,23,25-pentaenoate (77)

The procedure for 47 was used with 76 (0.38 g, 0.34 μmol) and DDQ (0.084 g, 0.37 mmol) to yield 77 (0.28 g, 82%) after flash column chromatography (EtOAc/hexane 1:9) as a colorless oil: IR (CHCl$_3$) 3542, 2956, 2856, 1722, 1640, 1462, 1254, 1175, 1086, 1004, 836, 773 cm$^{-1}$; $^1$H NMR (300 MHz, CDCl$_3$) δ 7.39 (dd, J=15.2, 11.2 Hz, 1H), 6.63 (ddd, J=16.9, 10.5, 10.4 Hz, 1H), 6.53 (t, J=11.3 Hz, 1H), 6.09 (t, J=1.0 Hz, 1H), 5.98 (dd, J=8.3, 7.1 Hz, 1H), 5.58 (d, J=11.3 Hz, 1H), 5.45-5.39 (m, 2H), 5.26 (dd, J=10.8, 8.4 Hz, 1H), 5.20 (d, J=16.9 Hz, 1H), 5.11(d, J=10.1 Hz, 1H), 4.53 (m, 1H), 3.95 (m, 1H), 3.76 (m, 1H), 3.71 (s, 3H), 3.47 (m, 1H), 3.40 (m, 1H), 2.82 (m, 1H), 2.55 (m, 1H), 2.20 (br, 1H), 1.72 (m, 2H), 1.60-1.35 (m, 5H), 1.32-1.10 (m, 5H), 1.04 (d, J=6.8 Hz, 3H), 0.99-0.83 (m, 48H), 0.12-0.03 (m, 24H); $^{13}$C NMR (75 MHz, CDCl$_3$) δ 166.7, 147.1, 145.4, 135.2, 132.6, 132.5, 132.3, 130.0, 126.8, 117.7, 115.5, 80.2, 77.3, 76.2, 72.1, 66.5, 50.9, 43.4, 42.5, 38.3, 38.1, 36.1, 35.8, 34.7, 33.7, 28.3, 26.2, 25.94, 25.89, 25.5, 19.5, 18.4, 18.1, 17.7, 14.9, 13.3, 7.2, −3.0, −3.6, −3.8, −4.18, −4.20, −4.37, −4.41; LRMS (ESI) 1029.7 [M+Na]$^+$, 875.6, 379.3; HRMS (ESI) calcd for C$_{56}$H$_{110}$O$_7$Si$_4$Na 1029.7226 [M+Na]$^+$, found 1029.7244; [α]$^{20}$$_D$−18.7 (c 0.62, CHCl$_3$).

(8S,10S,14R,20R)-tetrakis(tert-Butyldimethylsilyloxy)-(7R,13S,15S,21S)-tetramethyl-(22S)-((1S)-methylpenta-2,4-dienyl)-oxacyclodocosa-3,5,11-trien-2-one (78)

The procedure for 48 was used with 77 (0.28 g, 0.28 μmol) and 1N KOH (2.8 mL, 2.8 mmol) to yield the acid (0.27 g, quantitative) as a pale yellow oil, which was used directly in next step: IR (CHCl$_3$) 2930, 1693, 1635, 1462, 1387, 1255, 1089, 838, 773 cm$^{-1}$; $^1$H NMR (300 MHz, CDCl$_3$) δ 7.36 (dd, J=15.0, 11.4 Hz, 1H), 6.6-6.57 (m, 2H), 6.08 (t, J=10.9 Hz, 1H), 6.02 (dd, J=15.7, 7.0 Hz, 1H), 5.59 (d, J=11.3 Hz, 1H), 5.45-5.39 (m, 2H), 5.26 (m, 1H), 5.20 (d, J=17.8 Hz, 1H), 5.11 (d, J=10.2 Hz, 1H), 4.55 (m, 1H), 3.95 (m, 1H), 3.76 (m, 1H), 3.49 (m, 1H), 3.41 (m, 1H), 2.82 (m, 1H), 2.57 (m, 2H), 1.70 (m, 2H), 1.57-1.41 (m, 5H), 1.31-1.12 (m, 5H), 1.04 (d, J=6.7 Hz, 3H), 0.99-0.84 (m, 48H), 0.12-0.04 (m, 24H); $^{13}$C NMR (75 MHz, CDCl$_3$) δ 170.9, 147.7, 146.8, 134.9, 132.5, 132.4, 132.2, 130.0, 126.9, 117.6, 115.5, 80.1, 75.7, 72.0, 66.4, 58.1, 43.4, 42.5, 38.3, 38.1, 35.9, 35.6, 34.7, 33.5, 28.3, 26.2, 25.90, 25.85, 25.5, 25.1, 19.5, 18.4, 18.1, 18.0, 17.7, 14.9, 13.3, 7.3, −3.1, −3.7, −3.8, −3.9, −4.2, −4.3, −4.4, −4.5; LRMS (ESI) 1015.7 [M+Na]$^+$, 861.6, 729.5, 651.4; HRMS (ESI) calcd for C$_{55}$H$_{108}$O$_7$Si$_4$Na 1015.7070 [M+Na]$^+$, found 1015.7091; [α]$^{20}$$_D$−14.6 (c 1.4, CHCl$_3$). The procedure for 49 was used with the acid (0.26 g, 0.26 μmol), 2,4,6-trichlorobenzoyl chloride (0.21 mL, 1.30 mmol), Et$_3$N (0.22 mL, 1.56 mmol) and 4-DMAP (130 mL, 2.6 mmol) to yield 78 (0.19 g, 76% for 2 steps) by flash column chromatography (EtOAc/hexane 1:19) as a colorless oil: IR (CHCl$_3$) 2956, 2929, 2856, 1714, 1640, 1471, 1255, 1088, 836, 773 cm$^{-1}$; $^1$H NMR (300 MHz, CDCl$_3$) δ 7.16 (dd, J=15.6, 11.2 Hz, 1H), 6.61 (ddd, J=16.8, 10.6, 10.5 Hz; 1H), 6.52 (t, J=11.3 Hz, 1H), 6.03 (d, J=9.6, 5.9 Hz, 1H), 6.00 (t, J=10.6 Hz, 1H), 5.62 (t, J=10.5 Hz, 1H), 5.56 (d, J=11.3 Hz, 1H), 5.39 (t, J=10.5 Hz, 1H), 5.28 (dd, J=11.2, 8.0 Hz, 1H), 5.20-5.14 (m, 2H), 5.09 (d, J=10.3 Hz, 1H), 4.59 (m, 1H), 4.01 (m, 1H), 3.53 (m, 1H), 3.43 (m, 1H), 3.06 (m, 1H), 2.56 (m, 1H), 2.45 (m, 1H), 1.90 (m, 1H), 1.55-1.35 (m, 6H), 1.28 (m, 1H), 1.24-1.12 (m, 4H), 1.08 (d, J=6.7 Hz, 3H), 1.02 (d, J=5.9 Hz, 3H), 1.01 (d, J=6.0 Hz, 3H), 0.93-0.88 (m, 39H), 0.81 (d, J=6.9 Hz, 3H), 0.14-0.05 (m, 24H); $^{13}$C NMR (75 MHz, CDCl$_3$) δ 166.2, 144.1, 142.6, 133.9, 132.1, 131.5, 129.7, 128.0, 127.5, 117.8, 117.6, 80.3, 74.0, 71.2, 66.5, 62.4, 43.7, 39.8, 39.3, 34.9, 34.0, 33.0, 31.8, 27.8, 26.1, 26.05, 25.98, 20.1, 18.33, 18.28, 18.14, 18.11, 17.8, 16.1, 14.0, 10.7, −2.7, −3.8, −4.0, −4.1, −4.2, −4.3; LRMS (ESI) 997.7 [M+Na]$^+$, 843.6, 711.5, 579.4; HRMS (ESI) calcd for C$_{55}$H$_{106}$O$_6$Si$_4$Na 997.6964 [M+Na]$^+$, found 997.6989; [α]$^{20}$$_D$−26.4 (c 0.59, CHCl$_3$).

(8S,10S,14R,20R)-Tetrahydroxy-(7R,13S,15S,21S)-tetramethyl-(22S)-((1S)-methylpenta-2,4-dienyl)-oxacyclodocosa-3,5,11-trien-2-one (79)

The procedure for 1 was used with 78 (0.19 g, 0.19 μmol), 3N HCl in 15 ml of 2:1 MeOH/THF to yield 79 (25 mg, 24%) after flash column chromatography (EtOAc/hexane 3:7) as a colorless oil: IR (CHCl$_3$) 3414, 2965, 2930, 1708, 1637, 1454, 1375, 1273, 1182, 1046, 968 cm$^{-1}$; $^1$H NMR (600 MHz, CD$_3$OD) 6 7.22 (dd, J=15.4, 11.2 Hz, 1H), 6.67 (ddd, J=17.3, 11.0, 10.5 Hz, 1H), 6.64 (dd, J=11.4, 11.4 Hz, 1H), 6.07 (dd, J=15.4,7.7 Hz, 1H), 6.02 (dd, J=10.9,10.9 Hz, 1H), 5.55 (t, J=10.6 Hz, 1H), 5.52 (d, J=11.4 Hz, 1H), 5.43 (dd, J=10.9, 9.0 Hz, 1H), 5.35 (dd, J=10.7, 10.6 Hz, 1H), 5.20 (d, J=16.7 Hz, 1H), 5.12 (d, J=10.2 Hz, 1H), 5.08 (dd, J=5.9, 5.9 Hz, 1H), 4.64 (m, 1H), 3.86 (ddd, J=8.4, 4.7, 4.5 Hz, 1H), 3.43 (m, 1H), 3.16 (m, 1H), 3.14 (dd, J=8.1, 2.6 Hz, 1H), 2.73 (m, 1H), 2.37 (m, 1H), 1.84 (m, 1H), 1.68 (m, 1H), 1.51-1.45 (m, 3H), 1.31 (m, 1H), 1.20 (m, 1H), 1.14-1.11 (m, 1H), 1.08 (d, J=6.9 Hz, 6H), 1.07-1.01 (m, 2H), 0.99 (d, J=6.8 Hz, 3H), 0.98 (d, J=6.7 Hz, 3H), 0.95 (m, 1H), 0.92 (d, J=6.6 Hz, 3H); $^{13}$C NMR (150 MHz, CD$_3$OD) δ 168.2, 146.6, 144.8, 134.3, 133.8, 133.4, 132.2, 131.3, 129.1, 118.5, 118.0, 79.9, 79.3, 72.4, 71.0, 65.5, 44.9, 41.7, 40.7, 37.9, 36.0, 35.4, 35.2, 33.9, 27.4, 27.2, 19.5, 18.3, 16.4, 15.1, 10.1; LRMS (ESI) 541.3 [M+Na]$^+$, 483.3; HRMS (ESI) calcd for C$_{31}$H$_{50}$O$_6$Na 541.3505 [M+Na]$^+$, found 541.3521; [α]$^{20}$$_D$−34.4 (c 0. 18, MeOH).

(3S,4SE)-3-(tert-Butyldimethylsilyloxy)-N-methoxy-N,4-dimethyl-7-(trityloxy)hept-5-enamide (81)

(3S,4S,E)-3-(tert-Butyldimethylsilyloxy)-4-methyl-7-trityloxyhept-5-en-1-ol (0.34 g, 0.66 mmol) in CH$_2$Cl$_2$ (10 mL) was treated with Dess-Martin periodinane (0.41 g, 0.99 mmol). After 1 h, the mixture was quenched with saturated NaHCO$_3$ (10 mL). The aqueous layer was extracted with ethyl ether (10 mL×2) and the combined extracts were dried over anhydrous MgSO$_4$. Filtration and concentration followed by short flash column chromatography (hexane/EtOAc 8:2) to remove the Dess-Martin residue provided the aldehyde as a colorless oil, which was used for the next reaction without further purification. A solution of the above aldehyde in THF (10 mL) and H$_2$O (5 mL) was treated with a 2 M solution of 2-methyl-2-butene (1.9 mL, 0.95 mmol) in THF, NaH$_2$PO$_4$.H$_2$O (0.27 g, 1.96 mmol) and NaClO$_2$ (0.22 g, 1.96 mmol). The reaction mixture was stirred for 2 h, diluted with 1N HCl (20 mL) and extracted with CH$_2$Cl$_2$ (2×40 mL). The combined organic layers were dried over MgSO$_4$, concentrated in vacuo and the crude was used for the next reaction without further purification. To a solution of acid in CH$_2$Cl$_2$, N,O-dimethylhydroxylamine hydrochloride (0.064 g, 0.65 mmol), Et$_3$N (0.09 mL, 0.65 mmol), DMAP (8 mg, 0.065 mmol) were successively added. The reaction mixture was cooled to 0° C., DCC (0.14 g, 0.65 mmol) was added. The mixture was stirred at ambient temperature for 15 h and filtered. The filtrate was washed with 0.5 N HCl, saturated aqueous NaHCO$_3$, and brine, dried over anhydrous MgSO$_4$ and concentrated. Purification by column chromatography over silica gel (hexane/EtOAc 4:1) gave the Weinreb amide 81 (0.37 g, 81 % for 3 steps) as a colorless oil: IR (CHCl$_3$) 2956, 2929, 2855, 1661, 1448, 1385, 1251, 1089, 1054, 1003, 836, 775, 706 cm$^{-1}$; $^1$H NMR (300 MHz, CDCl$_3$) ε7.64-7.61. m, 6H), 7.45-7.33 (m, 9H), 6.09 (dd, J=15.7, 6.6 Hz, 1H), 5.75 (dt, J=15.7, 5.2 Hz, 1H), 4.42 (m, 1H), 3.76 (s, 3H), 3.70 (m, 2H), 3.29 (s, 3H), 2.88 (m, 1H), 2.55 (m, 1H), 1.18 (d, J=6.8 Hz, 3H), 1.06 (s, 9H), 0.27 (s, 3H), 0.20 (s, 3H); $^{13}$C NMR (75 MHz, CDCl$_3$) δ 172.5, 144.2, 133.5, 128.5, 127.6, 126.8, 86.5, 72.8, 64.6, 61.1, 42.2, 36.0, 31.9, 25.8, 18.0, 14.8, −4.7, −4.8; LRMS (EI) 573, 558, 516, 246, 165; HRMS (EI) calcd for C$_{35}$H$_{47}$O$_4$N$_1$Si$_1$ 573.3290, found 573.3290; [α]$^{20}$$_D$−40.1 (c 1.2, CHCl$_3$).

(4S,5S,10S,11R,12R,14R,E)-11-(4-Methoxybenzyloxy)-5,15-bis(tert-butyldimethylsilyloxy)-4,10,12,14-tetramethyl-1-(trityloxy)pentadec-2-en-8-yn-7-one (82)

Alkyne 80 (7.75 g, 18.5 mmol) was taken up in THF (185 mL) and cooled to −78° C. n-BuLi (11.6 mL, 1.6 M solution in hexane) was added slowly. After 5 min, the mixture was warmed to 0° C. and stirred for 30 min. The mixture was then cooled to −78° C. and amide 81 (5.31 g, 9.26 mmol) in THF (15 mL) was added slowly. After 5 min the solution was warmed to 0° C. and stirred for 1 h. The reaction was quenched with aq NH$_4$Cl and the mixture was partitioned in a separatory funnel. The aqueous phase was extracted with ether (50 mL×3) and combined organic extracts were washed with brine and dried over MgSO$_4$. Filtration and concentration under reduced pressure, followed by flash chromatography on silica gel (hexane/EtOAc 95:5) afforded ynone (8.45 g, 98%) as a pale yellow oil: IR (CHCl$_3$) 2955, 2929, 2856, 2208, 1674, 1514, 1470, 1249, 1092, 836, 775, 706 cm$^{-1}$; $^1$H NMR (300 MHz, CDCl$_3$) ε7.50-7.47. m, 6H), 7.35-7.22 (m, 1H), 6.88-6.84 (m, 2H), 5.81 (dd, J=15.6, 6.7 Hz, 1H), 5.58 (dt, J=15.6, 5.2 Hz, 1H), 4.64 (d, J=10.8 Hz, 1H), 4.54 (d, J=10.8 Hz, 1H), 4.27 (m, 1H), 3.80 (s, 3H), 3.59 (d, J=5.2 Hz, 2H), 3.44-3.34 (m, 2H), 3.18 (t, J=5.4 Hz, 1H), 2.94 (m, 1H), 2.62 (m, 1H), 2.38 (m, 1H), 1.89 (m, 1H), 1.68 (m, 1H), 1.26 (d, J=7.0 Hz, 3H), 1.24 (m, 1H), 0.99 (d, J=6.9 Hz, 3H), 0.97 (d, J=6.9 Hz, 3H), 0.92 (s, 9H), 0.91 (m, 1H), 0.89 (s, 9H), 0.84 (d, J=6.7 Hz, 3H), 0.09-0.05 (m, 12H); $^{13}$C NMR (75 MHz, CDCl$_3$) δ 186.4, 159.1, 144.3, 133.5, 130.7, 129.2, 128.7, 127.7, 127.3, 126.9, 113.7, 96.8, 86.8, 86.2, 82.6, 74.0, 72.3, 69.2, 64.9, 55.2, 50.5, 42.3, 34.9, 33.2, 33.0, 29.5, 26.0, 25.9, 18.3, 18.1, 17.2, 16.3, 15.9, 14.8, −4.50, −4.55, −5.3; LRMS (ESI) 953.6 [M+Na]+, 855.4, 797.4, 577.5, 413.4, 359.3, 328.4; HRMS (ESI) calcd for C$_{58}$H$_{82}$O$_6$Si$_2$Na 953.5548 [M+Na]+, found 953.5552; [α]$^{20}$$_D$−9.5 (c 2.8, CHCl$_3$).

(4S,5S,7S,10S,11R,12R,14R,)-11-(4-Methoxybenzyloxy)-5,15-bis(tert-butyldimethylsilyloxy)-4,10,12,14-tetramethyl-1-(trityloxy)pentadec-2-en-8-yn-7-ol (83)

Ynone 82 (7.06 g, 7.59 mmol) was taken up in i-PrOH (100 mL). Noyori catalyst (1.02 g, 1.52 mmol, 20 mol %) was added in one portion and the solution was stirred for 12 h. The solvent was removed under vacuum, and the crude residue was purified by flash chromatography on silica gel (hexane/EtOAc 9:1), affording propargylic alcohol 83 (6.16 g, 87%) as a pale yellow oil: IR (CHCl$_3$) 3434, 2955, 2928, 2855, 1613, 1513, 1462, 1250, 1091, 836, 775 cm$^{-1}$; $^1$H NMR (300 MHz, CDCl$_3$) δ 7.59-7.57 (m, 6H), 7.42-7.30 (m, 11H), 6.96-6.93 (m, 2H), 5.96 (dd, J=15.7, 6.4 Hz, 1H), 5.68 (dt, J=15.2, 5.3 Hz, 1H), 4.79 (d, j=10.8 Hz, 1H), 4.67 (m, 1H), 4.63 (d, J=10.9 Hz, 1H), 4.07 (m, 1H), 3.86 (s, 3H), 3.69 (d, J=4.7 Hz, 2H), 3.49 (m, 2H), 3.22 (t, J=5.5 Hz, 1H), 2.91 (m, 1H), 2.67 (d, J=5.3 Hz, 1H), 2.56 (m, 1H), 1.98 (m, 1H), 1.86 (m, 2H), 1.77 (m, 1H), 1.36 (m, 1H), 1.31 (d, J=7.0 Hz, 3H), 1.09 (d, J=7.1 Hz, 3H), 1.06 (d, J=7.1 Hz, 3H), 1.03 (s, 9H), 1.02 (s, 9H), 0.94 (d, J=6.6 Hz, 3H), 0.24 (s, 3H), 0.22 (s, 3H), 0.15 (s, 6H); $^{13}$C NMR (75 MHz, CDCl$_3$) δ 158.9, 144.3, 133.2, 131.0, 129.1, 128.6, 127.7, 127.0, 126.8, 113.5, 87.5, 86.79, 86.74, 82.6, 74.0, 73.3, 69.3, 65.0, 59.6, 55.1, 41.4, 40.2, 34.5, 33.1, 32.7, 29.1, 25.9, 18.3, 18.0, 17.9, 16.6, 15.8, 15.3, −4.3, −4.5, −5.4; LRMS (ESI) 955.6 [M+Na]+, 707.3, 633.3, 559.2, 413.3; HRMS (ESI) calcd for C$_{58}$H$_{84}$O$_6$Si$_2$Na 955.5704 [M+Na]+, found 955.5734; [α]$^{20}$$_D$−8.5 (c 1.5, CHCl$_3$).

(2E,4S,5S,7S,8Z,10S,11R,12R,14R)-11-(4-Methoxybenzyloxy)-5-(tert-butyldimethylsilyloxy)-15-(tert-butyldimethylsilyloxy))-4,10,12,14-tetramethyl-1-(trityloxy)pentadeca-2,8-dien-7-ol (84)

A catalytic amount of Lindlar catalyst (ca. 200 mg) was added to a solution of alcohol 83 (3.11 g, 3.33 mmol) in toluene (100 mL). The flask was fitted with a H$_2$ balloon, and stirred under an atmosphere of H$_2$ until starting material was consumed (usually 1 h), as indicated by TLC analysis. The mixture was filtered through a pad of celite and concentrated under reduced pressure to afford the olefin 84 as a colorless oil (2.81 g, 90%): IR (CHCl$_3$) 3434, 2956, 2928, 2856, 1613, 1514, 1471, 1249, 1062, 836, 774 cm$^{-1}$; $^1$H NMR (300 MHz, CDCl$_3$) δ 7.58-7.55 (m, 6H), 7.4-7.29 (m, 1H), 6.93 (m, 2H), 5.90 (dd, J=15.6, 6.6 Hz, 1H), 5.68 (dt, J=15.7, 5.4 Hz, 1H), 5.60 (dd, J=11.1, 8.9 Hz, 1H), 5.51 (dd, J=11.2, 7.3 Hz, 1H), 4.66 (m, 1H), 4.58 (d, J=10.9 Hz, 1H), 4.55 (d, J=10.9 Hz, 1H), 3.95 (m, 1H), 3.86 (s, 3H), 3.66 (dd, J=4.9 Hz, 1H), 3.52-3.38 (m, 2H), 3.01 (m, 2H), 2.89 (br, 1H), 2.55 (m, 1H), 1.79 (m, 1H), 1.70 (m, 1H), 1.62 (m, 2H), 1.33-1.29 (m, 2H), 1.12 (d, J=5.8 Hz, 3H), 1.10 (d, J=6.7 Hz, 3H), 1.02 (s, 9H), 1.01 (s, 9H), 0.89 (d, J=6.1 Hz, 3H), 0.87 (d, J=6.3 Hz, 3H), 0.19 (s, 6H), 0.14 (s, 6H); $^{13}$C NMR (75 MHz, CDCl$_3$) δ 158.9, 144.3, 134.1, 133.5, 132.6, 131.0, 129.0, 128.6, 127.7, 126.8, 126.7, 113.5, 88.4, 86.7, 74.9, 73.5, 69.4, 65.2, 65.1, 55.1, 41.8, 40.2, 35.0, 34.6, 33.1, 25.9, 19.1, 18.3, 18.0, 16.6, 15.8, 15.6, −4.4, −4.5, −5.3; LRMS (ESI) 957.6 [M+Na]+, 781.4, 707.3, 559.3, 485.2, 413.4; HRMS (ESI) calcd for C$_{58}$H$_{86}$O$_6$Si$_2$Na 957.5861 [M+Na]+, found 957.5900; [α]$^{20}$$_D$+2.0 (c 1.2, CHCl$_3$).

((2E,4S,5S,7S,8Z,10S,11R,12R,14R)-11-(4-Methoxybenzyloxy)-5,7,15-tris(tert-butyldimethylsilyloxy)-4,10,12,14-tetramethylpentadeca-2,8-dienyloxy)triphenylmethane (85)

TBSOTf (1.05 mL, 4.57 mmol) was added to a stirred solution of the alcohol 84 (3.89 g, 4.16 mmol) and 2,6-lutidine (0.58 mL, 5.01 mmol) in CH$_2$Cl$_2$ (14 mL) at 0° C. After stirring for 1 h at 0° C., the reaction mixture was quenched by the addition of water (25 mL), and extracted by CH$_2$Cl$_2$ and dried over MgSO$_4$, followed by the evaporation of the solvent under reduced pressure. The residue was purified by short column chromatography (hexane/EtOAc 9:1) to obtain the product 85 (4.36 g, quantitative) as a colorless oil: IR (CHCl$_3$) 2956, 2928, 2856, 1613, 1514, 1471, 1462, 1250, 1088, 836, 773, 705 cm$^{-1}$; $^1$H NMR (300 MHz, CDCl$_3$) δ 7.61-7.58 (m, 6H), 7.43-7.31 (m, 1H), 6.97-6.94 (m, 2H), 5.95 (dd, J=15.7, 6.0 Hz, 1H), 5.67 (dt, J=15.7, 5.6 Hz, 2H), 4.71 (m, 1H), 4.62 (m, 2H), 4.05 (m, 1H), 3.87 (s, 3H), 3.69 (d, J=5.3 Hz, 2H), 3.53-3.40 (m, 2H), 3.08 (m, 1H), 2.91 (m, 1H), 2.51 (m, 1H), 1.76 (m, 1H), 1.66 (m, 2H), 1.50-1.40 (m, 2H), 1.32 (m, 1H), 1.22 (d, J=6.8 Hz, 6H), 1.09 (d, J=6.9 Hz, 3H), 1.06-0.96 (m, 27H), 0.91 (d, J=6.6 Hz, 3H), 0.83 (d, J=6.5 Hz, 3H), 0.25-0.17 (m, 18H); $^{13}$C NMR (75 MHz, CDCl$_3$) δ 158.9, 144.4, 134.3, 133.7, 131.4, 129.4, 129.0, 128.6, 127.7, 126.8, 126.4, 113.5, 88.8, 86.7, 74.8, 72.8, 69.5, 66.3, 65.1, 55.1, 43.0, 42.3, 35.4, 35.1, 33.4, 33.1, 26.1, 26.0, 18.8, 18.3, 18.1, 16.7, 15.7, 14.6, −2.8, −3.9, −4.1, −4.2, −5.3; LRMS (ESI) 1071.9 [M+Na]+, 413.4, 359.3, 243.2; HRMS (ESI) calcd for C$_{64}$H$_{100}$O$_6$Si$_3$Na 1071.6725 [M+Na]+, found 1071.6779; $[α]^{20}_D$ −9.5 (c 3.0, CHCl$_3$).

(2R,4R,5R,6S,7Z,9S,11S,12S,13E)-1,9,11-tris(tert-Butyldimethylsilyloxy)-2,4,6,12-tetramethyl-15-(trityloxy)pentadeca-7,13-dien-5-ol (86)

The above PMB alcohol 85 (2.90 g, 2.77 mmol) was added to CH$_2$Cl$_2$ (25 mL) and H$_2$O (1 mL), and DDQ (0.94 g, 4.15 µmol) was added. After 1 h of stirring, the reaction mixture was quenched by adding sat'd NaHCO$_3$ (200 mL). The organic phase was washed by sat'd NaHCO$_3$ solution (3×100 mL) and brine, dried over MgSO$_4$ and concentrated. Purification by flash column chromatography (EtOAc/hexane 5:95) furnished 86 (2.16 g, 84%) as a colorless oil: IR (CHCl$_3$) 3477, 2956, 2928, 2856, 1471, 1386, 1254, 1088, 836, 774 cm$^{-1}$; $^1$H NMR (300 MHz, CDCl$_3$) δ 7.55-7.52 (m, 6H), 7.38-7.25 (m, 9H), 5.92 (dd, J=15.7, 6.0 Hz, 1H), 5.62 (dt, J=15.7, 5.5 Hz, 1H), 5.52 (dd, J=11.1, 9.3 Hz, 1H), 5.35 (t, J=10.5 Hz, 1H), 4.63 (m, 1H), 3.97 (m, 1H), 3.63 (d, J=5.4 Hz, 2H), 3.51-3.36 (m, 2H), 3.18 (m, 1H), 2.68 (m, 1H), 2.47 (m, 1H), 1.71-1.59 (m, 3H), 1.42-1.27 (m, 2H), 1.17 (m, 1H), 1.08 (d, J=6.7 Hz, 3H), 1.04 (d, J=6.9 Hz, 3H), 0.99 (s, 9H), 0.97 (s, 9H), 0.96 (s, 9H), 0.91 (d, J=6.8 Hz, 3H), 0.84 (d, J=6.6 Hz, 3H), 0.18 (s, 3H), 0.16 (s, 3H), 0.15 (s, 3H), 0.13 (s, 3H), 0.12 (s, 6H); $^{13}$C NMR (75 MHz, CDCl$_3$) δ 144.4, 135.2, 134.1, 131.1, 128.7, 127.7, 126.8, 126.4, 86.7, 79.8, 72.8, 69.6, 66.2, 65.2, 43.0, 42.1, 35.5, 33.7, 32.8, 32.5, 26.1, 26.0, 25.9, 18.4, 18.1, 17.6, 16.8, 16.3, 14.7, −2.9, −4.0, −4.15, −4.22, −5.3; LRMS (ESI) 951.7 [M+Na]+, 823.7, 577.4, 413.3, 328.4, 243.1; HRMS (ESI) calcd for C$_{56}$H$_{92}$O$_5$Si$_3$Na 951.6150 [M+Na]+, found 951.6165; $[α]^{20}_D$ 30.0 (c 3.6, CHCl$_3$).

((2E,4S,5S,7S,8Z,10S,11R,12R,14R)-5,7,11,15-tetrakis(tert-Butyldimethylsilyloxy)-4,10,12,14-tetramethylpentadeca-2,8-dienyloxy)triphenylmethane (87)

The procedure for 85 was used with above 86 (3.34 g, 3.60 µmol), TBSOTf (1.82 mL, 7.9 mmol) to yield 3.53 g (94%) of the product by flash column chromatography (EtOAc/Hexane 5:95) as a colorless oil: IR (CHCl$_3$) 2956, 2928, 2856, 1471, 1462, 1361, 1254, 1088, 836, 773, 705 cm$^{-1}$; $^1$H NMR (300 MHz, CDCl$_3$) δ 7.50-7.48 (m, 6H), 7.34-7.22 (m, 9H), 5.82 (dd, J=15.7, 6.0 Hz, 1H), 5.57 (dt, J=15.8, 5.9 Hz, 1H), 5.48 (dd, J=11.0, 9.9 Hz, 1H), 5.32 (dd, J=11.0, 8.7 Hz, 1H), 4.56 (m, 1H), 3.93 (m, 1H), 3.59 (d, J=5.5 Hz, 2H), 3.39 (dd, J=9.6, 5.8 Hz, 1H), 3.31-3.27 (m, 2H), 2.62(m, 1H), 2.40 (m, 1H), 1.58-1.50 (m, 3H), 1.35 (m, 1H), 1.20-1.09 (m, 2H), 1.02 (d, J=7.1 Hz, 3H), 1.00 (d, J=7.0 Hz, 3H), 0.94 (s, 9H), 0.92 (s, 9H), 0.91 (s, 9H), 0.90 (s, 9H), 0.78 (d, J=6.8 Hz, 3H), 0.74 (d, J=6.6 Hz, 3H), 0.13-0.05 (m, 24H); $^{13}$C NMR (75 MHz, CDCl$_3$) δ 144.4, 134.5, 133.0, 131.8, 128.7, 127.7, 126.8, 126.4, 86.7, 81.2, 72.8, 69.3, 66.6, 65.3, 43.1, 42.3, 35.9, 35.1, 33.3, 29.7, 26.2, 26.1, 26.0, 19.6, 18.4, 18.3, 18.2, 16.3, 16.0, 14.6, −2.8, −3.5, −3.6, −4.0, −4.1, −5.3; LRMS (ESI) 1065.7 [M+Na]+, 953.7, 615.1, 577.3, 359.2; HRMS (ESI) calcd for C$_{62}$H$_{106}$O$_5$Si$_4$Na 1065.7015 [M+Na]+, found 1065.7068; $[α]^{20}_D$ −22.5 (c 2.0, CHCl$_3$).

(2R,4R,5R,6S,7Z,9S,11S,12S,13E)-5,9,11-tris(tert-Butyldimethylsilyloxy)-2,4,6,12-tetramethyl-15-(trityloxy)pentadeca-7,13-dien-1-ol (88)

HF-pyridine in pyridine (40 mL, prepared by slow addition of 12 mL pyridine to 3 mL HF-pyridine complex followed by dilution with 25 mL THF) was slowly added to a solution of TBS ether 87 (3.54 g, 4.10 mmol) in THF (5 mL) at 0° C. The mixture was stirred for 2 days at 0° C. and quenched with sat'd NaHCO$_3$ (100 mL). The aqueous layer was separated and extracted with Et$_2$O (3×50 mL). The combined organic layers were washed with sat'd CuSO$_4$ (3×50 mL), dried over MgSO$_4$, and concentrated. Flash column chromatography (EtOAc/hexane 15:85) afforded 2.08 g (66%) of the alcohol as a colorless oil: IR (CHCl$_3$) 3400, 2956, 2928, 2856, 1471, 1448, 1254, 1075, 836, 773 cm$^{-1}$; $^1$H NMR (300 MHz, CDCl$_3$) δ 7.52-7.48 (m, 6H), 7.36-7.24 (m, 9H), 5.87 (dd, J=15.7, 5.9 Hz, 1H), 5.59 (dt, J=15.7, 5.7 Hz, 1H), 5.55 (dd, J=10.6, 10.4 Hz, 1H), 5.33 (dd, J=11.0, 8.7 Hz, 1H), 4.58 (m, 1H), 3.94 (m, 1H), 3.60 (d, J=5.5 Hz, 2H), 3.38-3.32 (m, 2H), 3.25 (m, 1H), 2.62 (m, 1H), 2.45 (m, 1H), 1.59 (m, 1H), 1.55 (m, 1H), 1.47 (m, 1H), 1.35 (m, 1H), 1.09 (m, 1H), 1.04 (d, J=7.6 Hz, 3H), 1.01 (d, J=7.2 Hz, 3H), 0.96 (s, 9H), 0.94 (s, 9H), 0.93 (s, 9H), 0.79 (d, J=6.8 Hz, 3H), 0.75 (d, J=6.6 Hz, 3H), 0.15 (s, 9H), 0.14 (s, 3H), 0.10 (s, 3H), 0.09 (s, 3H), 0.08 (s, 3H), 0.07 (s, 3H); $^{13}$C NMR (75 MHz, CDCl$_3$) δ 144.4, 134.0, 132.7, 131.3, 128.7, 127.7, 126.8, 126.5, 86.8, 81.0, 73.0, 69.2, 66.5, 65.3, 42.6, 42.2, 36.2, 35.5, 34.6, 33.3, 26.2, 26.1, 25.9, 20.0, 18.4, 18.2, 18.1, 15.7, 15.6, 14.9, −2.8, −3.7, −3.8, −4.0, −4.1, −4.2; LRMS (ESI) 951.6 [M+Na]+, 705.1, 631.1, 557.0, 397.2, 381.2, 353.2, 243.1; HRMS (ESI) calcd for C$_{56}$H$_{92}$O$_5$Si$_3$Na 951.6150 [M+Na]+, found 951.6158; $[α]^{20}_D$ −33.5 (c 2.0, CHCl$_3$).

(2R,4E,6R,8R,9R,10S,11Z,13S,15S,16S,17E)-9,13,15-tris(tert-Butyldimethylsilyloxy)-2-((4S,5S)-2-(4-methoxy)phenyl)-5-methyl-1,3-dioxan-4-yl) -6,8,10,16-tetramethyl-19-(trityloxy)nonadeca-4,11,17trien-3-one (89)

The alcohol 88 (2.04 g, 2.20 µmol) in CH$_2$Cl$_2$ (30 mL) was treated with Dess-Martin periodinane (1.40 g, 3.30 1mol). After 1 h, the mixture was quenched with saturated NaHCO$_3$ (30 mL) and Na$_2$S$_2$O$_3$ (30 mL). The aqueous layer was extracted with ethyl ether (30 mL×2) and the combined extracts were dried over anhydrous MgSO$_4$. Filtration and concentration followed by short flash column chromatography filtration (hexane/EtOAc 4:1) to remove the residue from the Dess-Martin reagent provided crude aldehyde as a colorless oil, which was used for the next reaction without further purification. A mixture of ketophosphonate 38 (0.85 g, 2.20 mmol) and Ba(OH)$_2$ (0.30 g, activated by heating to 100° C. for 1-2 h before use) in THF (40 mL) was stirred at room temperature for 30 min. A solution of the above aldehyde in wet THF (4 mL+4×1 mL washings, 40:1 THF/H$_2$O) was then added. After stirring for 12 h, the reaction mixture was diluted with Et$_2$O (30 mL) and washed with sat'd NaHCO$_3$ (50 mL) and brine (50 mL). The organic solution was dried (MgSO$_4$) and the solvent was evaporated in vacuo. The residue was chromatographed (hexane/EtOAc 9:1) to yield 89 (2.04 g, 78% for 2 steps) as a colorless oil: IR (CHCl$_3$) 2957, 2929, 2855, 1618, 1518, 1461, 1388, 1251, 1078, 1036, 836, 773 cm$^{-1}$; $^1$H NMR (300 MHz, CDCl$_3$) δ 7.49-7.46 (m, 6H), 7.39 (m, 2H), 7.33-7.21 (m, 9H), 6.89 (m, 2H), 6.79 (dd, J=15.7, 7.4 Hz, 1H), 6.20 (d, J=15.6 Hz, 1H), 5.85 (dd, J=15.7, 5.9 Hz, 1H), 5.58 (dt, J=15.7, 4.6 Hz, 1H), 5.49 (dd, J=11.0, 10.4 Hz, 1H), 5.46 (s, 1H), 5.34 (dd, J=11.1, 8.6 Hz, 1H), 4.56 (m, 1H), 4.12 (dd, J=11.3, 4.6 Hz, 1H), 3.92 (m, 2H), 3.81 (s, 3H), 3.57 (d, J=5.6 Hz, 1H), 3.54 (m, 1H), 3.29 (dd, J=5.6, 2.4 Hz, 1H), 2.93 (m, 1H), 2.61 (m, 1H), 2.43 (m, 1H), 2.18 (m, 1H), 2.01 (m, 1H), 1.59-1.46 (m, 2H), 1.43 (m, 1H), 1.35-1.29 (m, 2H), 1.25 (d, J=7.0 Hz, 3H), 1.03 (d, J=7.2 Hz, 3H), 1.00 (d, J=7.0 Hz, 3H), 0.94 (s, 9H), 0.92 (s, 9H), 0.91 (s, 9H), 0.82 (d, J=7.0 Hz, 3H), 0.79 (d, J=6.7 Hz, 3H), 0.77 (d, J=6.5 Hz, 3H), 0.13 (s, 3H), 0.12 (s, 3H), 0.09 (s, 3H), 0.08 (s, 3H), 0.05 (s, 3H), 0.02 (s, 3H); $^{13}$C NMR (75 MHz, CDCl$_3$) δ 200.7, 159.8, 153.3, 144.3, 134.0, 133.3, 131.1, 130.8, 128.6, 127.7, 127.2, 126.8, 126.5, 125.7, 113.4, 100.8, 86.7, 82.7, 80.4, 72.8, 66.5, 65.8, 65.2, 55.2, 47.0, 42.8, 42.1, 39.1, 35.6, 34.9, 34.0, 32.3, 26.1, 26.0, 25.9, 19.7, 18.39, 18.36, 18.1, 16.4, 15.2, 14.7, 12.4, 10.7, −2.8, −3.6, −3.7, −4.0, −4.1; LRMS (ESI) 1209.7 [M+Na]+, 577.4, 359.2, 243.1, 165.0; HRMS (ESI) calcd for C$_{72}$H$_{1108}$Si$_3$Na 1209.7406 [M+Na]+, found 1209.7466; [α]$^{21}_D$ 8.6 (c 2.5, CHCl$_3$).

(2R,6S,8R,9R,10S,11Z,13S,15S,16S,17E)-9,13,15-tris(tert-Butyldimethylsilyloxy)-2-((4S,5S)-2-(4-methoxyphenyl)-5-methyl-1,3-dioxan-4-yl)-6,8,10,16-tetramethyl-19-(trityloxy)nonadeca-11,17-dien-3-one (90)

NiCl$_2$.6H$_2$O (0.20 g, 0.84 mmol) then portion wise NaBH$_4$ (0.17 g, 4.49 mmol) were added to a stirred solution of unsaturated ketone 89 (2.60 g, 1.72 μmol) in MeOH (60 mL), THF (20 mL) at 0° C. After 1 h, the reaction mixture was evaporated and filtered with celite using Et$_2$O as an eluent (30 mL). The organic phase was concentrated and the residue was purified by flash chromatography (EtOAc/hexane 1:9) to yield 90 (1.55 g, 76%) as a colorless oil: IR (CHCl$_3$) 2956, 2929, 2855, 1713, 1616, 1518, 1462, 1251, 1076, 836, 773 cm$^{-1}$; $^1$H NMR (300 MHz, CDCl$_3$) δ 7.52-7.50 (m, 6H), 7.42-7.24 (m, 1H), 6.92-6.86 (m, 2H), 5.87 (dd, J=15.7, 6.0 Hz, 2H), 5.60 (dt, J=15.8, 5.9 Hz, 1H), 5.50 (m, 1H), 5.49 (s, 1H), 5.37 (dd, J=10.9, 8.5 Hz, 1H), 4.59 (m, 1H), 4.17 (dd, J=11.3, 4.7 Hz, 1H), 3.98 (m, 2H), 3.82 (s, 3H), 3.62-3.55 (m, 3H), 3.29 (m, 1H), 2.73 (m, 1H), 2.65 (m, 1H), 2.49 (m, 2H), 2.06 (m, 1H), 1.63-1.50 (m, 2H), 1.47-1.32 (m, 2H), 1.27 (d, J=7.1 Hz, 3H), 1.26 (m, 1H), 1.06 (d, J=7.3 Hz, 3H), 1.03 (d, J=7.2 Hz, 3H), 0.97-0.94 (m, 27H), 0.90-0.84 (m, 2H), 0.83 (d, J=6.7 Hz, 3H), 0.76 (d, J=7.0 Hz, 3H), 0.69 (d, J=5.7 Hz, 3H), 0.17-0.05 (m, 18H); $^{13}$C NMR (75 MHz, CDCl$_3$) δ 211.7, 159.8, 144.4, 134.3, 133.1, 131.4, 130.9, 128.6, 127.9, 127.6, 127.1, 126.8, 126.4, 113.4, 100.8, 86.7, 82.9, 81.0, 72.8, 66.5, 65.2, 55.2, 48.3, 43.0, 42.2, 39.8, 38.3, 35.2, 35.1, 31.9, 31.3, 29.7, 26.2, 26.0, 25.9, 19.6, 18.6, 18.4, 18.1, 16.3, 14.6, 12.1, 9.7, −2.9, −3.5, −3.6, −4.0, −4.1, −4.2; LRMS (ESI) 1211.8 [M+Na]+, 577.3, 463.3, 413.3, 359.2, 316.9, 284.3; HRMS (ESI) calcd for C$_{72}$H$_{112}$O$_8$Si$_3$Na 1211.7563 [M+Na]+, found 1211.7629; [α]$^{20}_D$ −4.3 (c 1.0, CHCl$_3$).

(2S,3R,6S,8R,9R,10S,11Z,13S,15S,16S,17E)-9,13,15-tris(tert-Butyldimethylsilyloxy)-2-((4S,5S)-2-(4-methoxyphenyl)-5-methyl-1,3-dioxan-4-yl)-6,8,10,16-tetramethyl-19-(trityloxy)nonadeca-11,17-dien-3-ol (91)

NaBH$_4$ (0.074 g, 1.96 mmol) was added to a solution of ketone 90 (1.55 g, 1.30 mmol) in MeOH (21 mL) at 0° C. After stirring for 2 h at 0° C., the reaction mixture was evaporated and water (30 mL) was added. The reaction mixture was extracted with ether (2×40 mL) and washed with brine (50 mL), dried over MgSO$_4$ and concentrated in vacuo. The residue was purified by flash chromatography (EtOAc/hexane 1:9) to yield 1.02 g of major product β (less polar, 62%) and 0.60 g (more polar, 36%) of minor product α as colorless oils: (91β) IR (CHCl$_3$) 3540, 2956, 2929, 2855, 1615, 1518, 1461, 1385, 1252, 1074, 835, 773, 706 cm$^{-1}$; $^1$H NMR (300 MHz, CDCl$_3$) δ 7.54-7.50 (m, 6H), 7.42 (m, 2H), 7.37-7.25 (m, 9H), 6.94-6.91 (m, 2H), 5.88 (dd, J=15.7, 6.0 Hz, 1H), 5.61 (dt, J=16.0, 5.7 Hz, 1H), 5.56 (s, 1H), 5.50 (m, 1H), 5.37 (dd, J=10.8, 8.6 Hz, 1H), 4.60 (m, 1H), 4.17 (dd, J=11.2, 4.6 Hz, 1H), 3.96 (m, 1H), 3.87 (m, 1H), 3.84 (s, 3H), 3.74 (m, 1H), 3.64-3.53 (m, 3H), 3.32 (m, 1H), 3.20 (br, 1H), 2.67 (m, 1H), 2.44 (m,1H), 2.18 (m, 1H), 1.83 (m, 1H), 1.67-1.51 (m, 2H), 1.50-1.32 (m, 3H), 1.26 (m, 1H), 1.08 (d, J=6.8 Hz, 3H), 1.07 (m, 2H), 1.06 (d, J=7.0 Hz, 3H), 1.04 (d, J=7.4 Hz, 3H), 0.98-0.85 (m, 2H), 0.82 (d, J=6.7 Hz, 3H), 0.81 (d, J=6.7 Hz, 3H), 0.77 (d, J=6.0 Hz, 3H), 0.18-0.09 (m, 18H); $^{13}$C NMR (75 MHz, CDCl$_3$) δ 160.0, 144.5, 144.4, 134.4, 132.9, 131.6, 130.7, 128.6, 127.6, 127.2, 126.8, 126.7, 126.4, 113.6, 101.2, 89.1, 86.7, 81.1, 76.8, 73.1, 72.8, 66.5, 55.2, 43.0, 42.3, 39.9, 37.2, 35.3, 35.1, 34.7, 32.3, 30.4, 30.2, 26.2, 26.1, 25.9, 19.6, 18.8, 18.4, 18.13, 18.10, 16.3, 14.6, 11.9, 5.5, −2.8, −3.56, −3.61, −4.0, −4.1, −4.16, −4.25; LRMS (API-ES) 1213.6 [M+Na]+, 557.0, 359.2, 243.1; HRMS (ESI) calcd for C$_{72}$H$_{114}$O$_8$Si$_3$Na 1213.7719 [M+Na]+, found 1213.7717; [α]$^{20}_D$ −0.68 (c 7.1, CHCl$_3$): (91α) IR (CHCl$_3$) 3531, 2956, 2929, 2855, 1615, 1518, 1462, 1383, 1252, 1075, 836, 773 cm$^{-1}$; $^1$H NMR (300 MHz, CDCl$_3$) δ 7.53-7.49 (m, 6H), 7.44-7.41 (m, 2H), 7.36-7.24 (m, 9H), 6.94-6.91 (m, 2H), 5.86 (dd, J=15.7, 6.0 Hz, 1H), 5.60 (dt, J=15.7, 5.7 Hz, 1H), 5.54 (s, 1H), 5.56-5.47 (m, 1H), 5.36 (dd, J=11.0, 8.6 Hz, 1H), 4.60 (m, 1H), 4.17 (dd, J=11.2, 4.6 Hz, 1H), 3.97-3.91 (m, 2H), 3.84 (s, 3H), 3.62 (d, J=4.9 Hz, 2H), 3.61-3.53 (m, 2H), 3.32 (m, 1H), 2.67 (m, 1H), 2.44 (m,1H), 2.16 (m, 1H), 1.82 (m, 1H), 1.72-1.50 (m, 4H), 1.42-1.33 (m, 2H), 1.32-1.22 (m, 2H), 1.14 (d, J=7.1 Hz, 3H), 1.06 ((d, J=7.0 Hz, 3H), 1.03 (d, J=7.0 Hz, 3H), 0.97-0.92 (m, 27H), 0.90-0.85 (m, 2H), 0.81 (d, J=6.4 Hz, 3H), 0.79 (d, J=6.6 Hz, 3H), 0.76 (d, J=5.7 Hz, 3H), 0.17-0.09 (m, 18H); $^{13}$C NMR (75 MHz, CDCl$_3$) δ 160.0, 144.6, 144.4, 134.4, 133.0, 131.6, 131.1, 128.7, 127.7, 127.6, 127.3, 126.8, 126.7, 126.4, 113.6, 101.0, 86.7, 82.8, 81.2, 75.1, 73.3, 72.8, 66.6, 65.2, 55.2, 43.0, 42.3, 39.9, 37.9, 35.3, 35.1, 34.6, 33.4, 30.3, 26.3, 26.1, 26.0, 19.7, 19.0, 18.4, 18.1, 16.4, 14.6, 11.9, 11.1, −2.8, −3.5, −4.0, −4.07, −4.13; LRMS (ESI) 1213.8 [M+Na]+, 633.2, 359.2; HRMS (ESI) calcd for C$_{72}$H$_{114}$O$_8$Si$_3$Na 1213.7719 [M+Na]+, found 1213.7766; [α]$^{20}_D$ −1.4 (c 4.7, CHCl$_3$).

(4S,5S)-4-((2R,3R,6S,8R,9R,10S,11Z,13S,15S,16S,17E)-3,9,13,15-tetrakis(tert-Butyldimethylsilyloxy)-6,8,10,16-tetramethyl-19-(trityloxy)nonadeca-11,17-dien-2-yl)-2-(4-meyhoxypheny)-5-methyl-1,3-dioxane (92)

TBSOTf (0.30 mL, 2.57 mmol) was added to a stirred solution of alcohol 91β (1.02 g, 0.86 mmol) and 2,6-lutidine (0.20 mL, 1.71 mmol) in CH$_2$Cl$_2$ (17 mL) at 0° C. and the reaction mixture was stirred for 1 h at ambient temperature. The reaction mixture was quenched by the addition of water (50 mL). The reaction mixture was extracted by CH$_2$Cl$_2$ and dried over MgSO$_4$ followed by the evaporation of the solution under reduced pressure. The residue was purified by short column chromatography (hexane/EtOAc 9:1) to yield product (0.97 g, 86%) as a colorless oil: IR (CHCl$_3$) 2955, 2928, 2856, 1615, 1518, 1471, 1462, 1387, 1251, 1074, 1038, 835, 773 cm$^{-1}$; $^1$H NMR (300 MHz, CDCl$_3$) δ 7.52-7.46 (m, 6H), 7.45-7.42 (m, 2H), 7.35-7.22 (m, 9H), 6.92-6.89 (m, 2H), 5.86 (dd, J=15.7, 6.0 Hz, 1H), 5.59 (dt, J=15.7, 4.9 Hz, 1H), 5.48 (m, 1H), 5.47 (s, 1H), 5.36 (dd, J=11.1, 8.6 Hz, 1H), 4.58 (m, 1H), 4.15 (dd, J=11.2, 4.6 Hz, 1H), 3.96 (m, 1H), 3.81 (s, 3H), 3.73-3.66 (m, 2H), 3.60 (d, J=5.6 Hz, 2H), 3.55 (m, 1H), 3.19 (m, 1H), 2.65 (m 1H), 2.42 (m, 1H), 2.07 (m, 1H), 1.91 (m, 1H), 1.57 (m, 2H), 1.40-1.21 (m, 3H), 1.14 (m, 1H), 1.06 (d, J=6.7 Hz, 3H), 1.04 (d, J=5.9 Hz, 3H), 1.02 (d, J=6.9 Hz, 3H), 0.96-0.92 (m, 36H), 0.88-0.84 (m, 3H), 0.80 (m, 1H), 0.77 (d, J=6.5 Hz, 3H), 0.76 (d, J=6.4 Hz, 3H), 0.71 (d, J=5.1 Hz, 3H), 0.16-0.03 (m, 24H); $^{13}$C NMR (75 MHz, CDCl$_3$) δ 159.7, 144.6, 144.4, 134.4, 133.2, 131.7, 131.4, 128.7, 127.7, 127.2, 126.8, 126.4, 113.4, 100.4, 86.7, 81.8, 81.4, 75.0, 73.3, 72.8, 66.5, 65.2, 55.2, 43.1, 42.3, 39.7, 38.9, 35.3, 35.0, 34.0, 31.2, 30.7, 30.6, 26.2, 26.1, 26.00, 25.95, 19.5, 19.1, 18.4, 18.13, 18.10, 16.5, 14.5, 12.4, 10.6, -2.8, -3.4, -3.95, -3.98, -4.2, -4.3; LRMS (ESI) 1327.8 [M+Na]+, 977.8, 739.6; HRMS (ESI) calcd for C$_{78}$H$_{128}$O$_8$Si$_4$Na 1327.8584 [M+Na]+, found 1327.8534; [α]$^{20}_D$+6.7 (c 0.65, CHCl$_3$).

(2S,3S,4R,5R,8S,10R,11R,12S,13Z,15S,17S,18S, 19E)-3-(4-Methoxybenzyloxy)-5,11,15,17-tetrakis (tert-butyldimethylsilyloxy)-2,4,8,10,12,18-hexamethyl-21-(trityloxy)henicosa-13,19-dien-1-ol (93)

DIBAL (1.0 M in hexane, 7.4 mL, 7.4 mmol) was added to a stirred solution of TBS protected acetal 92 (0.97 g, 0.74 mmol) in anhydrous CH$_2$Cl$_2$ (3 mL), under an atmosphere of N$_2$ at 0° C. dropwise. After stirring for additional 30 min at 0° C., the reaction mixture was quenched by the careful addition of aqueous sat'd potassium sodium tartrate solution (30 mL) and stirred for 3 h at room temperature. The organic layer was separated, and the aqueous layer was extracted with CH$_2$Cl$_2$ (20 mL). The combined organic layers were washed with brine and dried over MgSO$_4$ followed by the evaporation of the organic solution under reduced pressure. The residue was purified by column chromatography (EtOAc/hexane 1:9) to obtain 93 (0.94 g, 97 %) as a colorless oil: IR (CHCl$_3$) 3501, 2956, 2929, 2856, 1613, 1514, 1471, 1462, 1251, 1075, 835, 773, 705 cm$^{-1}$; $^1$H NMR (300 MHz, CDCl$_3$) δ 7.55-7.51 (m, 6H), 7.37-7.25 (m, 11H), 6.94-6.92 (m, 2H), 5.90 (dd, J=15.7, 5.9 Hz, 1H), 5.62 (dt, J=15.6, 5.6 Hz, 1H), 5.56-5.48 (m, 1H), 5.40 (dd, J=11.2, 8.5 Hz, 1H), 4.61 (m, 1H), 4.60 (s, 2H), 3.99 (m, 1H), 3.90 (m, 1H), 3.83 (s, 3H), 3.69 (m, 1H), 3.64 (d, J=5.3 Hz, 1H), 3.53 (m, 1H), 3.31 (m, 1H), 2.99 (m 1H), 2.70 (m, 1H), 2.47 (m, 1H), 2.00 (m, 2H), 1.65-1.52 (m, 3H), 1.45-1.37 (m, 1H), 1.33 (m, 1H), 1.30 (m, 1H), 1.20 (d, J=6.9 Hz, 3H), 1.10 (d, J=6.6 Hz, 3H), 1.09 (d, J=6.9 Hz, 3H), 1.05 (d, J=7.0 Hz, 3H), 1.00-0.96 (m, 36H), 0.92-0.86 (m, 2H), 0.82 (d, J=6.6 Hz, 3H), 0.76 (d, J=5.5 Hz, 3H), 0.19-0.11 (m, 24H); $^{13}$C NMR (75 MHz, CDCl$_3$) δ 159.2, 144.5, 144.4, 134.3, 133.1, 131.5, 130.5, 129.2, 128.6, 127.6, 126.8, 126.4, 113.8, 86.7, 86.0, 81.1, 75.3, 73.6, 72.8, 66.5, 65.1, 65.0, 55.1, 43.0, 42.3, 40.5, 40.0, 36.8, 35.2, 35.1, 34.0, 32.1, 30.4, 26.2, 26.1, 26.0, 25.9, 19.6, 18.9, 18.4, 18.1, 16.5, 15.8, 14.6, 9.9, -2.8, -3.4, -3.5, -3.8, -4.0, -4.2, -4.4; LRMS (ESI) 1329.8 [M+Na]+, 1087.7, 801.5, 669.4, 537.3, 480.2, 359.2, 243.1; HRMS (ESI) calcd for C$_{78}$H$_{130}$O$_8$Si$_4$Na 1329.8741 [M+Na]+, found 1329.8778; [α]$^{20}_D$-9.9 (c 0.36, CHCl$_3$).

((2E,4S,5S,7S,8Z,10S,11R,12R,14S,17R,18R,19S, 20S,21Z)-19-(4-Methoxybenzyloxy)-7,11,17-tris(tert -butyldimethylsilyloxy)-5-(tert-butyldimethylsilyloxy))-4,10,12,14, 18,20-hexamethyltetracosa-2,8, 21,23-tetraenyloxy)triphenylmethane (94)

The alcohol 93 (0.94 g, 0.72 μmol) in CH$_2$Cl$_2$ (20 mL) was treated with Dess-Martin periodinane (0.46 g, 1.08 μmol). After 1 h, the mixture was quenched with saturated NaHCO$_3$ (20 mL) and Na$_2$S$_2$O$_3$ (20 mL). The aqueous layer was extracted with ethyl ether (20 mL×2) and the combined extracts were dried over anhydrous MgSO$_4$. Filtration and concentration followed by short flash column chromatography (hexane/EtOAc 9:1) to remove Dess-Martin residue provided crude aldehyde as a colorless oil, which was used for the next reaction without further purification. To a stirred solution of the above crude aldehyde and 1-bromoallyl trimethylsilane (0.89 g) in anhydrous THF (18 mL) under an atmosphere of N$_2$ at room temperature was added CrCl$_2$ (0.73 g, 5.94 mmol), and the mixture was stirred for additional 14 h at ambient temperature. The reaction mixture was diluted with hexane followed by filtration through celite. After the evaporation of the solvent under reduced pressure, the residue was purified by short silica gel column chromatography using EtOAc/hexane (1:9) as an eluent. The foregoing product in THF (40 mL) was cooled to 0° C. and NaH (95% w/w, 0.36 g, 14.4 mmol) was added in one portion. The ice bath was removed after 15 min and the mixture was stirred for 2 h at ambient temperature. The reaction mixture was cooled to 0° C., quenched with H$_2$O (5 mL), extracted with ethyl ether (20 mL×2). The combined organic layers were washed with brine and dried over MgSO$_4$ followed by the evaporation of the organic solution under reduced pressure. The residue was purified by column chromatography (hexane/EtOAc 98:2) to obtain 94 (0.81 g, 85% for 3 steps) as a colorless oil: IR (CHCl$_3$) 2955, 2928, 2856, 1614, 1514, 1471, 1462, 1249, 1076, 835, 772, 705 cm$^{-1}$; $^1$H NMR (300 MHz, CDCl$_3$) δ 7.60-7.56 (m, 6H), 7.43-7.27 (m, 1H), 6.99-6.96 (m, 1H), 6.71 (ddd, J=16.9, 10.6, 10.5 Hz, 1H), 6.14 (t, J=11.0 Hz, 1H), 5.97 (dd, J=15.7, 5.9 Hz, 1H), 5.82-5.77 (m, 1H), 5.74-5.70 (m, 1H), 5.68-5.62 (m, 1H), 5.61-5.56 (m, 1H), 5.46 (dd, J=11.1, 8.6 Hz, 1H), 5.28 (d, J=16.9 Hz, 1H), 5.20 (d, J=10.3 Hz, 1H), 4.66 (m, 3H), 4.05 (m, 1H), 3.86 (s, 3H), 3.76 (m, 1H), 3.69 (d, J=5.2 Hz, 1H), 3.48 (m, 1H), 3.35 (m, 1H), 3.15 (m, 1H), 2.76 (m, 1H), 2.53 (m, 1H), 2.34 (m, 1H), 1.82 (m, 1H), 1.70-1.57 (m, 3H), 1.56-1.32 (m, 3H), 1.25 (d, J=6.8 Hz, 3H), 1.14 (d, J=7.1 Hz, 3H), 1.12 (m, 2H), 1.11 (d, J=7.1 Hz, 3H), 1.08-1.03 (m, 36H), 0.98-0.90 (m, 2H), 0.86 (d, J=6.6 Hz, 3H), 0.76 (d, J=5.1 Hz, 3H), 0.25-0.13 (m, 24H); $^{13}$C NMR (75 MHz, CDCl$_3$) δ 159.0, 146.2, 144.6, 144.4, 134.5, 134.3, 133.2, 132.4, 131.4, 130.2, 129.0, 128.7, 127.7, 126.8, 126.5, 117.2, 113.7, 86.7, 84.5, 81.3, 75.1, 72.9, 66.6, 65.2, 55.1, 43.0, 42.3, 40.6, 40.2, 35.6, 35.25, 35.19, 33.9, 32.6, 30.3, 26.3, 26.1, 26.04, 25.99, 19.6, 18.9, 18.4, 18.2, 16.6, 14.7, 9.2, -2.8, -3.36, -3.4, -3.5, -3.9, -4.1, -4.4; LRMS (ESI) 1351.8 [M+Na]+, 837.1, 763.1, 689.541.0; HRMS (ESI) calcd for C$_{81}$H$_{132}$O$_7$Si$_4$Na 1351.8948 [M+Na]+, found 1351.8973; [α]$^{20}_D$+0.4 (c 0.51, CHCl$_3$).

(2E,4S,5S,7S,8Z,10S,11R,12R,14S,17R,18R,19S, 20S,21Z)-19-(4-Methoxybenzyloxy)-5,7,11,17-tetrakis(tert-butyldimethylsilyloxy)-4,10,12,14,18,20-hexamethyltetracosa-2, 8,21,23-tetrean-1-ol (95)

ZnBr$_2$ solution (0.42 g in 5 mL CH$_2$Cl$_2$ and 0.8 mL of MeOH) was added to a stirred solution of trityl ether 94

(0.50 g, 0.38 μmol) in MeOH (3 mL), CH$_2$Cl$_2$ (18 mL) at 0° C. dropwise for 30 min. After 4 h, the reaction mixture was quenched with saturated NaHCO$_3$ solution (20 mL) and extracted with Et$_2$O (10 mL×2). The organic phase was separated, dried with MgSO$_4$ and concentrated. The residue was purified by flash chromatography (EtOAc/hexane 1:9) to yield 0.34 g of product 95 (83%) as a colorless oil: IR (CHCl$_3$) 3410, 2956, 2929, 2856, 1613, 1514, 1471, 1251, 1076, 836, 773 cm$^{-1}$; $^1$H NMR (300 MHz, CDCl$_3$) δ 7.31-7.29 (m, 2H), 6.90-6.87 (m, 2H), 6.60 (ddd, J=16.8, 10.6, 10.5 Hz, 1H), 6.02 (t, J=11.0 Hz, 1H), 5.79 (dd, J=15.6, 5.8 Hz, 1H), 5.62 (d, J=9.3 Hz, 1H), 5.60 (m, 1H), 5.47 (t, J=10.3 Hz, 1H), 5.32 (dd, J=10.7, 8.9 Hz, 1H), 5.18 (d, J=16.8 Hz, 1H), 5.10 (d, J=10.2 Hz, 1H), 4.54 (m, 3H), 4.07 (d, J=5.9 Hz, 2H), 3.89 (m, 1H), 3.81 (s, 3H), 3.64 (m, 1H), 3.35 (m, 1H), 3.24 (br, 1H), 3.00 (m, 1H), 2.61 (m, 1H), 2.40 (m, 1H), 1.68 (m, 1H), 1.55-1.42 (m, 3H), 1.38-1.21 (m, 3H), 1.12 (d, J=6.7 Hz, 3H), 1.02-0.99 (m, 3H), 0.98 (d, J=7.0 Hz, 3H), 0.94-0.89 (m, 40H), 0.79 (d, J=6.9 Hz, 3H), 0.76 (d, J=6.3 Hz, 3H), 0.11-0.06 (m, 24H); $^{13}$C NMR (75 MHz, CDCl$_3$) δ 159.0, 134.9, 134.5, 133.1, 132.4, 131.5, 131.4, 129.1, 128.9, 128.7, 117.2, 113.7, 84.5, 81.3, 75.1, 72.7, 66.4, 64.1, 55.3, 42.7, 42.0, 40.5, 40.4, 35.5, 35.23, 35.20, 33.9, 32.6, 30.5, 26.3, 26.03, 26.00, 25.96, 19.7, 18.9, 18.8, 18.5, 18.2, 18.1, 16.6, 14.7, 9.2, −2.8, −3.47, −3.53, −4.03, −4.05, −4.2, −4.5, −4.7; LRMS (ESI) 1109.7 [M+Na]+, 945.3, 797.3, 723.2, 577.4, 499.2, 413.3, 359.3; HRMS (ESI) calcd for C$_{62}$H$_{180}$O$_7$Si$_4$Na 1109.7852 [M+Na]+, found 1109.7898; [α]$^{20}_D$ −2.0 (c 2.6, CHCl$_3$).

(2Z,4E,6S,7S,9S,10Z,12S,13R,14R,16S,19R,20R, 21S,22S,23Z)-Methyl-21-(4-methoxybenzyloxy)-7, 9,13,19-tetrakis(tert-butyldimethylsilyloxy)-6,12,14, 16,20,22-hexamethylhexacosa-2,4,10,23,25-pentaenoate (96)

The alcohol 95 (0.34 g, 0.31 μmol) in CH$_2$Cl$_2$ (20 mL) was treated with Dess-Martin periodinane (0.20 g, 0.47 μmol). After 1 h, the mixture was quenched with saturated NaHCO$_3$ (5 mL) and Na$_2$S$_2$O$_3$ (5 mL). The aqueous layer was extracted with ethyl ether (10 mL×2) and the combined extracts were dried over anhydrous MgSO$_4$. Filtration and concentration followed by short flash column chromatography (hexane/EtOAc 9:1) to remove the Dess-Martin residue provided the crude aldehyde as a colorless oil, which was used for the next reaction without further purification. To a stirred solution of bis(2,2,2-trifluoroethyl)-(methoxycarbonylmethyl) phosphate (0.080 mL, 0.37 μmol), 18-crown-6 (0.41 g, 1.55 mmol) in THF (6 mL) cooled to −78° C. was added dropwise potassium bis(trimethylsilyl)amide (0.75 mL, 0.37 μmol, 0.5M solution in toluene). Thereafter the above aldehyde in THF (1 mL) was added and the solution was stirred for 4 h at −78° C. The reaction mixture was quenched by addition of a sat'd NH$_4$Cl solution (5 mL) and diluted with diethyl ether (20 mL). The layers were separated and organic phase was washed with brine (30 mL) and dried with MgSO$_4$, filtered, and concentrated. The residue was purified by flash chromatography (EtOAc/hexane 5:95) to obtain (E,Z)-doubly unsaturated ester 96 (0.32 g, 90% for 2 steps) as a colorless oil: IR (CHCl$_3$) 2956, 2929, 2885, 1722, 1641, 1514, 1471, 1250, 1174,1075, 836, 773 cm$^{-1}$; $^1$H NMR (300 MHz, CDCl$_3$) δ 7.34 (dd, J=15.5, 11.2 Hz, 1H), 7.29-7.26 (m, 2H), 6.87-6.84 (m, 2H), 6.56 (ddd, J=17.0, 10.6, 10.5 Hz, 1H), 6.52 (t, J=11.4 Hz, 1H), 6.19 (dd, J=15.5, 6.4 Hz, 1H), 5.99 (t, J=11.0 Hz, 1H), 5.57 (t, J=10.5 Hz, 1H), 5.54 (d, J=11.3 Hz, 1H), 5.42 (m, 1H), 5.30 (m, 1H), 5.15 (d, J=16.8 Hz, 1H), 5.07 (d, J=10.1 Hz, 1H), 4.51 (m, 3H), 3.92 (m, 1H), 3.78 (s, 3H), 3.70 (s, 3H), 3.61 (m, 1H), 3.32 (dd, J=7.9, 2.8 Hz, 1H), 3.20 (m, 1H), 2.97 (m, 2H), 2.57 (m, 2H), 1.65 (m, 1H), 1.56-1.39 (m, 3H), 1.29-1.16 (m, 3H), 1.10 (d, J=6.8Hz, 3H), 1.03 (d, J=6.9 Hz, 3H), 0.98 (d, J=7.0 Hz, 3H), 0.94 (d, J=6.9 Hz, 3H), 0.93-0.83(m, 39H), 0.77 (m, 1H), 0.91 (s, 9H), 0.87 (s, 9H), 0.83 (d, J=6.4 Hz, 3H), 0.82 (d, J=6.0 Hz, 3H), 0.13 (s, 3H), 0.76 (d, J=6.6 Hz, 3H), 0.71 (d, J=5.9 Hz, 3H), 0.10-0.02 (m, 24H); $^{13}$C NMR (75 MHz, CDCl$_3$) δ 166.8, 159.0, 147.2, 145.6, 134.5, 133.1, 132.4, 131.5, 131.4, 129.0, 128.9, 126.4, 117.1, 115.1, 113.7, 84.4, 81.3, 75.0, 72.8, 72.7, 66.4, 55.2, 50.9, 42.9, 42.6, 40.5, 40.2, 35.3, 35.2, 33.8, 32.6, 30.5, 26.3, 26.0, 25.9, 19.6, 18.9, 18.8, 18.4, 18.2, 18.1, 16.7, 14.5, 9.2, −2.8, −3.4, −3.5, −3.6, −4.07, −4.14, −4.24, −4.49; LRMS (ESI) 1163.8 [M+Na]+, 1107.9, 782.5; HRMS (ESI) calcd for C$_{65}$H$_{120}$O$_8$Si$_4$Na 1163.7958 [M+Na]+, found 1163.8004; [α]$^{20}_D$ −27.3 (c 5.0, CHCl$_3$).

(2Z,4E,6S,7S,9S,10Z,12S,13R,14R,16S,19R,20R, 21S,22S,23Z)-Methyl-7,9,13,19-tetrakis(tert-butyldimethylsilyloxy)-21-hydroxy-6,12,14,16,20,22-hexamethylhexacosa-2,4,10,23, 25-pentaenoate (97)

The ester 96 (0.15 g, 0.14 μmol) was added to CH$_2$Cl$_2$ (5 mL) and H$_2$O (0.2 mL) and DDQ (34 mg, 0.15 μmol) was added at 0° C. After 1 h of stirring at 0° C., the reaction mixture was quenched by adding sat'd NaHCO$_3$ (5 mL). The organic phase was washed by sat'd NaHCO$_3$ solution (3×10 mL) and brine, dried over MgSO$_4$ and concentrated. Purification by flash column chromatography (EtOAc/hexane 1:9) furnished 97 (0.12 g, 90%) as a colorless oil: IR (CHCl$_3$) 3540, 2956, 2929, 2856, 1641, 1601, 1471, 1462, 1407, 1379, 1361, 1255, 1174, 1089, 1004, 836, 773 cm$^{-1}$; $^1$H NMR (300 MHz, CDCl$_3$) δ 7.33 (dd, J=15.5, 11.2 Hz, 1H), 6.61 (ddd, J=16.9, 10.5, 10.4 Hz, 1H), 6.51 (t, J=11.4 Hz, 1H), 6.17 (dd, J=15.5, 5.9 Hz, 1H), 6.07 (t, J=11.0 Hz, 1H), 5.54 (d, J=11.3 Hz, 1H), 5.45-5.37 (m, 2H), 5.28 (m, 1H), 5.18 (d, J=16.8 Hz, 1H), 5.09 (d, J=10.1 Hz, 1H), 4.51 (m, 1H), 3.91 (m, 1H), 3.74 (m, 1H), 3.69 (s, 3H), 3.45 (m, 1H), 3.23 (m, 1H), 3.76 (m, 1H), 2.56 (m, 2H), 2.29 (br, 1H), 1.68 (m, 1H), 1.56-1.41 (m, 3H), 1.34-1.17 (m, 3H), 1.02 (d, J=6.9 Hz, 3H), 0.97 (d, J=6.9 Hz, 3H), 0.94 (d, J=6.8 Hz, 3H), 0.90-0.84 (m, 40H), 0.81 (d, J=5.8 Hz, 3H), 0.77 (d, J=6.5 Hz, 3H), 0.76 (d, J=6.2 Hz, 3H), 0.08-0.01 (m, 24H); $^{13}$C NMR (75 MHz, CDCl$_3$) δ 166.8, 147.3, 145.5, 135.3, 133.0, 132.3, 131.5, 129.9, 126.4, 117.6, 115.2, 81.3, 77.5, 76.7, 72.7, 66.4, 50.9, 42.9, 42.6, 40.1, 37.9, 36.1, 35.4, 35.2, 33.8,.32.2, 30.6, 26.2, 26.0, 25.9, 19.6, 19.0, 18.4, 18.10, 18.05, 17.7, 16.6, 14.4, 6.9, −2.8, −3.5, −3.6, −3.7, −4.1, −4.15, −4.21, −4.4; LRMS (ESI) 1043.7 [M+Na]+, 889.8, 757.6, 625.5, 544.3, 364.4; HRMS (ESI) calcd for C$_{57}$H$_{112}$O$_7$Si$_4$Na 1043.7383 [M+Na]+, found 1043.7433; [α]$^{20}_D$ −40.3 (c 2.1, CHCl$_3$).

(2Z,4E,6S,7S,9S,10Z,12S,13R,14R,16S,19R,20R, 21S,22S,23Z)-7,9,13,19-tetrakis(tert-Butyldimethylsilyloxy)-21-hydroxy-6,12,14,1 6,20,22-hexamethylhexacosa-2,4,10,23,25-pentaenoic acid (98)

1N aqueous KOH solution (1.2 mL) was added to a stirred solution of the above 97 (0.12 g, 0.12 μmol) in EtOH (12 mL), THF (1 mL) and the mixture was refluxed gently until the ester disappeared (about 5 h) as determined by TLC analysis. The ethanolic solution was concentrated and then diluted with ether (4 mL). After the solution was acidified to pH3 with 1N HCl solution, organic phase was separated and aqueous phase was extracted with Et$_2$O (2×5 mL). The combined organic phases were dried with MgSO$_4$, concentrated and used without further purification: IR (CHCl$_3$) 2957, 2929, 2857, 1692, 1471, 1462, 1254, 1089, 836, 773 cm$^{-1}$; $^1$H NMR (300 MHz, CDCl$_3$) δ 7.34 (dd, J=15.1, 11.4 Hz, 1H), 6.64 (ddd, J=16.0, 10.8, 10.5 Hz, 1H), 6.61 (t, J=11.2 Hz, 1H), 6.22 (dd, J=15.4, 6.0 Hz, 1H), 6.09 (t, J=11.0 Hz, 1H), 5.58 (d, J=11.3 Hz, 1H), 5.49-5.39 (m, 2H), 5.34-5.28 (m, 1H), 5.20 (d, J=16.7 Hz, 1H), 5.11 (d, J=10.2 Hz, 1H), 4.55 (m, 1H), 3.95 (m, 1H), 3.76 (m, 1H), 3.50 (m, 1H), 3.27 (m, 1H), 2.81 (m, 1H), 2.58 (m, 2H), 1.71 (m, 1H), 1.57-1.50 (m, 3H), 1.44-1.31 (m, 3H), 1.25 (d, J=7.3 Hz, 3H), 1.21 (d, J=6.1 Hz, 3H), 1.04 (d, J=6.9 Hz, 3H), 0.99 (d, J=7.0 Hz, 3H), 0.96-0.89 (m, 40H), 0.81 (d, J=6.2 Hz, 3H), 0.79 (d, J=5.9 Hz, 3H), 0.11-0.05 (m, 24H); $^{13}$C NMR (75 MHz, CDCl$_3$) δ 171.1, 148.1, 147.3, 135.2, 132.8, 132.3, 131.6, 129.9, 126.6, 117.6, 115.0, 81.3, 77.6, 72.7, 66.4, 58.3, 43.0, 42.6, 40.1, 37.9, 36.0, 35.4, 35.2, 33.8, 32.2, 30.6, 26.3, 26.0, 25.9, 25.2, 19.6, 19.0, 18.4, 18.09, 18.05, 17.7, 16.6, 14.5, 7.0, −2.8, −3.45, −3.54, −3.7, −4.1, −4.2, −4.4; LRMS (ESI) 1029.7 [M+Na]+, 915.7, 897.7; HRMS (ESI) calcd for C$_{56}$H$_{110}$O$_7$Si$_4$Na 1029.7226 [M+Na]+, found 1029.7257; [α]$^{20}_D$−41.7 (c 1.4, CHCl$_3$).

8(S),10(S),14(R),20(R)-tetrakis(tert-Butyldimethyl-silyloxy)-7(S),13(S),15(R),17(S),21 (S)-pentam-ethyl-22(S)-(1(S)-methylpenta-2,4-dienyl)oxacy-clodocosa-3,5,11-trien-2-one (99)

A solution of above acid 98 in THF (2mL) was treated at 0° C. with Et$_3$N (0.10 mL, 0.72 μmol) and 2,4,6-trichlo-robenzoyl chloride (0.095 mL, 0.60 μmol). The reaction mixture was stirred at 0° C. for 30 min and then added to 4-DMAP (60 mL, 0.02 M solution in toluene) at 25° C. and stirred overnight. The reaction mixture was concentrated, Et$_2$O (10 mL) was added and the crude was washed with 0.5 N HCl (2×10 mL), dried over MgSO$_4$. Purification by flash column chromatography (EtOAc/hexane 2:98) furnished macrolactone 99 (93 mg, 78% for 2 steps) as a colorless oil: IR (CHCl$_3$) 2957, 2929, 2856, 1745, 1715, 1581, 1471, 1369, 1270, 1117, 1082, 836, 773 cm$^1$; $^1$H NMR (300 MHz, CDCl$_3$) δ 7.11 (dd, J=15.3, 10.5 Hz, 1H), 6.59 (ddd, J=16.8, 10.7, 10.5 Hz, 1H), 6.22 (dd, J=15.4, 6.0 Hz, 1H), 6.07 (dd, J=15.4, 10.6 Hz, 1H), 5.92 (t, J=10.9 Hz, 1H), 5.70 (d, J=15.4 Hz, 1H), 5.46 (t, J=10.5 Hz, 1H), 5.35-5.27 (m, 2H), 5.20 (d, J=8.4 Hz, 1H), 5.12 (d, J=16.8 Hz, 1H), 5.04 (d, J=10.3 Hz, 1H), 4.53 (m, 1H), 3.91 (m, 1H), 3.41 (m, 1H), 3.19 (m, 1H), 2.94 (m, 1H), 2.55 (m, 2H), 1.94 (m, 1H), 1.40-1.29 (m, 3H), 1.26-1.15 (m, 3H), 1.00-0.85 (m, 52H), 0.74 (d, J=6.7 Hz, 3H), 0.63 (d, J=6.2 Hz, 3H), 0.08-0.00 (m, 24H); $^{13}$C NMR (75 MHz, CDCl$_3$) δ 166.9, 144.93, 144.88, 136.0, 135.0, 133.5, 132.4, 130.7, 129.3, 120.2, 117.2, 80.3, 75.7, 73.9, 72.7, 66.3, 42.4, 41.0, 40.6, 39.3, 36.5, 35.8, 35.1, 34.5, 31.9, 29.7, 26.2, 26.0, 25.9, 21.6, 19.8, 19.7, 18.4, 18.11, 18.07, 17.9, 14.9, 11.3, −2.6, −3.6, −3.8, −4.2, −4.5, −4.6; LRMS (ESI) 1011.8 [M+Na]+, 857.7, 725.6, 633.2, 413.3, 375.3; HRMS (ESI) calcd for C$_{56}$H$_{108}$O$_6$Si$_4$Na 1011.7121 [M+Na]+, found 1011.7148; [α]$^{20}_D$−16.9 (c 1.24, CHCl$_3$).

8(S),10(S),14(R),20(R)-Tetrahydroxy-7(S),13(S),15 (R),17(S),21 (S)-pentamethyl-22(S)-(1(S)-methyl-penta-2,4-dienyl)-oxa-cyclodocosa-3(E),5(E),11(Z)-trien-2-one (100, YSS665-2)

3 N HCl (10 mL, prepared by adding 2.5 mL of conc. HCl to 7.5 mL MeOH) was added to a stirred solution of the above macrolactone 99 (61 mg, 6.17 μmol) in THF (3 mL) at 0° C. After 24 h at room temperature, the reaction mixture was diluted with EtOAc (4 mL) and H$_2$O (4 mL) and the organic phase was separated and aqueous phase was extracted with EtOAc (2×4 mL). The combined organic phases were washed with sat'd NaHCO$_3$ (10 mL), dried with MgSO$_4$, concentrated and the residue was purified by flash chromatography (EtOAc/hexane 3:2) to yield the product 100 (8.2 mg, 25%) as a colorless oil: IR (CHCl$_3$) 3404, 2962, 2916, 1692, 1639, 1455, 1244, 1061, 1001 cm$^{-1}$; $^1$H NMR (600 MHz, CD$_3$OD) δ 7.15 (dd, J=15.3, 10.5 Hz, 1H), 6.64 (ddd, J=16.8, 10.6, 10.3 Hz, 1H), 6.29 (dd, J=15.4, 6.3 Hz, 1H), 6.22 (dd, J=15.5, 10.5 Hz, 1H), 5.92 (t, J=10.9 Hz, 1H), 5.72 (d, J=15.3 Hz, 1H), 5.44-5.37 (m, 2H), 5.25 (t, J=10.3 Hz, 1H), 5.13 (dd, J=16.8, 1.8 Hz, 1H), 5.06 (d, J=10.8 Hz, 1H), 5.04 (dd, J=9.1, 1.8 Hz, 1H), 4.68 (ddd, J=9.9, 7.2, 2.4 Hz, 1H), 3.82 (ddd, J=9.2, 6.2, 2.7 Hz, 1H), 3.40 (ddd, J=10.2, 6.2, 2.3 Hz, 1H), 3.06 (m, 1H), 2.99 (dd, J=8.0, 3.3 Hz, 1H), 2.62 (m, 1H), 2.58 (m, 1H), 1.88 (m, 1H), 1.62 (m, 1H), 1.55 (ddd, J=14.0, 10.5, 2.7 Hz, 1H), 1.38 (ddd, J=12.3, 9.6, 2.7 Hz, 1H), 1.34-1.23 (m, 4H), 1.12 (d, J=7.0 Hz, 3H), 1.06 (d, J=6.9 Hz, 3H), 1.04 (d, J=6.9 Hz, 3H), 1.00 (d, J=6.7 Hz, 3H), 0.95-0.88 (m, 2H), 0.87-0.82 (m, 1H), 0.79 (d, J=5.3 Hz, 3H), 0.68 (d, J=6.7 Hz, 3H); $^{13}$C NMR (150 MHz, CD$_3$OD) δ 168.5, 147.7, 147.4, 135.7, 134.4, 133.5, 131.7, 130.8, 129.1, 120.7, 118.0, 80.7, 76.9, 74.2, 72.8, 65.9, 44.0, 42.5, 40.9, 39.5, 36.5, 36.3, 36.1, 35.5, 31.7, 31.2, 21.1, 19.0, 17.9, 17.7, 15.7, 11.3; LRMS (ESI) 555.6 [M+Na]+, 541.4; HRMS (ESI) calcd for C$_{32}$H$_{52}$O$_6$ 555.3662 [M+Na]+, found 555.3684; [α]$^{20}_D$−6.5 (c 0.17, MeOH).

(4S,5S)-4-((2R,3S,6S,8R,9R,10S,11Z,13S,15S,16S, 17E)-3,9,13,15-tetrakis(tert-Butyldimethylsilyloxy)-6,8,10,16-tetramethyl-19-(trityloxy)nonadeca-11,17-dien-2-yl)-2-(4-methoxyphenyl)-5-methyl-1,3-dioxane (101)

The same procedure for 92 was used with above 91α (0.60 g, 0.50 μmol), TBSOTf (0.17 mL, 0.75 mmol) and 2,6-lutidine (0.12 mL, 1.0 mmol) to yield 0.61 g (93%) of the product by flash column chromatography (EtOAc/Hexane 1:9) as a colorless oil: IR (CHCl$_3$) 2956, 2928, 2856, 1518, 1471, 1462, 1251, 1075, 835, 773 cm$^{-1}$; $^1$H NMR (300 MHz, CDCl$_3$) δ 7.56-7.48 (m, 8H), 7.38-7.26 (m, 9H), 6.97-6.94 (m, 1H), 5.91 (dd, J=15.6, 5.9 Hz, 1H), 5.63 (dt, J=15.7, 5.3 Hz, 1H), 5.58-5.50 (m, 1H), 5.52 (s, 1H), 5.41 (dd, J=10.8, 8.6 Hz, 1H), 4.65 (m, 1H), 4.19 (dd, J=11.1, 4.5 Hz, 1H), 4.01 (m, 1H), 3.90 (m, 1H), 3.84 (s, 3H), 3.66 (d, J=5.0 Hz, 2H), 3.56 (t, J=11.1 Hz, 1H), 3.36 (m, 1H), 2.71 (m 1H), 2.48 (m, 1H), 2.12 (m, 1H), 1.88 (m, 1H), 1.76-1.56 (m, 3H), 1.52-1.42 (m, 2H), 1.40-1.31 (m, 2H), 1.09 (d, J=7.7 Hz, 3H), 1.07 (d, J=7.5 Hz, 3H), 1.05-0.94 (m, 42H), 0.93-0.90 (m, 2H), 0.86 (d, J=6.6 Hz, 3H), 0.81 (d, J=6.3 Hz, 3H), 0.21-0.13 (m, 24H); $^{13}$C NMR (75 MHz, CDCl$_3$) δ 159.7, 144.6, 144.4, 134.4, 133.0, 131.9, 131.8, 128.7, 127.7, 127.3, 126.8, 126.4, 113.4, 100.8, 86.7, 81.6, 81.3, 73.4, 72.8, 72.0, 66.6, 65.2, 55.1, 43.1, 42.3, 39.7, 38.2, 35.4, 35.3, 31.3, 30.8, 30.7, 30.3, 26.2, 26.1, 26.04, 25.97, 19.5, 18.8, 18.4, 18.1, 16.6, 14.6, 12.2, 9.1, −2.8, −3.4, −3.6, −3.9, −4.0, −4.1, −4.3; LRMS (ESI) 1327.9 [M+Na]+, 1037.9, 803.6, 647.6, 619.6, 413.3, 359.2, 229.1; HRMS (ESI) calcd for C$_{78}$H$_{128}$O$_8$Si$_4$Na 1327.8584 [M+Na]+, found 1327.8622; [α]$^{20}_D$+5.9 (c 0.3, CHCl$_3$).

(2S,3S,4R,5S,8S,10R,11R,12S,13Z,15S,17S,18S, 19E)-3-(4-Methoxybenzyloxy)-5,11,15,17-tetrakis(tert-butyldimethylsilyloxy)-2,4,8,10,12,18-hexamethyl-21-(trityloxy)henicosa-13,19-dien-1-ol (102)

The procedure for 93 was used with 101 (0.61 g, 0.47 μmol), DIBAL (4.6 mL, 4.6 mmol) to yield 0.53 g (87%) of the product by flash column chromatography (EtOAc/Hexane 0.5:9.5) as a colorless oil: IR (CHCl$_3$) 3453, 2956, 2929, 1514, 1471, 1251, 1075, 835, 773 cm$^{-1}$; $^1$H NMR (300 MHz, CDCl$_3$) δ 7.56-7.52 (m, 6H), 7.38-7.26 (m, 11H), 6.96-6.93 (m, 2H), 5.91(dd, J=15.7, 6.0 Hz, 1H), 5.64 (dt, J=15.4, 5.5 Hz, 1H), 5.55-5.50 (m, 1H), 5.42 (dd, J=11.1, 8.4 Hz, 1H), 4.70-4.58 (m, 3H), 4.01 (m, 1H), 3.83 (s, 3H), 3.79 (m, 2H), 3.67-3.61 (m, 3H), 3.35 (m, 1H), 3.30 (m 1H), 2.72 (m, 1H), 2.48 (m, 1H), 1.93 (m, 2H), 1.76-1.55 (m, 3H), 1.51-1.26 (m, 1H), 1.10 (d, J=6.6 Hz, 3H), 1.09 (d, J=6.6 Hz, 3H), 1.07 (d, J=6.7 Hz, 3H), 1.01-0.98 (m, 39H), 0.93-0.89 (m, 2H), 0.86 (d, J=6.6 Hz, 3H), 0.78 (d, J=4.6 Hz, 3H), 0.21-0.13 (m, 24H); $^{13}$C NMR (75 MHz, CDCl$_3$) δ 159.2, 144.5, 144.4, 134.3, 133.1, 131.7, 130.6, 129.1, 128.6, 127.6, 126.8, 126.7, 126.4, 113.8, 86.7, 85.1, 81.3, 74.9, 74.4, 72.8, 66.5, 65.9, 65.1, 55.1, 43.0, 42.3, 41.8, 40.1, 38.4, 35.3, 35.1, 32.8, 30.7, 30.5, 26.2, 26.1, 26.0, 25.9, 19.5, 18.6, 18.4, 18.13, 18.10, 16.5, 15.4, 14.6, 10.5, −2.8, −3.4, −3.6, −3.9, −4.0, −4.2, −4.4; LRMS (ESI) 1329.8 [M+Na]+, 801.6, 659.3, 637.3, 437.2, 243.1; HRMS (ESI) calcd for C$_{78}$H$_{130}$O$_8$Si$_4$Na 1329.8741 [M+Na]+, found 1329.8788; [α]$^{20}_D$ −9.8 (c 2.6, CHCl$_3$).

((2E,4S,5S,7S,8Z,10S,11R,12R,14S,17S,18R,19S, 20S,21z)-19-(4-Methoxybenzyloxy)-5,7,11,17-tetrakis(tert-butyldimethylsilyloxy)-4,10,12,14,18,20-hexamethyltetracosa-2,8,21,23-tetraenyloxy) triphenylmethane (103)

The procedure for 94 was used with 102 (0.52 g, 0.40 μmol), Dess-Martin reagent (0.25 g, 0.59 mmol) and 1-bromoallyl trimethylsilane (0.49 g, 2.0 mmol), CrCl$_2$ (0.41 g, 3.32 mmol) and NaH (0.20 g, 8.0 mmol) to yield 0.46 g (88%) of the product by flash column chromatography (EtOAc/hexane 1:19) as a colorless oil: IR (CHCl$_3$) 2956, 2856, 1614, 1514, 1471, 1249, 1074, 835, 773 cm$^{-1}$; $^1$H NMR (300 MHz, CDCl$_3$) δ 7.59-7.56 (m, 6H), 7.41-7.27(m, 1H), 6.98-6.95 (m, 2H), 6.71 (ddd, J=16.7, 10.6, 10.5 Hz, 1H), 6.14 (t, J=11.0 Hz, 1H), 5.94 (dd, J=15.6, 5.6 Hz, 1H), 5.80-5.67 (m, 2H), 5.64-5.55 (m, 1H), 5.46 (dd, J=11.0, 8.5 Hz, 1H), 5.31 (d, J=16.8 Hz, 1H), 5.21 (d, J=10.2 Hz, 1H), 4.70-4.62 (m, 3H), 4.04 (m, 1H), 3.86 (s, 3H), 3.69 (d, J=4.7 Hz, 1H), 3.34 (m, 2H), 2.96 (m, 1H), 2.77 (m, 1H), 2.51 (m, 1H), 1.93 (m, 1H), 1.78 (m, 1H), 1.75-1.63 (m, 3H), 1.57-1.31 (m, 5H), 1.21 (d, J=6.7 Hz, 3H), 1.15 (d, J=6.1 Hz, 3H), 1.12 (d, J=6.7 Hz, 3H), 1.00 (d, J=7.3 Hz, 3H), 1.05-1.01 (m, 36H), 0.96-0.93 (m, 2H), 0.89 (d, J=6.7 Hz, 3H), 0.81 (d, J=5.3 Hz, 3H), 0.25-0.11 (m, 24H); $^{13}$C NMR (75 MHz, CDCl$_3$) δ 159.1, 146.2, 144.6, 144.4, 134.4, 134.3, 132.2, 131.3, 130.2, 129.0, 128.7, 127.7, 126.8, 126.5, 117.5, 113.7, 86.7, 84.9, 81.4, 74.9, 73.1, 72.9, 66.6, 65.2, 55.1, 43.1, 42.9, 42.3, 40.4, 35.9, 35.6, 35.3, 35.1, 34.5, 30.2, 29.4, 26.3, 26.1, 26.0, 19.6, 18.8, 18.6, 18.5, 18.2, 18.14, 18.11, 16.5, 14.7, 10.5, −1.1, −2.8, −3.0, −3.3, −3.5, −3.9, −4.2, −4.3; LRMS (ESI) 1351.8 [M+Na]+, 911.1, 837.1, 763.1, 689.1, 541.1, 413.2; HRMS (ESI) calcd for C$_{81}$H$_{132}$O$_7$Si$_4$Na 1351.8948 [M+Na]+, found 1351.8998; [α]$^{20}_D$ −9.3 (c 1.5, CHCl$_3$).

(2E,4S,5S,7S,8Z,10S,11R,12R,14S,17S,18R,19S, 20S,21Z)-19-(4-Methoxybenzyloxy)-5,7,11,17-tetrakis(tert-butyldimethylsilyloxy)-4,10,12,14,18,20-hexamethyltetracosa-2, 8,21,23-tetraen-1-ol (104)

The procedure for 95 was used with 103 (0.33 g, 0.25 μmol) and ZnBr (0.28 g, 1.25 mmol) to yield 0.18 g (65%) of the product by flash column chromatography (EtOAc/hexane 1:9) as a colorless oil: IR (CHCl$_3$) 3417, 2956, 2856, 1613, 1514, 1471, 1250, 1074, 836, 773 cm$^{-1}$; $^1$H NMR (300 MHz, CDCl$_3$) δ 7.31-7.27 (m, 2H), 6.90-6.87 (m, 2H), 6.60 (ddd, J=16.9, 10.6, 10.5 Hz, 1H), 6.04 (t, J=11.0 Hz, 1H), 5.81 (dd, J=15.7, 5.9 Hz, 1H), 5.67-5.60 (m, 2H), 5.51-5.44 (m, 1H), 5.34 (dd, J=11.2, 8.7 Hz, 1H), 5.21 (d, J=16.8 Hz, 1H), 5.12 (d, J=10.2 Hz, 1H), 4.60-4.52 (m, 3H), 4.10 (d, J=5.7 Hz, 1H), 3.91 (m, 1H), 3.81 (s, 3H), 3.59 (m, 1H), 3.31-3.23 (m, 2H), 2.86 (m, 1H), 2.65 (m, 1H), 2.40 (m, 1H), 1.82 (m, 1H), 1.66-1.42 (m, 5H), 1.36-1.20 (m, 3H), 1.11 (d, J=6.8 Hz, 3H), 1.03 (d, J=7.3 Hz, 3H), 1.01 (d, J=6.6 Hz, 3H), 0.99 (d, J=5.8 Hz, 3H), 0.94-0.89 (m, 38H), 0.84 (d, J=7.2 Hz, 3H), 0.82 (d, J=6.4 Hz, 3H), 0.13-0.00 (m, 24H); $^{13}$C NMR (75 MHz, CDCl$_3$) δ 159.0, 135.0, 134.5, 133.2, 132.2, 131.5, 131.4, 129.1, 129.0, 128.7, 117.4, 113.7, 84.8, 81.4, 74.8, 73.1, 72.7, 66.5, 64.1, 55.2, 42.8, 42.7, 42.0, 40.4, 35.9, 35.4, 35.2, 34.4, 30.3, 29.4, 26.3, 26.03, 26.97, 25.95, 19.6, 18.7, 18.6, 18.5, 18.1, 16.6, 14.7, 10.5, −2.8, −3.4, −3.5, −4.0, −4.1, −4.2, −4.3, −4.4; LRMS (ESI) 1109.8 [M+Na]+, 707.2, 633.2, 541.1, 429.1, 355.1; HRMS (ESI) calcd for C$_{62}$H$_{118}$O$_7$Si$_4$Na 1109.7852 [M+Na]+, found 1109.7874; [α]$^{20}_D$ −15.0 (c 0.94, CHCl$_3$).

(2Z,4E,6S,7S,9S,10Z,12S,13R,14R,16S,19S,20R, 21S,22S,23Z)-Methyl-21-(4-methoxybenzyloxy)-7, 9,13,19-tetrakis(tert-butyldimethylsilyloxy)-6,12,14, 16,20,22-hexamethylhexacosa-2,4,10,23,25-pentaenoate (105)

The procedure for 96 was used with 104 (0.18 g, 0.16 μmol), Dess-Martin reagent (0.10 g, 0.24 mmol) and bis(2, 2,2-trifluoroethyl)-(methoxycarbonylmethyl) phosphate (0.041 mL, 0.19 μmol), 18-crown-6 (0.21 g, 0.19 mmol) and KHMDS (0.39 mL, 0.19 mmol) to yield 0.16 g (84%) of the product by flash column chromatography (EtOAc/hexane 1:19) as a colorless oil: IR (CHCl$_3$) 2956, 2929, 2856, 1721, 1514, 1462, 1250, 1174, 1074, 836, 773 cm$^{-1}$; $^1$H NMR (300 MHz, CDCl$_3$) δ 7.38 (dd, J=15.4, 11.2 Hz, 1H), 7.32-7.29 (m, 2H), 6.91-6.86 (m, 2H), 6.60 (ddd, J=17.0, 10.6, 10.5 Hz, 1H), 6.56 (t, J=11.3 Hz, 1H), 6.23 (dd, J=15.5, 5.9 Hz, 1H), 6.05 (t, J=11.0 Hz, 1H), 5.68-5.56 (m, 2H), 5.50-5.43 (m, 1H), 5.38-5.31 (m, 1H), 5.23 (d, J=16.8 Hz, 1H), 5.12 (d, J=10.2 Hz, 1H), 4.61-4.52 (m, 3H), 3.98 (m, 1H), 3.81 (s, 3H), 3.73 (s, 3H), 3.59 (m, 1H), 3.29-3.23 (m, 2H), 2.86 (m, 1H), 2.68-2.59 (m, 2H), 1.83 (m, 1H), 1.63-1.51 (m, 2H), 1.49-1.35 (m, 3H), 1.34-1.22 (m, 2H), 1.12 (d, J=6.8 Hz, 3H), 1.07 (d, J=6.9 Hz, 3H), 1.03 (d, J=5.0 Hz, 3H), 1.01 (d, J=6.7 Hz, 3H), 0.94-0.89 (m, 38H), 0.84 (d, J=6.6 Hz, 3H), 0.80 (d, J=6.1 Hz, 3H), 0.14-0.00 (m, 24H); $^{13}$C NMR (75 MHz, CDCl$_3$) δ 166.8, 159.1, 147.2, 145.7, 134.4, 133.2, 132.2, 131.6, 131.4, 129.2, 129.0, 126.4, 117.5, 115.2, 113.7, 84.7, 81.5, 74.9, 73.0, 72.7, 66.4, 55.2, 50.9, 42.9, 42.8, 42.6, 40.3, 35.9, 35.4, 35.2, 34.4, 30.4, 29.5, 26.3, 26.03, 25.98, 19.6, 18.8, 18.7, 18.5, 18.1, 16.7, 14.5, 10.5, 2.8, −3.3, −3.5, −4.0, −4.1, −4.17, −4.22, −4.4; LRMS (ESI) 1163.8 [M+Na]+, 1009.7, 877.6, 513.4; HRMS (ESI) calcd for C$_{65}$H$_{120}$O$_8$Si$_4$Na 1163.7958 [M+Na]+, found 1163.7981; [α]$^{20}_D$ −45.3 (c 0.36, CHCl$_3$)

(2Z,4E,6S,7S,9S,10Z,12S,13R,14R,16S,19S,20R, 21S,22S,23Z)-Methyl-7,9,13,19-tetrakis(tert-butyldimethylsilyloxy)-21-hydroxy-6,12,14,16,20,22-hexamethylhexacosa-2,4,10,23, 25-pentaenoate (106)

The procedure for 97 was used with 105 (0.16 g, 0.14 μmol) and DDQ (0.034 g, 0.15 mmol) to yield 0.13 g (90%) of the product by flash column chromatography (EtOAc/hexane 1:19) as a colorless oil: IR (CHCl$_3$) 3512, 2956, 2929, 2857, 1772, 1639, 1471, 1462, 1255, 1193, 1076, 836, 773 cm$^{-1}$; $^1$H NMR (300 MHz, CDCl$_3$) δ 7.35 (dd, J=15.4, 11.2 Hz, 1H), 6.61 (ddd, J=16.9, 10.6, 10.5 Hz, 1H), 6.53 (t, J=11.3 Hz, 1H), 6.19 (dd, J=15.6, 6.0 Hz, 1H), 6.09 (t, J=11.0 Hz, 1H), 5.56 (d, J=11.3 Hz, 1H), 5.44 (t, J=11.0 Hz, 1H), 5.31 (dd, J=11.0, 8.4 Hz, 1H), 5.19 (d, J=16.8 Hz, 1H), 5.10 (d, J=10.1 Hz, 1H), 4.55 (m, 1H), 3.94 (m, 1H), 3.71 (s, 3H), 3.25 (m, 2H), 2.75 (m, 1H), 2.58 (m, 2H), 1.72 (m, 1H), 1.67-1.60 (m, 1H), 1.59-1.49 (m, 2H), 1.40 (m, 1H), 1.32-1.25 (m, 2H), 1.22-1.13 (m, 2H), 1.04 (d, J=7.0 Hz, 3H), 1.01 (d, J=7.1 Hz, 3H), 0.99 (d, J=6.8 Hz, 3H), 0.91-0.86 (m, 41H), 0.81 (d, J=6.5 Hz, 3H), 0.79 (d, J=6.0 Hz, 3H), 0.11-0.05 (m, 24H); $^{13}$C NMR (75 MHz, CDCl$_3$) δ 166.8, 147.2, 145.6, 136.4, 133.2, 132.6, 131.5, 129.5, 126.4, 117.3, 115.2, 81.3, 78.6, 74.3, 72.7, 66.4, 50.9, 42.9, 42.6, 39.7, 36.2, 35.8, 35.4, 35.3, 34.1, 32.4, 30.6, 26.3, 26.0, 25.9, 19.6, 19.2, 18.5, 18.1, 18.0, 17.4, 16.7, 14.5, 10.9, −2.8, −3.4, −3.5, −4.06, −4.11, −4.2, −4.3, −4.4; LRMS (ESI) 1043.7 [M+Na]+; HRMS (ESI) calcd for C$_{57}$H$_{112}$O$_7$Si$_4$Na 1043.7383 [M+Na]+, found 1043.7424; [α]$^{21}_D$−37.8 (c 1.4, CHCl$_3$).

(2Z,4E,6S,7S,9S,10Z,12S,13R,14R,16S,19S,20R, 21S,22S,23Z)-7,9,13,19-tetrakis(tert-Butyldimethylsilyloxy)-21-hydroxy-6,12,14,16,20,22-hexamethylhexacosa-2,4,10,23,25-pentaenoic acid (107)

The procedure for 99 was used with 106 (0.13 g, 0.13 μmol) and 1N KOH (1.2 mL, 1.3 mmol), 2,4,6-trichlorobenzoyl chloride (0.094 mL, 0.60 μmol) and Et$_3$N (0.10 mL, 0.78 mmol), 4-DMAP (60 mL, 1.3 mmol) to yield 0.054 g (45% for 2 steps) of the product by flash column chromatography (EtOAc/hexane 1:19) as a colorless oil: (seco acid) IR (CHCl$_3$) 2956, 2857, 1692, 1634, 1471, 1462, 1254, 1076, 836, 773 cm$^{-1}$; $^1$H NMR (300 MHz, CDCl$_3$) δ 7.34 (dd, J=15.2, 11.3 Hz, 1H), 6.66 (ddd, J=16.8, 10.8, 10.6 Hz, 1H), 6.62 (t, J=11.3 Hz, 1H), 6.23 (dd, J=15.3, 6.0 Hz, 1H), 6.09 (t, J=11.0 Hz, 1H), 5.57 (d, J=11.2 Hz, 1H), 5.48-5.42 (m, 1H), 5.35-5.28 (m, 1H), 5.20 (d, J=16.8 Hz, 1H), 5.10 (d, J=10.2 Hz, 1H), 4.55 (m, 1H), 3.95 (m, 1H), 3.74 (m, 1H), 3.26 (m, 1H), 2.78 (m, 1H), 2.58 (m, 2H), 1.75-1.64 (m, 2H), 1.62-1.49 (m, 3H), 1.44-1.37 (m, 1H), 1.32-1.19 (m, 3H), 1.04 (d, J=7.0 Hz, 3H), 1.01 (d, J=7.0 Hz, 3H), 1.00 (d, J=6.4 Hz, 3H), 0.95-0.86 (m, 41H), 0.82 (d, J=7.1 Hz, 3H), 0.81 (d, J=6.4 Hz, 3H), 0.12-0.05 (m, 24H); $^{13}$C NMR (75 MHz, CDCl$_3$) δ 171.5, 148.3, 147.4, 136.4, 133.1, 132.6, 131.5, 129.5, 126.6, 117.3, 115.0, 81.3, 78.6, 74.3, 72.7, 66.4, 43.0, 42.7, 39.7, 36.2, 35.5, 35.3, 34.1, 32.4, 30.6, 26.3, 26.0, 25.94, 25.92, 19.6, 19.2, 18.5, 18.1, 18.0, 17.4, 16.7, 14.5, 11.0, −2.8, −3.4, −3.5, −4.1, −4.25, −4.32, −4.7; LRMS (ESI) 1029.7 [M+Na]+, 915.8; HRMS (ESI) calcd for C$_{56}$H$_{110}$O$_7$Si$_4$Na 1029.7226 [M+Na]+, found 1029.7252; [α]$^{20}_D$−32.7 (c 0.51, CHCl$_3$).

8(S),10(S),14(R),20(S)-Tetrahydroxy-7(S),13(S),15(R),17(S),21(S)-pentamethyl-22(S)-(1(S)-methyl-penta-2,4-dienyl)oxacyclodocosa-3(Z),5(E),11(Z)-trien-2-one (194, YSS675-1) and 8(S),10(S),14(R), 20(S)-Tetrahydroxy-7(S),13(S),15(R),17(S),21(S)-pentamethyl-22(S)-(1(S)-methyl-penta-2,4-dienyl) oxacyclodocosa-3(E),5(E),11(Z)-trien-2-one (108, YSS675-2)

The procedure for 100 was used with 107 (0.054 g, 0.054 μmol) in 3N HCl (5 mL) and THF (2 mL) to yield 13 mg (45%) of 108 and 4.5 mg (15%) of the 109 by flash column chromatography (EtOAc/hexane 7:3) as a colorless oil: (108) IR (CHCl$_3$) 3416, 2961, 2927, 2873, 1692, 1635, 1455, 1421, 1379, 1190, 1086, 998 cm$^{-1}$; $^1$H NMR (600 MHz, CD$_3$OD) δ 7.26 (dd, J=15.2, 11.3 Hz, 1H), 6.65 (ddd, J=16.8, 10.6, 10.3 Hz, 1H), 6.56 (t, J=11.3 Hz, 1H), 5.97 (t, J=10.9 Hz, 1H), 5.91 (dd, J=15.2, 9.3 Hz, 1H), 5.49 (d, J=10.7 Hz, 1H), 5.42 (t, J=8.6 Hz, 1H), 5.20 (t, J=10.4 Hz, 1H), 5.15 (dd, J=16.9, 1.3 Hz, 1H), 5.08 (d, J=10.1 Hz, 1H), 5.05 (dd, J=9.6, 1.3 Hz, 1H), 4.62 (ddd, J=11.5, 7.7, 4.3 Hz, 1H), 3.65 (ddd, J=10.0, 7.3, 3.1 Hz, 1H), 3.07 (dd, J=6.7, 4.0 Hz, 1H), 3.01 (m, 1H), 2.66 (m, 1H), 2.26 (m, 1H), 1.90 (m, 1H), 1.66 (ddd, J=11.5, 8.4, 3.4 Hz, 1H), 1.49 (ddd, J=14.1, 10.0, 4.0 Hz, 1H), 1.45 (m, 1H), 1.38 (m, 1H), 1.32 (m, 1H), 1.27 (m, 1H), 1.11 (d, J=6.7 Hz, 3H), 1.06 (m, 1H), 1.03 (ddd, J=11.3, 7.2, 4.4 Hz, 3H), 1.01 (d, J=6.9 Hz, 3H), 0.99 (d, J=6.7 Hz, 3H), 0.96 (d, J=7.0 Hz, 3H), 0.93 (m, 1H), 0.89 (m, 1H), 0.85 (d, J=6.7 Hz, 3H), 0.75 (d, J=5.9 Hz, 3H); $^{13}$C NMR (150 MHz, CD$_3$OD) δ 168.1, 148.7, 146.6, 135.7, 134.0, 133.7, 132.9, 131.1, 128.2, 118.0, 117.0, 80.9, 78.4, 74.4, 72.4, 66.3, 46.4, 43.4, 42.5, 40.9, 36.3, 35.90, 35.88, 35.7, 31.8, 31.5, 19.9, 19.3, 18.3, 17.5, 8.5; LRMS (ESI) 555.3 [M+Na]+, 537.4; HRMS (ESI) calcd for C$_{32}$H$_{52}$O$_6$ 555.3662 [M+Na]+, found 555.3680; [α]$^{20}_D$+76.5 (c 0.52, MeOH): (109) IR (CHCl$_3$) 3428, 2962, 2928, 1690, 1635, 1380, 1243, 1145, 1064, 1000 cm$^{-1}$; $^1$H NMR (600 MHz, CD$_3$OD) δ 7.20 (dd, J=15.2, 10.8 Hz, 1H), 6.65 (ddd, J=17.0, 10.6, 10.5 Hz, 1H), 6.38 (dd, J=15.5, 5.4 Hz, 1H), 6.23 (dd, J=14.4, 10.9 Hz, 1H), 5.95 (t, J=11.0 Hz, 1H), 5.77 (d, J=15.3 Hz, 1H), 5.40-5.39 (m, 2H), 5.23 (t, J=10.5 Hz, 1H), 5.13 (d, J=18.1 Hz, 1H), 5.12 (dd, J=8.2, 1.5 Hz, 1H), 5.07 (d, J=10.2 Hz, 1H), 4.66 (m, 1H), 3.90 (ddd, J=7.6, 5.1, 2.5 Hz, 1H), 3.22 (dd, J=9.8, 7.9 Hz, 1H), 3.04 (m, 1H), 2.95 (dd, J=9.7, 2.1 Hz, 1H), 2.72 (m, 1H), 2.65 (m, 1H), 1.83 (m, 1H), 1.58 (m, 1H), 1.46 (m, 1H), 1.35-1.23 (m, 4H), 1.05 (d, J=6.8 Hz, 3H), 1.04 (d, J=6.9 Hz, 3H), 0.98 (d, J=6.8 Hz, 3H), 0.97 (d, J=7.0 Hz, 3H), 0.94 (m, 2H), 0.78 (m, 1H), 0.71 (d, J=6.4 Hz, 3H), 0.68 (d, J=6.5 Hz, 3H); $^{13}$C NMR (150 MHz, CD$_3$OD) δ 169.4, 147.5, 147.4, 135.9, 134.3, 133.7, 131.0, 128.9, 120.0, 118.0, 80.5, 78.5, 72.6, 72.0, 65.2, 43.6, 42.6, 42.1, 39.3, 36.3, 35.8, 35.6, 35.3, 31.4, 29.7, 19.3, 18.5, 17.4, 17.1, 14.8, 9.0; LRMS (ESI) 555.5 [M+Na]+; HRMS (ESI) calcd for C$_{32}$H$_{52}$O$_6$ 555.3662 [M+Na]+, found 555.3687; [α]$^{20}_D$−17.3 (c 0.15, MeOH).

Biology

Tubulin Polymerization Assay

Tubulin assembly was monitored turbidimetrically in Gilford 250 spectrophotometers equipped with electronic temperature controllers as described previously (ter Haar et al., 1996). The reaction mixtures without the compounds consisted of tubulin (1 mg/ml), heat-treated MAPs (0.75 mg/ml, if present), GTP (100 μM, if present), and 0.1M (4-morpholinyl)ethane sulfonate (MeS). Baselines were established after addition of all reaction components except the compounds to the cuvettes held at 0° C. Compounds, at 10 μM or 40 μM final concentration, were then added and each reaction mixture (0.25 mL final volume) was subjected to the indicated temperature changes.

Antiproliferative Assay

The effects of dictyostatin and its analogs on growth inhibition of parental (A549) and paclitaxel-resistant (1A9/Ptx10 and Ptx22) ovarian adenocarcinoma cell lines were evaluated following the antiproliferative assay protocol as described earlier (Minguez et al., 2003; Choy et al., 2003; Lazo et al., 2001). Cells were maintained in RPMI medium with 10% FBS in it, plated in tissue culture plates, and allowed to grow for 48-72 h before transferring them into 96-well plates. Cells were allowed to attach and grow for 48 h in 96-well plates after which they were treated with either control (DMSO) or drug in triplicate/quadruplicate. Cells were incubated with the compounds for 72 h. Cells were treated with MTS reagent before reading the plate in a Dynamax plate reader for determining the cell number. The fifty percent growth inhibition values ($GI_{50}$ values) were calculated for the compounds against all the three cell lines.

Pelleting Assay (Determination of $EC_{50}$)

The assay was performed under three different reaction conditions following the procedure reported earlier (Gapud et al., 2004). Reaction condition 1 included 0.2 M monosodium glutamate (MSG), 10 μM tubulin, 5% DMSO and varying concentrations of test agents. Reaction condition 2 included 0.8 M MSG, 400 μM GTP, 10 μM tubulin, 5% DMSO, and varying concentrations of test agents. Reaction condition 3 had 0.6 M MSG, 200 μM GTP, and 10 μM tubulin, and 5% DMSO, and varying concentrations of the test agents. The experimental protocol for all the three reaction conditions was the following. The reaction mixtures were incubated at room temperature (20-22° C.) for 15 min and spun for 10 min at 14,000 rpm in an Eppendorf microtube centrifuge. Aliquots of the supernatants were removed and assayed for protein content by the method of Lowry. The $EC_{50}$ was defined as drug concentration required to polymerize 50% of tubulin compared to the pellet found in the DMSO control reaction determined for each test system. On average 5.5±4.0% of the tubulin pelleted in the DMSO control.

Multiparameter Fluorescence Microscopy High Information Content Cell-Based Fluorescence Screening HeLa cells growing at log phase were trypsinized and plated in 40 μL at a density of 7,000-8,000 cells per well in calf skin collagen I-coated 384-well plates (Falcon #3962; Fisher Scientific). Cells were exposed to test agents or 0.5% DMSO within 2-8 h of plating. Concentrated DMSO stock solutions of all test agents were diluted into solutions of HBSS medium plus 10% FBS and added to the microplate wells (10 μL per well), using an automated liquid handling system (Biomek® 2000; Beckman-Coulter, Inc.) to provide a serial 2-fold dilution of each test agent. The cells were incubated in the presence of test agents for 24 h. At the end of the incubation, the medium was removed and replaced with HBSS containing 4% formaldehyde and 10 μg/mL Hoechst 33342 (25 μL/well) to fix the cells and fluorescently label their chromatin. After incubation at room temperature for 20-30 min, the solution was removed from each well and replaced with HBSS (100 μL/well). Further reagent additions were made to the microplates using the Biomek 2000. After removing the HBSS from each well, cells were permeabilized for 5 min at room temperature with 0.5% (w/w) Triton X-100 in HBSS (10 μL/well). This step extracts a fraction of the soluble cellular components, including soluble tubulin. The wells were washed with HBSS (100 μL/well), followed by addition of a primary antibody solution containing mouse anti-α-tubulin (1:3000) and rabbit anti-phosphohistone H3 (1:500) in HBSS (10 μL/well). After 1 h at room temperature, the wells were washed with HBSS as above, followed by the addition of a secondary antibody solution containing fluorescein-5-isothiocyanate (FITC)-labeled donkey anti-mouse (1:300) and Cy3-labeled donkey anti-rabbit (1:300) antibodies diluted in HBSS (10 μL/well). After 1 h at room temperature, the wells were washed as above, and HBSS was added (100 μL/well). The plates were placed in an ArrayScan® HCS Reader with the Target Activation BioApplication Software coupled to Cellomics® Store and the vHCS™ Discovery Toolbox (Cellomics, Inc.) to analyze images. Briefly, the instrument was used to scan multiple optical fields, each with multiparameter fluorescence, within a subset of the wells of the 384-well microplate. The BioApplication software produced multiple numerical feature values, such as subcellular object intensities, shapes, and location for each cell within an optical field. Data were acquired from a minimum of 1,000 cells per well, except in cases where added test agents reduced the attachment of cells to the substrate. A nuclear mask was generated from Hoechst 33342-stained nuclei, and object identification thresholds and shape parameters were set such that the algorithm identified over 90% of the nuclei in each field. Objects that touched each other or the edge of the image were excluded from the analysis. Tubulin mass was defined as the average green (FITC) pixel intensity in an area defined by the Hoechst-defined nuclear mask. This cytoplasmic area around the nucleus contains cytoskeletal components is a region from which sensitive measurements of cytoplasmic characteristics can be made. The percentage of phospho-histone H3 positive cells was defined as the number of cells whose average red (Cy3) staining intensity exceeded the average Cy3 intensity plus two standard deviations of vehicle-treated cells, divided by the total number of cells.

Radiolabeled Ligand Binding Assays

[$^3$H]Paclitaxel, [$^3$H]discodermolide and [$^{14}$C]epothilone B solutions were prepared as 125 μM stock solutions in 50% DMSO. Radiolabeled compound (final concentration, 4.0 μM) and test agents at final concentrations noted in the text and tables were mixed in 50 μL of 4:1 (v/v) 0.75 M aqueous MSG/DMSO and warmed to 37° C. Meanwhile, a reaction mixture containing 0.75 M MSG, 2.5 μM tubulin, and 25 μM ddGTP was prepared and incubated at 37° C. for 30 min to form microtubuless. A 200 μL aliquot of the microtubule mixture was added to the drug mixtures, and incubation continued for 30 min at 37° C. Reaction mixtures were centrifuged in an Eppendorf 5417C centrifuge at 14,000 rpm for 20 min at room temperature. Radiolabel in the supernatants (100 μL) was determined by scintillation spectrometry. Bound radiolabeled compound was calculated from the total radiolabel added to each reaction mixture minus the amount of radiolabel found in the supernatant.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A compound of the following structure or its enantiomer

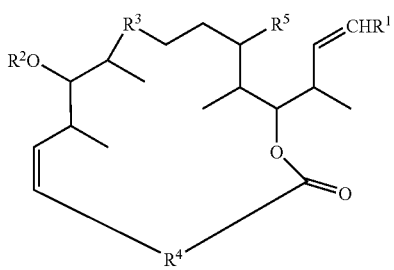

wherein $R^1$ is H, an alkyl group, an aryl group, an alkenyl group, an alkynyl group, or a halogen atom;

$R^2$ is H, a protecting group, an alkyl group, a benzyl group, a trityl group, —SiR$^a$R$^b$R$^c$, CH$_2$OR$^d$, or COR$^e$;

$R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein $R^i$ is an alkylene group;

$R^e$ is an alkyl group, an allyl group, a benzyl group, an aryl group, an alkoxy group, or —NR$^g$R$^h$, wherein $R^g$ and $R^h$ are independently H, an alkyl group or an aryl group;

$R^3$ is (CH$_2$)$_n$ where n is an integer in the range of 0 to 5, —CH$_2$CH(CH$_3$)—, —CH=CH—, —CH=C(CH$_3$)—, or —C≡C—;

$R^4$ is

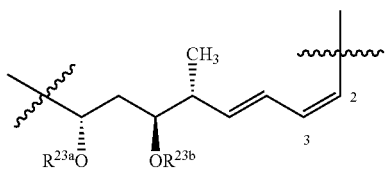

wherein $R^{23a}$ is H, a protecting group, an alkyl group, a benzyl group, a trityl group, —SiR$^a$R$^b$R$^c$, CH$_2$OR$^d$, or COR$^e$, $R^{23b}$ is H, a protecting group, an alkyl group, a benzyl group, a trityl group, —SiR$^a$R$^b$R$^c$, CH$_2$OR$^d$, or COR$^e$, or $R^{23a}$ and $R^{23b}$ together form a portion of six-membered acetal ring incorporating CR$^t$R$^u$;

$R^t$ and $R^u$ are independently H, an alkyl group, an aryl group or an alkoxyaryl group; and $R^5$ is H or OR$^{2b}$, wherein $R^{2b}$ is H, a protecting group, an alkyl group, an aryl group, a benzyl group, a trityl group, —SiR$^a$R$^b$R$^c$, CH$_2$OR$^d$, or COR$^e$; provided that the compound is not dictyostatin 1.

2. The compound of claim 1 with the following stereostructure, or its enantiomer

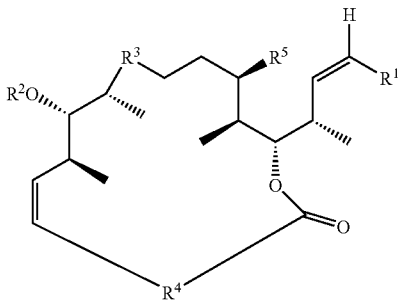

wherein $R^1$ is alkenyl; $R^2$ is H; $R^3$ is —CH$_2$CH(CH$_3$), CH$_2$CH$_2$CH=CH, or —CH=C(CH$_3$).

3. The compound of claim 2 wherein the compound is 16-desmethyldictyostatin and wherein $R^3$ is CH$_2$CH$_2$, $R^5$ is OH, $R^1$ is CH=CH$_2$ and $R^{23a}$, $R^{23b}$ are H.

4. The compound of claim 2 wherein R is OH or OSiR$^a$R$^b$R$^c$.

5. The compound of claim 1 wherein the compound is the C2-C3 E-stereoisomer or its enantioner.

6. The compound of claim 2 wherein the compound is the C2-C3 E-stereoisomer or its enantioner.

* * * * *

UNITED STATES PATENT AND TRADEMARK OFFICE
CERTIFICATE OF CORRECTION

PATENT NO. : 7,321,046 B2  Page 1 of 1
APPLICATION NO. : 11/139949
DATED : January 22, 2008
INVENTOR(S) : Dennis P. Curran et al.

It is certified that error appears in the above-identified patent and that said Letters Patent is hereby corrected as shown below:

Col. 88;
In Claim 4, line 45, "wherein R" should be deleted and --wherein $R^5$-- should be inserted therefor.

Signed and Sealed this

Eleventh Day of November, 2008

JON W. DUDAS
*Director of the United States Patent and Trademark Office*